United States Patent
Hatakeyama et al.

(10) Patent No.: US 12,204,245 B2
(45) Date of Patent: Jan. 21, 2025

(54) POSITIVE RESIST COMPOSITION AND PATTERNING PROCESS

(71) Applicant: Shin-Etsu Chemical Co., Ltd., Tokyo (JP)

(72) Inventors: Jun Hatakeyama, Joetsu (JP); Takeshi Nagata, Joetsu (JP); Chuanwen Lin, Joetsu (JP); Shun Kikuchi, Joetsu (JP)

(73) Assignee: SHIN-ETSU CHEMICAL CO., LTD., Tokyo (JP)

( * ) Notice: Subject to any disclaimer, the term of this patent is extended or adjusted under 35 U.S.C. 154(b) by 595 days.

(21) Appl. No.: 17/484,343

(22) Filed: Sep. 24, 2021

(65) Prior Publication Data

US 2022/0107559 A1 Apr. 7, 2022

(30) Foreign Application Priority Data

Oct. 1, 2020 (JP) .................................. 2020-166646

(51) Int. Cl.

| | |
|---|---|
| G03F 7/004 | (2006.01) |
| C07C 309/12 | (2006.01) |
| C07C 381/12 | (2006.01) |
| C07D 307/00 | (2006.01) |
| C07D 327/04 | (2006.01) |
| C07D 327/08 | (2006.01) |
| C07D 333/76 | (2006.01) |
| C07J 31/00 | (2006.01) |
| G03F 7/039 | (2006.01) |

(52) U.S. Cl.
CPC .......... *G03F 7/0045* (2013.01); *C07C 309/12* (2013.01); *C07C 381/12* (2013.01); *C07D 307/00* (2013.01); *C07D 327/04* (2013.01); *C07D 327/08* (2013.01); *C07D 333/76* (2013.01); *C07J 31/006* (2013.01); *G03F 7/039* (2013.01); *C07C 2602/42* (2017.05); *C07C 2603/74* (2017.05)

(58) Field of Classification Search
CPC ............................ C07C 309/12; C07C 381/12
See application file for complete search history.

(56) References Cited

U.S. PATENT DOCUMENTS

| | | | | |
|---|---|---|---|---|
| 11,592,746 | B2 * | 2/2023 | Kiriyama | C09D 133/062 |
| 2014/0356787 | A1 * | 12/2014 | Komuro | G03F 7/0045 |
| | | | | 560/190 |
| 2017/0205709 | A1 * | 7/2017 | Hatakeyama | C07C 69/635 |
| 2017/0369616 | A1 | 12/2017 | Hatakeyama et al. | |
| 2018/0275512 | A1 | 9/2018 | Hatakeyama et al. | |
| 2019/0155152 | A1 * | 5/2019 | Aqad | C07D 333/76 |
| 2020/0089112 | A1 | 3/2020 | Hatakeyama et al. | |
| 2020/0183273 | A1 * | 6/2020 | Nguyen | C07C 65/11 |
| 2020/0289112 | A1 * | 9/2020 | Whitfield | A61B 17/07207 |
| 2022/0043347 | A1 | 2/2022 | Takada et al. | |
| 2022/0066319 | A1 * | 3/2022 | Hatakeyama | G03F 7/0397 |

FOREIGN PATENT DOCUMENTS

| | | | |
|---|---|---|---|
| JP | 2018118962 A | * | 8/2018 |
| JP | 2018-159744 A | | 10/2018 |
| TW | 201805269 A | | 2/2018 |
| TW | 202016653 A | | 5/2020 |
| WO | 2019/054282 A1 | | 3/2019 |
| WO | 2020/255964 A1 | | 12/2020 |

OTHER PUBLICATIONS

Office Action dated Jun. 15, 2022, issued in counterpart TW Application No. 110136185. (7 pages).
Office Action dated Jan. 25, 2024 issued in counterpart TW Application No. 110136185. (4 pages).
Hutchinson, "The Shot Noise Impact on Resist Roughness in EUV Lithography", SPIE, 1998, vol. 3331, pp. 531-536, cited in Specification (7 pages).
Lio, "EUV Resists: What's Next?", SPIE, 2016, vol. 9776, pp. 97760V-1-14, cited in Specification (14 pages).
Office Action dated Apr. 16, 2024, issued in counterpart JP Application No. 2021-146779, with English translation. (9 pages).

* cited by examiner

*Primary Examiner* — Amanda C. Walke

(74) *Attorney, Agent, or Firm* — WHDA, LLP

(57) ABSTRACT

A positive resist composition is provided comprising (A) an acid generator in the form of a sulfonium salt consisting of a fluorine-containing sulfonate anion and a fluorine-containing sulfonium cation, (B) a quencher in the form of a sulfonium salt containing at least two fluorine atoms in its cation or containing at least 5 fluorine atoms in its anion and cation, and (C) a base polymer comprising repeat units (a1) having a carboxy group whose hydrogen is substituted by an acid labile group and/or repeat units (a2) having a phenolic hydroxy group whose hydrogen is substituted by an acid labile group. The resist composition exhibits a high sensitivity, high resolution and improved LWR or CDU.

13 Claims, No Drawings

POSITIVE RESIST COMPOSITION AND PATTERNING PROCESS

CROSS-REFERENCE TO RELATED APPLICATION

This non-provisional application claims priority under 35 U.S.C. § 119(a) on Patent Application No. 2020-166646 filed in Japan on Oct. 1, 2020, the entire contents of which are hereby incorporated by reference.

TECHNICAL FIELD

This invention relates to a positive resist composition and a pattern forming process.

BACKGROUND ART

To meet the demand for higher integration density and operating speed of LSIs, the effort to reduce the pattern rule is in rapid progress. In particular, the enlargement of the logic memory market to comply with the wide-spread use of smart phones drives forward the miniaturization technology. As the advanced miniaturization technology, manufacturing of microelectronic devices at the 10-nm node by double patterning of the ArF immersion lithography has been implemented in a mass scale. Manufacturing of 7-nm node devices as the next generation by the double patterning technology is approaching to the verge of high-volume application. The candidate for 5-nm node devices as the next generation but one is EUV lithography.

The EUV lithography enables to form small size patterns because the wavelength (13.5 nm) of EUV is as short as 1/14.3 of the wavelength (193 nm) of ArF excimer laser light. However, since the number of photons available from EUV exposure is accordingly 1/14.3 of that from ArF excimer laser exposure, there arises the problem of shot noise that a variation in number of photons causes an increase in edge roughness (LER or LWR) and a lowering of CDU (Non-Patent Document 1).

In addition to the variations due to shot noise, it is pointed out in Non-Patent Document 2 that the uneven distribution of acid generator and quencher components in a resist film causes a variation in feature size. In the EUV lithography for forming very small size patterns, there exists a need for a resist material of uniform distribution system.

CITATION LIST

Non-Patent Document 1: SPIE Vol. 3331, p531 (1998)
Non-Patent Document 2: SPIE Vol. 9776, p97760V-1 (2016)

DISCLOSURE OF INVENTION

An object of the invention is to provide a positive tone resist composition which exhibits a higher sensitivity and resolution than prior art positive resist compositions, and forms a pattern of good profile with a reduced LWR or improved CDU after exposure; and a pattern forming process using the same.

The inventors presumed that for obtaining a positive tone resist composition having a high sensitivity, high resolution, reduced LWR and improved CDU as desired in the recent market, it is necessary to prevent resist material components such as acid generator and quencher from agglomerating together and to disperse or distribute them uniformly. It is believed effective for this purpose to utilize the electrical repulsion force of fluorine atoms to prevent the relevant components from agglomeration. The inventors have found that when a sulfonium salt consisting of a sulfonate anion and a sulfonium cation which both contain at least one fluorine atom is added as the acid generator, and a sulfonium salt consisting of an anion and a cation, the cation containing at least two fluorine atoms or the anion and cation containing at least 5 fluorine atoms in total, is added as the quencher, there is formulated a resist composition in which the acid generator and the quencher are uniformly distributed because of their mutual repulsion.

In one aspect, the invention provides a positive resist composition comprising:
(A) an acid generator in the form of a sulfonium salt consisting of a sulfonate anion having at least one fluorine atom and a sulfonium cation having at least one fluorine atom,
(B) a quencher in the form of a sulfonium salt consisting of a cation and an anion, the cation containing at least two fluorine atoms or the anion and cation containing at least 5 fluorine atoms in total, and
(C) a base polymer comprising repeat units of at least one type selected from repeat units (a1) having a carboxy group whose hydrogen is substituted by an acid labile group and repeat units (a2) having a phenolic hydroxy group whose hydrogen is substituted by an acid labile group.

In a preferred embodiment, the quencher (B) is a sulfonium salt in which the cation contains at least 3 fluorine atoms or the anion and cation contain at least 6 fluorine atoms in total.

In a preferred embodiment, the sulfonate anion in the acid generator (A) further contains an iodine atom.

In a preferred embodiment, the sulfonate anion in the acid generator (A) has the formula (1-1) or (1-2).

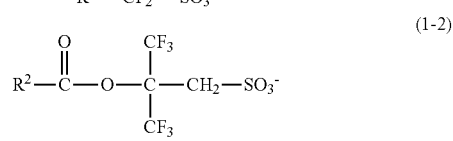

Herein $R^1$ is fluorine or a $C_1$-$C_{40}$ hydrocarbyl group which may contain a heteroatom exclusive of iodine. $R^2$ is a $C_1$-$C_{40}$ hydrocarbyl group which may contain a heteroatom exclusive of iodine.

In a preferred embodiment, the sulfonate anion has the formula (1-3).

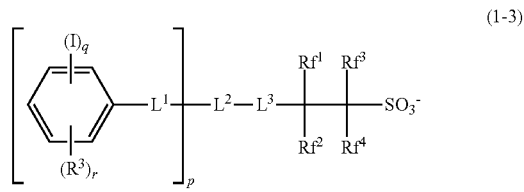

Herein p is an integer of 1 to 3, q is an integer of 1 to 5, r is an integer of 0 to 3, and q+r is from 1 to 5. $L^1$ is a single bond, ether bond, ester bond, amide bond, imide bond or a $C_1$-$C_6$ saturated hydrocarbylene group in which any constituent —$CH_2$— may be replaced by an ether bond or ester bond. $L^2$ is a single bond or $C_1$-$C_{20}$ hydrocarbylene group which may contain a heteroatom in case of p=1, and a $C_1$-$C_{20}$ (p+1)-valent hydrocarbon group which may contain a heteroatom in case of p=2 or 3. $L^3$ is a single bond, ether bond or ester bond. $Rf^1$ to $Rf^4$ are each independently hydrogen, fluorine or trifluoromethyl, at least one of $Rf^1$ to $Rf^4$ being fluorine or trifluoromethyl, and $Rf^1$ and $Rf^2$, taken together, may form a carbonyl group. $R^3$ is a hydroxy group, carboxy group, fluorine, chlorine, bromine, or amino group, or a $C_1$-$C_{20}$ hydrocarbyl group, $C_1$-$C_{20}$ hydrocarbyloxy group, $C_2$-$C_{20}$ hydrocarbyloxycarbonyl group, $C_2$-$C_{20}$ hydrocarbyloxycarbonyl group, $C_2$-$C_{20}$ hydrocarbylcarbonyloxy group, or $C_1$-$C_{20}$ hydrocarbylsulfonyloxy group, which may contain fluorine, chlorine, bromine, hydroxy, amino or ether bond,
or —N($R^{3A}$)($R^{3B}$), —N($R^{3C}$)—C(=O)—$R^{3D}$ or —N($R^{3C}$)—C(=O)—O—$R^{3D}$. $R^{3A}$ and $R^{3B}$ are each independently hydrogen or a $C_1$-$C_6$ saturated hydrocarbyl group, $R^{3C}$ is hydrogen or a $C_1$-$C_6$ saturated hydrocarbyl group, in which some or all hydrogen may be substituted by a halogen, hydroxy moiety, $C_1$-$C_6$ saturated hydrocarbyloxy moiety, $C_2$-$C_6$ saturated hydrocarbylcarbonyl moiety, or $C_2$-$C_6$ saturated hydrocarbylcarbonyloxy moiety, and $R^{3D}$ is a $C_1$-$C_{16}$ aliphatic hydrocarbyl group, $C_6$-$C_{12}$ aryl group or $C_7$-$C_{15}$ aralkyl group, in which some or all hydrogen may be substituted by a halogen, hydroxy moiety, $C_1$-$C_6$ saturated hydrocarbyloxy moiety, $C_2$-$C_6$ saturated hydrocarbylcarbonyl moiety, or $C_2$-$C_6$ saturated hydrocarbylcarbonyloxy moiety.

In a preferred embodiment, the anion of the sulfonium salt as quencher (B) is a carboxylate, sulfonamide, alkoxide or non-α-fluorinated sulfonate anion.

More preferably, the carboxylate anion has the formula (2-1), the sulfonamide anion has the formula (2-2), the alkoxide anion has the formula (2-3), and the non-α-fluorinated sulfonate anion has the formula (2-4).

$$R^{11}\!-\!\!\overset{\displaystyle O}{\underset{\displaystyle }{\text{C}}}\!\!-\!O^- \tag{2-1}$$

$$R^{12}\!-\!\!\overset{\displaystyle O}{\underset{\displaystyle O}{\overset{\|}{\text{S}}\|}}\!\!-\!N^-\!-\!R^{13} \tag{2-2}$$

$$R^{14}\!-\!O^- \tag{2-3}$$

$$R^{15}\!-\!\!\overset{\displaystyle O}{\underset{\displaystyle O}{\overset{\|}{\text{S}}\|}}\!\!-\!O^- \tag{2-4}$$

Herein $R^{11}$ is fluorine or a $C_1$-$C_{40}$ hydrocarbyl group which may contain fluorine and/or a heteroatom exclusive of fluorine. $R^{12}$ is fluorine or a $C_1$-$C_{40}$ hydrocarbyl group which may contain fluorine and/or a heteroatom exclusive of fluorine. $R^{13}$ is hydrogen or a $C_1$-$C_{20}$ hydrocarbyl group which may contain a heteroatom. $R^{14}$ is a $C_1$-$C_8$ saturated hydrocarbyl group having at least two fluorine atoms or a $C_6$-$C_{10}$ aryl group having at least two fluorine atoms. $R^{15}$ is a $C_1$-$C_{12}$ aliphatic hydrocarbyl group or $C_6$-$C_{10}$ aryl group, any constituent —$CH_2$— in the aliphatic hydrocarbyl group may be replaced by —N(H)—, ether bond, or ester bond, some or all of the hydrogen atoms in the aliphatic hydrocarbyl group may be substituted by a halogen atom, hydroxy moiety, carboxy moiety, $C_6$-$C_{10}$ aryl moiety, $C_1$-$C_{12}$ hydrocarbyloxy moiety, $C_2$-$C_{12}$ hydrocarbylcarbonyl moiety, or $C_1$-$C_{12}$ hydrocarbylcarbonyloxy moiety, some or all of the hydrogen atoms in the aryl group may be substituted by a halogen atom, hydroxy moiety, carboxy moiety, $C_1$-$C_{12}$ hydrocarbyloxy moiety, $C_2$-$C_{12}$ hydrocarbylcarbonyl moiety, or $C_1$-$C_{12}$ hydrocarbylcarbonyloxy moiety, with the proviso that $R^{15}$ has no fluorine on the α-carbon relative to the sulfo group.

In the sulfonium salt (A), the sulfonium cation having at least one fluorine atom preferably has the formula (3).

(3)

Herein $R^{a1}$ is a $C_1$-$C_{20}$ hydrocarbyl group substituted with at least one fluorine, which may contain at least one atom selected from oxygen, sulfur, nitrogen, and halogen exclusive of fluorine. $R^{a2}$ and $R^{a3}$ are each independently a $C_1$-$C_{20}$ hydrocarbyl group or $C_1$-$C_{20}$ hydrocarbyl group substituted with at least one fluorine, which may contain at least one atom selected from oxygen, sulfur, nitrogen, and halogen exclusive of fluorine. $R^{a1}$ and $R^{a2}$, or $R^{a2}$ and $R^{a3}$ may bond together to form a ring with the sulfur atom to which they are attached.

In a preferred embodiment, the repeat unit (a1) has the formula (a1) and the repeat unit (a2) has the formula (a2).

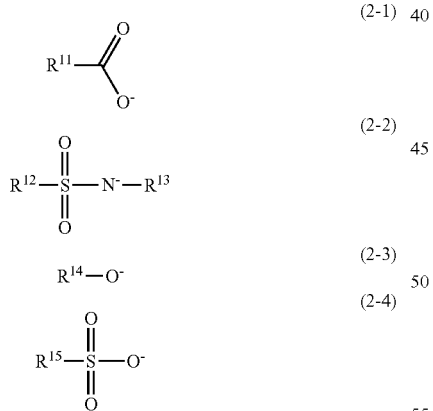

(a1)

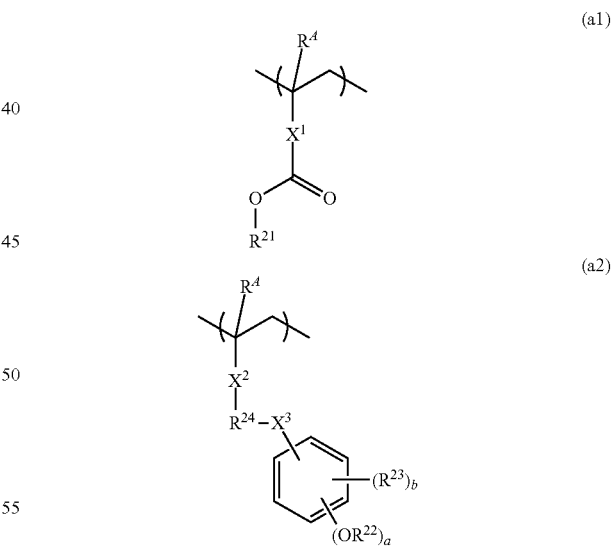

(a2)

Herein $R^A$ is each independently hydrogen or methyl. $X^1$ is a single bond, phenylene group, naphthylene group, or a $C_1$-$C_{12}$ linking group containing at least one moiety selected from an ether bond, ester bond and lactone ring. $X^2$ is a single bond, ester bond or amide bond. $X^3$ is a single bond, ether bond or ester bond. $R^{21}$ and $R^{22}$ are each independently an acid labile group. $R^{23}$ is fluorine, trifluoromethyl, cyano or a $C_1$-$C_6$ saturated hydrocarbyl group. $R^{24}$ is a single bond or a $C_1$-$C_6$ alkanediyl group in which some carbon may be replaced by an ether bond or ester bond; a is 1 or 2, b is an integer of 0 to 4, and 1≤a+b≤5.

In a preferred embodiment, the base polymer further comprises repeat units containing an adhesive group selected from among hydroxy, carboxy, lactone ring, carbonate, thiocarbonate, carbonyl, cyclic acetal, ether bond, ester bond, sulfonic ester bond, cyano, amide bond, —O—C(=O)—S—, and —O—C(=O)—NH—.

The resist composition may further comprise (D) an organic solvent and/or (E) a surfactant.

In another aspect, the invention provides a pattern forming process comprising the steps of applying the positive resist composition defined above to form a resist film on a substrate, exposing the resist film to high-energy radiation, and developing the exposed resist film in a developer.

The high-energy radiation is typically i-line, KrF excimer laser, ArF excimer laser, EB, or EUV of wavelength 3 to 15 nm.

In a further aspect, the invention provides a sulfonium salt having the formula (1-3-1):

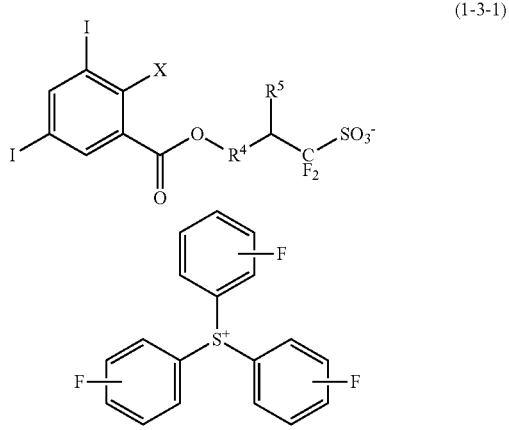

(1-3-1)

wherein $R^4$ is a single bond or $C_1$-$C_6$ alkanediyl group, $R^5$ is hydrogen or trifluoromethyl, and X is hydroxy or iodine.

Advantageous Effects of Invention

The positive resist composition of the invention forms a resist film having a high sensitivity and reduced LWR or improved CDU because the acid generator and the quencher are uniformly distributed in the resist film. By virtue of these advantages, the resist composition is fully useful in commercial application and suited as a micropatterning material for the fabrication of VLSIs, micropatterning material for the fabrication of photomasks by EB writing, and micropatterning material adapted for EB or EUV lithography. The resist composition may be used not only in the lithography for forming semiconductor circuits, but also in the formation of mask circuit patterns, micromachines, and thin-film magnetic head circuits.

DESCRIPTION OF EMBODIMENTS

As used herein, the singular forms "a," "an" and "the" include plural referents unless the context clearly dictates otherwise. The notation ($C_n$-$C_m$) means a group containing from n to m carbon atoms per group. The term "group" and "moiety" are interchangeable. The fluorine-containing compound is also referred to as fluorinated compound. In chemical formulae, the broken line designates a valence bond, and Me stands for methyl and Ac for acetyl.

The abbreviations and acronyms have the following meaning.
EB: electron beam
EUV: extreme ultraviolet
Mw: weight average molecular weight
Mn: number average molecular weight
Mw/Mn: molecular weight dispersity
GPC: gel permeation chromatography
PEB: post-exposure bake
PAG: photoacid generator
LWR: line width roughness
CDU: critical dimension uniformity Positive Resist Composition The positive resist composition of the invention is defined as comprising (A) an acid generator in the form of a sulfonium salt consisting of a sulfonate anion having at least one fluorine atom and a sulfonium cation having at least one fluorine atom, (B) a quencher in the form of a sulfonium salt consisting of a cation and an anion, the cation containing at least two fluorine atoms or the anion and cation containing at least 5 fluorine atoms in total, and (C) a base polymer comprising repeat units of at least one type selected from repeat units (a1) having a carboxy group whose hydrogen is substituted by an acid labile group and repeat units (a2) having a phenolic hydroxy group whose hydrogen is substituted by an acid labile group. Since the sulfonium salt as component (A) or acid generator contains fluorine in both the cation and the anion, and the sulfonium salt as component (B) or quencher contains at least 2 fluorine atoms in its cation or totally at least 5 fluorine atoms in its anion and cation, their molecules do not agglomerate together due to the electric repulsion of negatively charged fluorine atoms, and are uniformly distributed. As a consequence, the resist pattern after development is improved in LWR and CDU.

In the acid generator (A), preferably the sulfonate anion further contains iodine. Since iodine is highly absorptive to EUV, the number of photons available upon exposure is increased, and the physical contrast is improved. There is obtained a resist composition having a higher sensitivity and contrast.

(A) Acid Generator

Component (A) is an acid generator which is a sulfonium salt consisting of a sulfonate anion having at least one fluorine atom (referred to as fluorinated sulfonate anion, hereinafter) and a sulfonium cation having at least one fluorine atom (referred to as fluorinated sulfonium cation, hereinafter).

Typically, the fluorinated sulfonate anion has the formula (1-1) or (1-2).

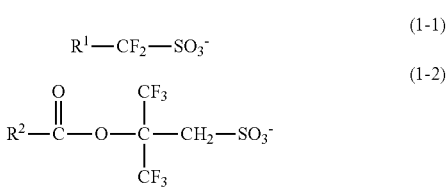

In formula (1-1), $R^1$ is fluorine or a $C_1$-$C_{40}$ hydrocarbyl group which may contain a heteroatom exclusive of iodine. The $C_1$-$C_{40}$ hydrocarbyl group may be saturated or unsaturated and straight, branched or cyclic. Examples thereof are the same as will be exemplified below for the hydrocarbyl group $R^{1a}$ in formula (1-1-1).

Of the anions having formula (1-1), anions having the formula (1-1-1) are preferred.

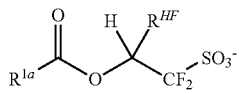
(1-1-1)

Herein, $R^{HF}$ is hydrogen or trifluoromethyl, preferably trifluoromethyl. $R^{1a}$ is a $C_1$-$C_{38}$ hydrocarbyl group which may contain a heteroatom. Suitable heteroatoms include oxygen, nitrogen, sulfur and halogen, with oxygen being preferred. Of the hydrocarbyl groups, those of 6 to 30 carbon atoms are preferred because a high resolution is available in fine pattern formation.

The hydrocarbyl group $R^{1a}$ may be saturated or unsaturated and straight, branched or cyclic. Suitable hydrocarbyl groups include $C_1$-$C_{38}$ alkyl groups such as methyl, ethyl, propyl, isopropyl, butyl, isobutyl, sec-butyl, tert-butyl, pentyl, neopentyl, hexyl, heptyl, 2-ethylhexyl, nonyl, undecyl, tridecyl, pentadecyl, heptadecyl, icosanyl; $C_3$-$C_{38}$ cyclic saturated hydrocarbyl groups such as cyclopentyl, cyclohexyl, 1-adamantyl, 2-adamantyl, 1-adamantylmethyl, norbornyl, norbornylmethyl, tricyclodecanyl, tetracyclododecanyl, tetracyclododecanylmethyl, dicyclohexylmethyl; $C_2$-$C_{38}$ unsaturated hydrocarbyl groups such as allyl, 3-cyclohexenyl, tetracyclododecenyl; $C_6$-$C_{38}$ aryl groups such as phenyl, 1-naphthyl, 2-naphthyl; $C_7$-$C_{38}$ aralkyl groups such as benzyl and diphenylmethyl; $C_{20}$-$C_{38}$ hydrocarbyl groups of steroid skeleton which may contain a heteroatom; and combinations thereof.

In these groups, some or all of the hydrogen atoms may be substituted by a moiety containing a heteroatom such as oxygen, sulfur, nitrogen or halogen, or some carbon may be replaced by a moiety containing a heteroatom such as oxygen, sulfur or nitrogen, so that the group may contain a hydroxy, cyano, carbonyl, ether bond, ester bond, sulfonic ester bond, carbonate, lactone ring, sultone ring, carboxylic anhydride or haloalkyl moiety. Examples of the heteroatom-containing hydrocarbyl group include tetrahydrofuryl, methoxymethyl, ethoxymethyl, methylthiomethyl, acetamidomethyl, trifluoroethyl, (2-methoxyethoxy)methyl, acetoxymethyl, 2-carboxy-1-cyclohexyl, 2-oxopropyl, 4-oxo-1-adamantyl, and 3-oxocyclohexyl.

Examples of the anion having formula (1-1) are shown below, but not limited thereto.

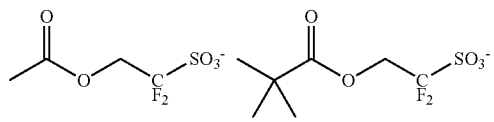

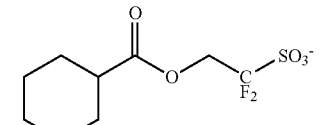

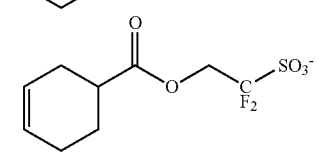

-continued

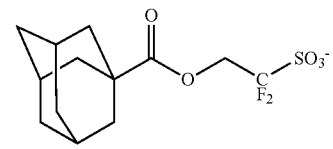

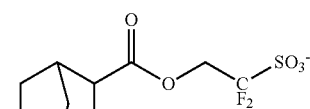

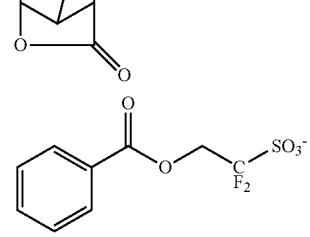

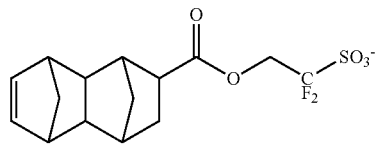

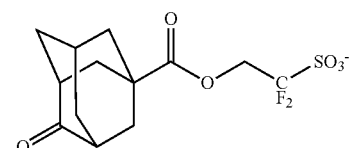

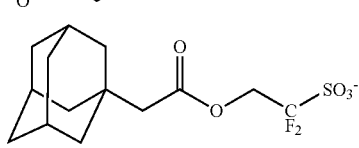

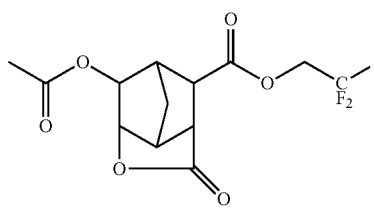

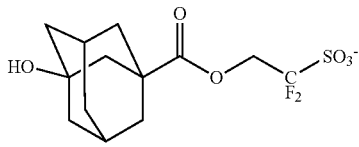

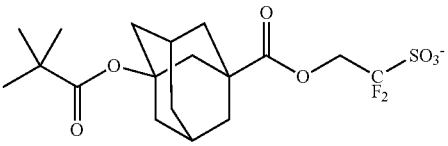

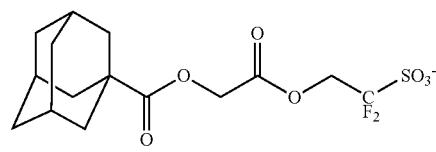

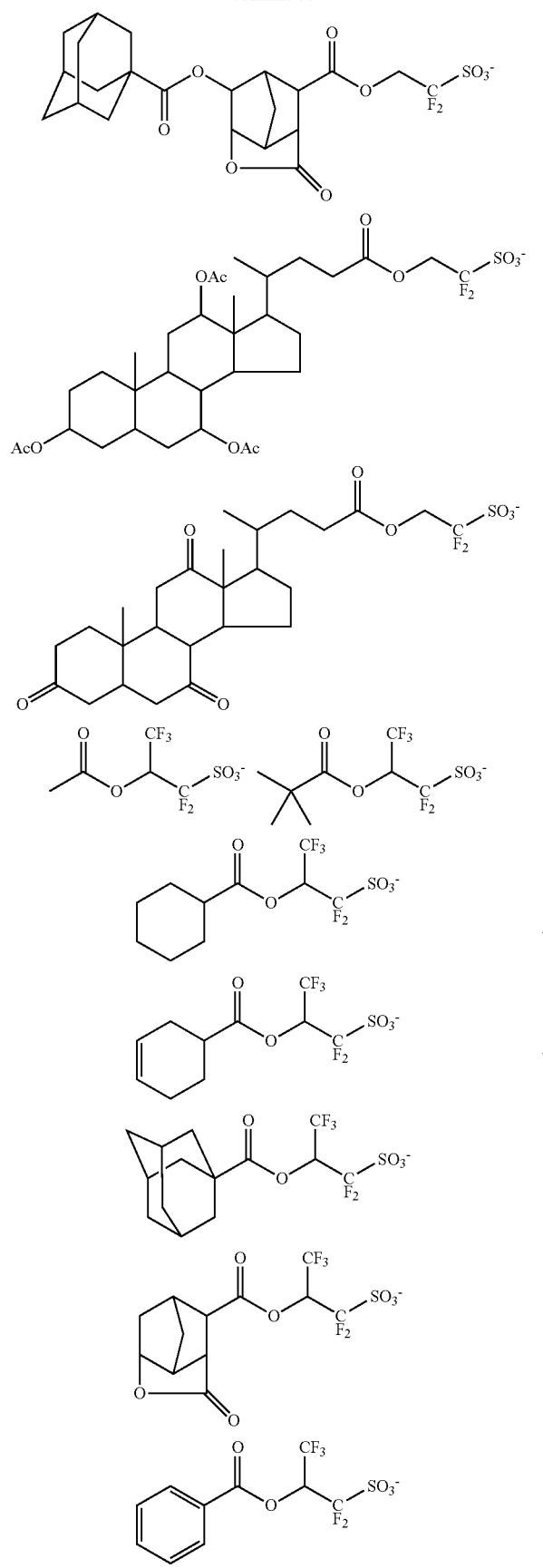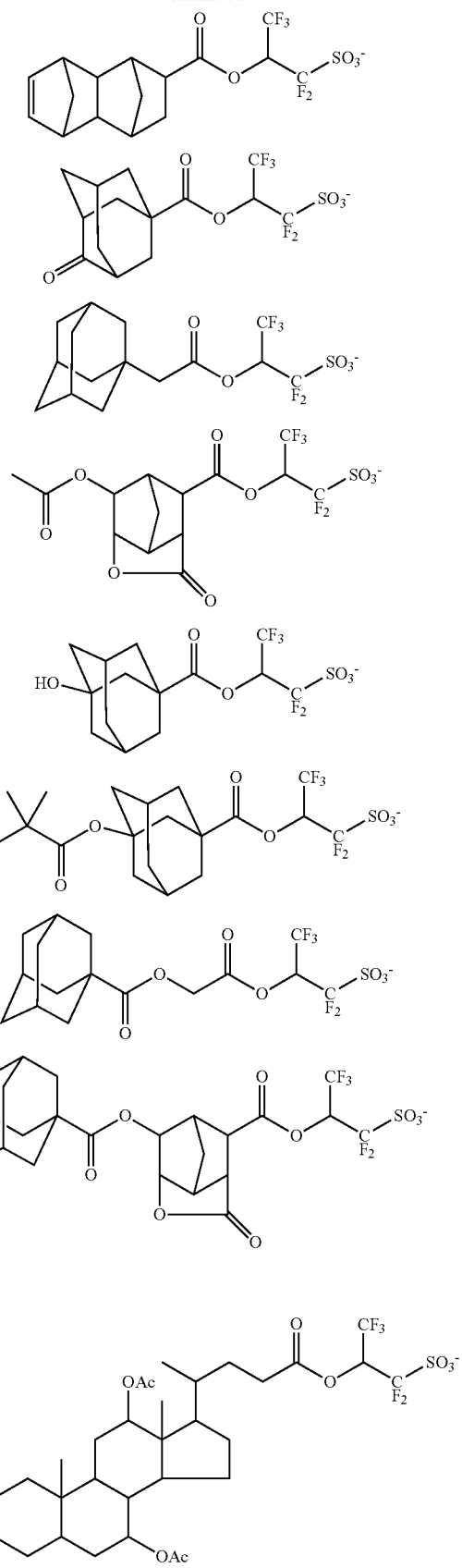

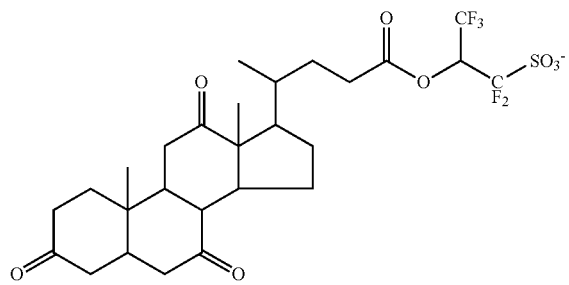

In formula (1-2), $R^2$ is a $C_1$-$C_{40}$ hydrocarbyl group which may contain a heteroatom exclusive of iodine. The hydrocarbyl group may be saturated or unsaturated and straight, branched or cyclic. Examples thereof are as exemplified above for the hydrocarbyl group $R^{1a}$ in formula (1-1-1).

Examples of the anion having formula (1-2) are shown below, but not limited thereto.

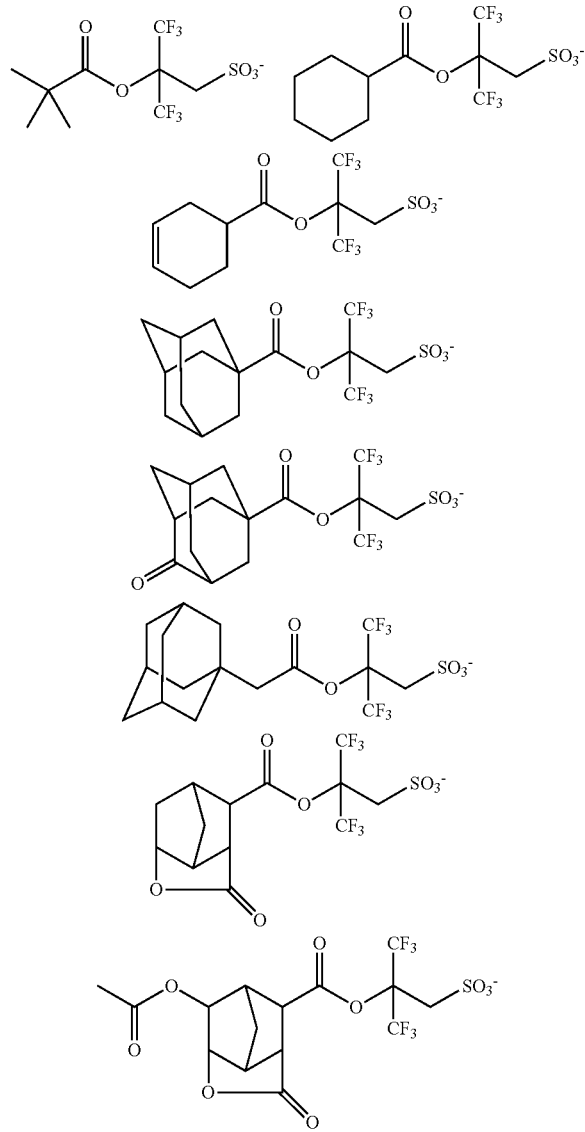

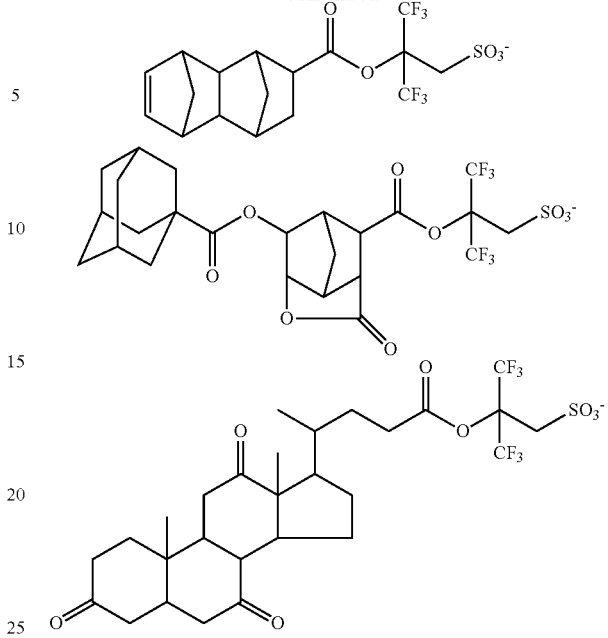

In the embodiment wherein the sulfonate anion further contains iodine, a sulfonate anion having the formula (1-3) is preferred.

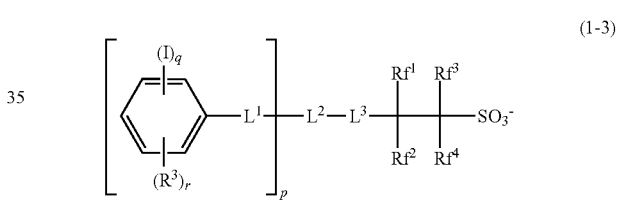

(1-3)

In formula (1-3), p is an integer of 1 to 3; q is an integer of 1 to 5, r is an integer of 0 to 3, and 1≤q+r≤5.

In formula (1-3), $L^1$ is a single bond, ether bond, ester bond, amide bond, imide bond, or a $C_1$-$C_6$ saturated hydrocarbylene group in which any constituent —$CH_2$— may be replaced by an ether bond or ester bond. Notably, the constituent —$CH_2$— may be positioned at the end of the saturated hydrocarbylene group.

The $C_1$-$C_6$ saturated hydrocarbylene group L may be straight, branched or cyclic. Examples thereof include $C_1$-$C_6$ alkanediyl groups such as methanediyl, ethane-1,1-diyl, ethane-1,2-diyl, propane-1,3-diyl, butane-1,4-diyl, pentane-1,5-diyl, and hexane-1,6-diyl; $C_3$-$C_6$ cyclic saturated hydrocarbylene groups such as cyclopropanediyl, cyclobutanediyl, cyclopentanediyl, and cyclohexanediyl; and combinations thereof.

In formula (1-3), $L^2$ is a single bond or a $C_1$-$C_{20}$ hydrocarbylene group which may contain a heteroatom in case of p=1; and a $C_1$-$C_{20}$ (p+1)-valent hydrocarbon group which may contain a heteroatom in case of p=2 or 3.

The $C_1$-$C_{20}$ hydrocarbylene group $L^2$ may be saturated or unsaturated and straight, branched or cyclic. Examples thereof include $C_1$-$C_{20}$ alkanediyl groups such as methanediyl, ethane-1,1-diyl, ethane-1,2-diyl, propane-1,3-diyl, butane-1,4-diyl, pentane-1,5-diyl, hexane-1,6-diyl, heptane-1,7-diyl, octane-1,8-diyl, nonane-1,9-diyl, decane-1,10-diyl, undecane-1,11-diyl, and dodecane-1,12-diyl; $C_3$-$C_{20}$ cyclic saturated hydrocarbylene groups such as cyclopentanediyl, cyclohexanediyl, norbornanediyl and adamantanediyl; $C_2$-$C_{20}$ unsaturated aliphatic hydrocarbylene groups such as vinylene and propene-1,3-diyl; $C_6$-$C_{20}$ arylene groups such as phenylene and naphthylene; and combinations thereof. The $C_1$-$C_{20}$ (p+1)-valent hydrocarbon group $L^2$ may be saturated or unsaturated and straight, branched or cyclic. Examples thereof include groups obtained by removing one or two hydrogen atoms from the above-described examples of the $C_1$-$C_{20}$ hydrocarbylene group.

In formula (1-3), $L^3$ is a single bond, ether bond or ester bond.

In formula (1-3), $R^3$ is a hydroxy group, carboxy group, fluorine, chlorine, bromine or amino group, or a $C_1$-$C_{20}$ hydrocarbyl group, $C_1$-$C_{20}$ hydrocarbyloxy group, $C_2$-$C_{20}$ hydrocarbylcarbonyl group, $C_2$-$C_{20}$ hydrocarbyloxycarbonyl group, $C_2$-$C_{20}$ hydrocarbylcarbonyloxy group or $C_1$-$C_{20}$ hydrocarbylsulfonyloxy group, which may contain fluorine, chlorine, bromine, hydroxy, amino or ether bond, or —N($R^{3A}$)($R^{3B}$), —N($R^{3C}$)—C(=O)—$R^{3D}$ or —N($R^{3C}$)—C(=O)O—$R^{3D}$. $R^{3A}$ and $R^{3B}$ are each independently hydrogen or a $C_1$-$C_6$ saturated hydrocarbyl group. $R^{3C}$ is hydrogen or a $C_1$-$C_6$ saturated hydrocarbyl group in which some or all of the hydrogen atoms may be substituted by halogen, hydroxy, $C_1$-$C_6$ saturated hydrocarbyloxy, $C_2$-$C_6$ saturated hydrocarbylcarbonyl or $C_2$-$C_6$ saturated hydrocarbylcarbonyloxy moiety. $R^{3D}$ is a $C_1$-$C_{16}$ aliphatic hydrocarbyl group, $C_6$-$C_{12}$ aryl group or $C_7$-$C_{15}$ aralkyl group, in which some or all of the hydrogen atoms may be substituted by halogen, hydroxy, $C_1$-$C_6$ saturated hydrocarbyloxy, $C_2$-$C_6$ saturated hydrocarbylcarbonyl or $C_2$-$C_6$ saturated hydrocarbylcarbonyloxy moiety. When p and/or r is 2 or more, groups $R^3$ may be the same or different.

The $C_1$-$C_{20}$ hydrocarbyl group, and hydrocarbyl moiety in the $C_1$-$C_{20}$ hydrocarbyloxy group, $C_2$-$C_{20}$ hydrocarbylcarbonyl group, $C_2$-$C_{20}$ hydrocarbyloxycarbonyl group, $C_2$-$C_{20}$ hydrocarbylcarbonyloxy group or $C_1$-$C_{20}$ hydrocarbylsulfonyloxy group, represented by $R^3$, may be saturated or unsaturated and straight, branched or cyclic. Examples thereof include $C_1$-$C_{20}$ alkyl groups such as methyl, ethyl, n-propyl, isopropyl, n-butyl, isobutyl, sec-butyl, tert-butyl, n-pentyl, n-hexyl, n-octyl, n-nonyl, n-decyl, undecyl, dodecyl, tridecyl, tetradecyl, pentadecyl, heptadecyl, octadecyl, nonadecyl and icosyl; $C_3$-$C_{20}$ cyclic saturated hydrocarbyl groups such as cyclopropyl, cyclopentyl, cyclohexyl, cyclopropylmethyl, 4-methylcyclohexyl, cyclohexylmethyl, norbornyl, adamantyl; $C_2$-$C_{20}$ alkenyl groups such as vinyl, propenyl, butenyl and hexenyl; $C_2$-$C_{20}$ cyclic unsaturated aliphatic hydrocarbyl groups such as cyclohexenyl and norbornenyl; $C_2$-$C_{20}$ alkynyl groups such as ethynyl, propynyl and butynyl; $C_6$-$C_{20}$ aryl groups such as phenyl, methylphenyl, ethylphenyl, n-propylphenyl, isopropylphenyl, n-butylphenyl, isobutylphenyl, sec-butylphenyl, tert-butylphenyl, naphthyl, methylnaphthyl, ethylnaphthyl, n-propylnaphthyl, isopropylnaphthyl, n-butylnaphthyl, isobutylnaphthyl, sec-butylnaphthyl, tert-butylnaphthyl; $C_7$-$C_{20}$ aralkyl groups such as benzyl and phenethyl; and combinations thereof.

The $C_1$-$C_6$ saturated hydrocarbyl groups represented by $R^{3A}$, $R^{3B}$ and $R^{3C}$ may be straight, branched or cyclic. Examples thereof include $C_1$-$C_6$ alkyl groups such as methyl, ethyl, n-propyl, isopropyl, n-butyl, isobutyl, sec-butyl, tert-butyl, n-pentyl and n-hexyl; and $C_3$-$C_6$ cyclic saturated hydrocarbyl groups such as cyclopropyl, cyclobutyl, cyclopentyl and cyclohexyl. Examples of the saturated hydrocarbyl moiety in the $C_1$-$C_6$ saturated hydrocarbyloxy group represented by $R^{3C}$ are as exemplified above for the saturated hydrocarbyl group. Examples of the saturated hydrocarbyl moiety in the $C_2$-$C_6$ saturated hydrocarbylcarbonyl group and $C_2$-$C_6$ saturated hydrocarbylcarbonyloxy group represented by $R^{3C}$ are as exemplified above for the $C_1$-$C_6$ saturated hydrocarbyl group, but of 1 to 5 carbon atoms.

The aliphatic hydrocarbyl group represented by $R^{3D}$ may be saturated or unsaturated and straight, branched or cyclic. Examples thereof include $C_1$-$C_{16}$ alkyl groups such as methyl, ethyl, n-propyl, isopropyl, n-butyl, isobutyl, sec-butyl, tert-butyl, n-pentyl, n-hexyl, n-octyl, n-nonyl, n-decyl, undecyl, dodecyl, tridecyl, tetradecyl, and pentadecyl; $C_3$-$C_{16}$ cyclic saturated hydrocarbyl groups such as cyclopropyl, cyclopentyl, cyclohexyl, cyclopropylmethyl, 4-methylcyclohexyl, cyclohexylmethyl, norbornyl, adamantyl; $C_2$-$C_{16}$ alkenyl groups such as vinyl, propenyl, butenyl and hexenyl; $C_2$-$C_{16}$ alkynyl groups such as ethynyl, propynyl and butynyl; $C_3$-$C_{16}$ cyclic unsaturated aliphatic hydrocarbyl groups such as cyclohexenyl and norbornenyl; and combinations thereof. Examples of the $C_6$-$C_{12}$ aryl group $R^{3D}$ include phenyl and naphthyl. Examples of the $C_7$-$C_{15}$ aralkyl group $R^{3D}$ include benzyl and phenethyl. Of the groups represented by $R^{3D}$, examples of the hydrocarbyl moiety in the $C_1$-$C_6$ saturated hydrocarbyloxy group are as exemplified above for the $C_1$-$C_6$ saturated hydrocarbyl group represented by $R^{3A}$, $R^{3B}$ and $R^{3C}$; examples of the hydrocarbyl moiety in the $C_2$-$C_6$ saturated hydrocarbylcarbonyl group or $C_2$-$C_6$ saturated hydrocarbylcarbonyloxy group are as exemplified above for the $C_1$-$C_6$ saturated hydrocarbyl group, but of 1 to 5 carbon atoms.

In formula (1-3), $Rf^1$ to $Rf^4$ are each independently hydrogen, fluorine or trifluoromethyl, at least one thereof being fluorine or trifluoromethyl. Also $Rf^1$ and $Rf^2$, taken together, may form a carbonyl group. The total number of fluorine atoms in $Rf^1$ to $Rf^4$ is preferably at least 2, more preferably at least 3.

Examples of the anion having formula (1-3) are shown below, but not limited thereto.

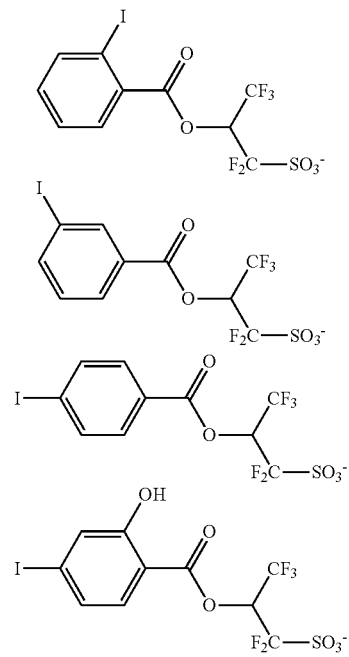

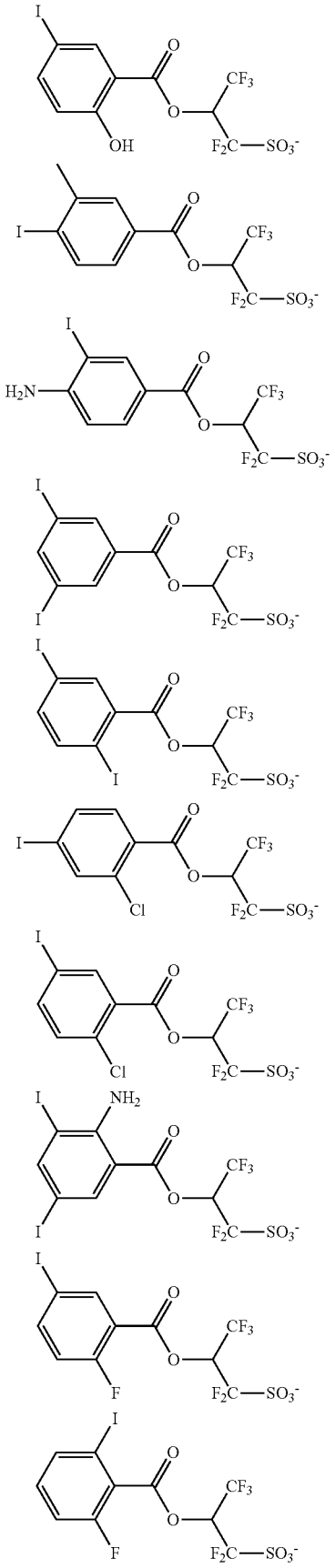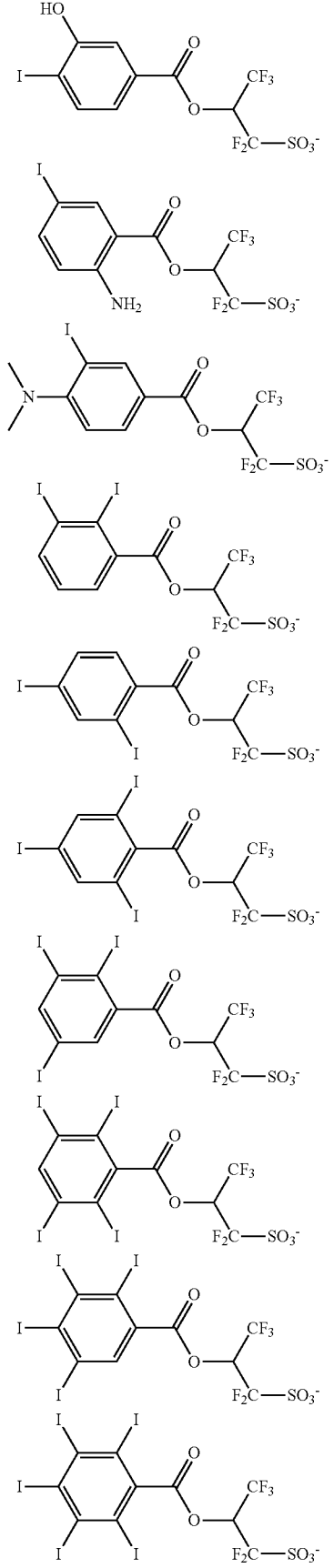

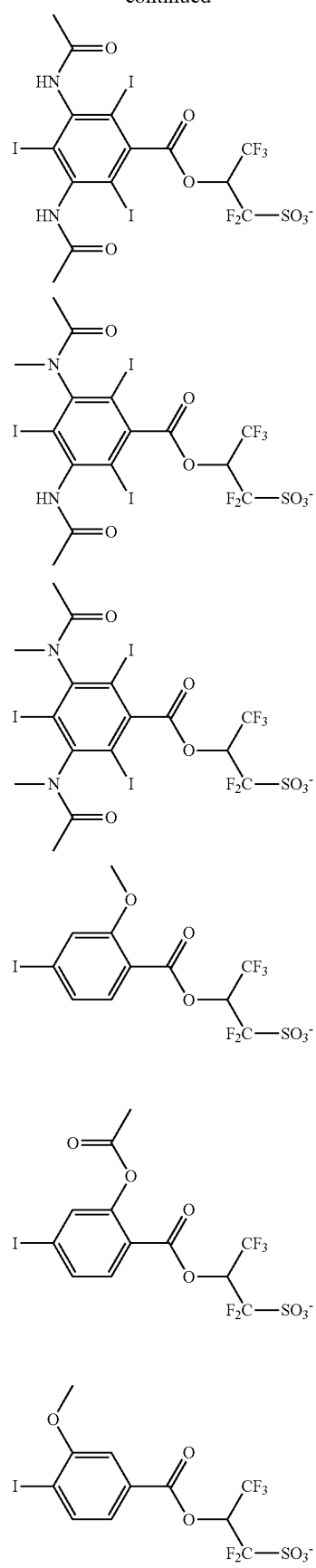
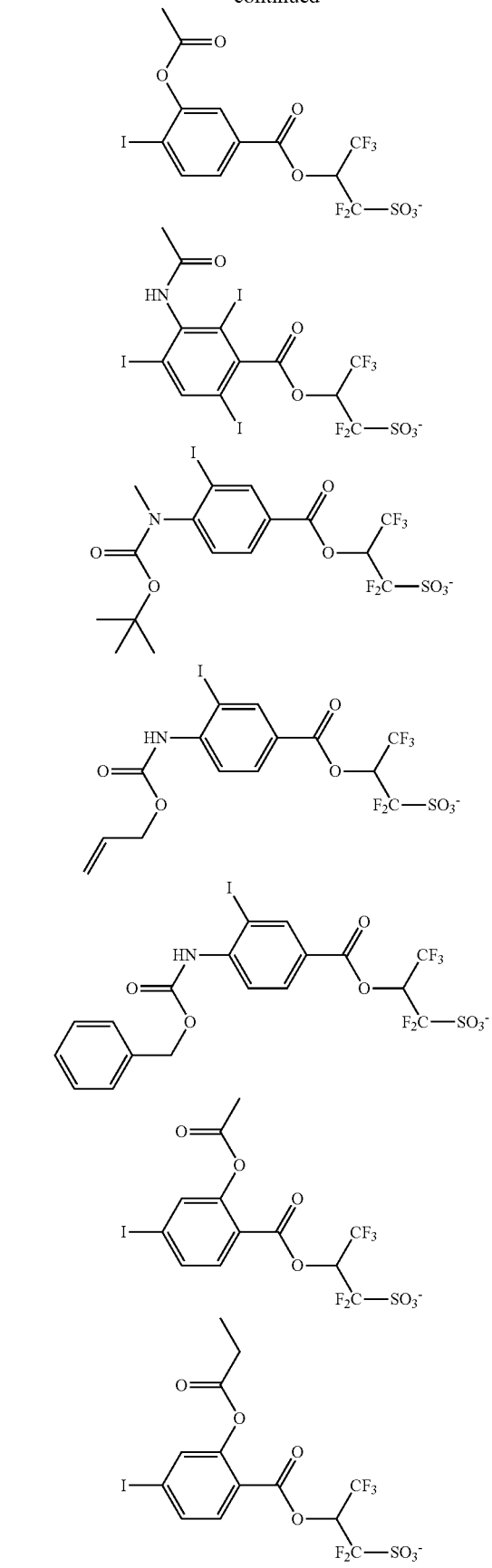

-continued
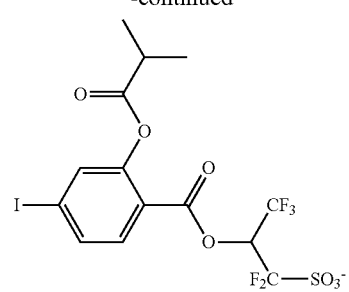
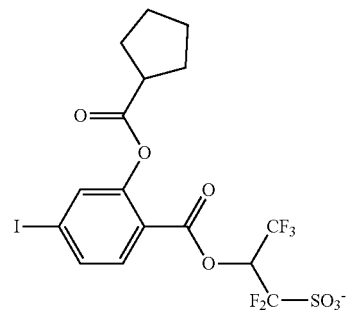
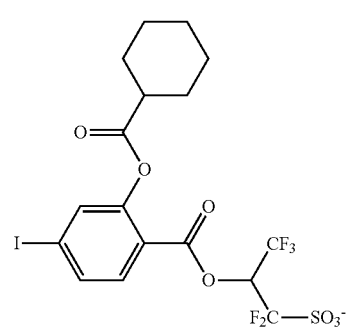
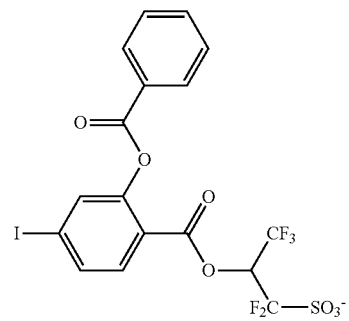
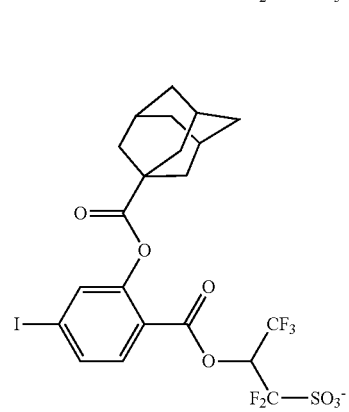
-continued
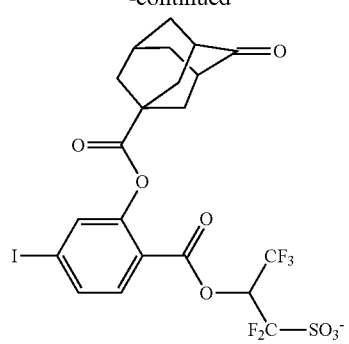
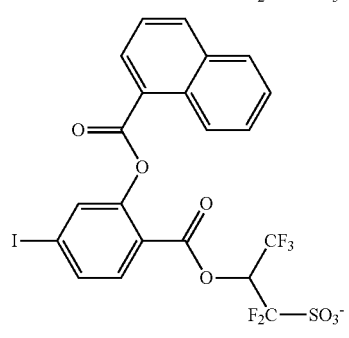
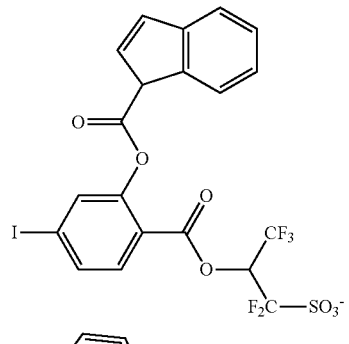
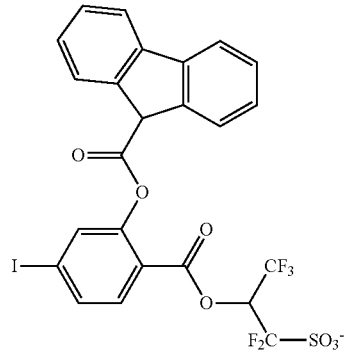
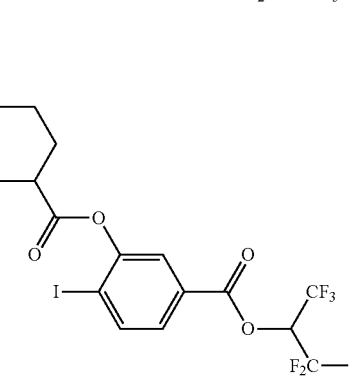

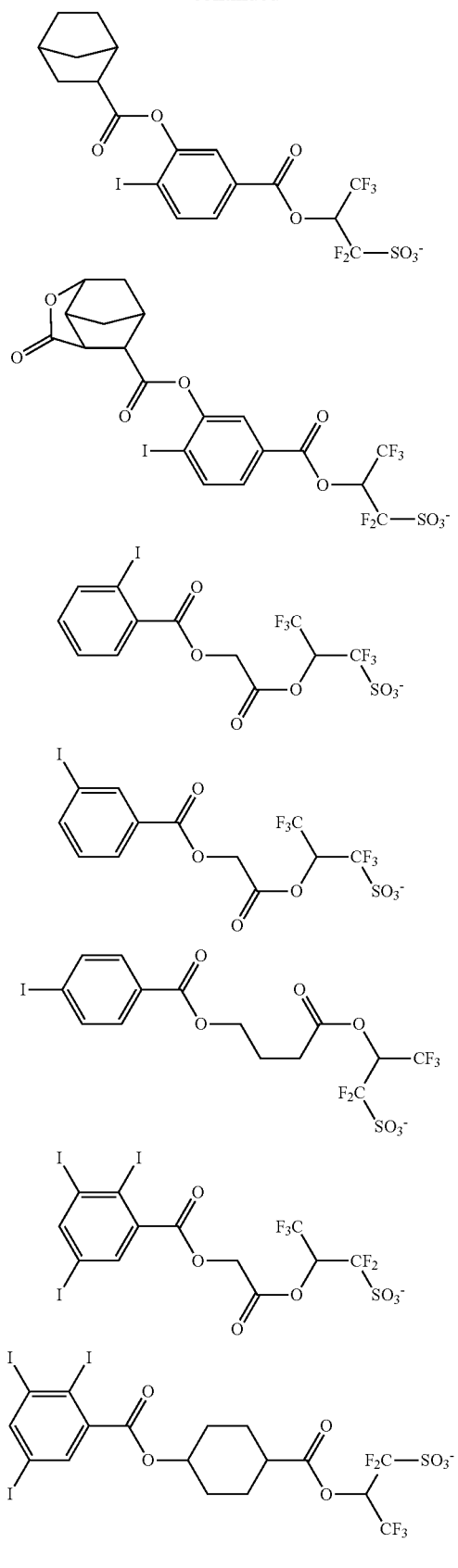
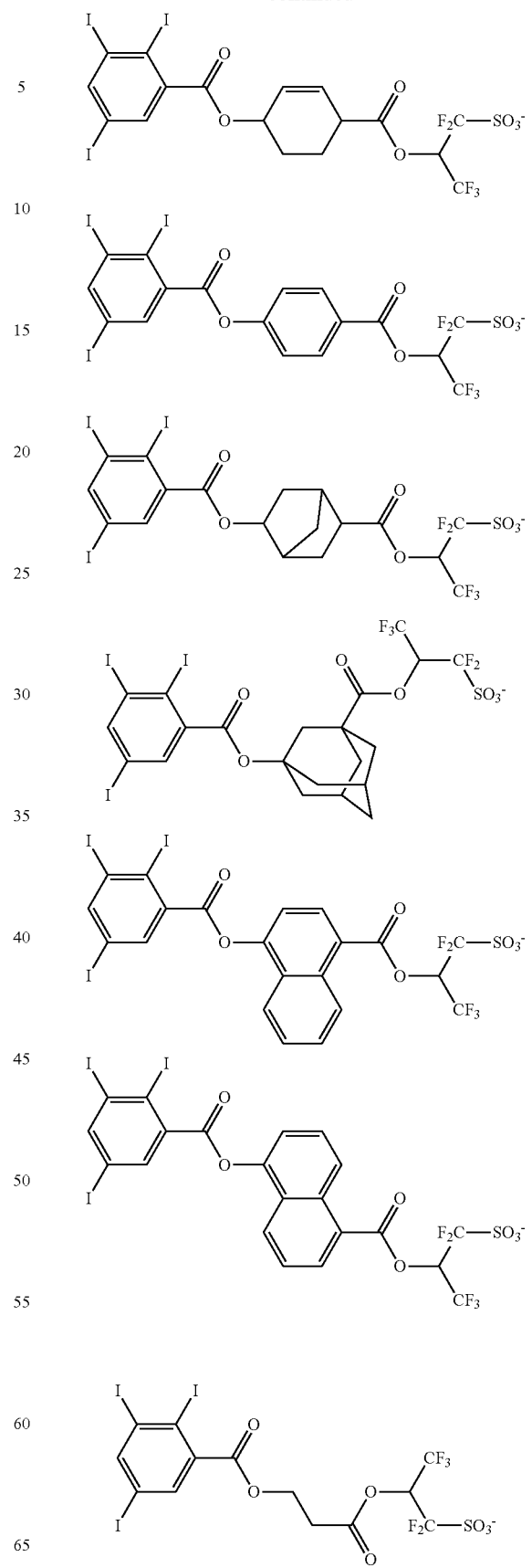

23
-continued
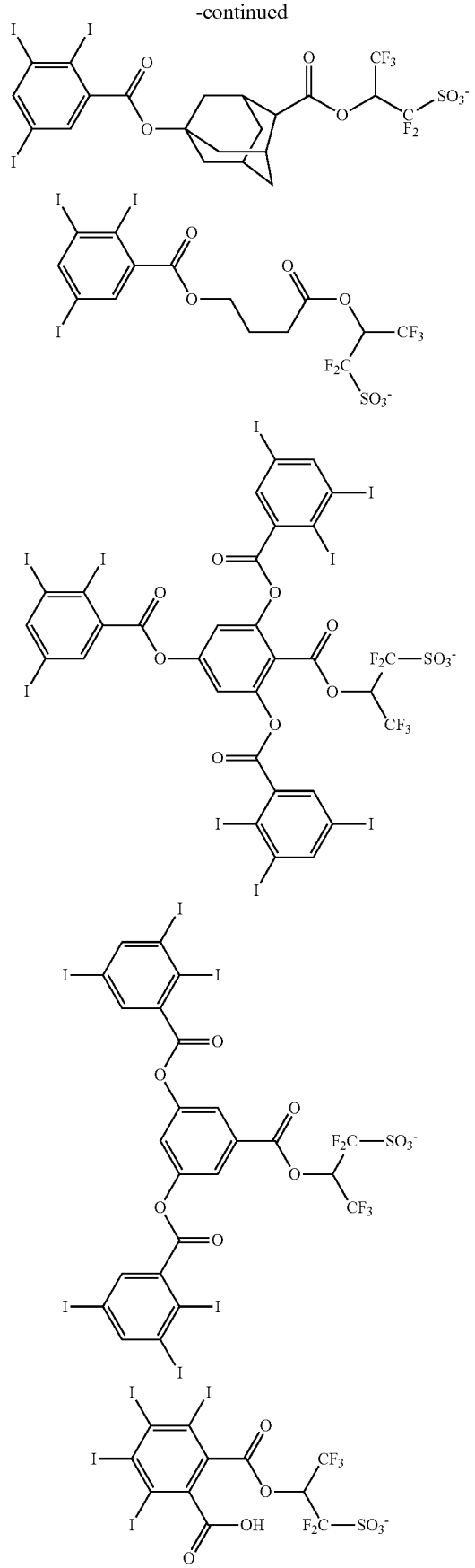
24
-continued
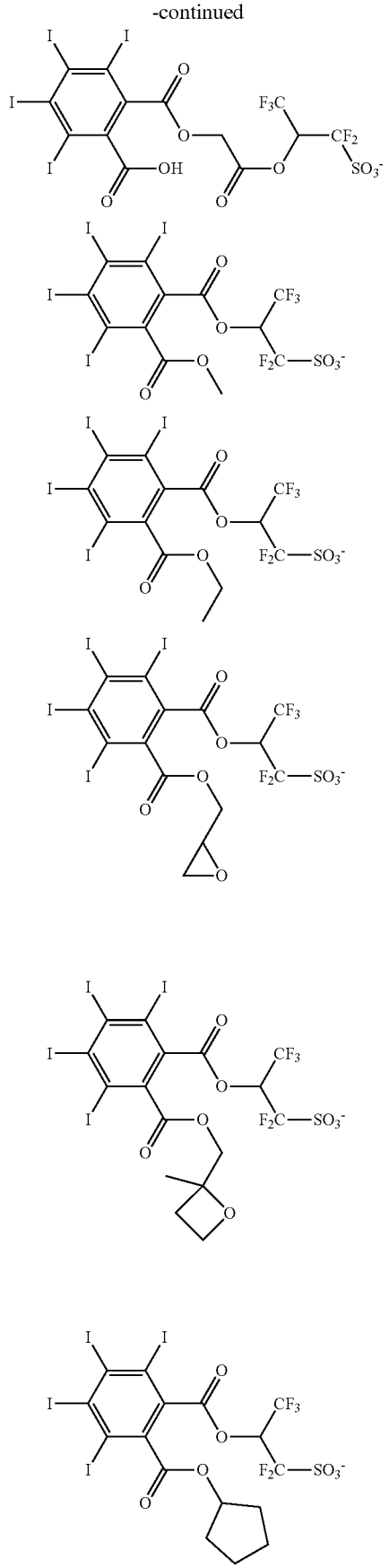

-continued
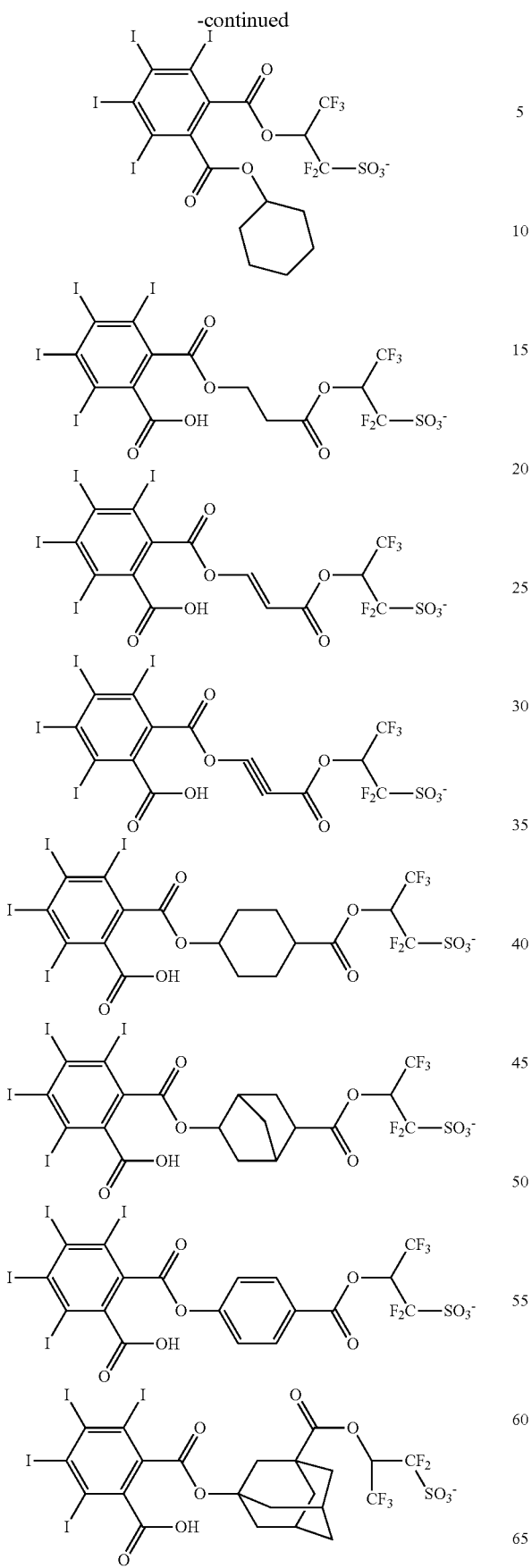
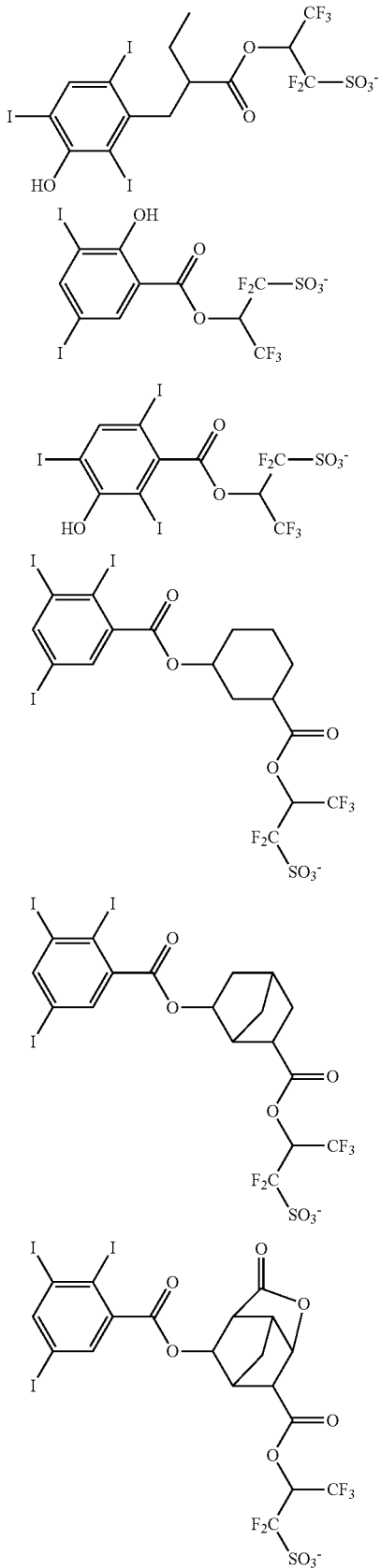

27
-continued
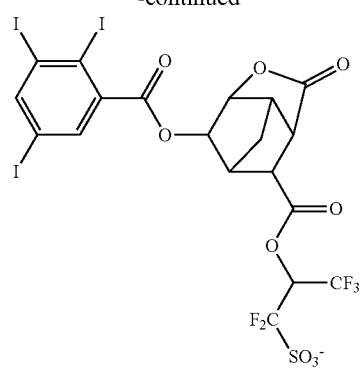
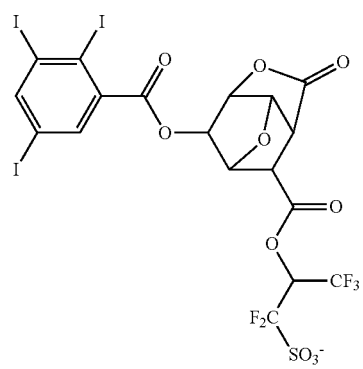
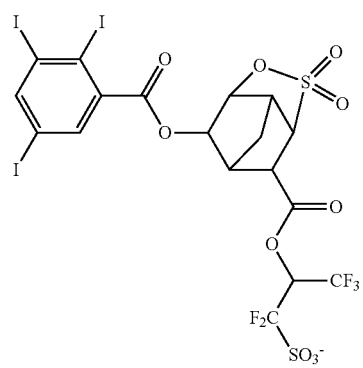
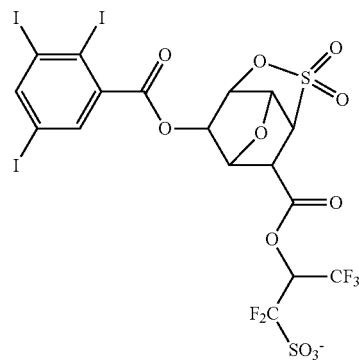
28
-continued
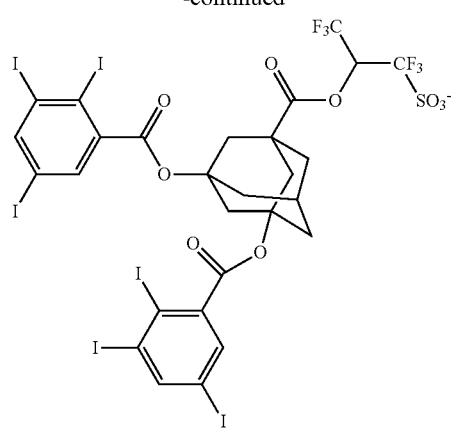
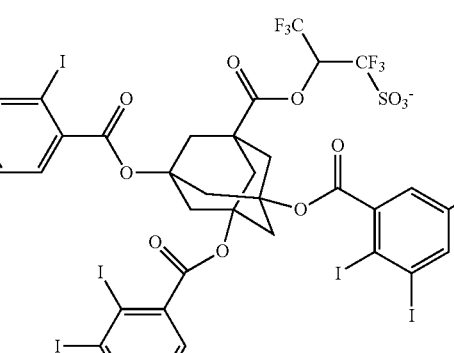
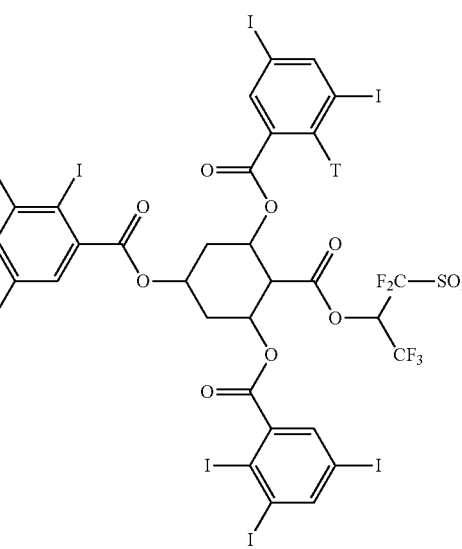

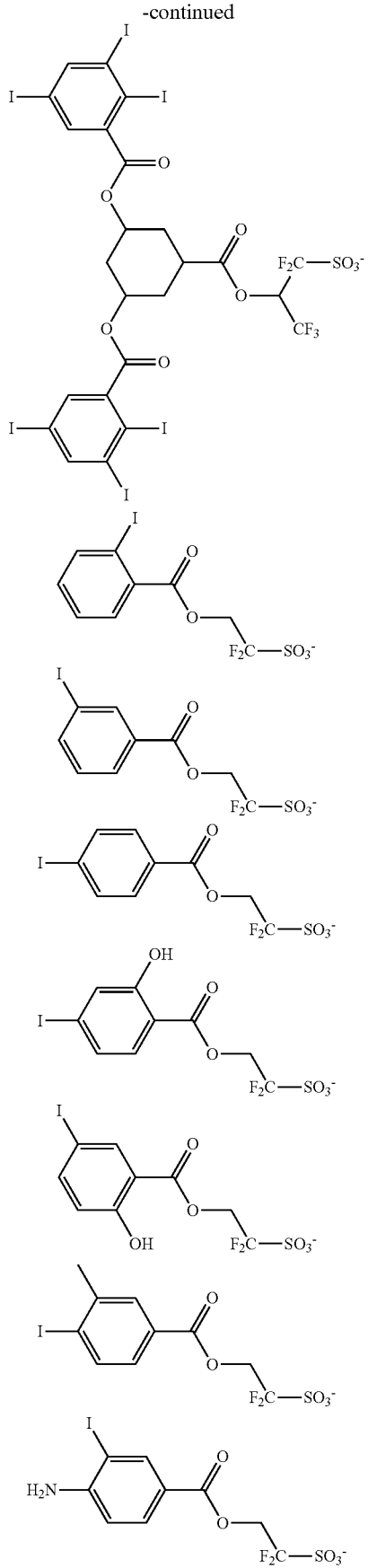
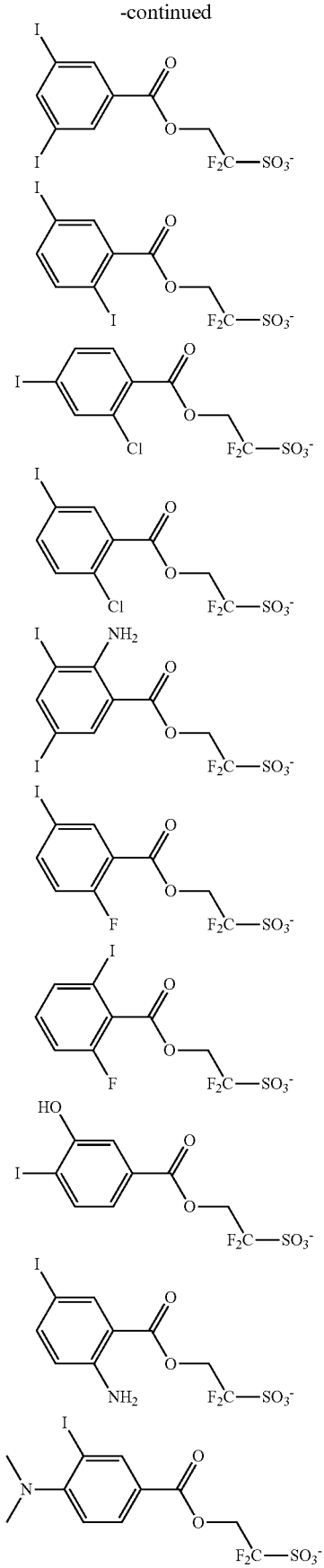

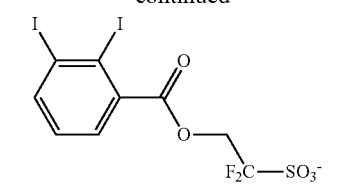
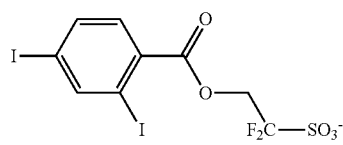
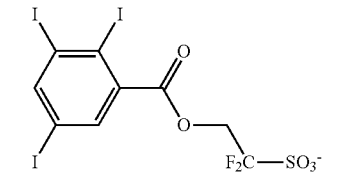

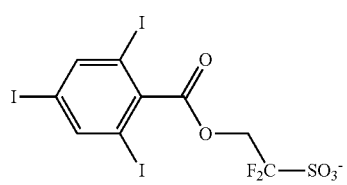
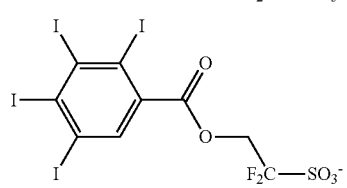
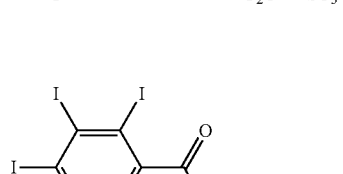
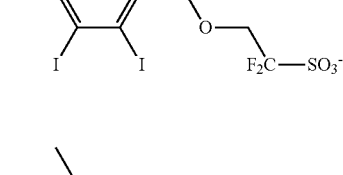
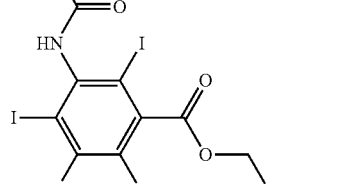
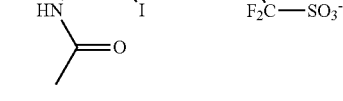
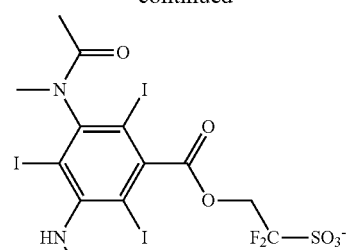
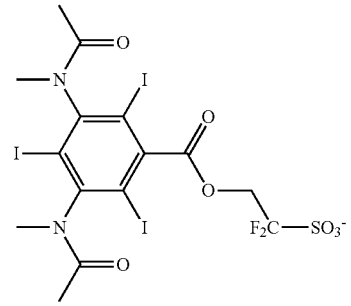
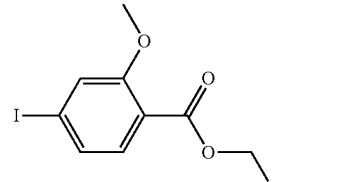
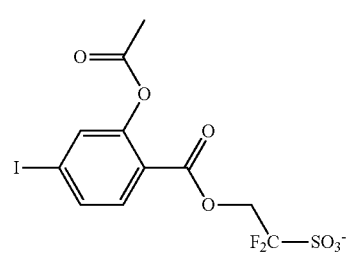
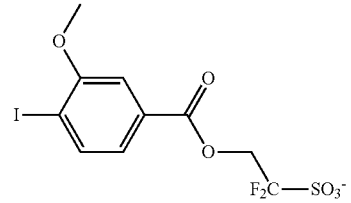
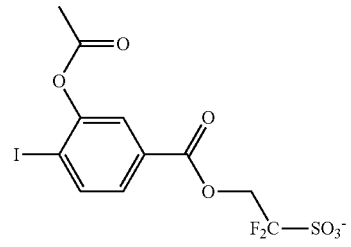

33
-continued
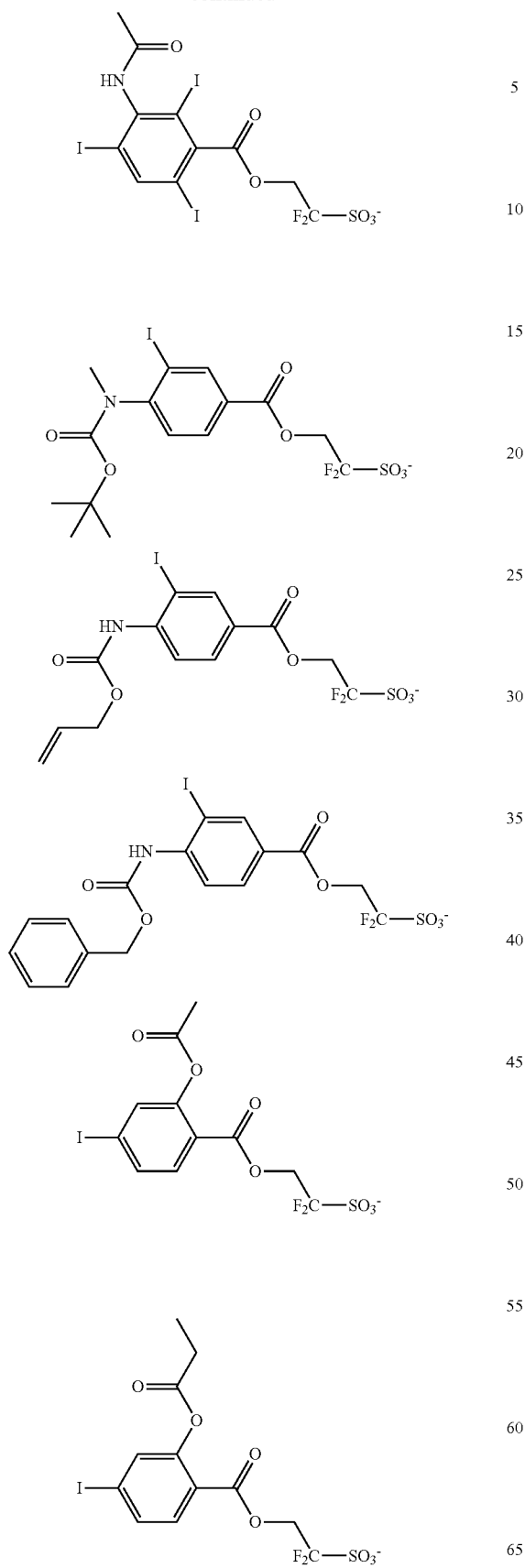
34
-continued
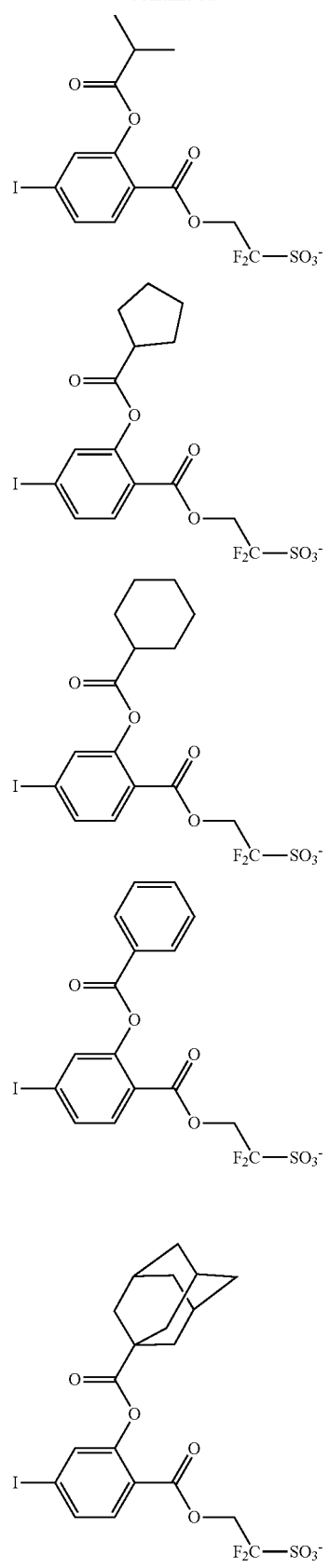

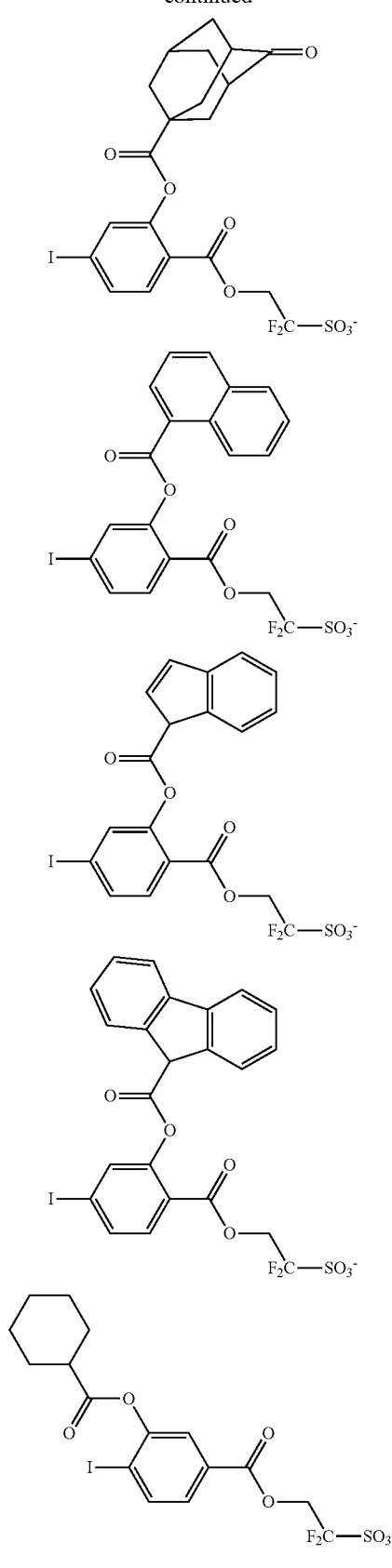
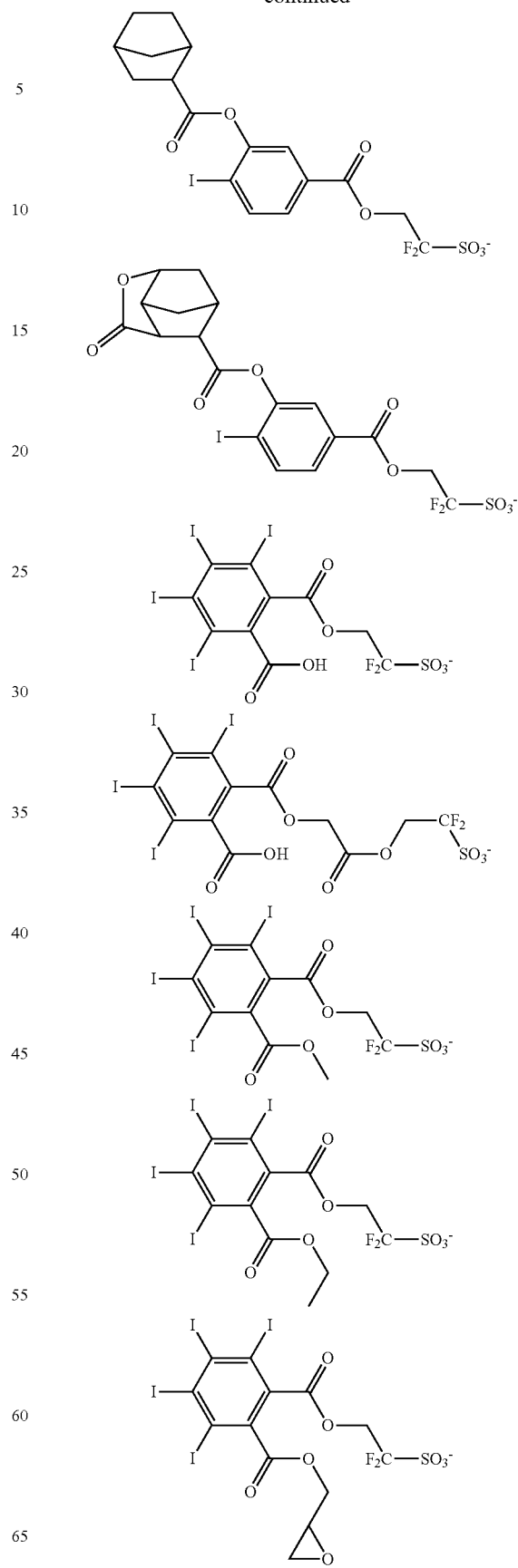

37
-continued
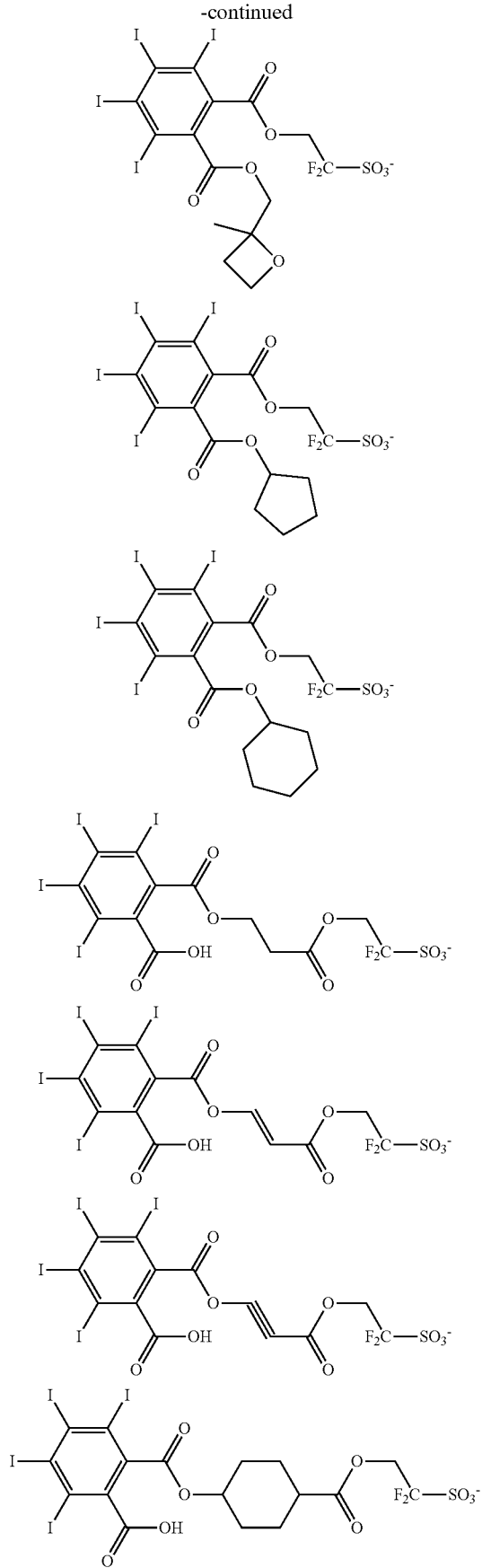
38
-continued
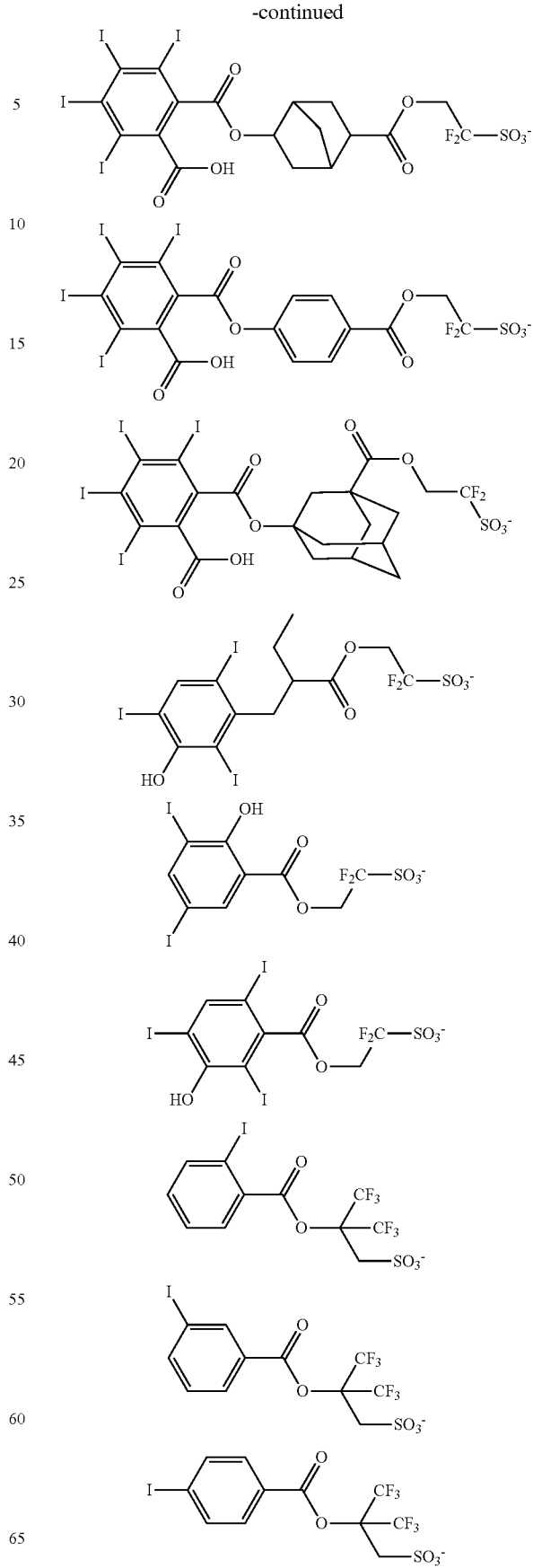

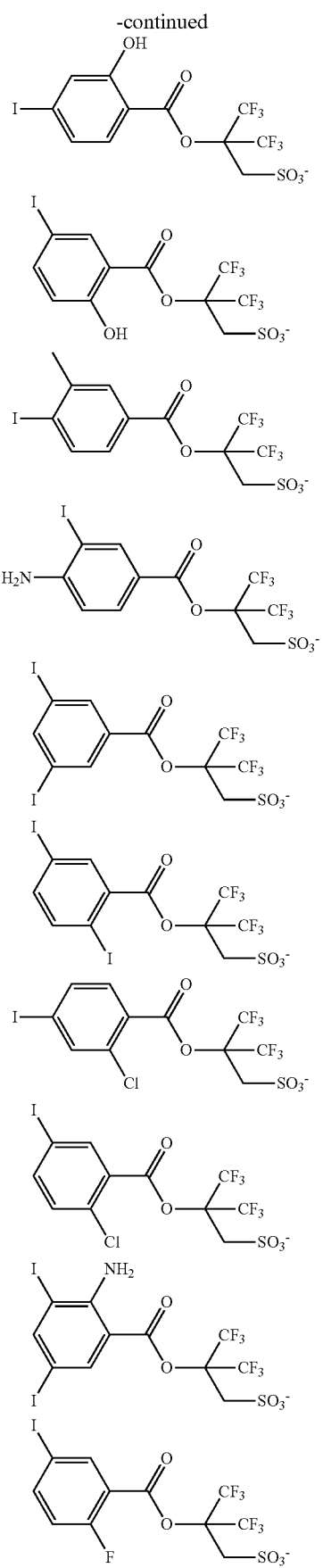
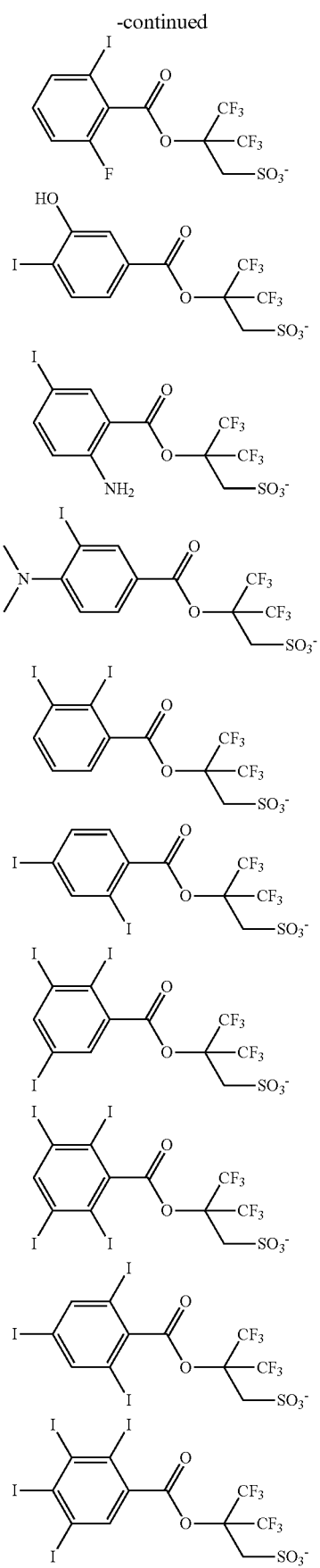

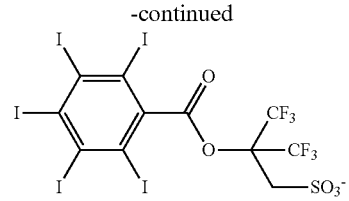
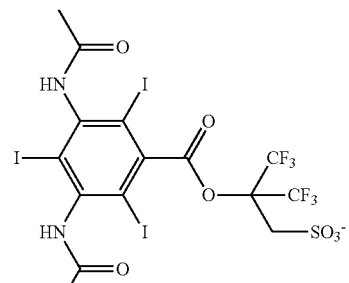
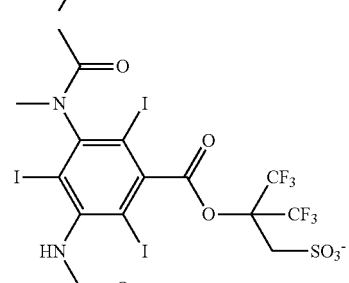
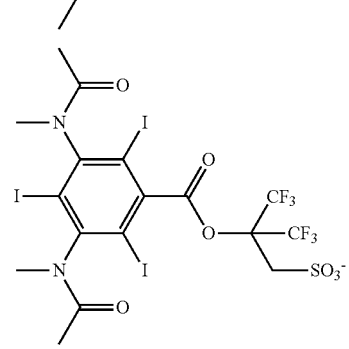
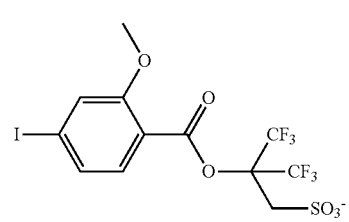
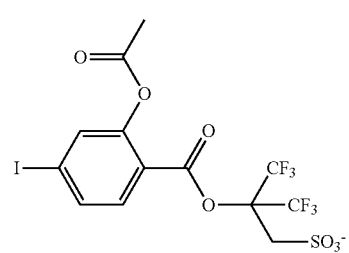
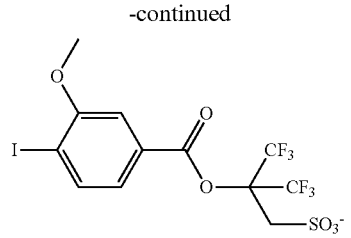
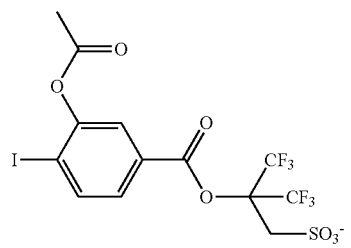
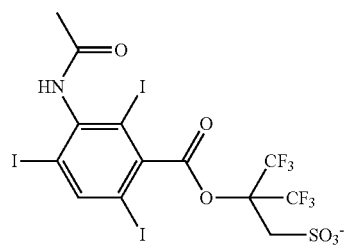
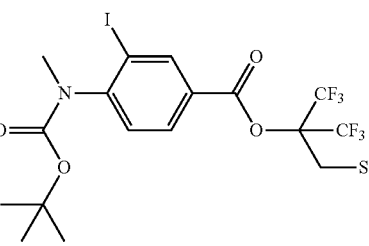
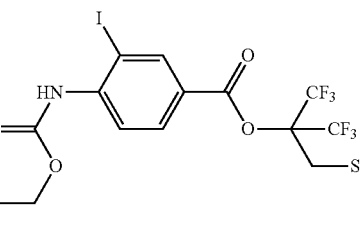
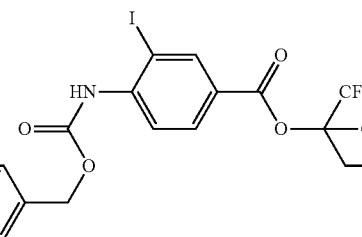
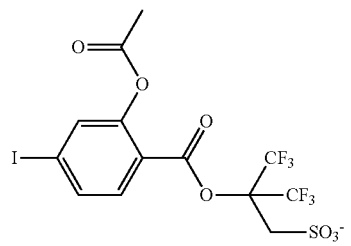

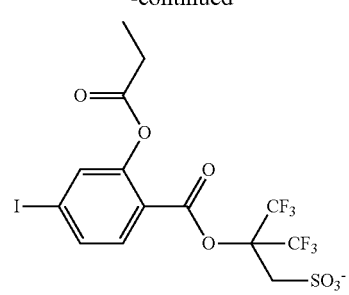
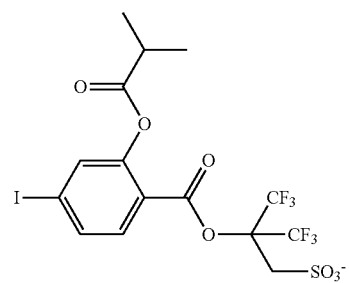
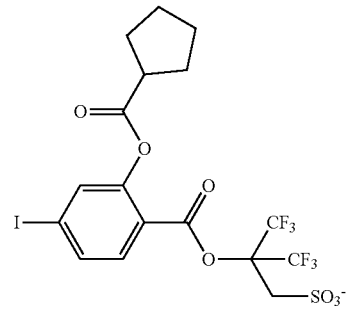
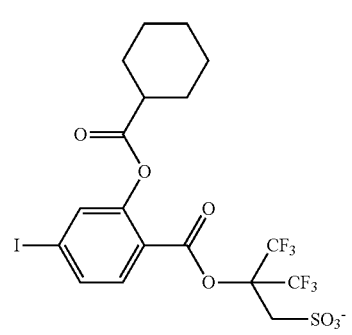
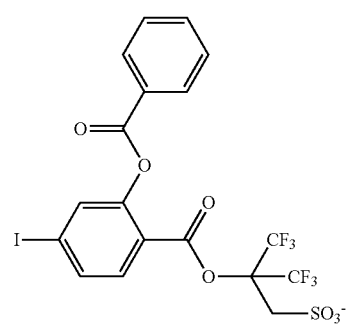
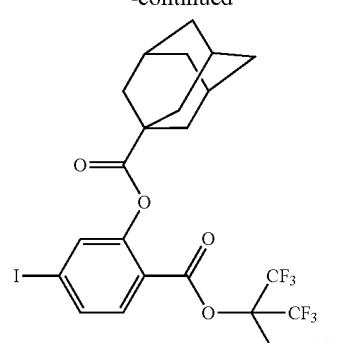
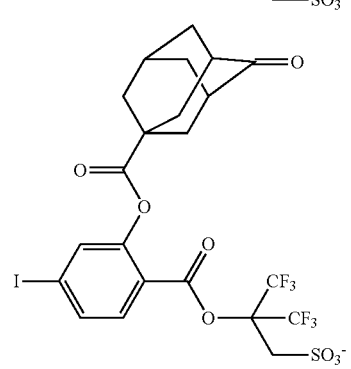
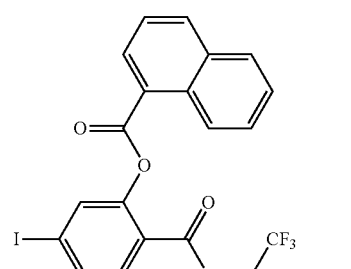
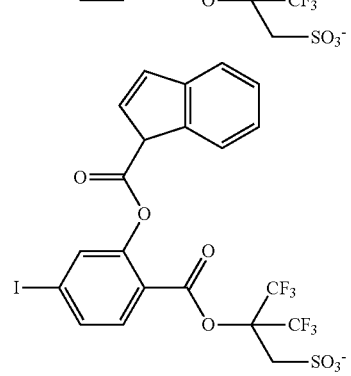
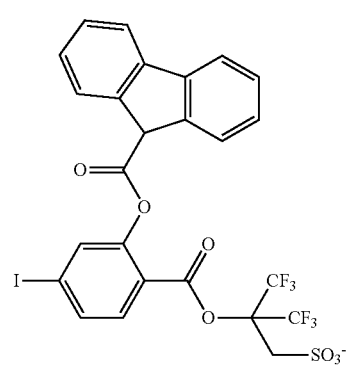

-continued
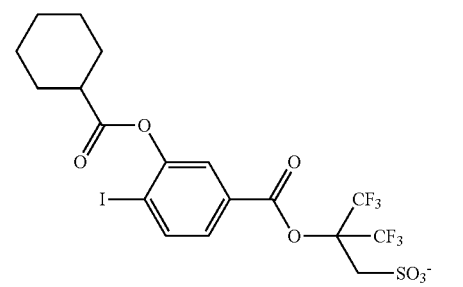
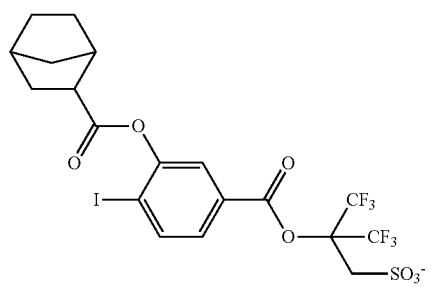
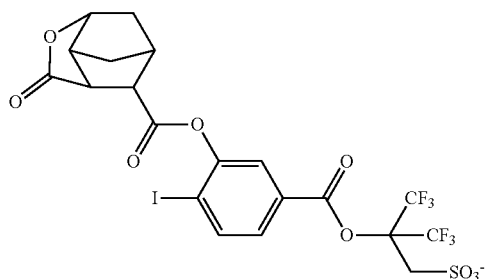
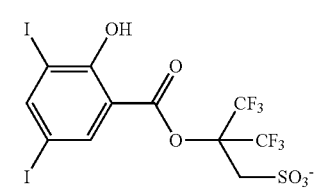
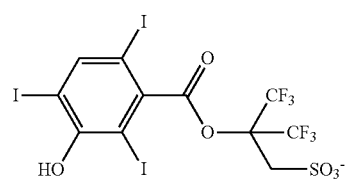
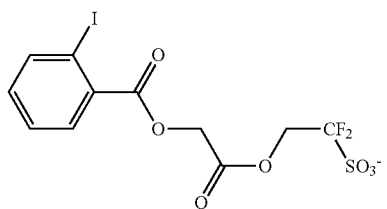
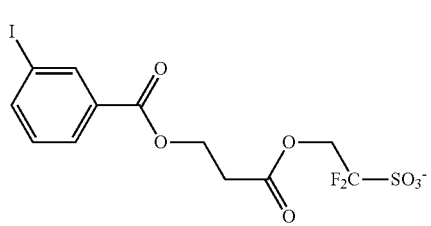
-continued
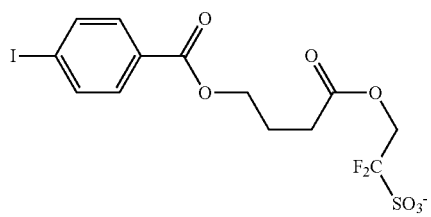
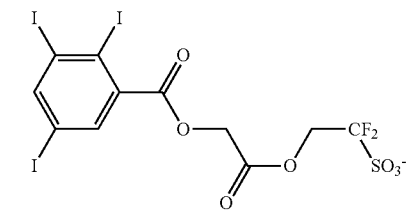
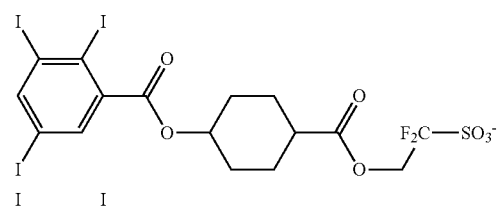
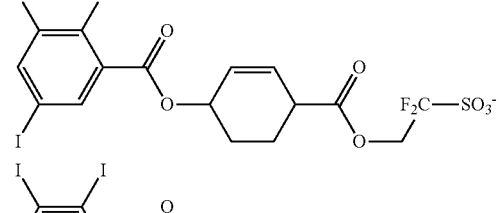
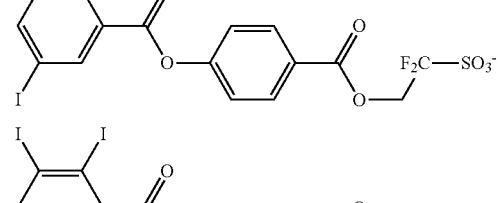
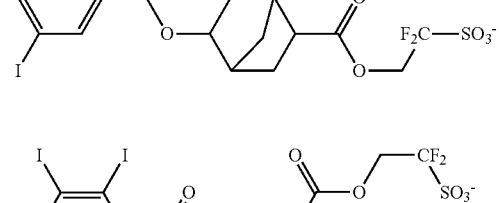
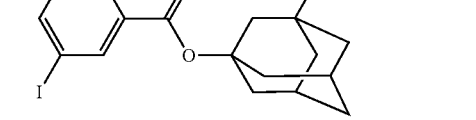
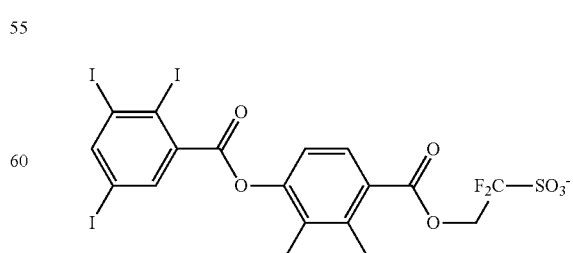

-continued
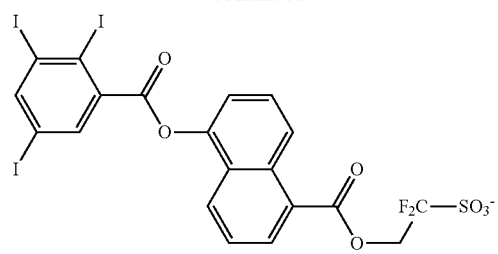
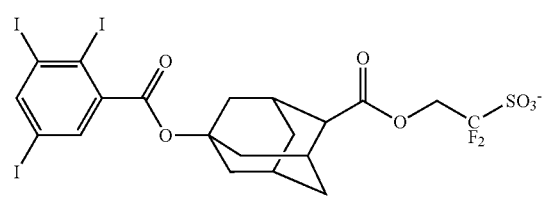
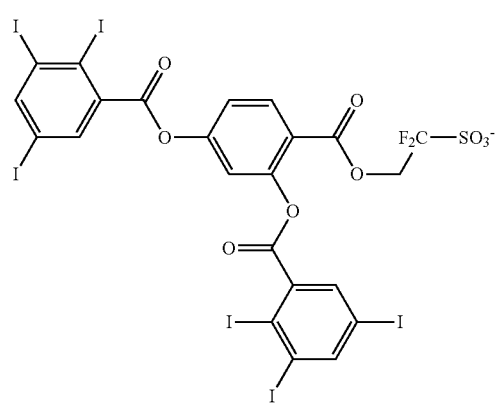
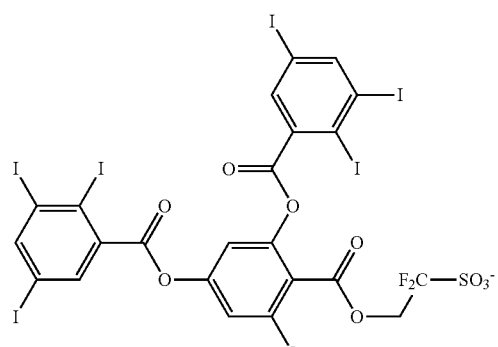
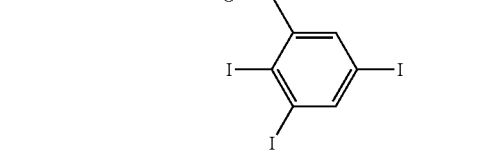
-continued
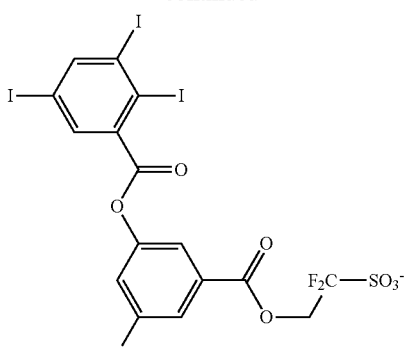
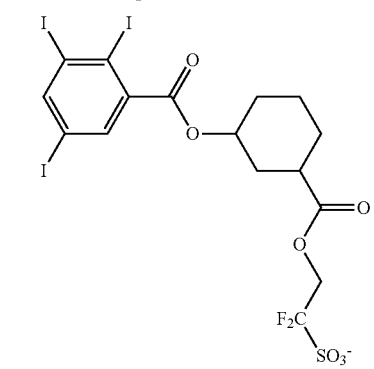
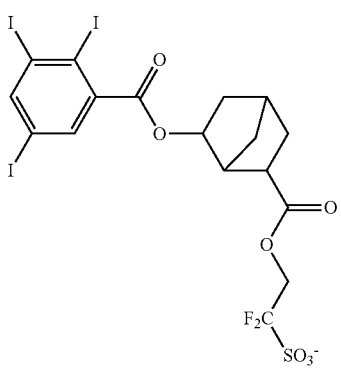
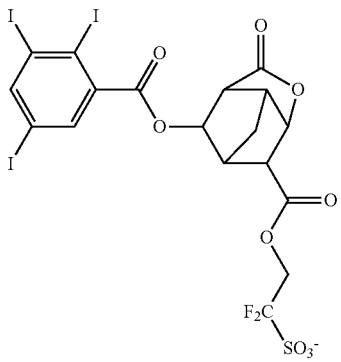

49
-continued
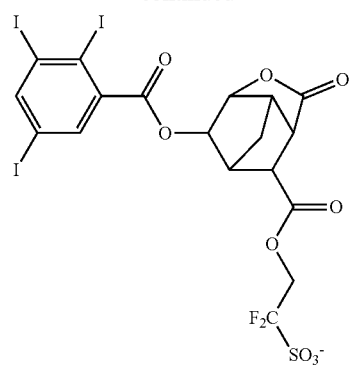
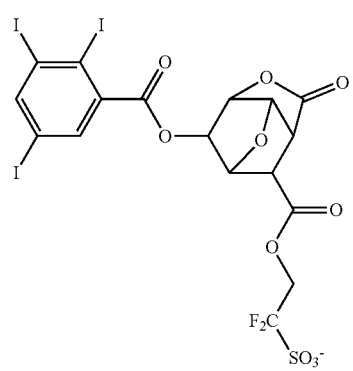
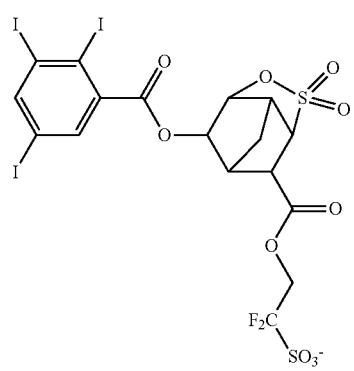
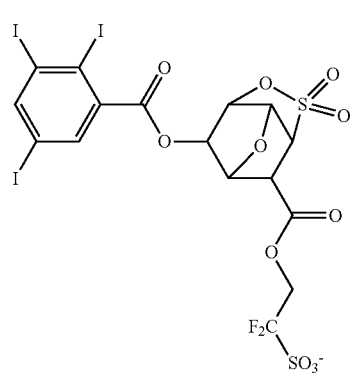
50
-continued
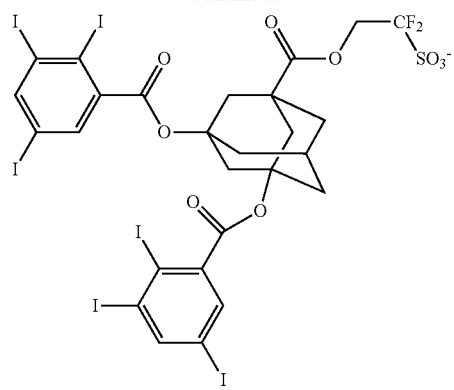
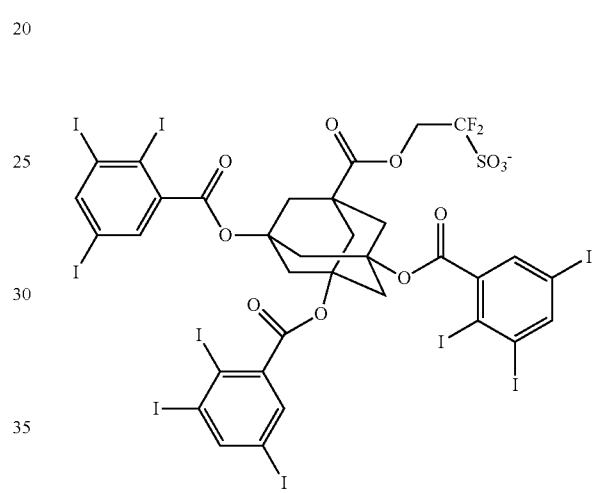
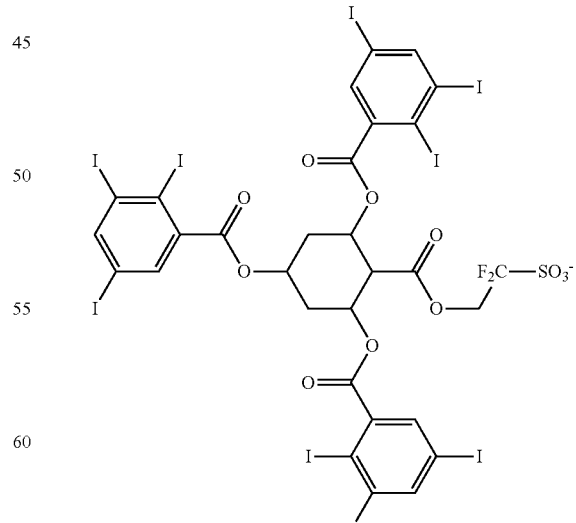

51
-continued
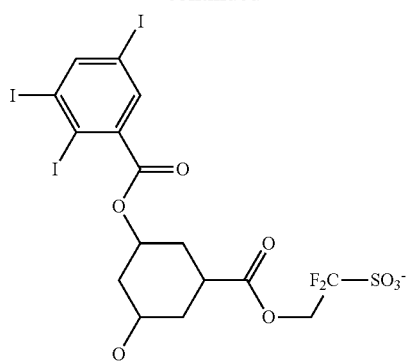
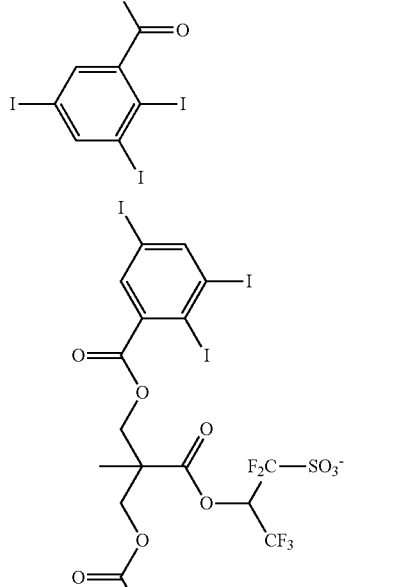
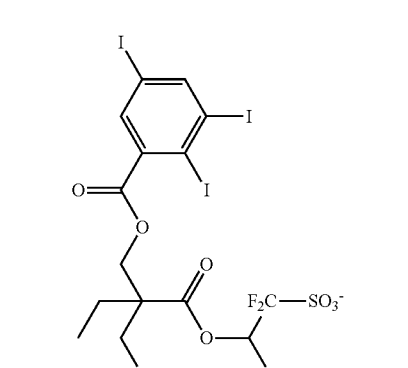
52
-continued
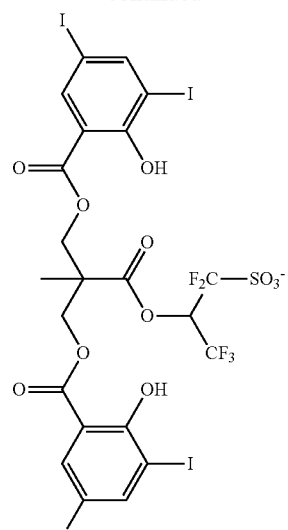
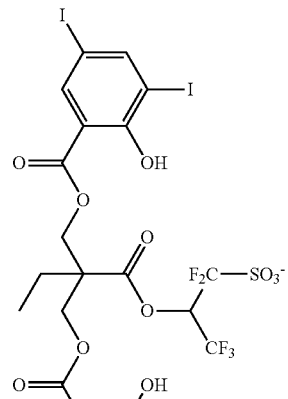
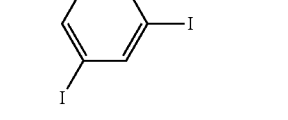
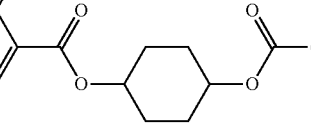
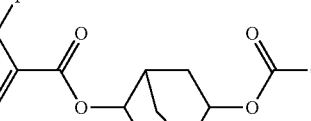

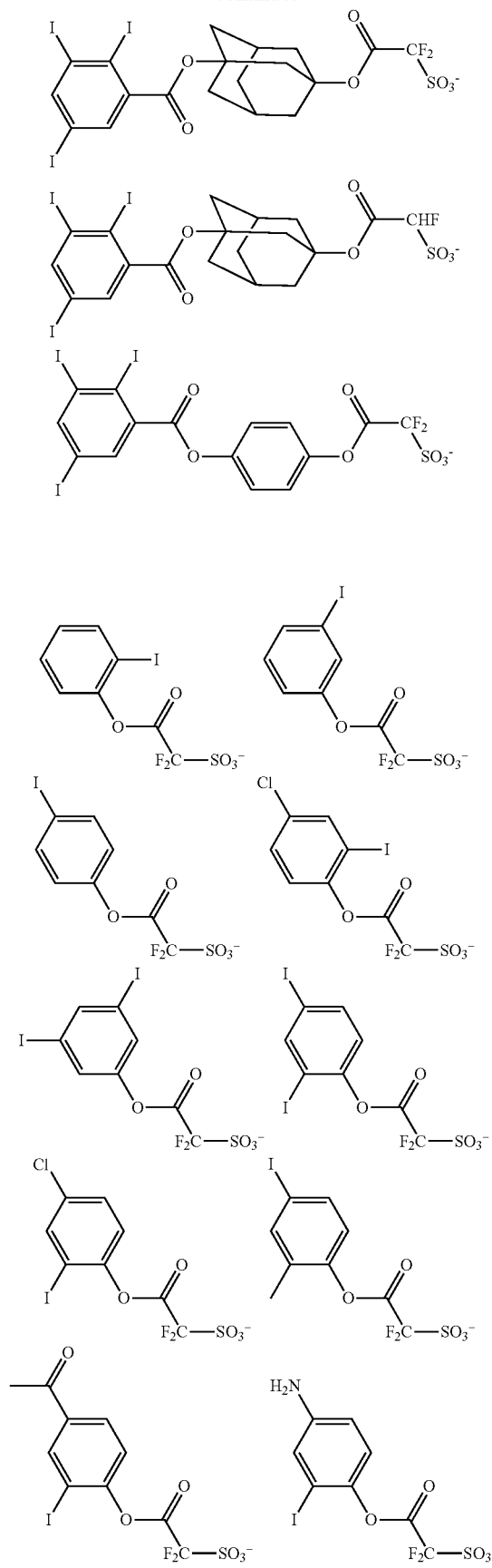
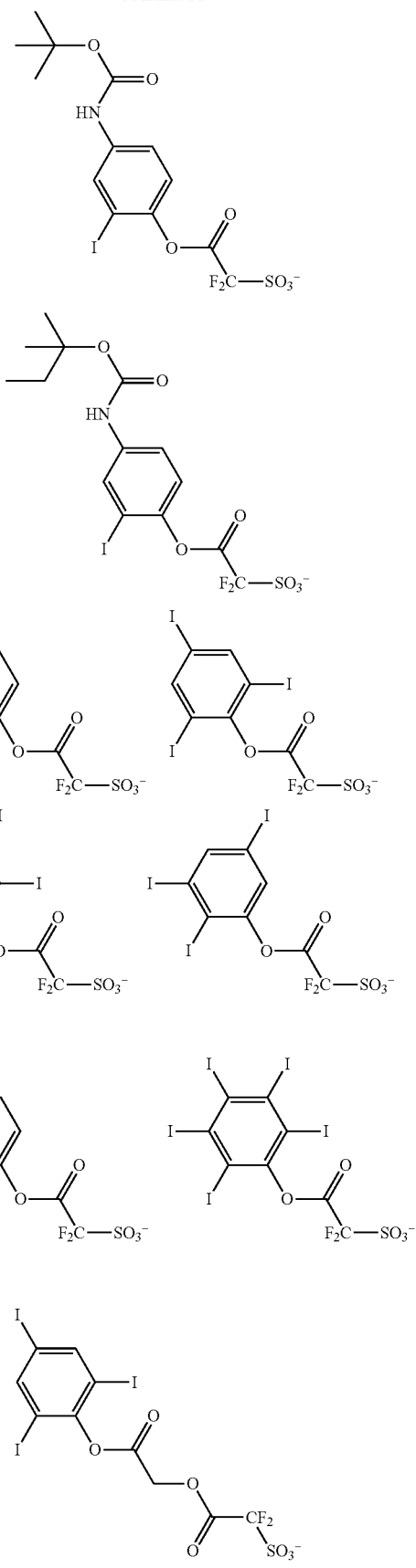

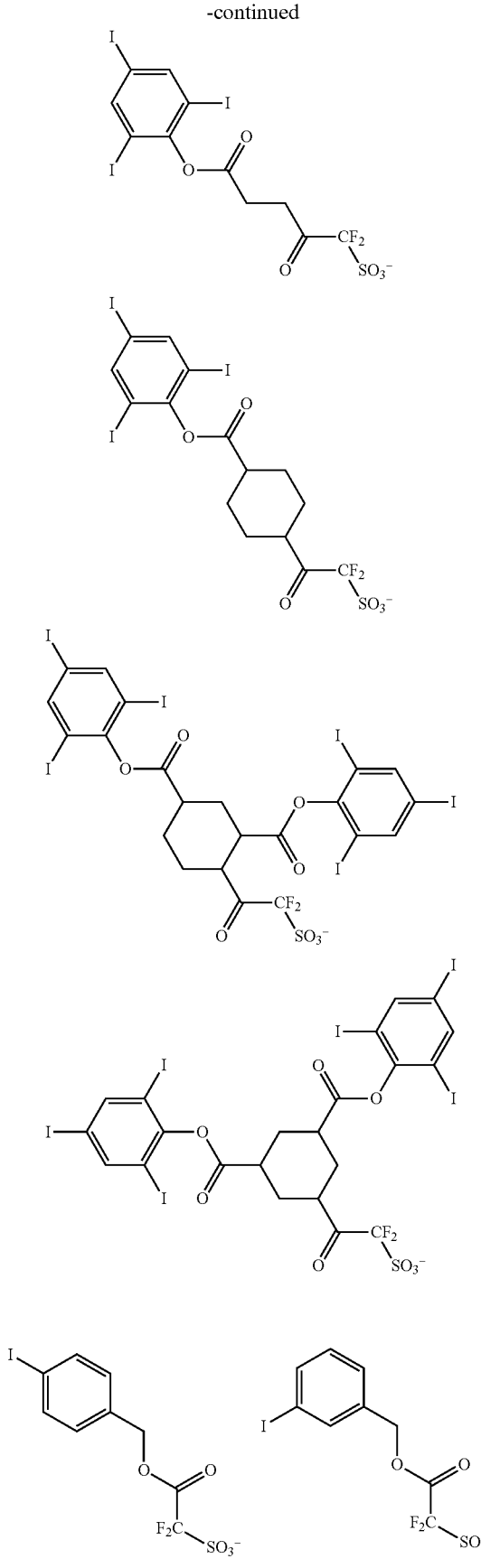
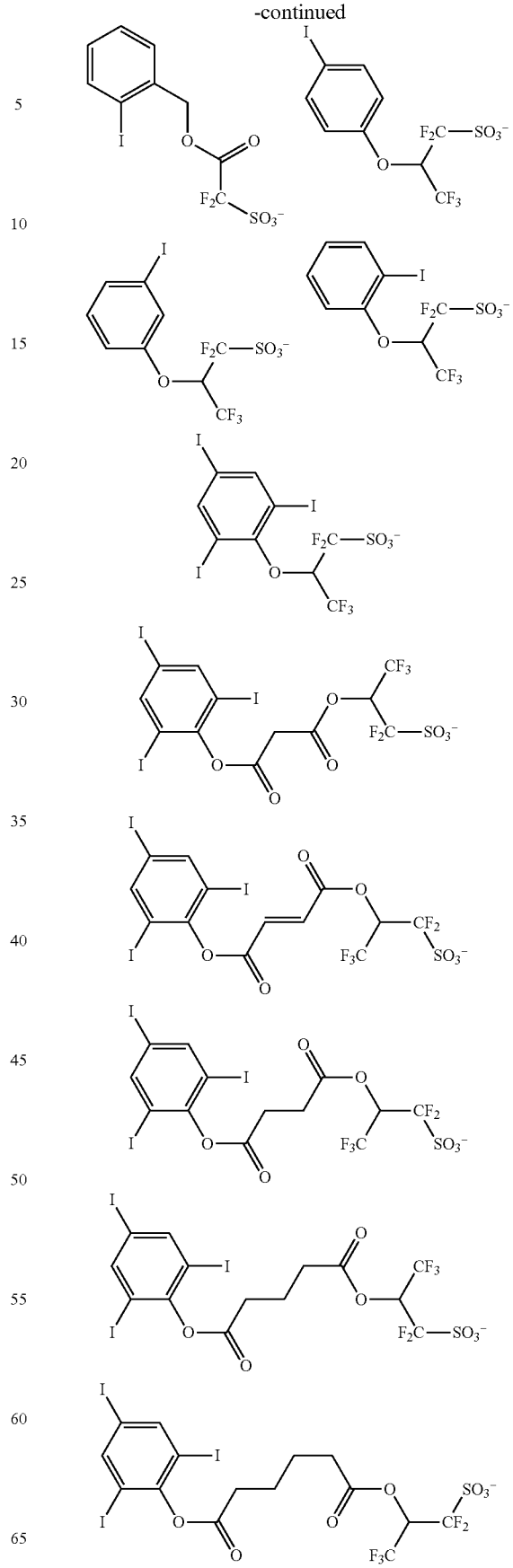

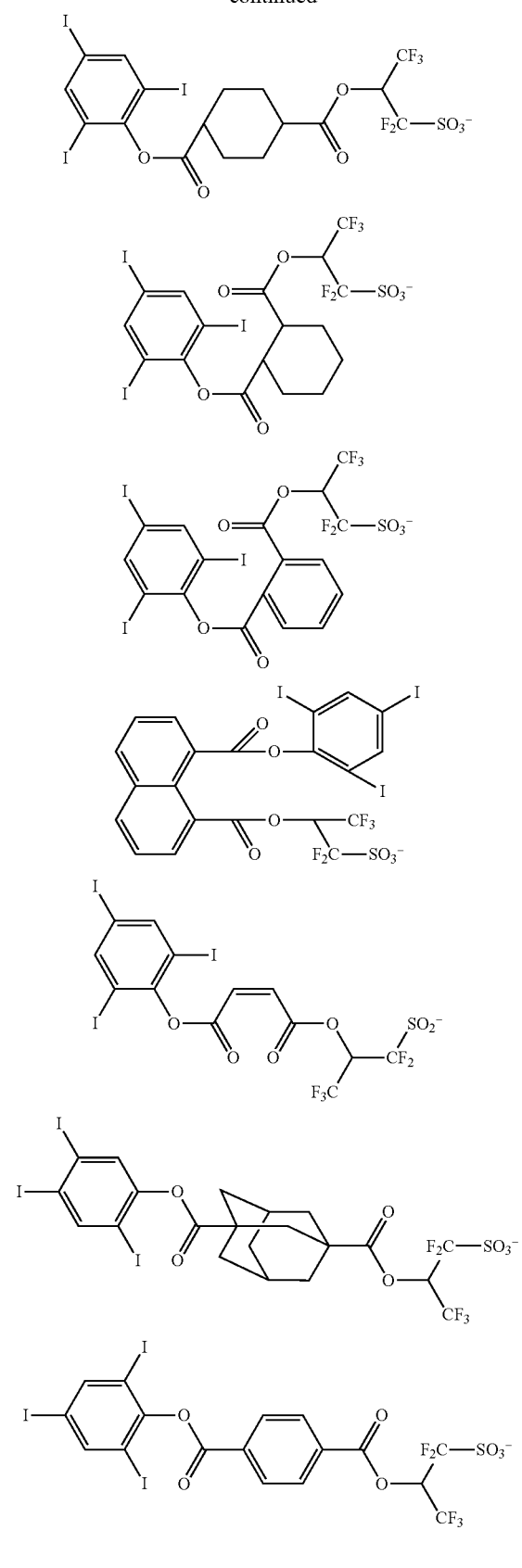
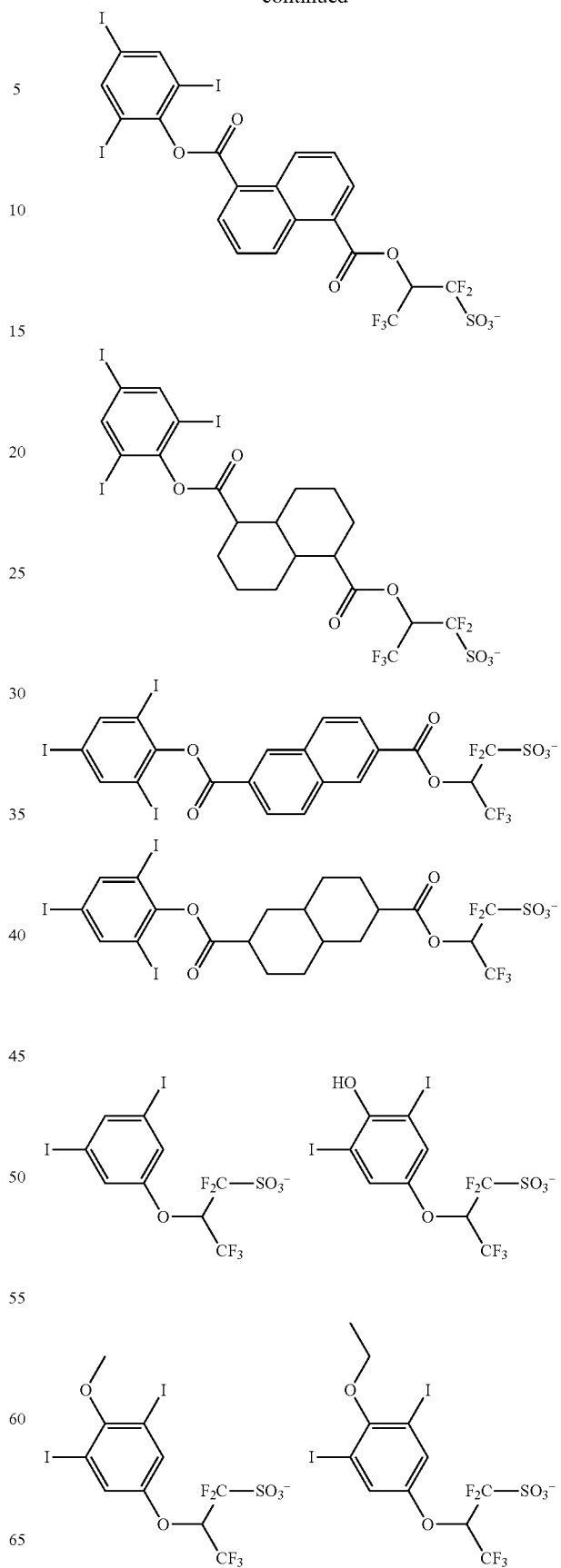

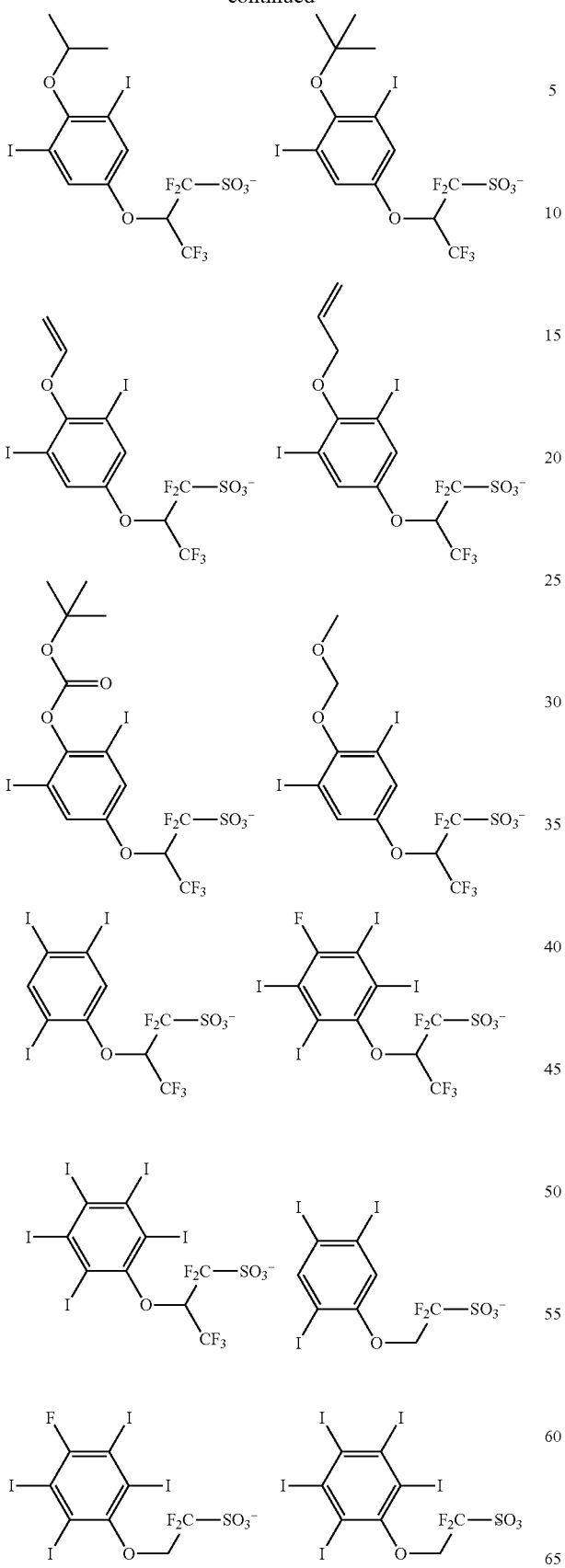

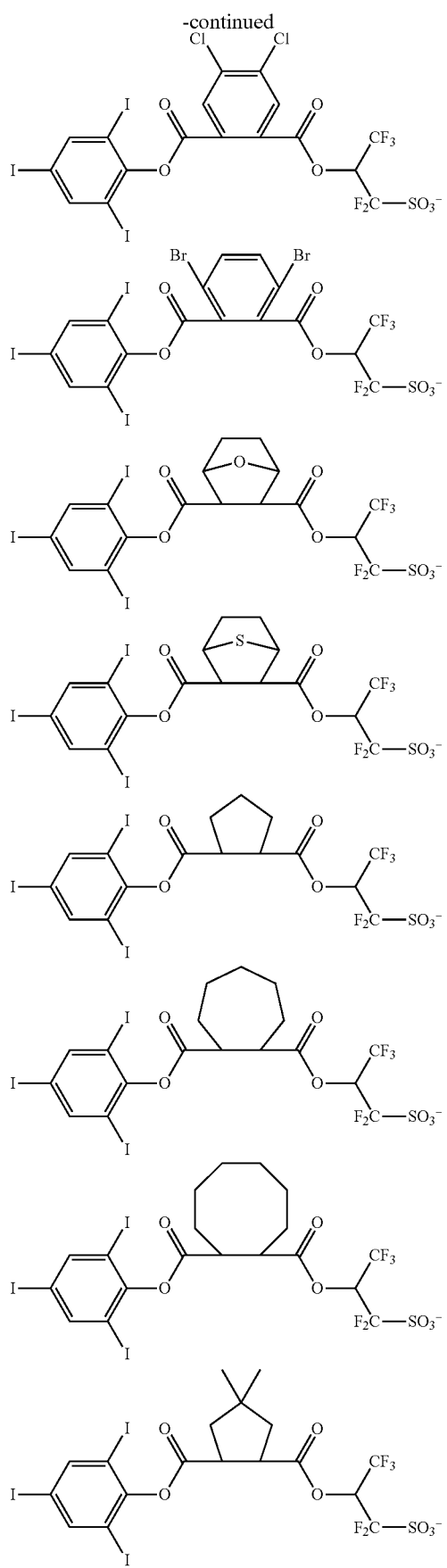
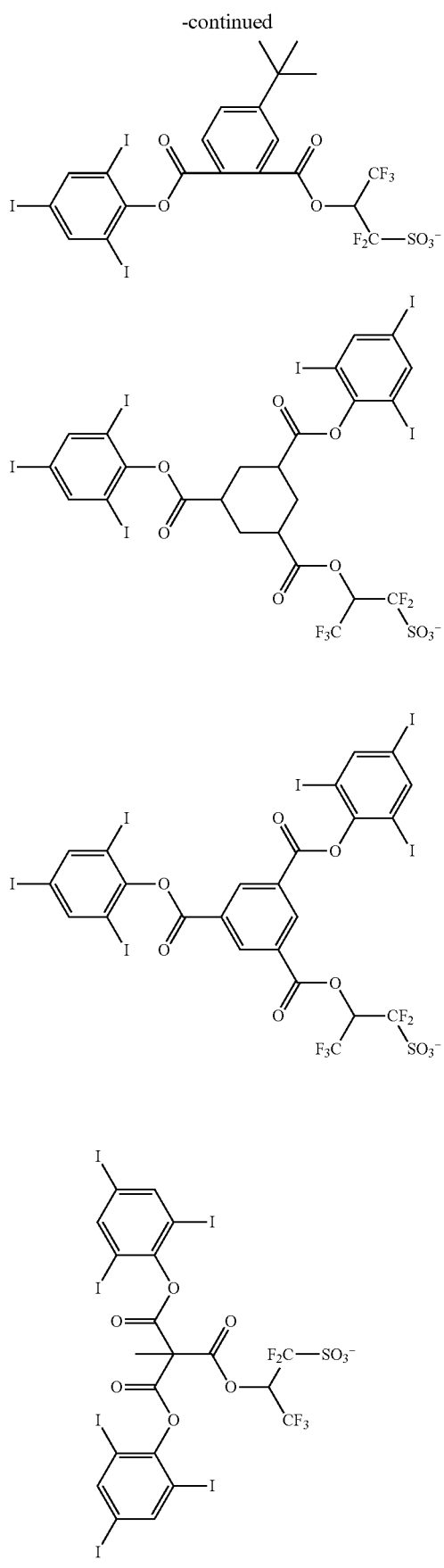

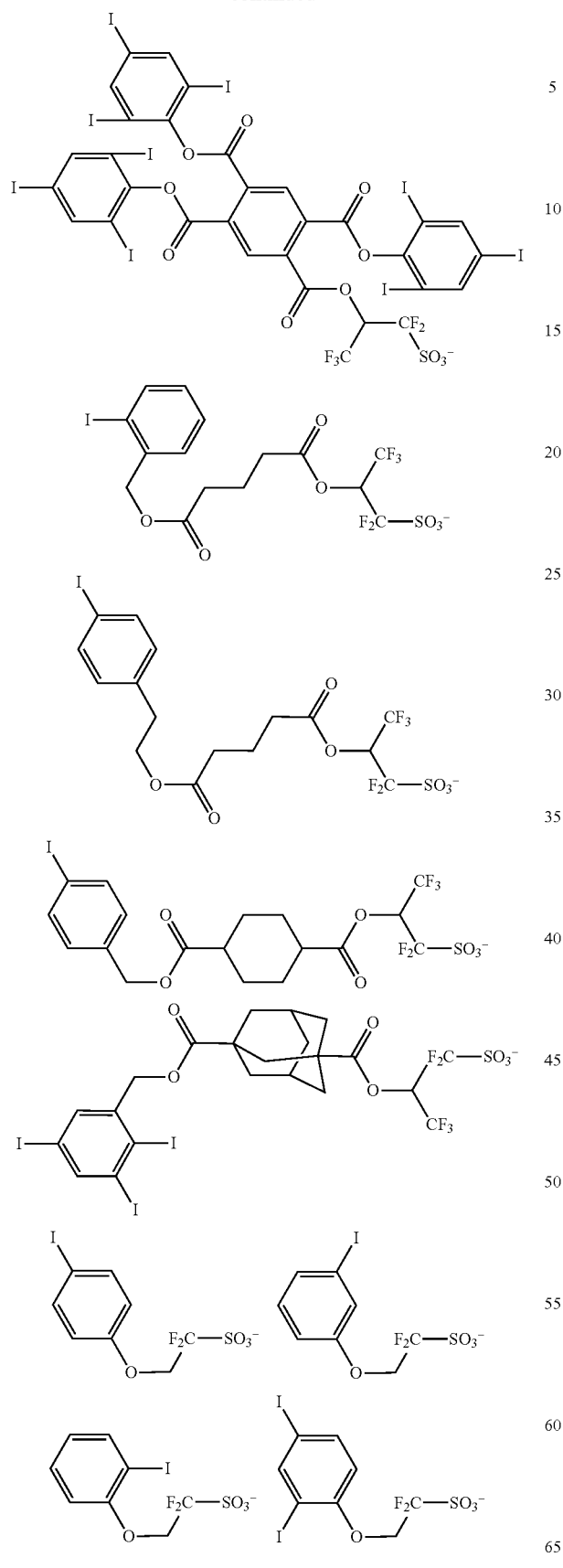
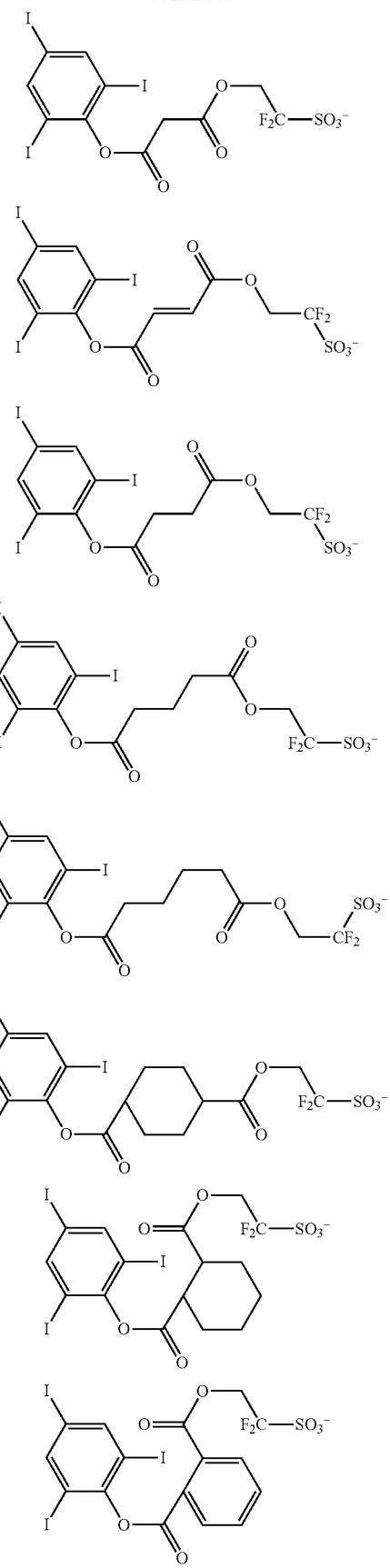

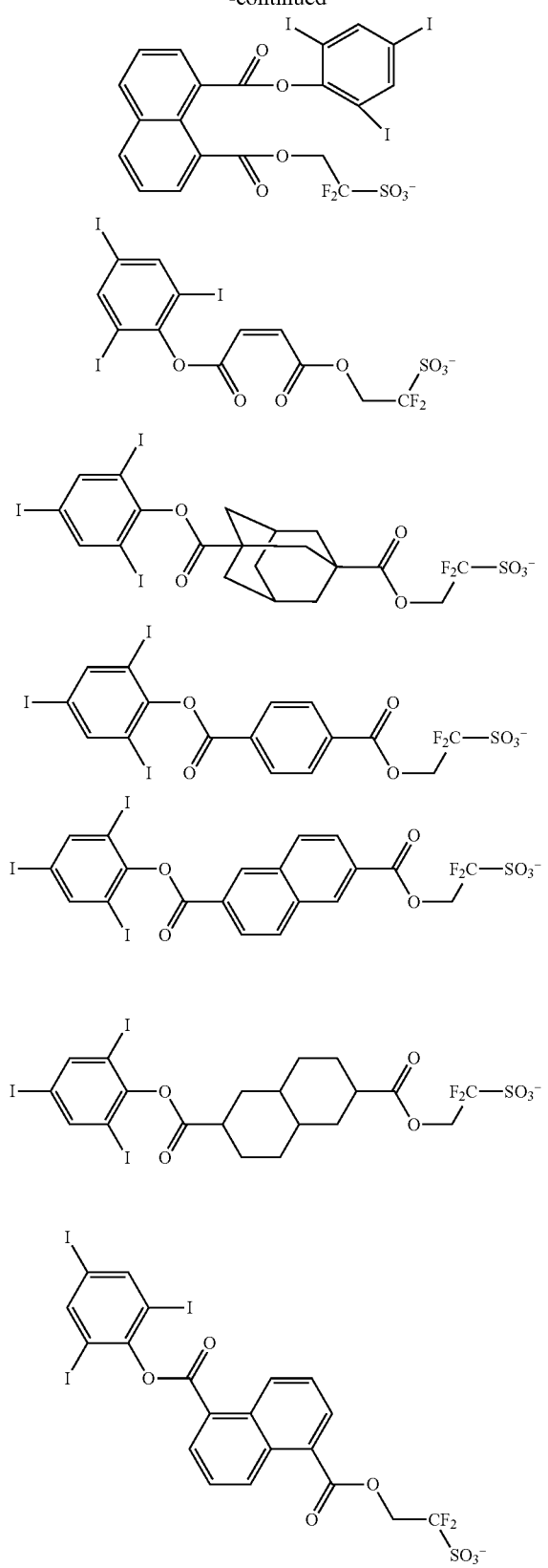
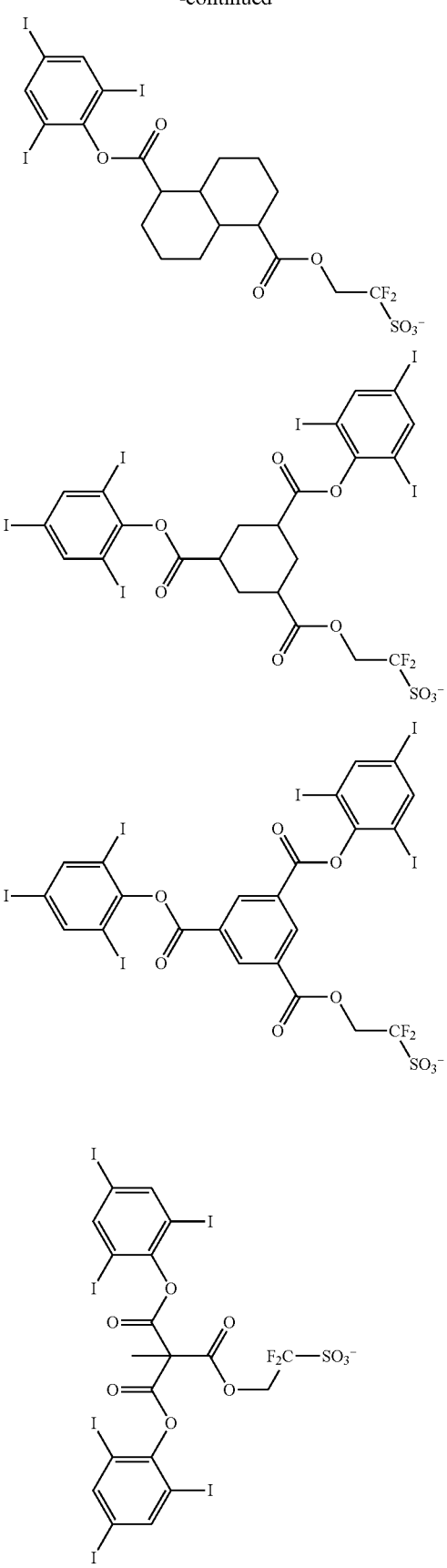

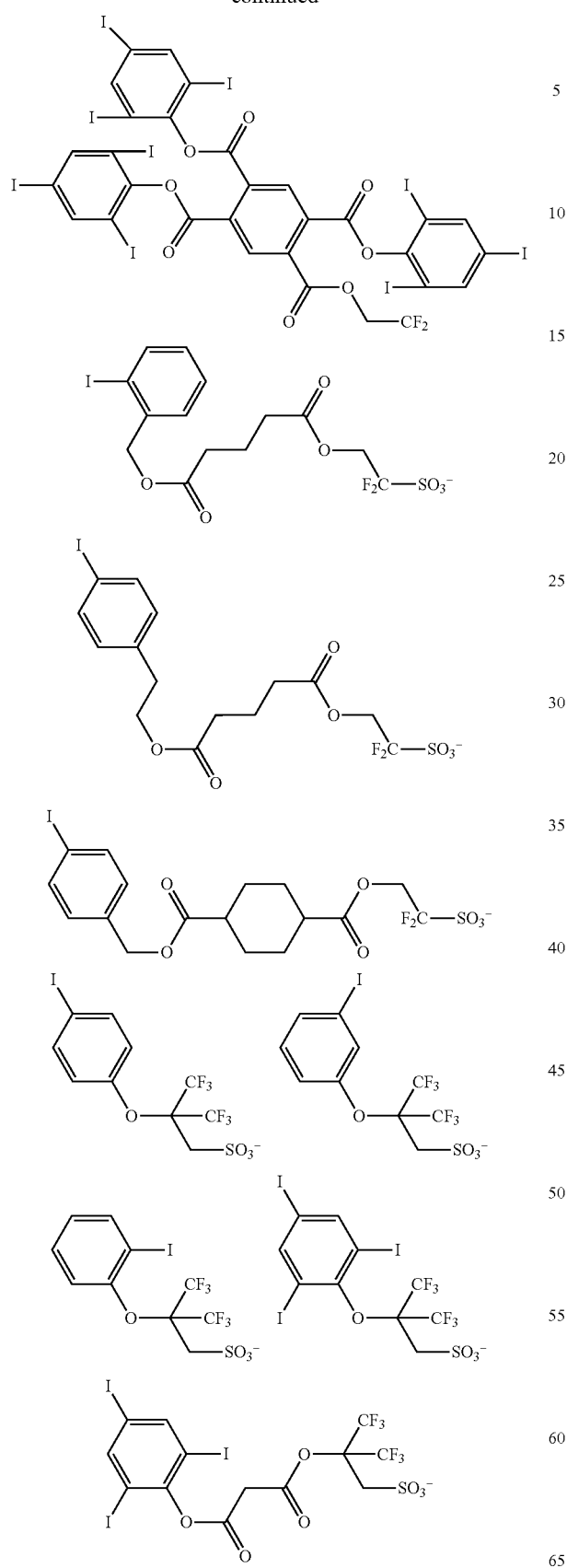
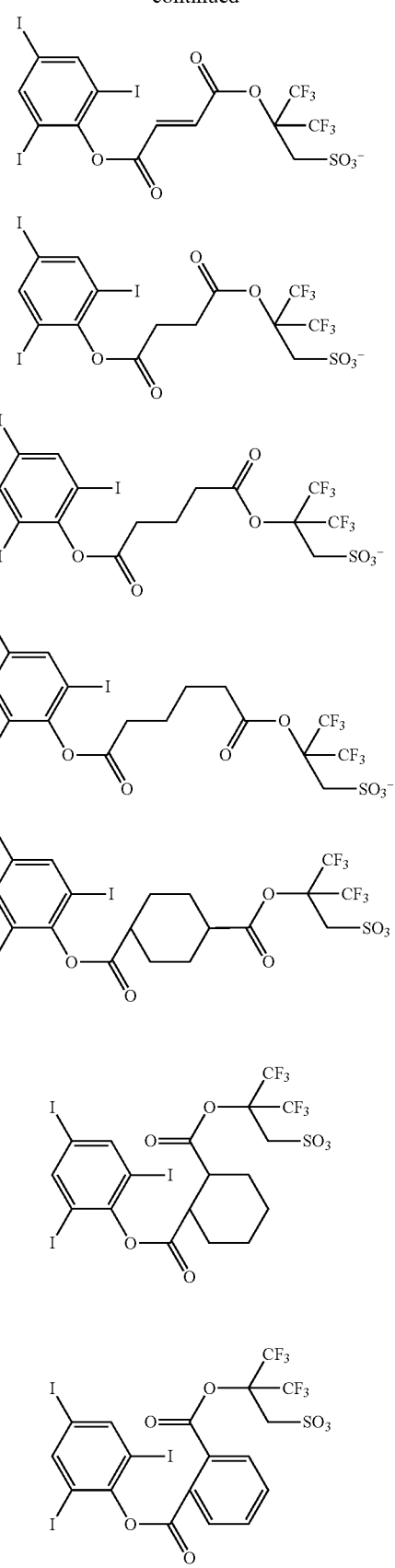

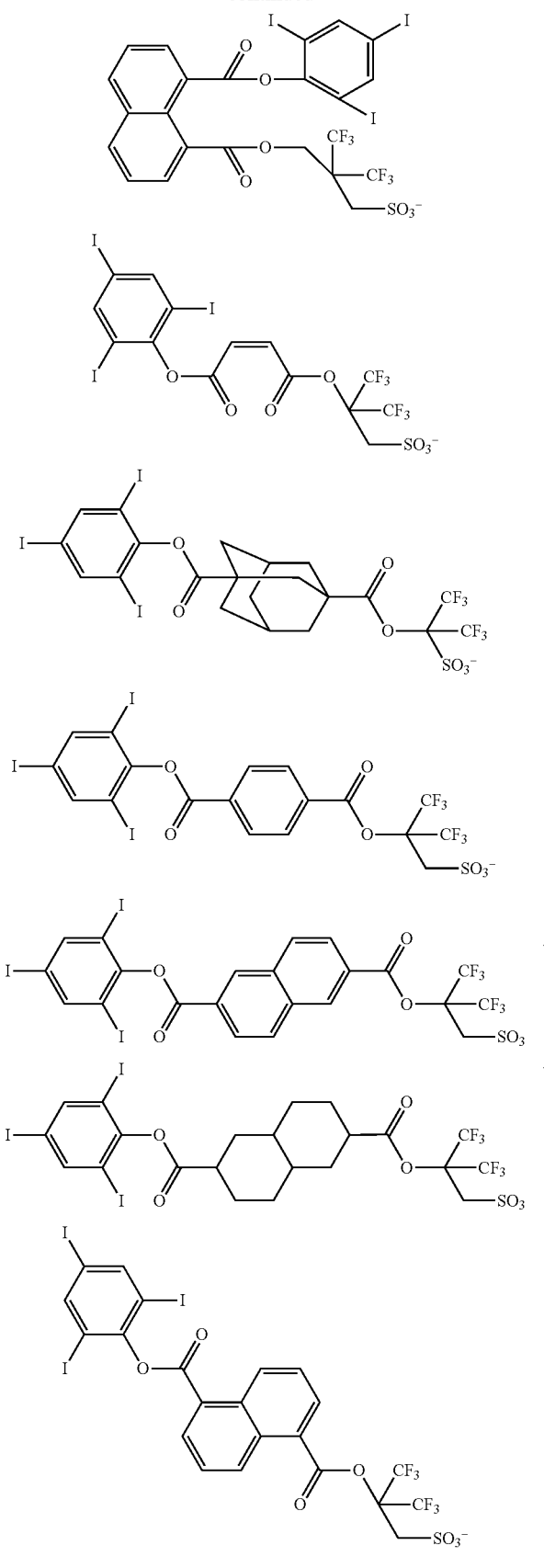
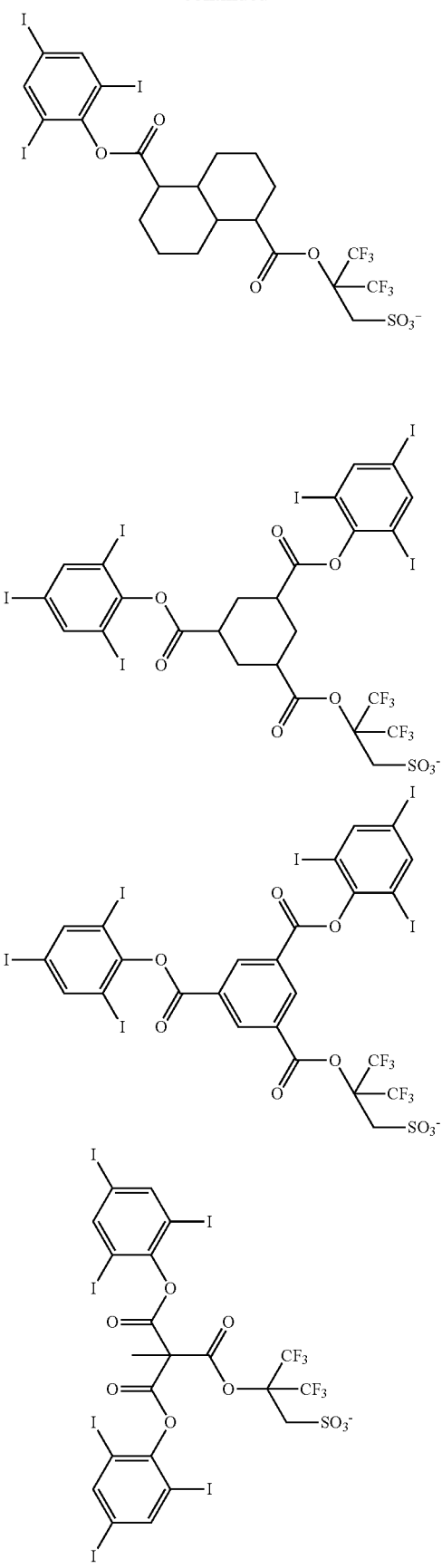

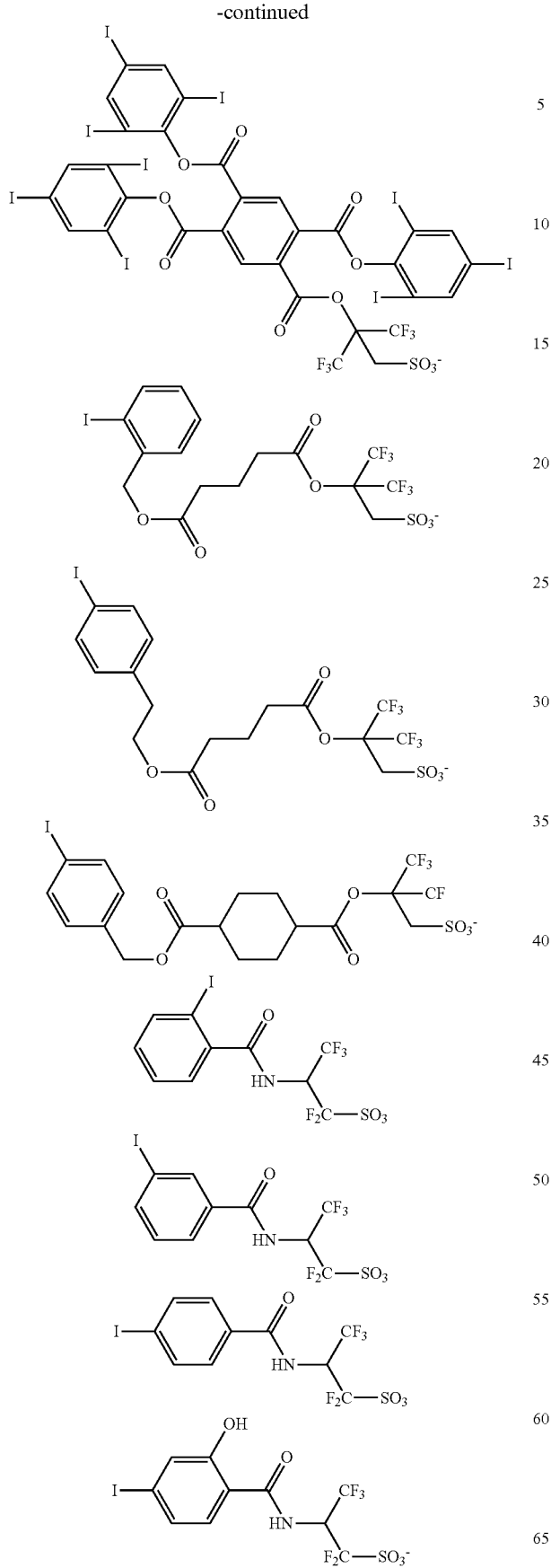
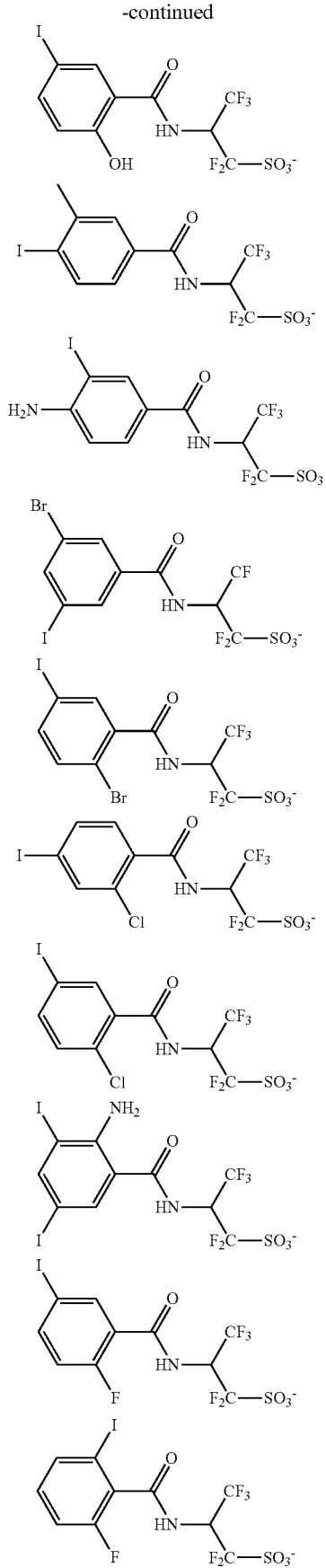

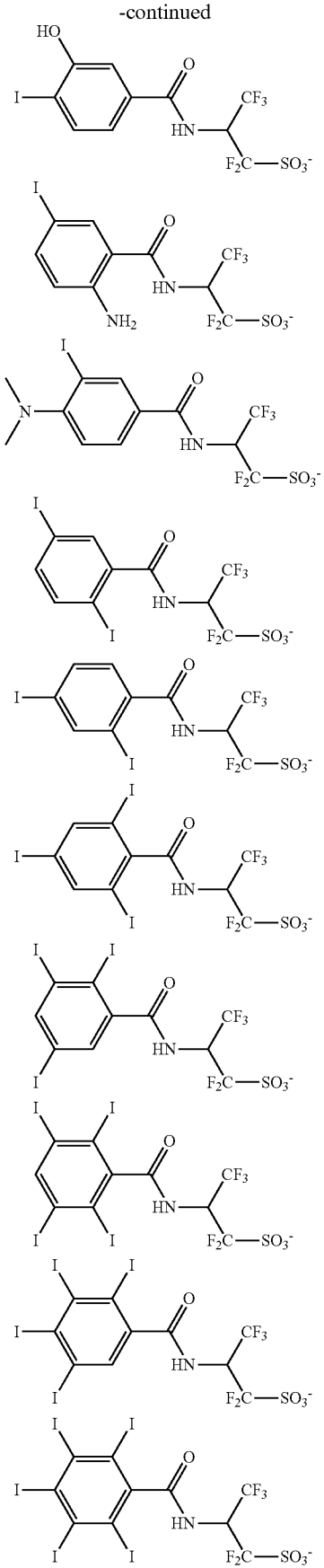
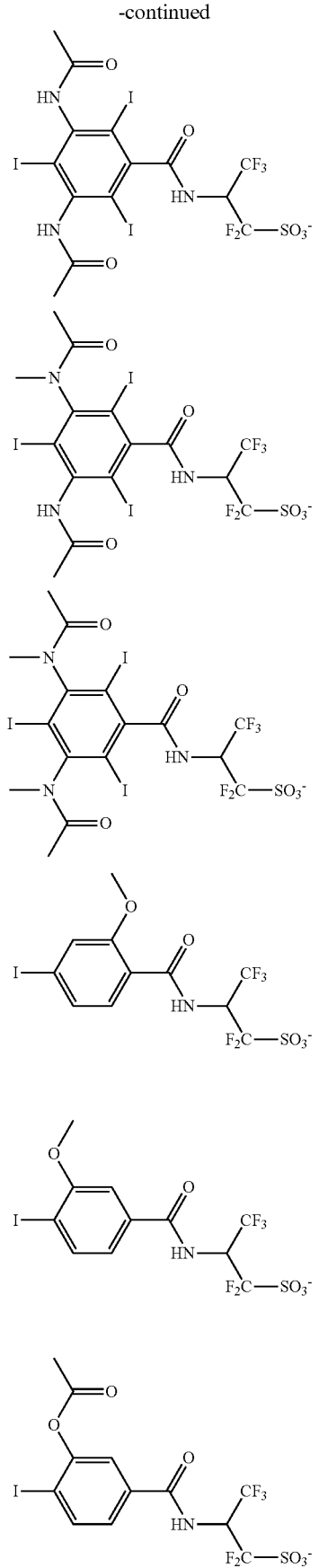

75
-continued
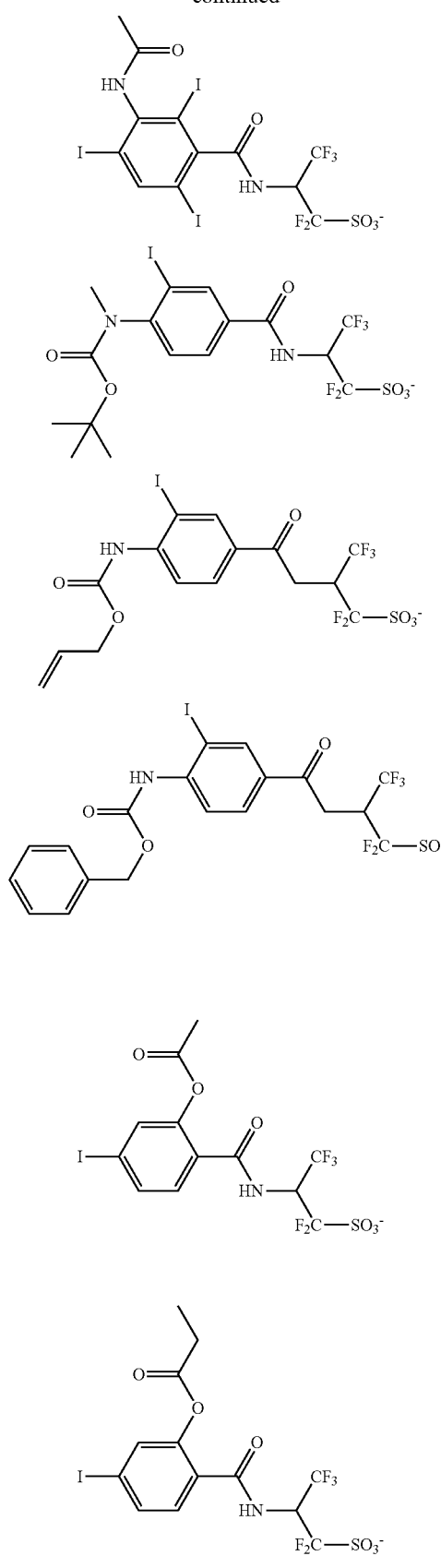
76
-continued
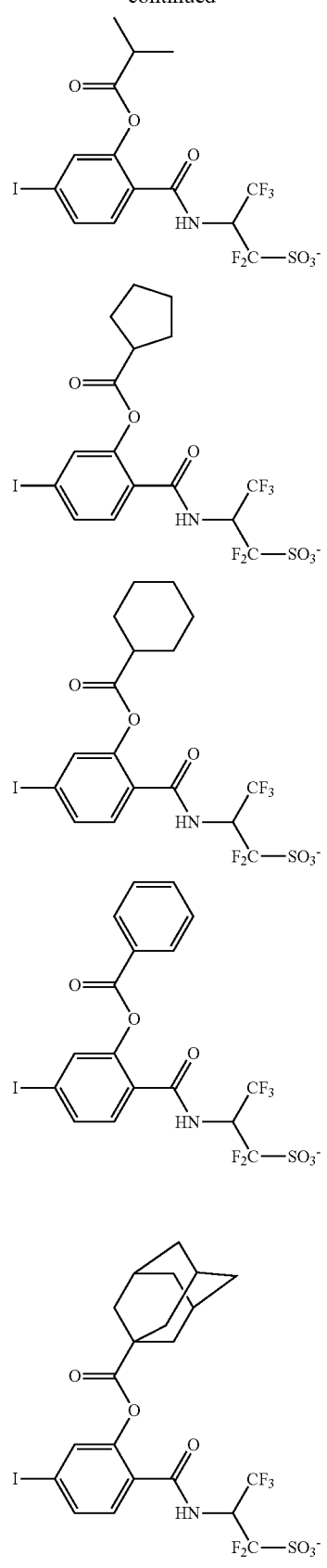

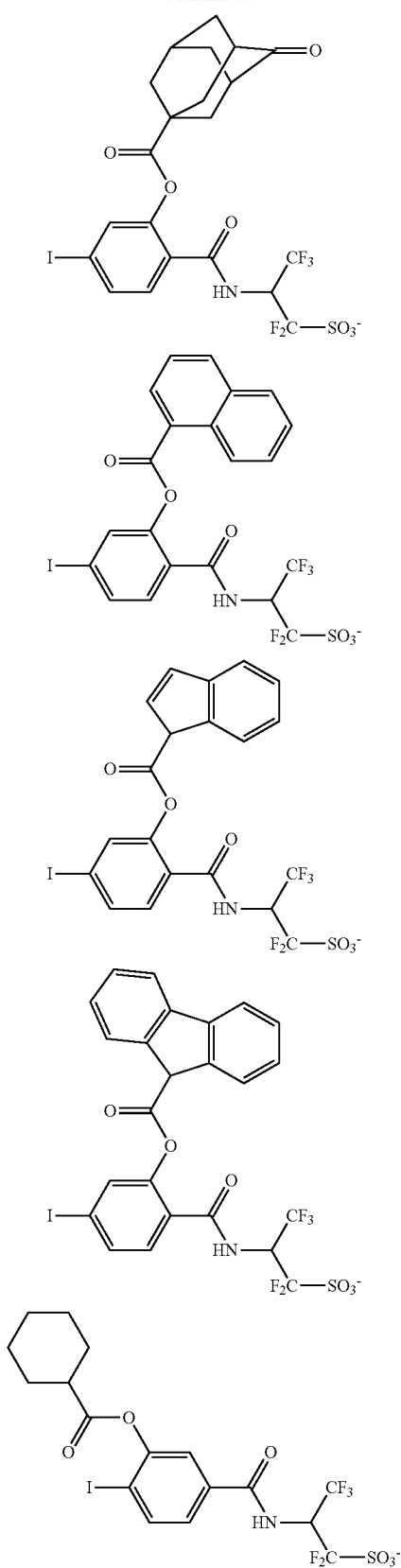
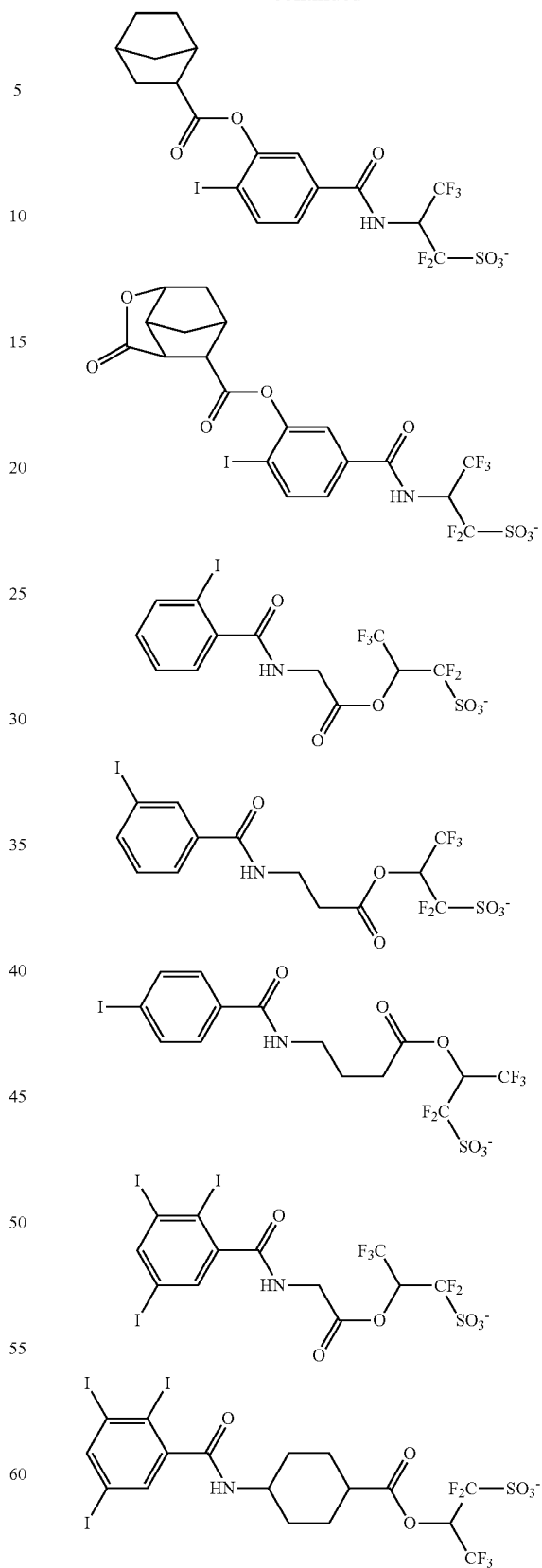

-continued
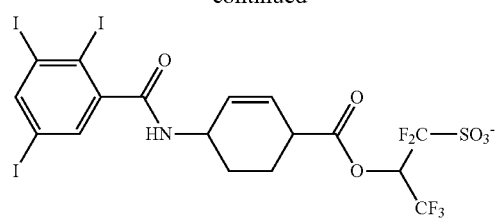
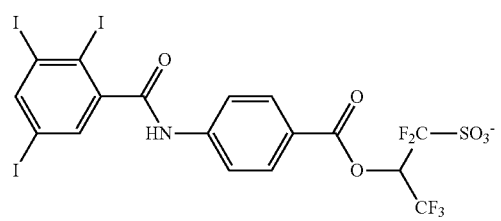
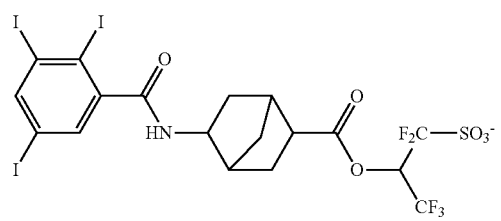
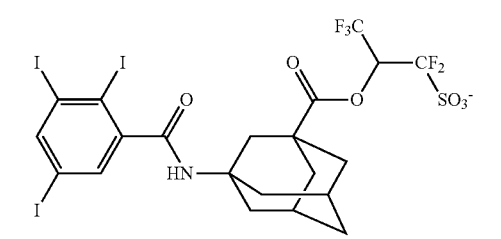
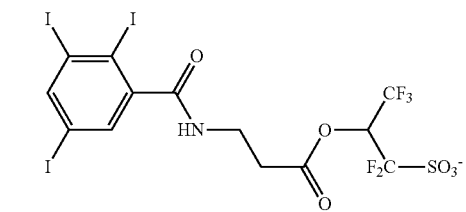
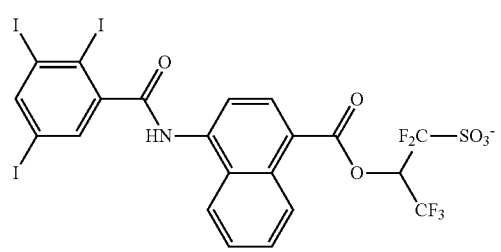
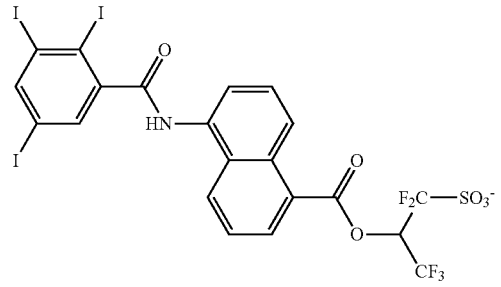
-continued
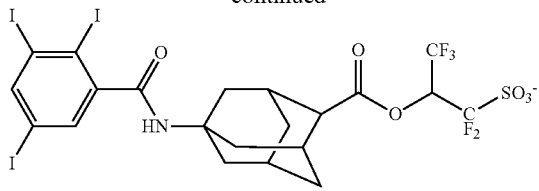
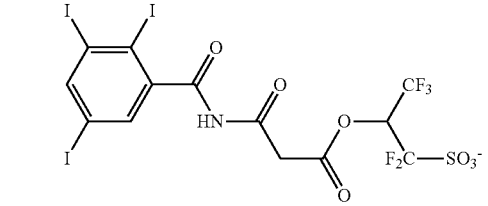
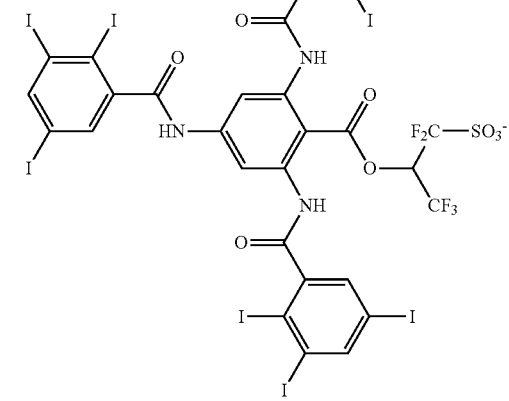
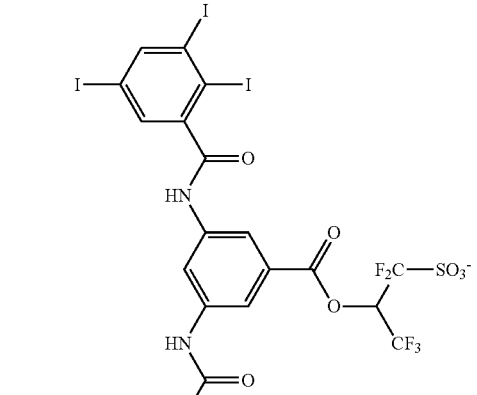
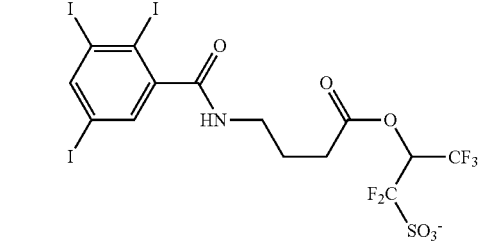

-continued
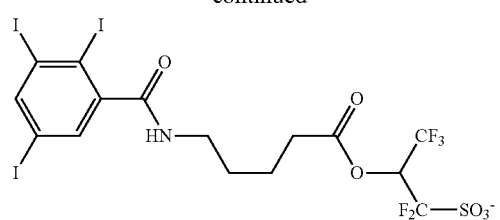
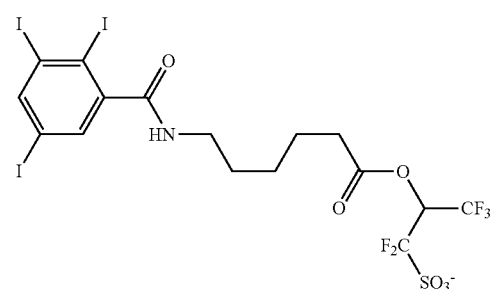
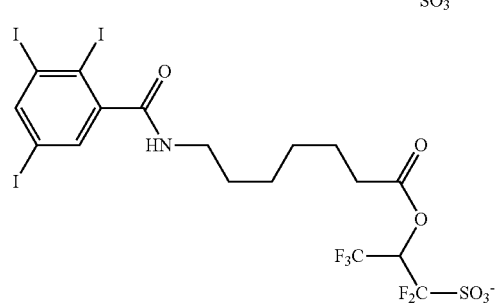
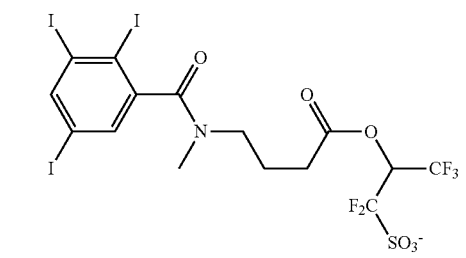
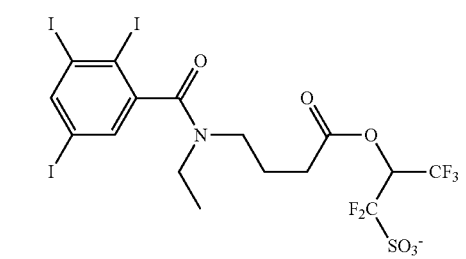
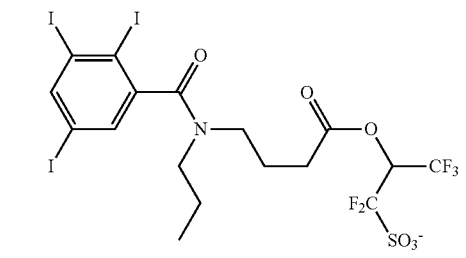
-continued
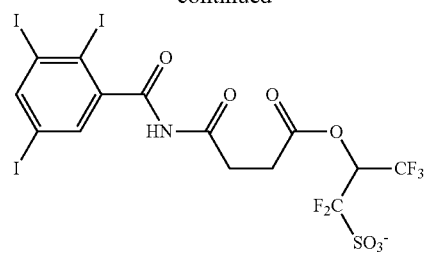
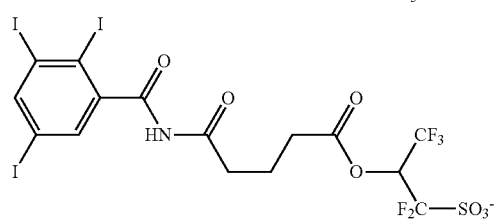
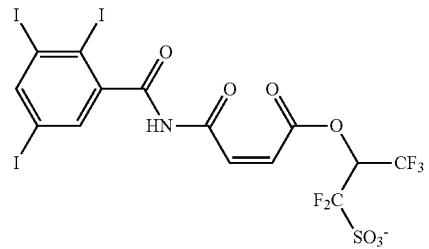
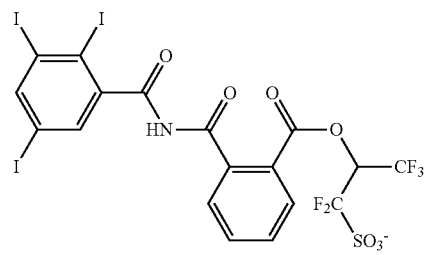
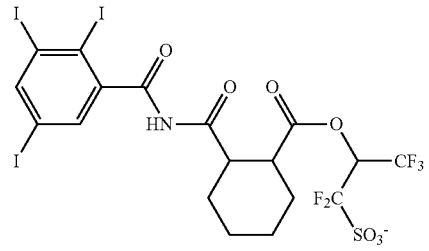
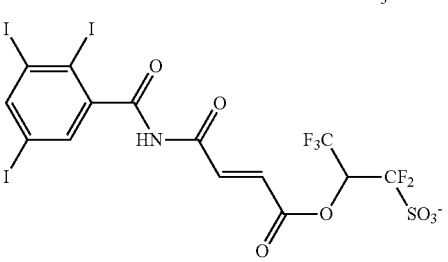
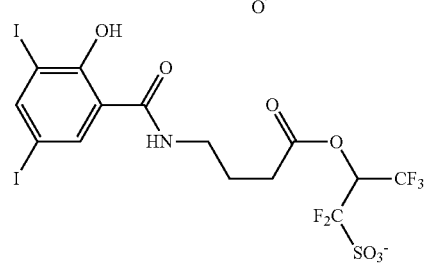

-continued
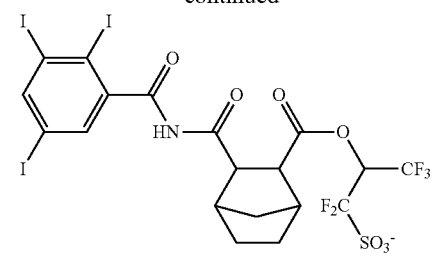
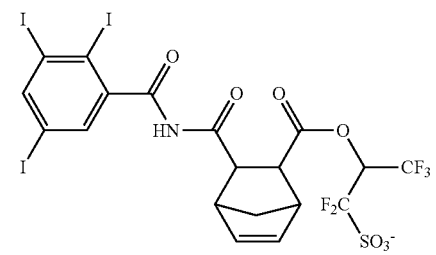
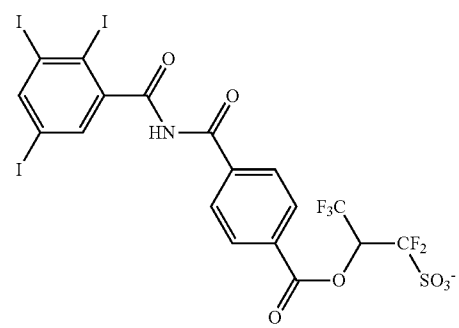
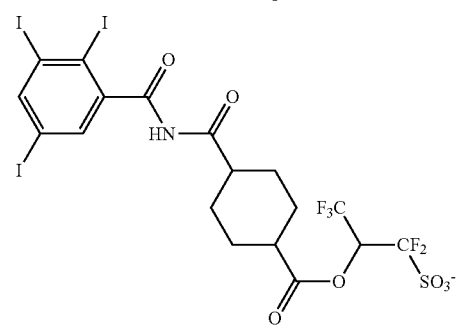
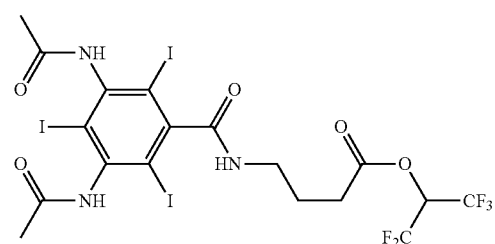
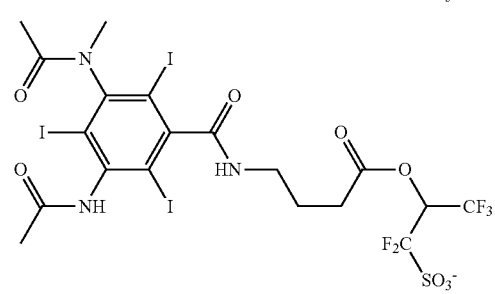
-continued
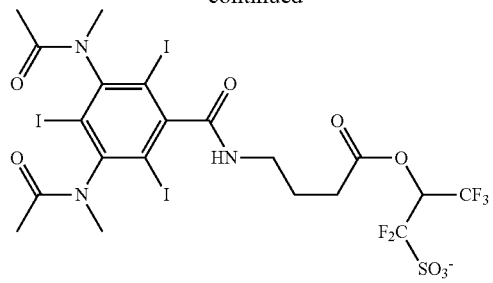
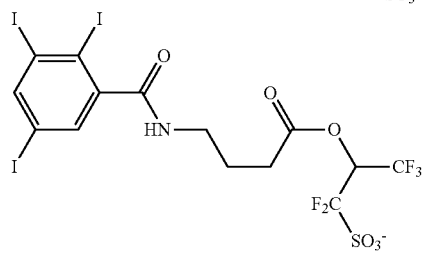
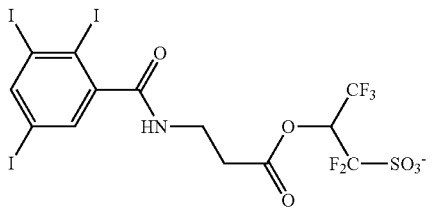
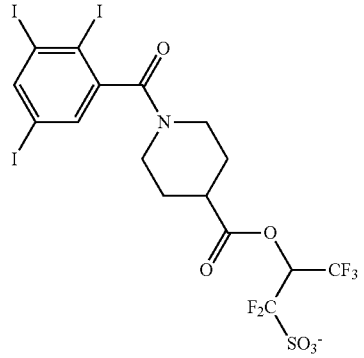
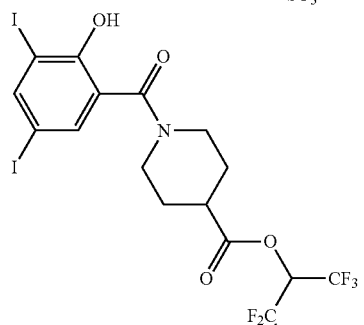
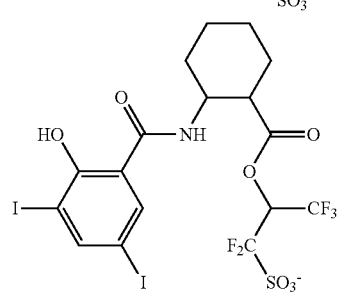

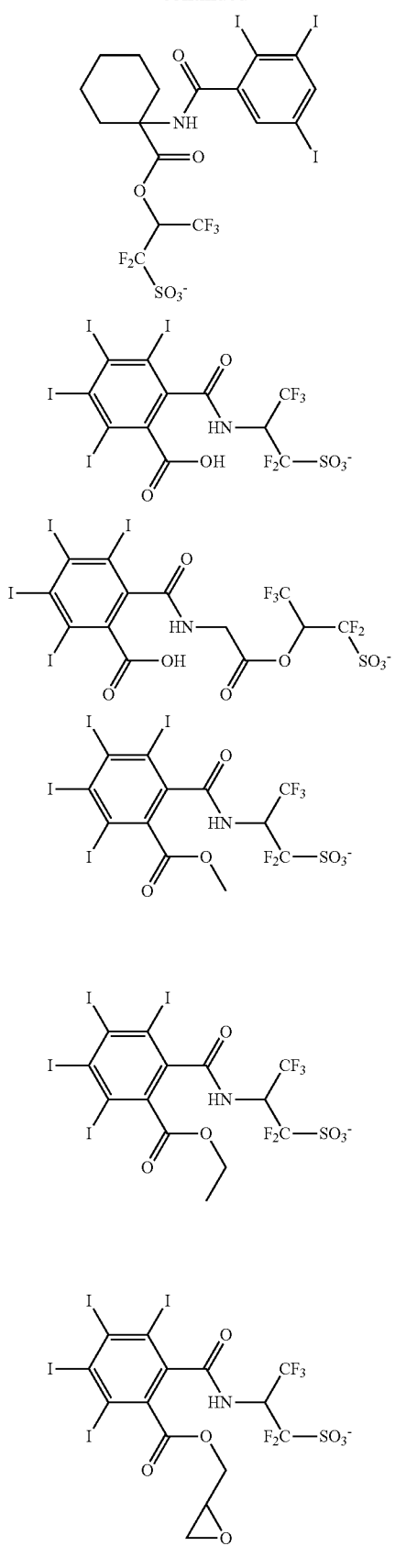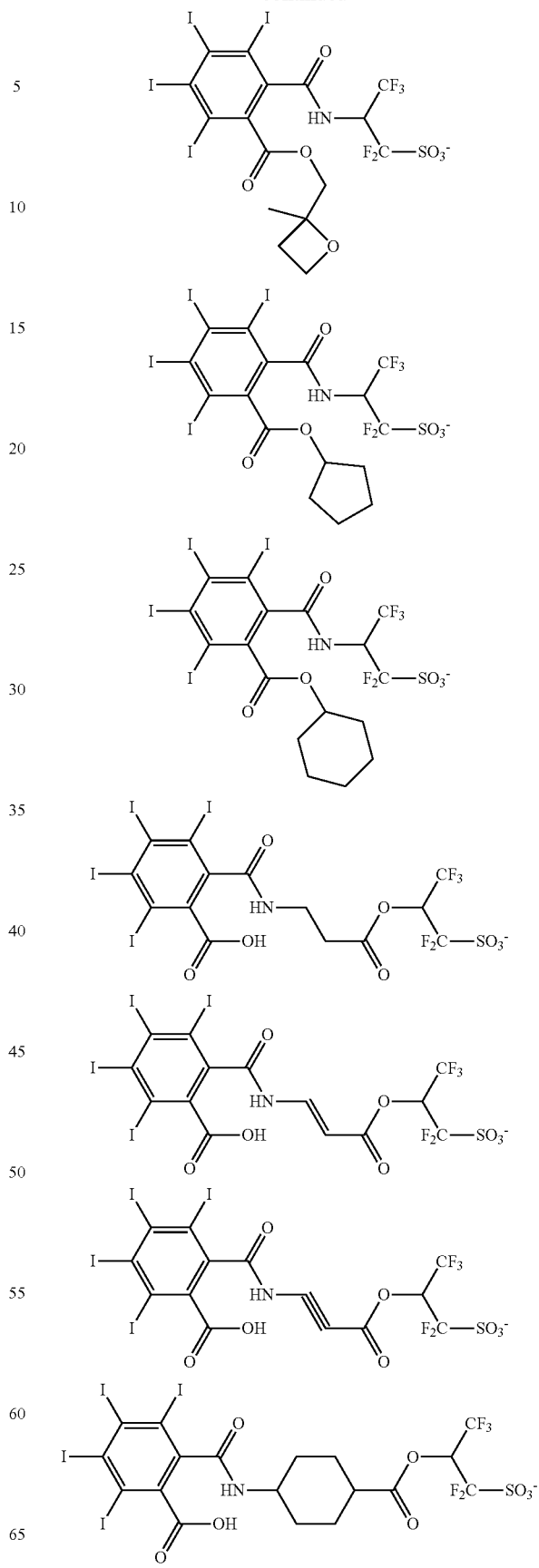

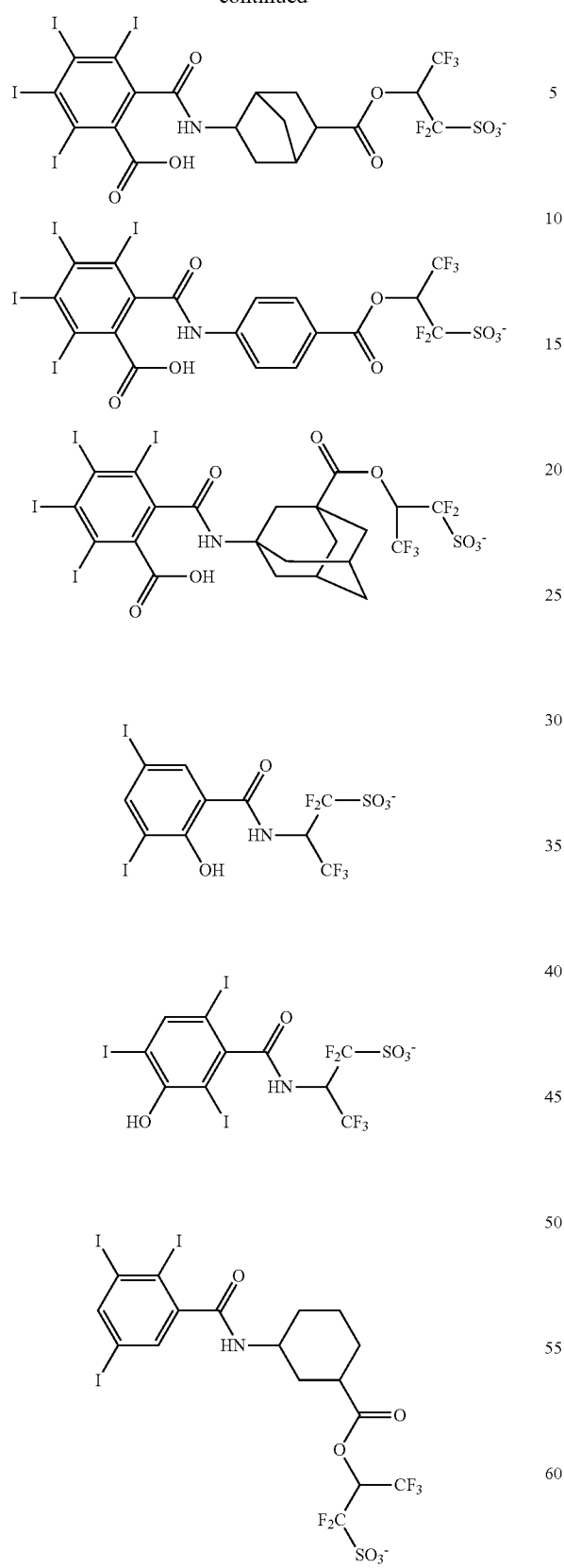
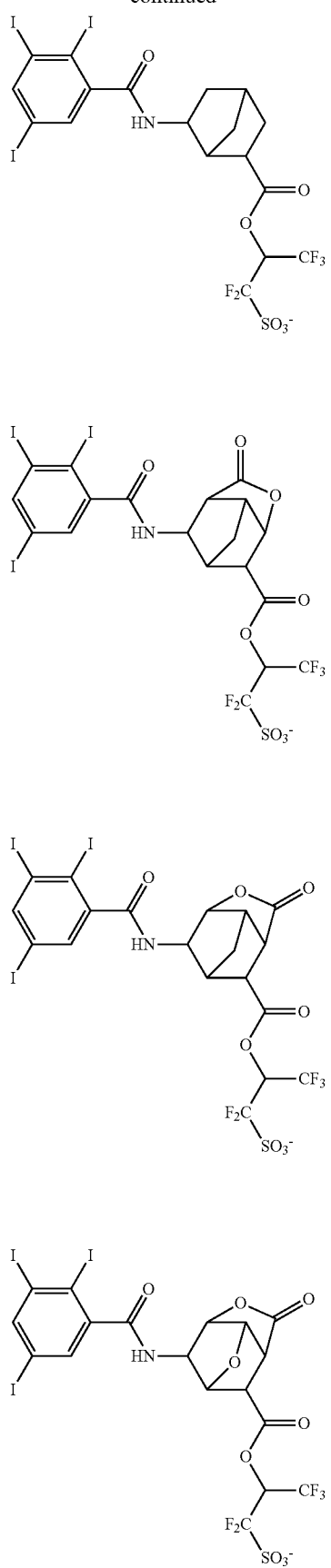

89
-continued
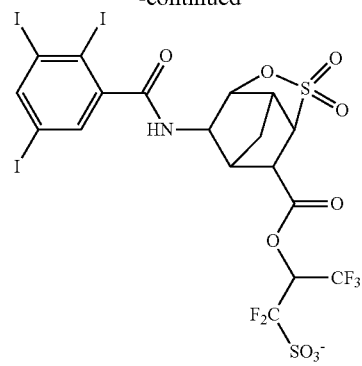
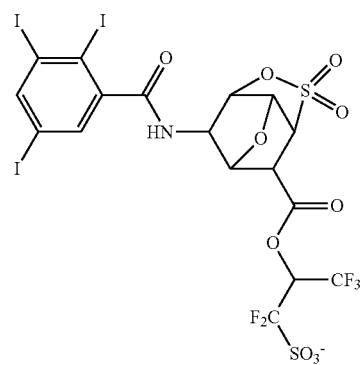
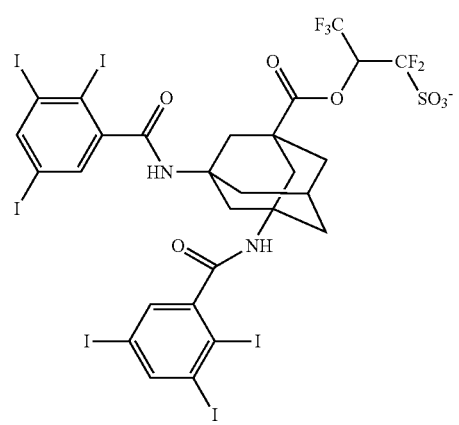
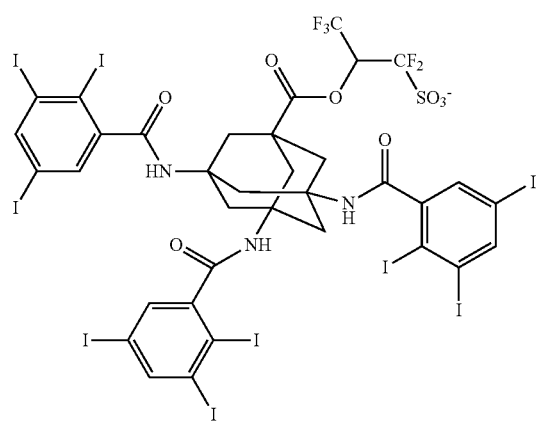
90
-continued
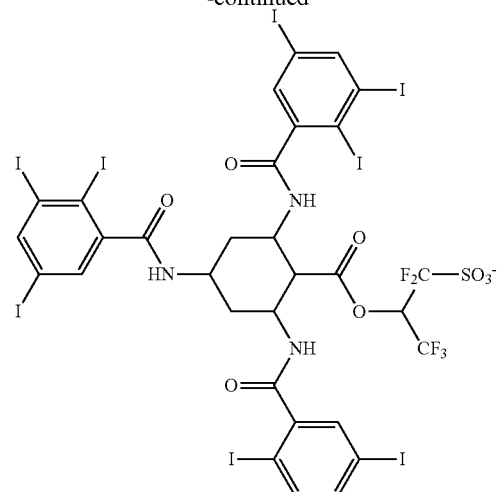
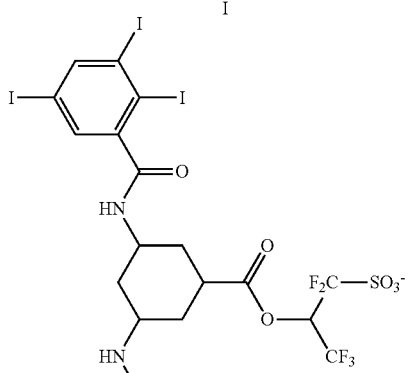
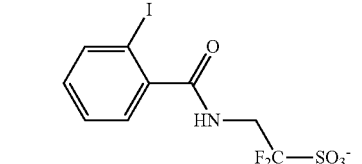
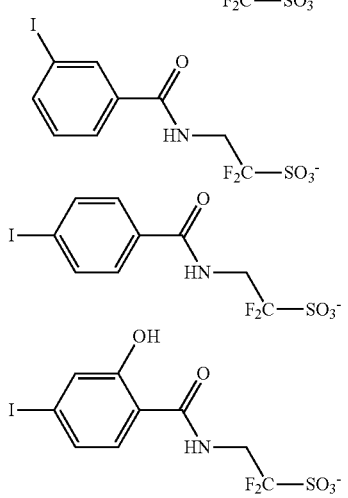

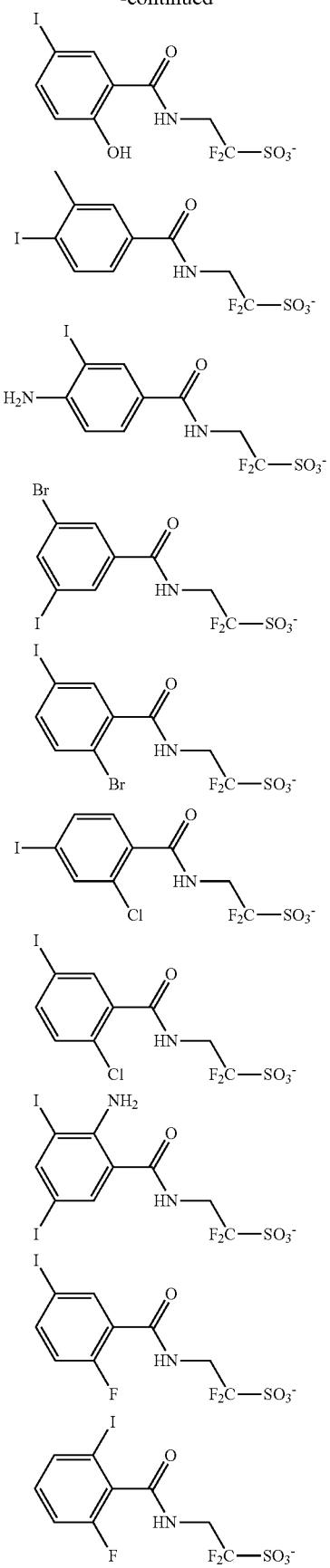
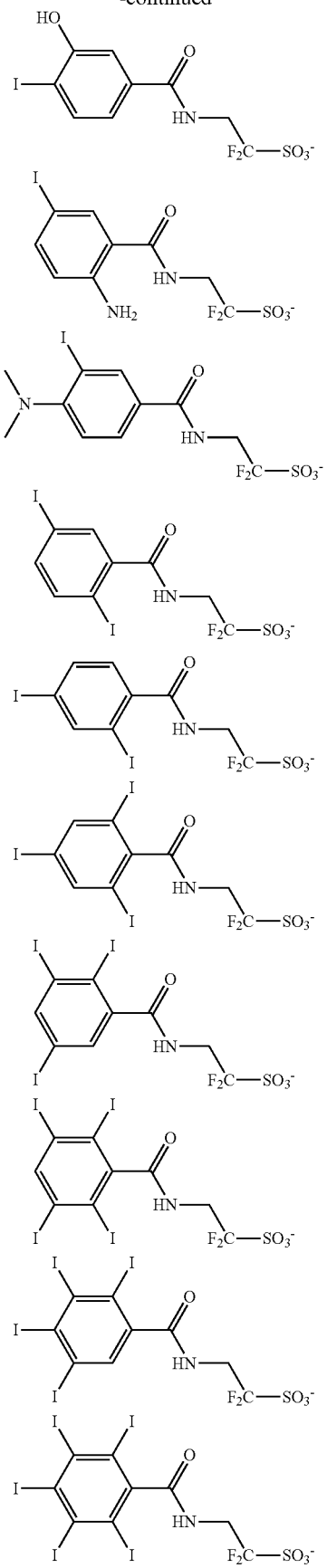

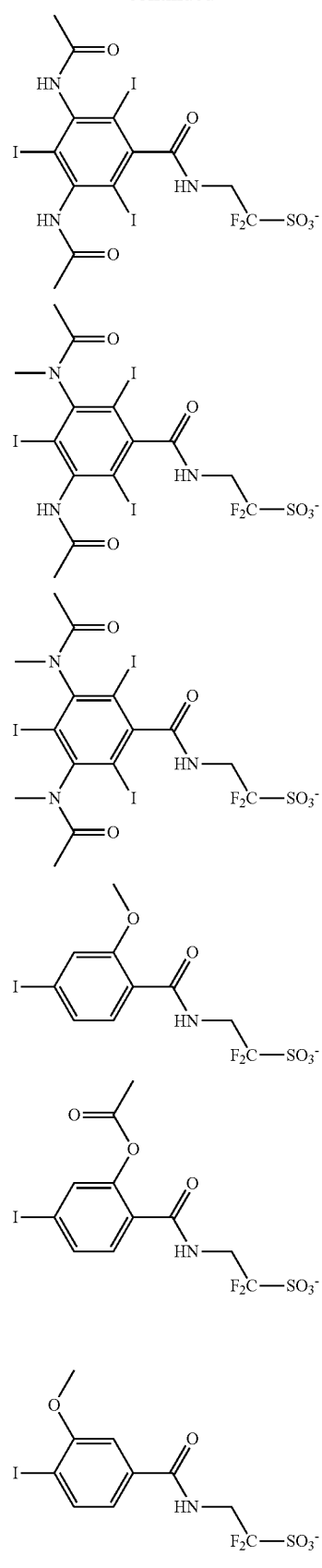
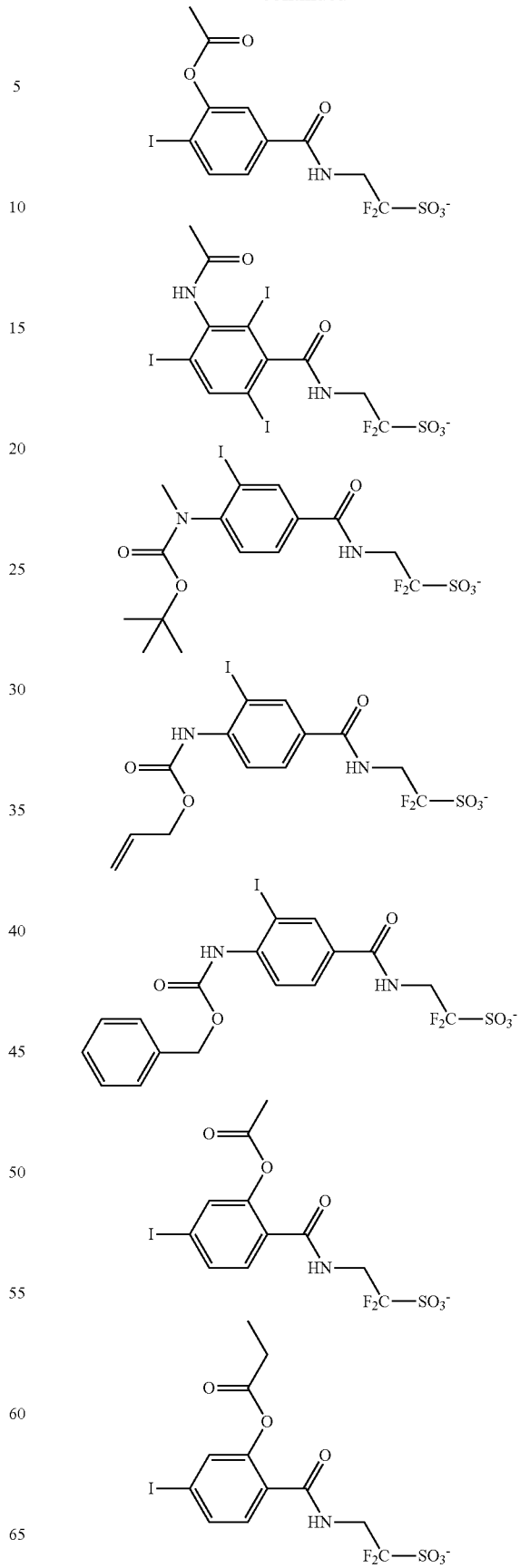

-continued
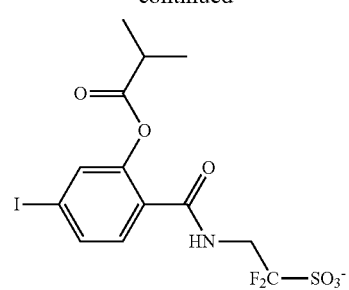
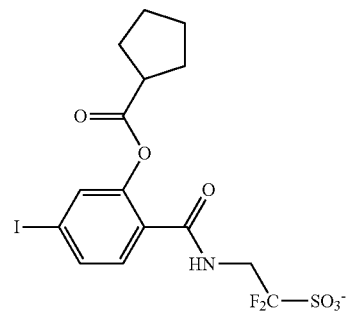
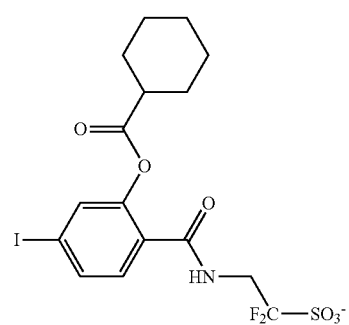
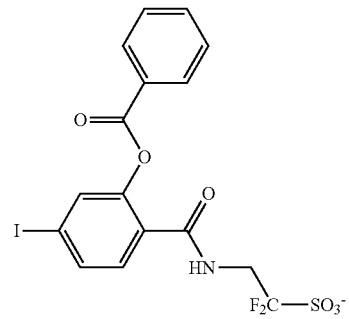
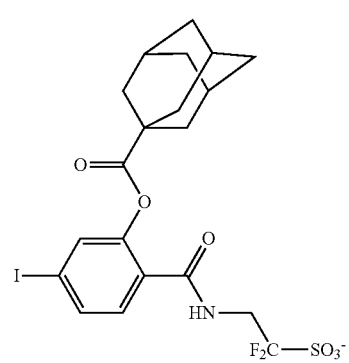
-continued
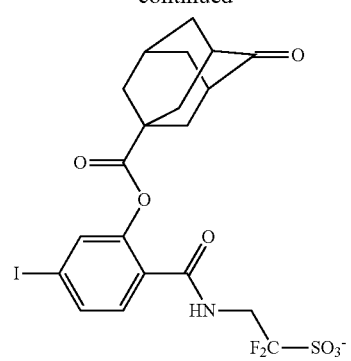
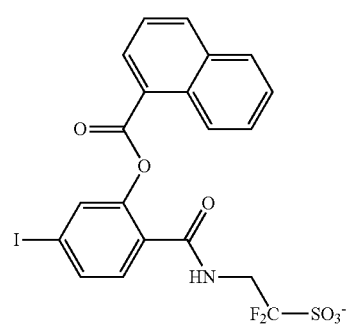
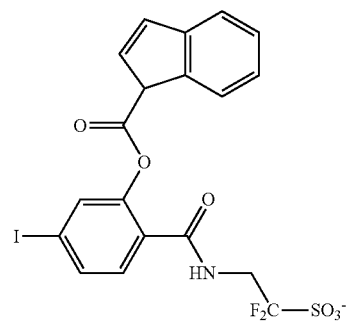
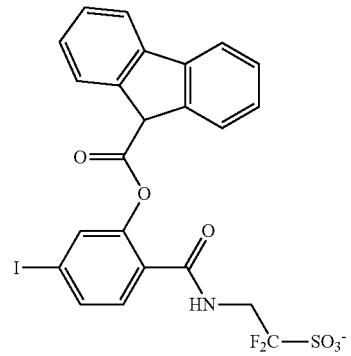
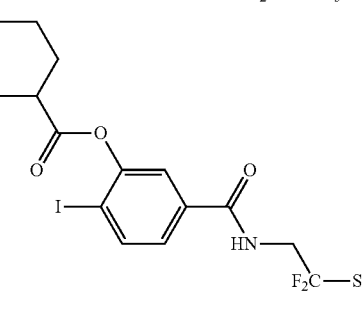

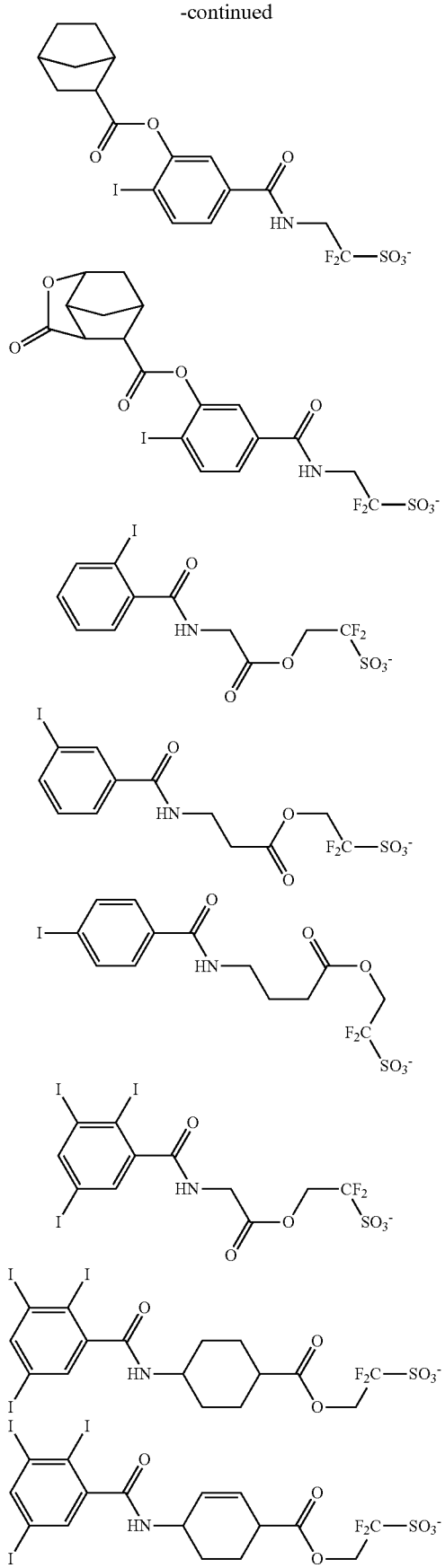
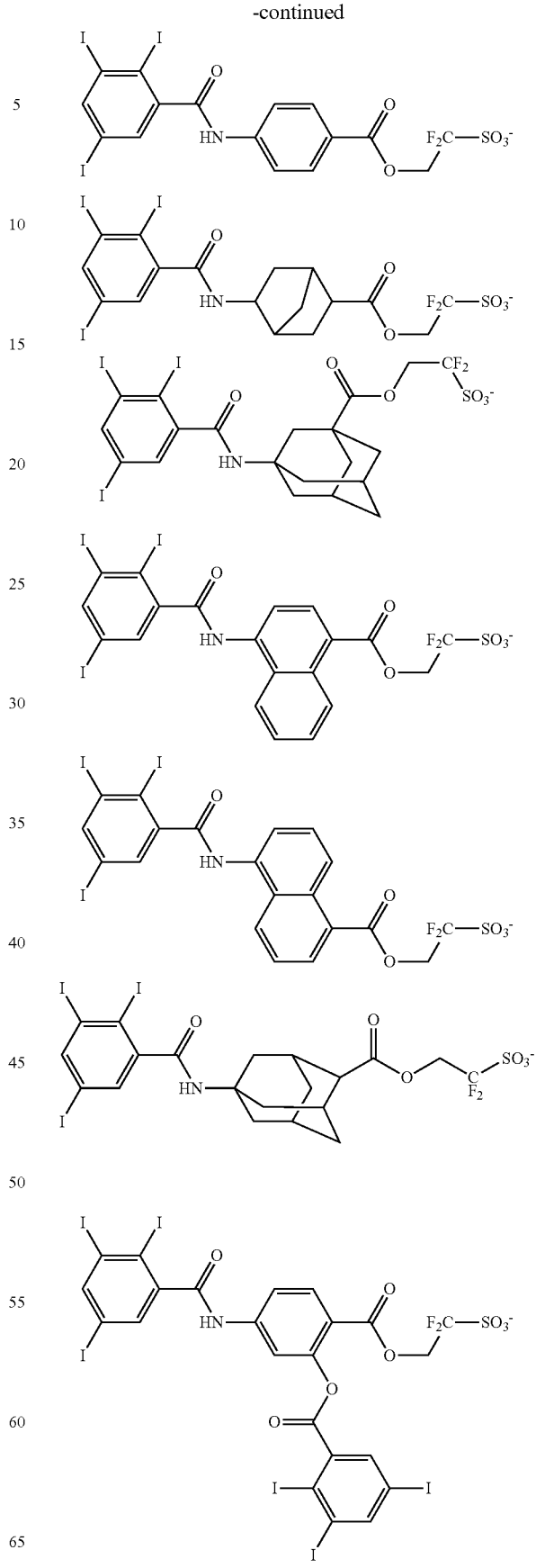

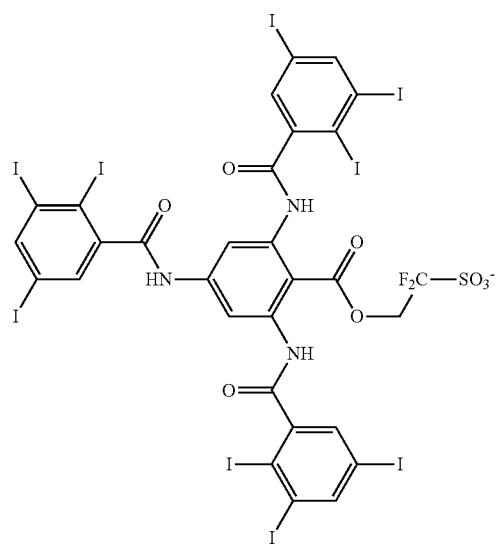
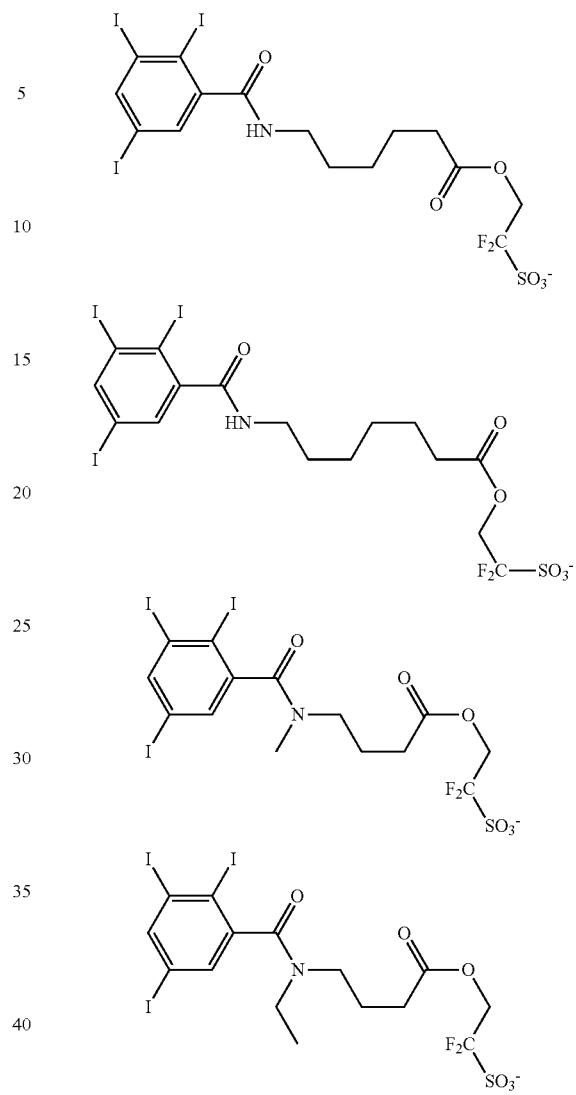
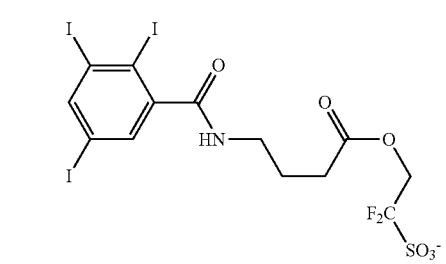
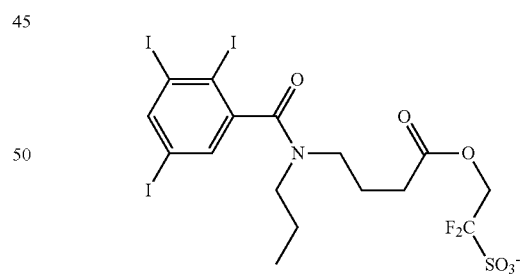
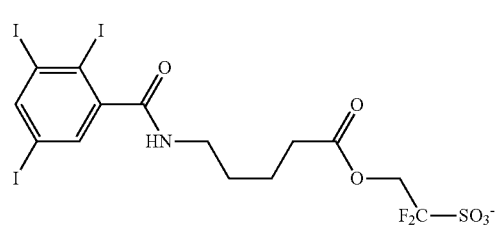

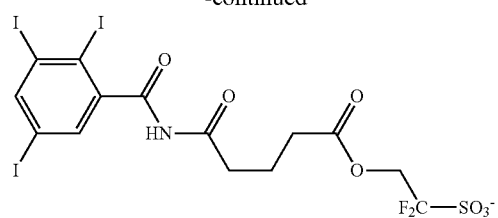
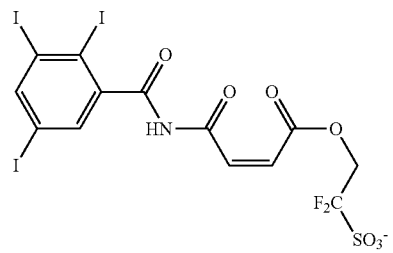
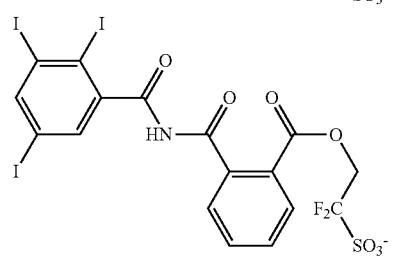
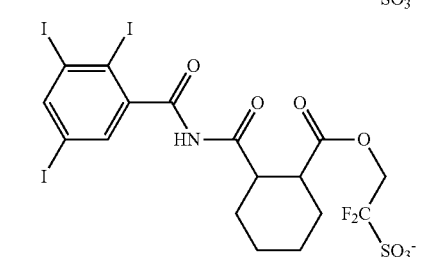
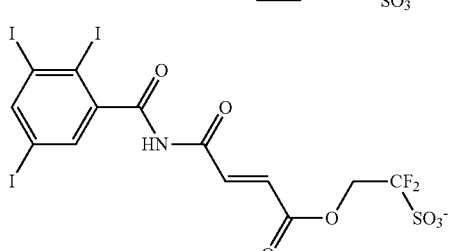
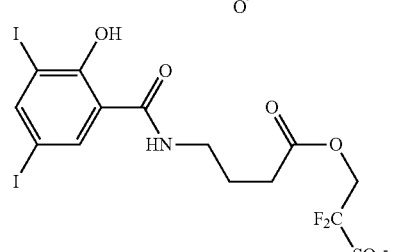
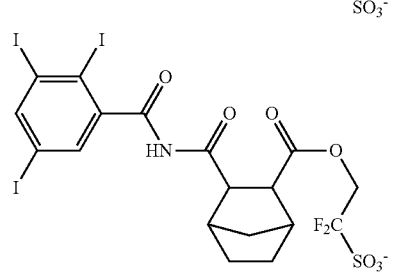
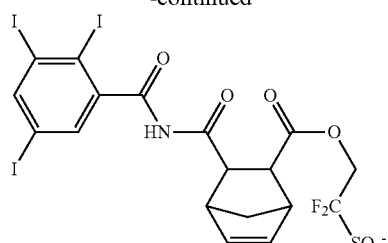
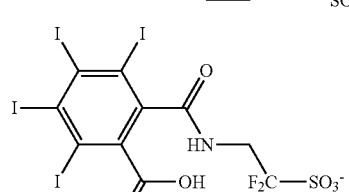
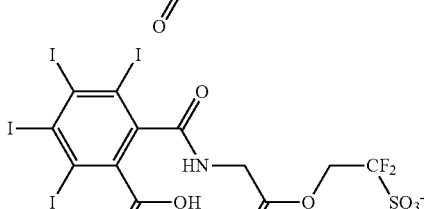
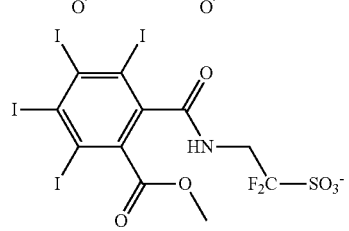
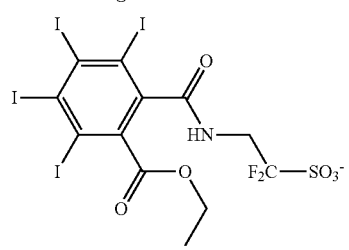
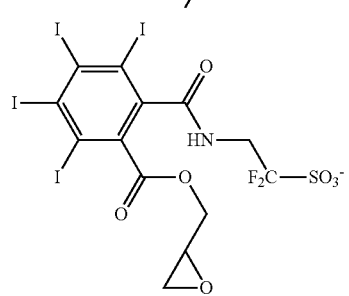
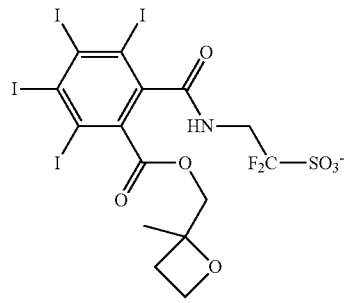

103
-continued
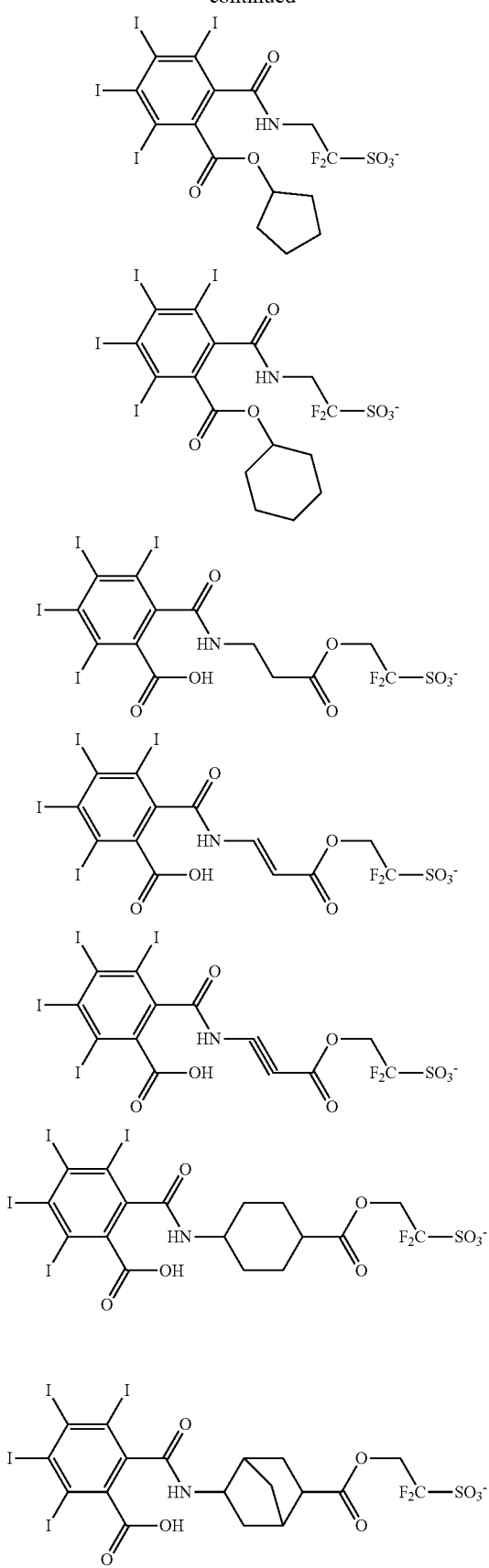
104
-continued
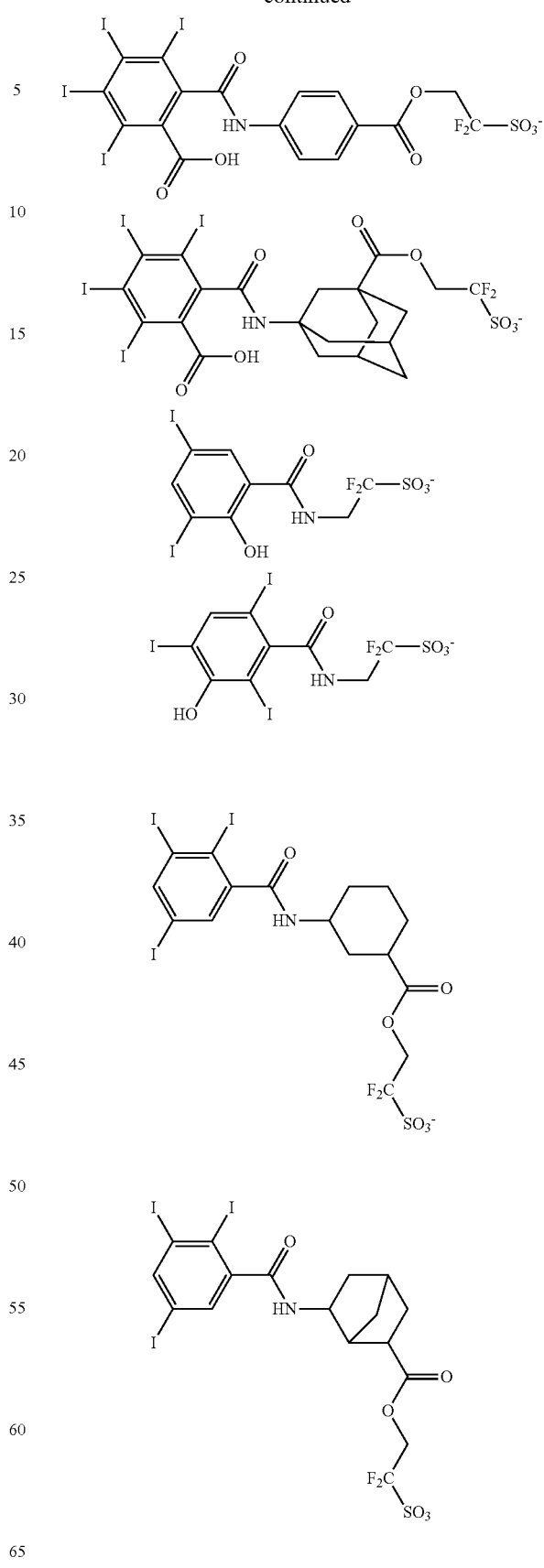

105
-continued
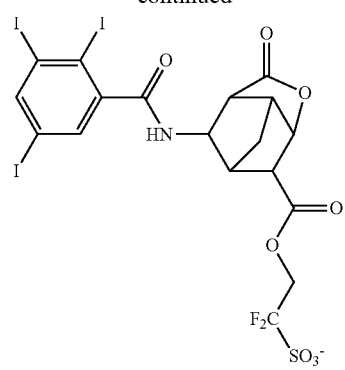
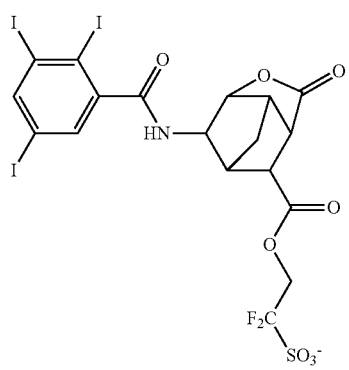
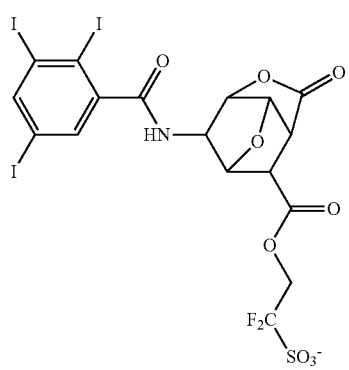
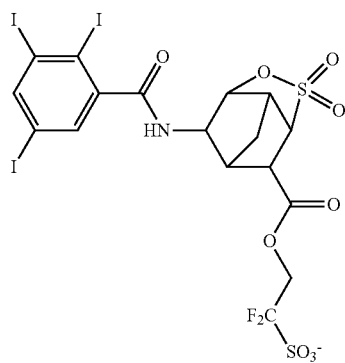
106
-continued
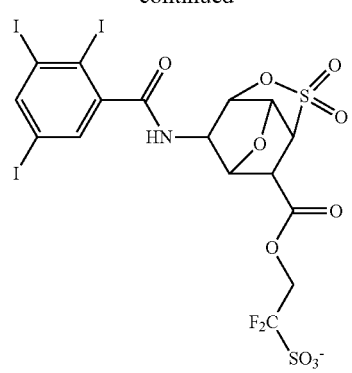
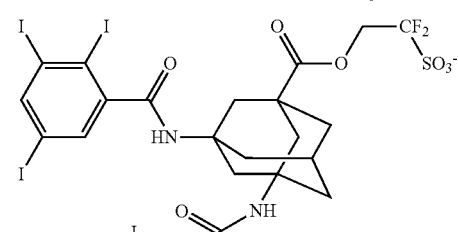
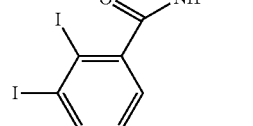
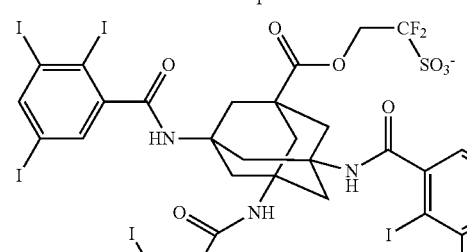
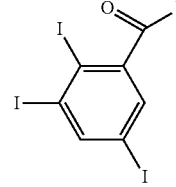
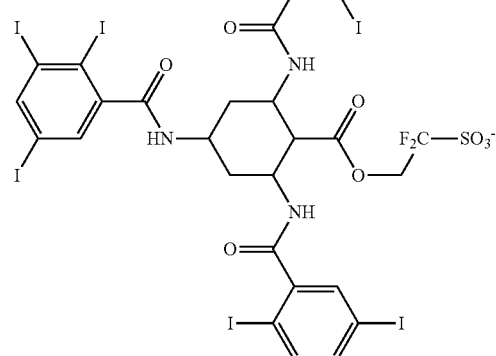

107
-continued
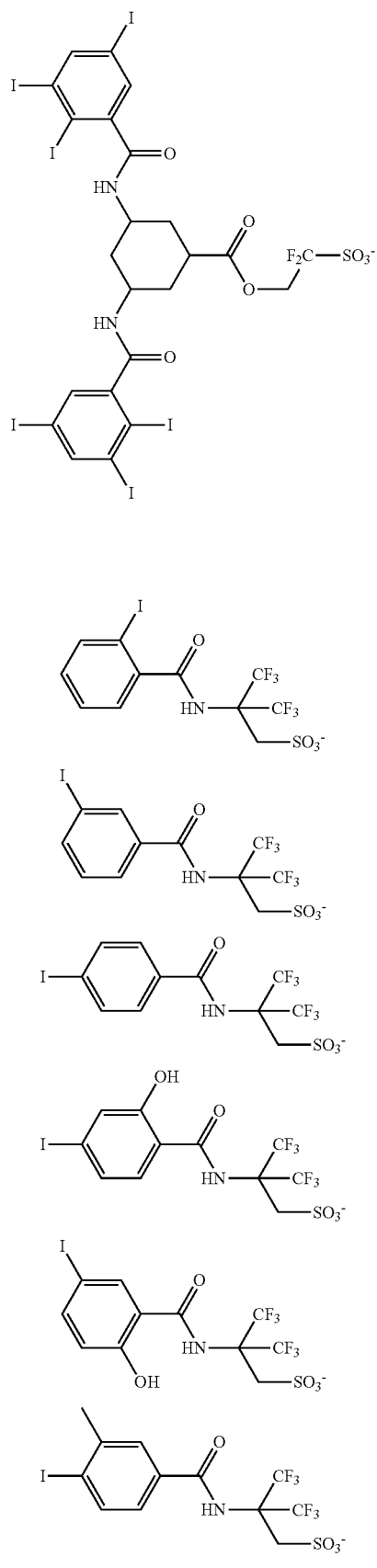
108
-continued
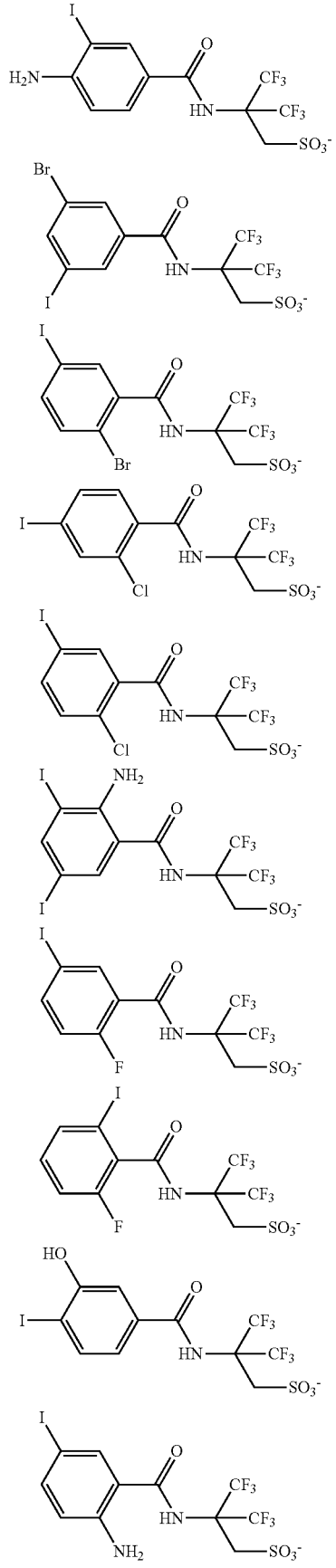

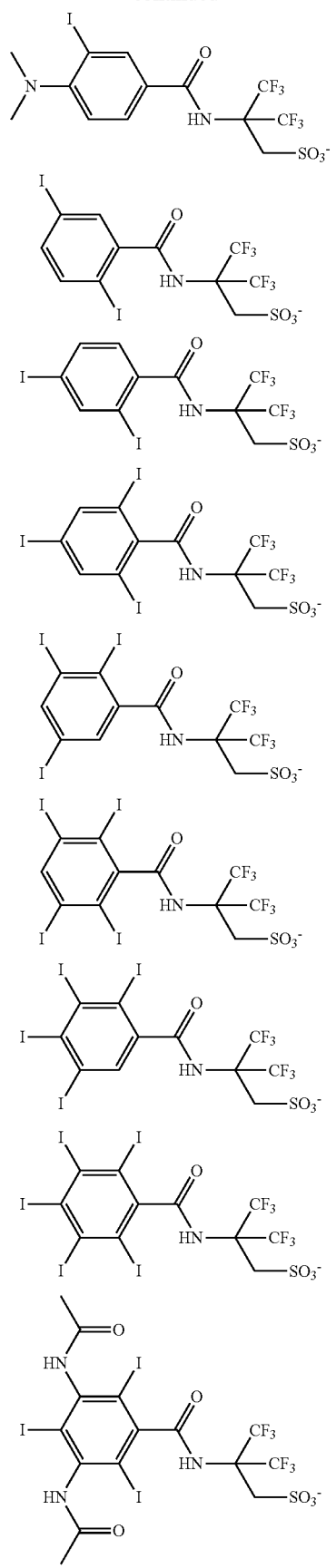
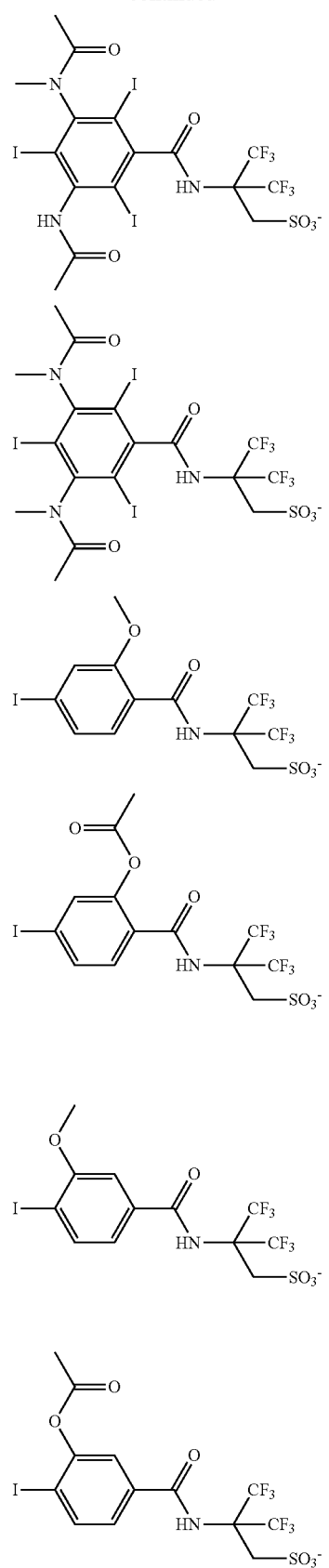

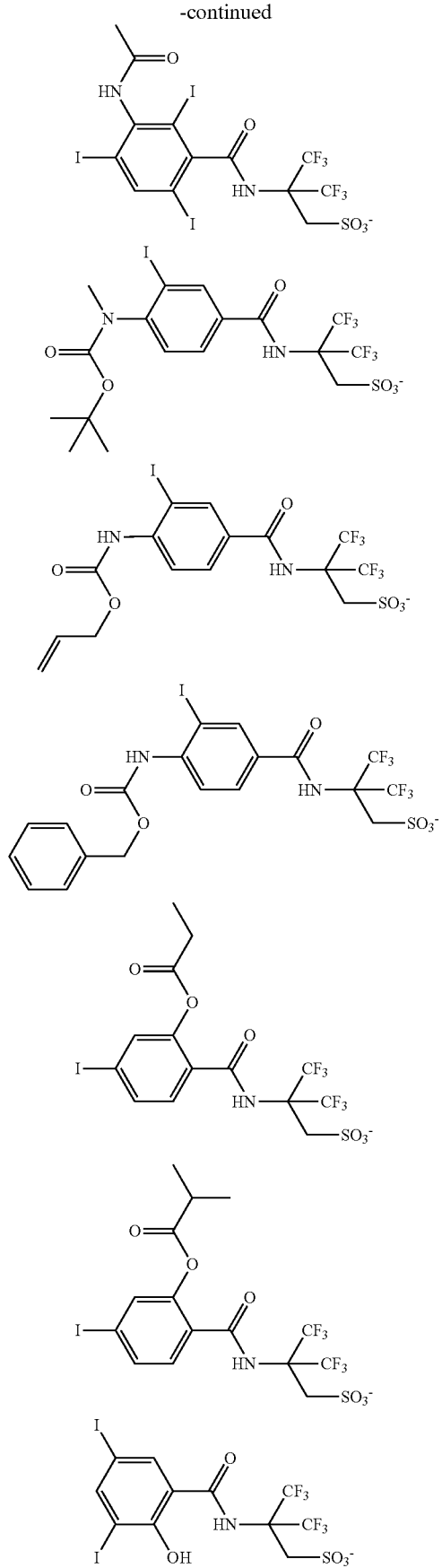
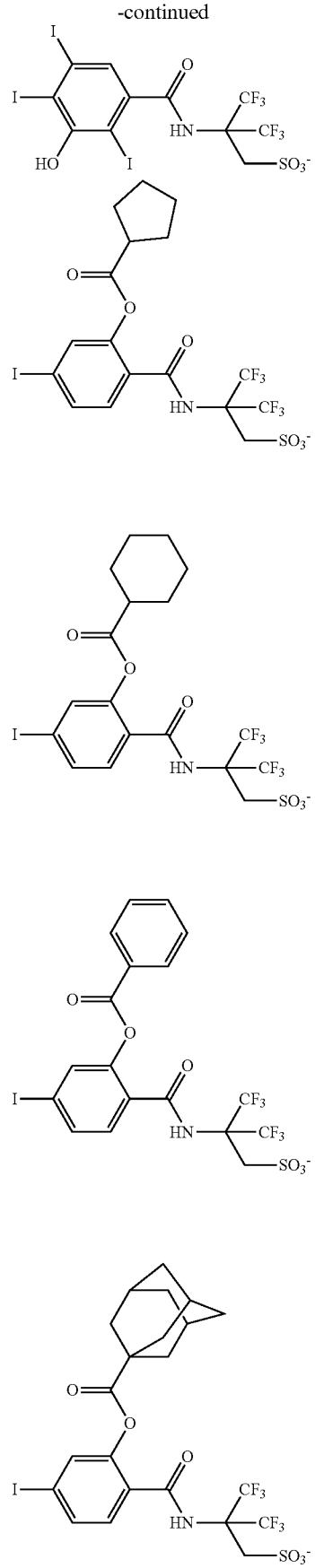

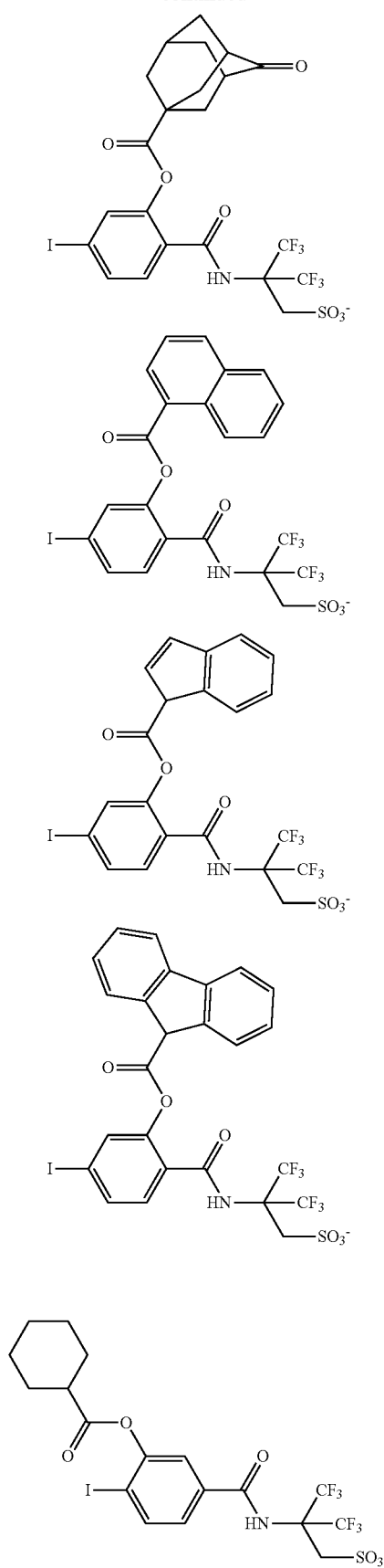
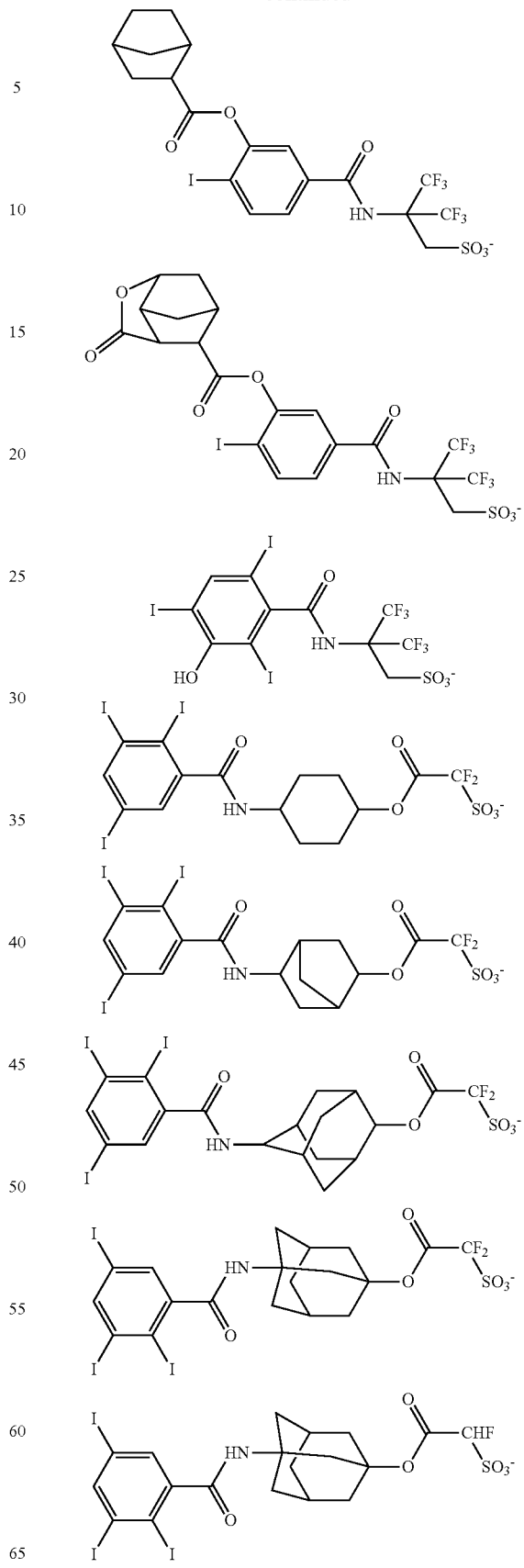

-continued
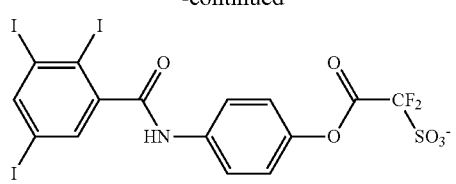
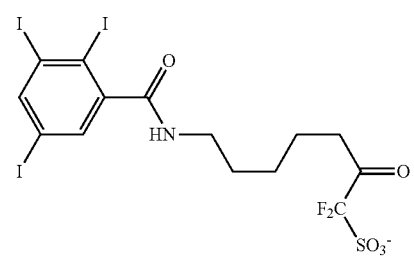
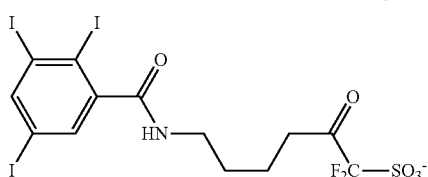
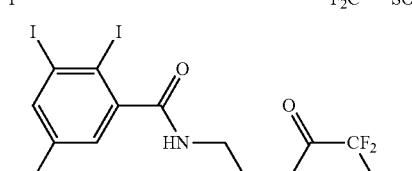
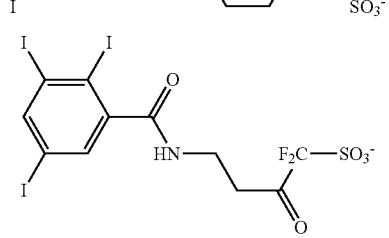
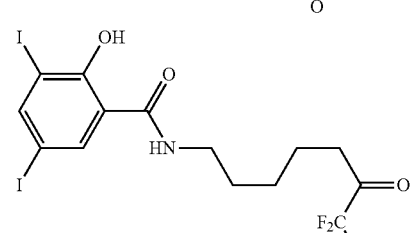
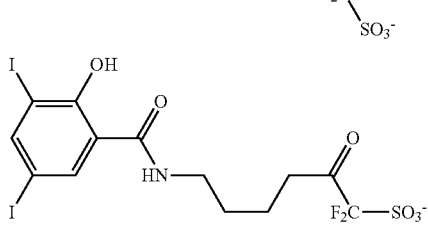
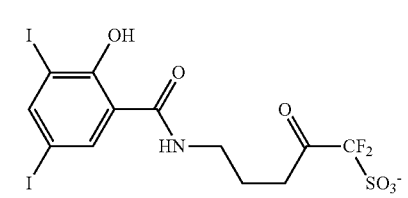
-continued
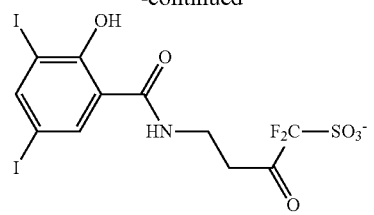
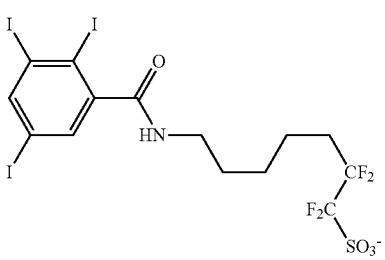
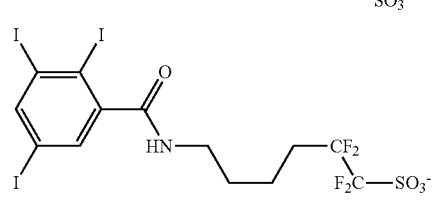
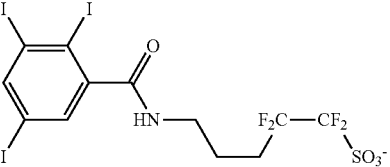
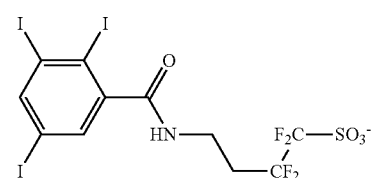
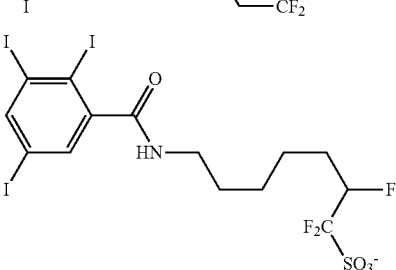
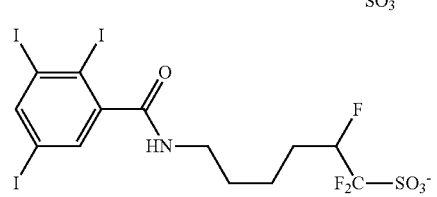
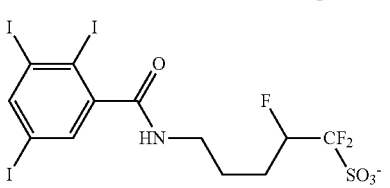

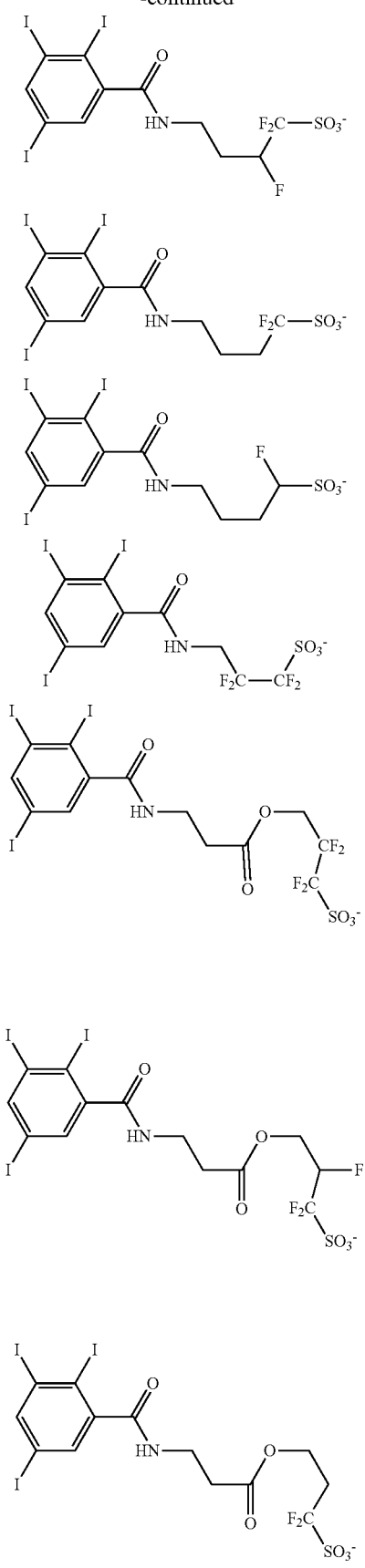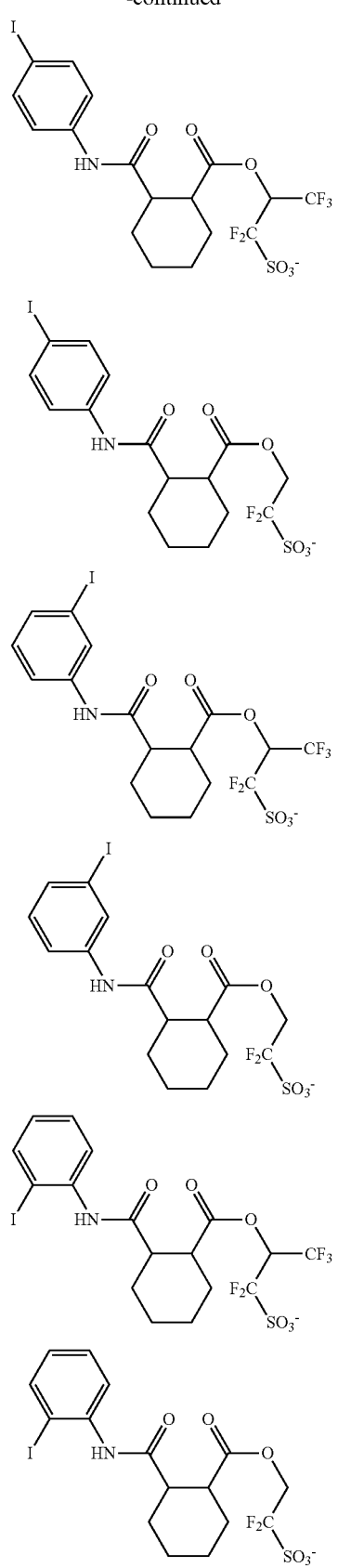

-continued

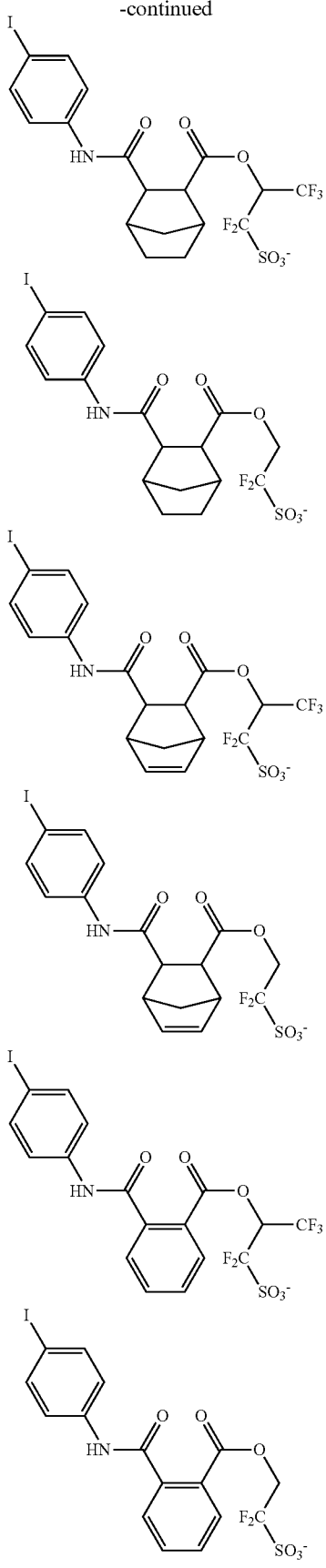

The fluorinated sulfonium cation preferably has the formula (3).

In formula (3), $R^{a1}$ is a $C_1$-$C_{20}$ hydrocarbyl group substituted with at least one fluorine, which may contain at least one element selected from oxygen, sulfur, nitrogen, and halogen exclusive of fluorine. $R^{a2}$ and $R^{a3}$ are each independently a $C_1$-$C_{20}$ hydrocarbyl group or $C_1$-$C_{20}$ hydrocarbyl group substituted with at least one fluorine, which may contain at least one element selected from oxygen, sulfur, nitrogen, and halogen exclusive of fluorine.

The total number of fluorine atoms in $R^{a1}$, $R^{a2}$ and $R^{a3}$ is preferably at least 2, more preferably at least 3.

The $C_1$-$C_{20}$ hydrocarbyl group may be saturated or unsaturated and straight, branched or cyclic. Examples thereof include $C_1$-$C_{20}$ alkyl groups such as methyl, ethyl, n-propyl, isopropyl, n-butyl, isobutyl, sec-butyl, tert-butyl, n-pentyl, n-hexyl, n-octyl, n-nonyl, n-decyl, undecyl, dodecyl, tridecyl, tetradecyl, pentadecyl, heptadecyl, octadecyl, nonadecyl and icosyl; $C_3$-$C_{20}$ cyclic saturated hydrocarbyl groups such as cyclopropyl, cyclopentyl, cyclohexyl, cyclopropylmethyl, 4-methylcyclohexyl, cyclohexylmethyl, norbornyl, adamantyl; $C_2$-$C_{20}$ alkenyl groups such as vinyl, propenyl, butenyl and hexenyl; $C_2$-$C_{20}$ alkynyl groups such as ethynyl, propynyl and butynyl; $C_3$-$C_{20}$ cyclic unsaturated aliphatic hydrocarbyl groups such as cyclohexenyl and norbornenyl; $C_6$-$C_{20}$ aryl groups such as phenyl, methylphenyl, ethylphenyl, n-propylphenyl, isopropylphenyl, n-butylphenyl, isobutylphenyl, sec-butylphenyl, tert-butylphenyl, naphthyl, methylnaphthyl, ethylnaphthyl, n-propylnaphthyl, isopropylnaphthyl, n-butylnaphthyl, isobutylnaphthyl, sec-butylnaphthyl, tert-butylnaphthyl; $C_7$-$C_{20}$ aralkyl groups such as benzyl and phenethyl; and combinations thereof.

In the $C_1$-$C_{20}$ hydrocarbyl group substituted with at least one fluorine, some or all of the hydrogen atoms may be substituted by a moiety containing a heteroatom such as oxygen, sulfur, nitrogen, or halogen exclusive of fluorine, and some carbon may be replaced by a moiety containing a heteroatom such as oxygen, sulfur, or nitrogen, so that the group may contain a hydroxy moiety, chlorine, bromine, iodine, cyano moiety, nitro moiety, carbonyl moiety, ether bond, ester bond, sulfonic ester bond, carbonate bond, lactone ring, sultone ring, carboxylic anhydride or haloalkyl moiety.

A pair of $R^{a1}$ and $R^{a2}$, or $R^{a2}$ and $R^{a3}$ may bond together to form a ring with the sulfur atom to which they are attached. In this case, rings of the following structure are preferred.

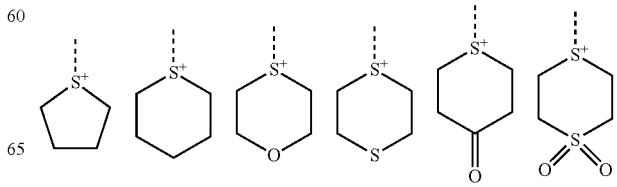

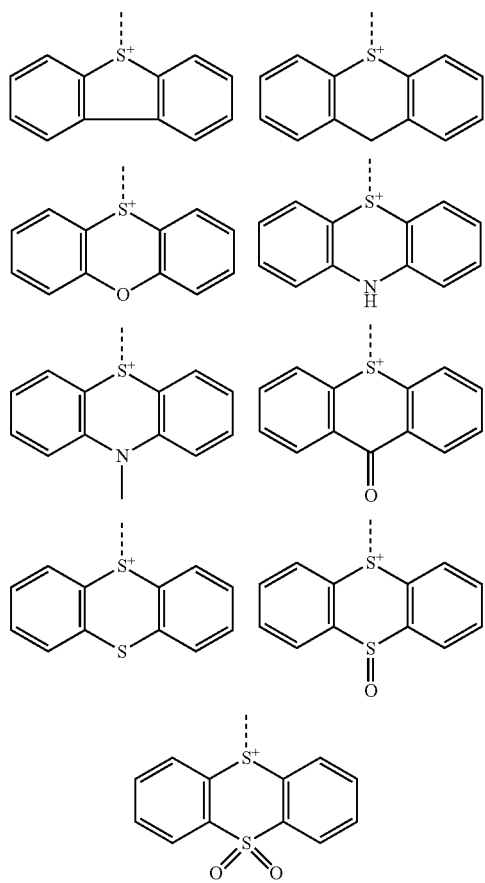
Examples of the sulfonium cation having formula (3) are shown below, but not limited thereto.
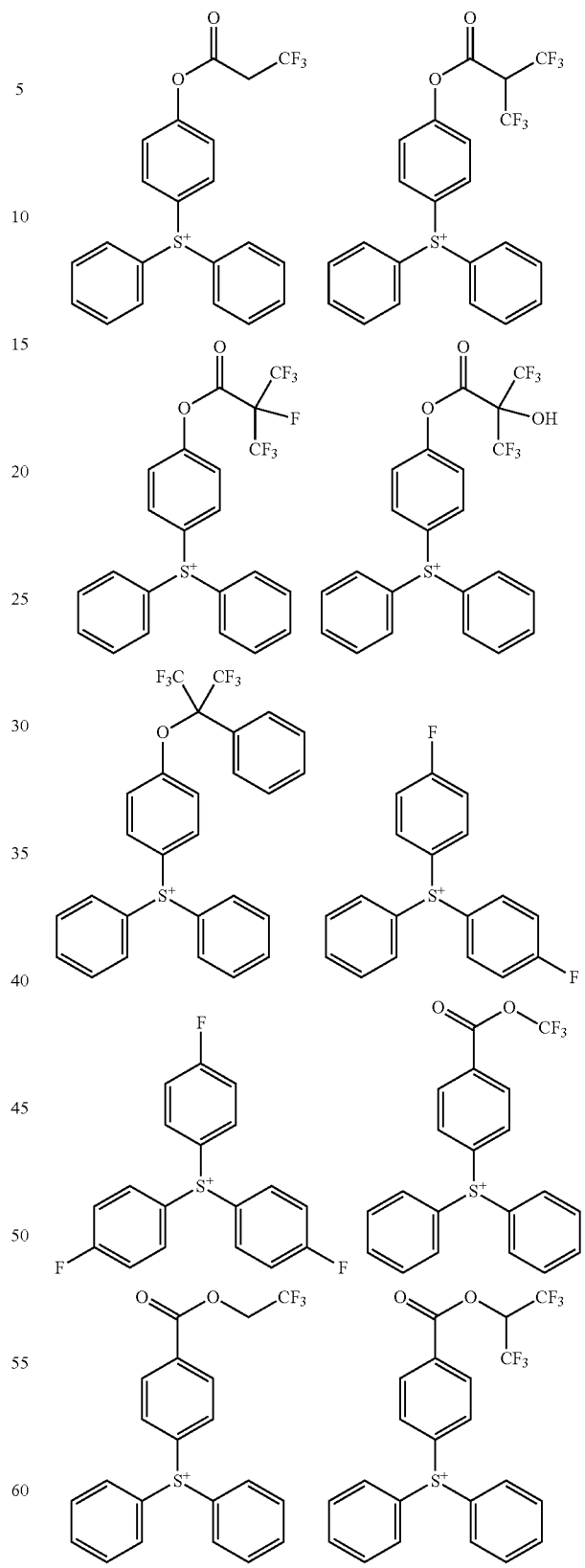

123
-continued
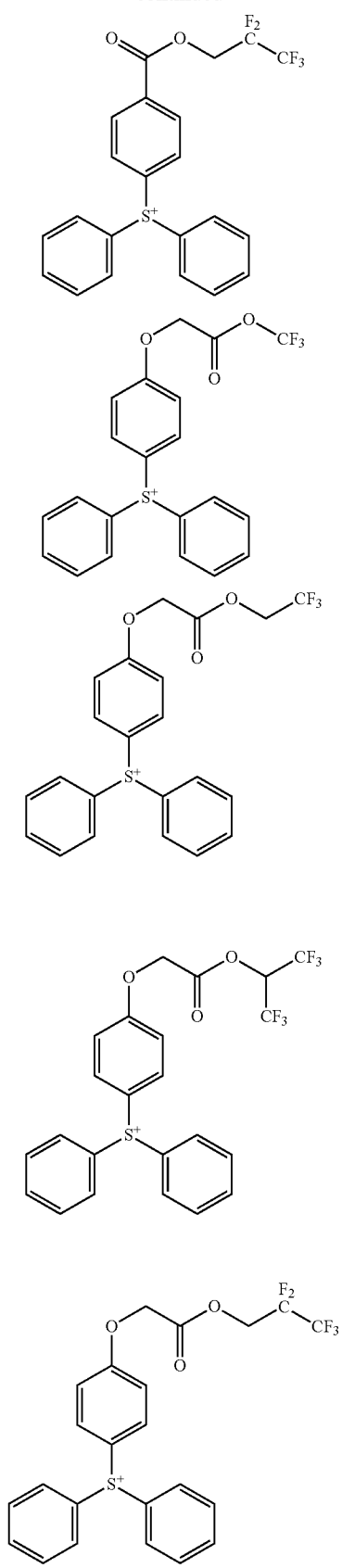
124
-continued
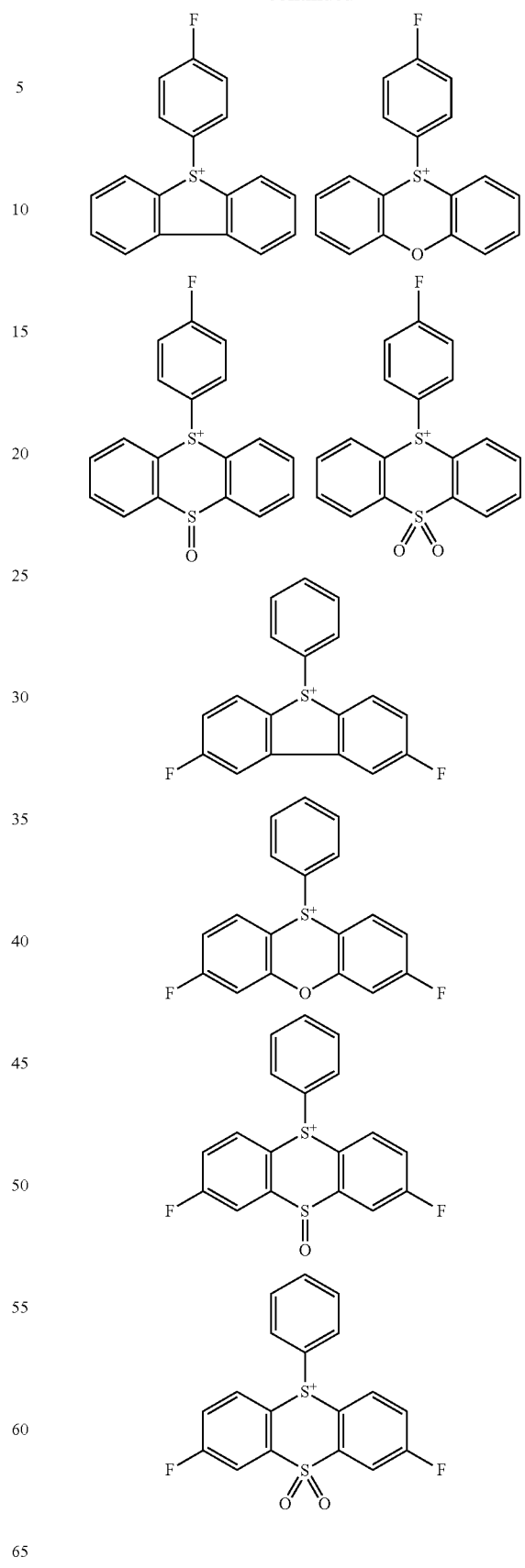

-continued
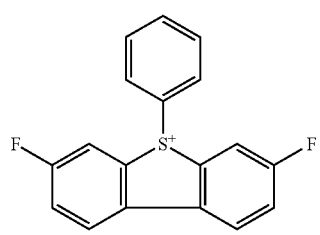
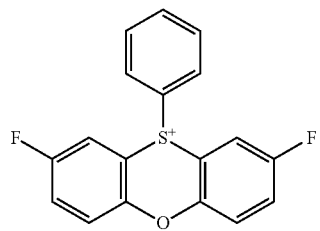
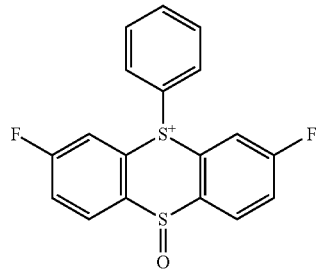
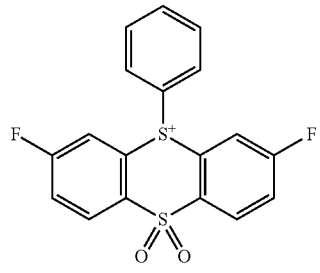
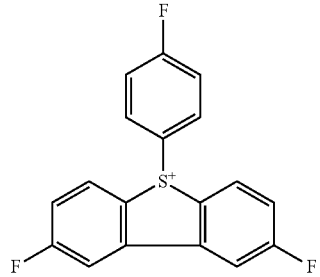
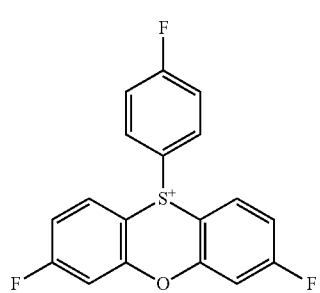
-continued
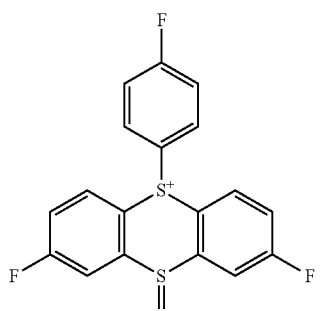
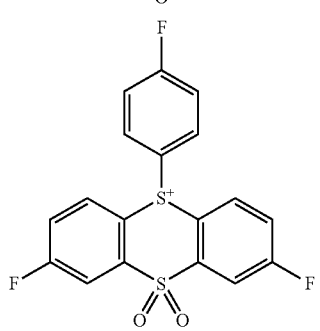
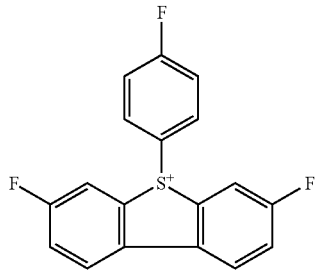
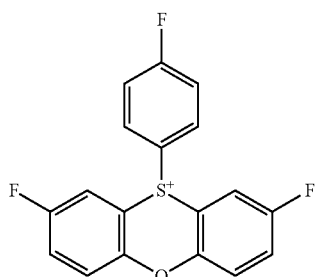
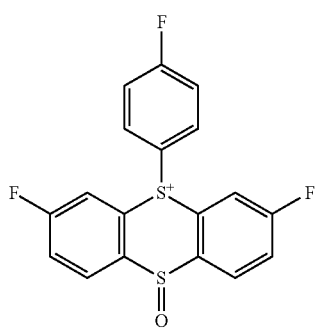

127
-continued
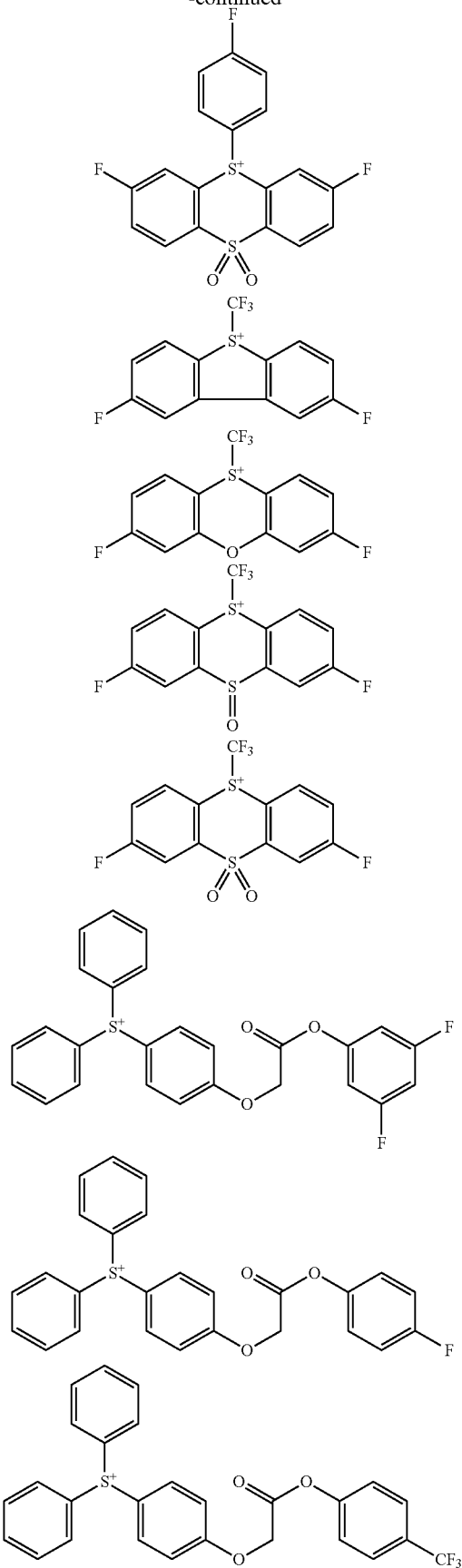
128
-continued
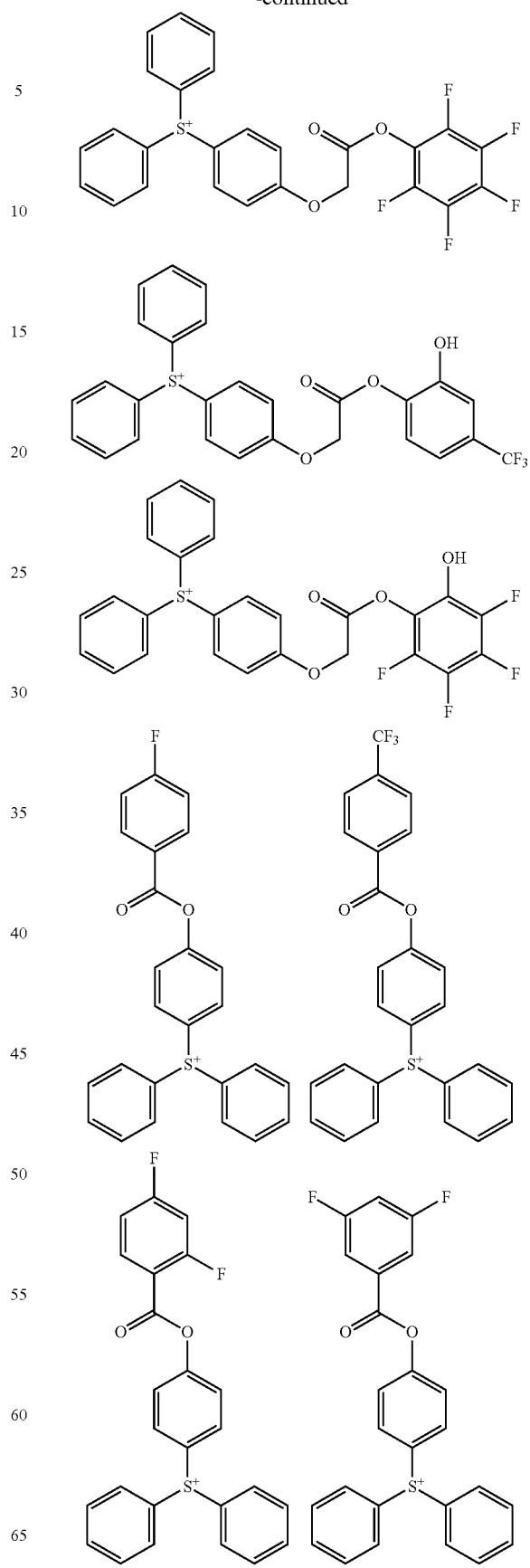

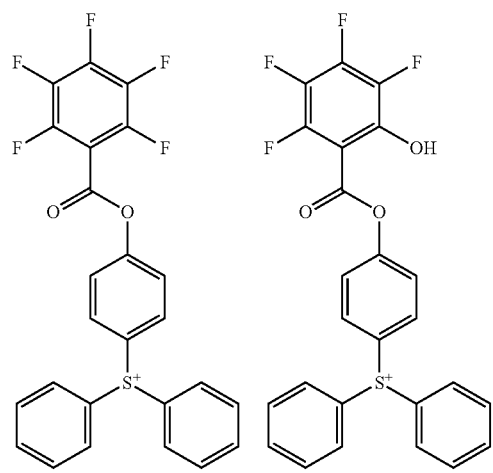
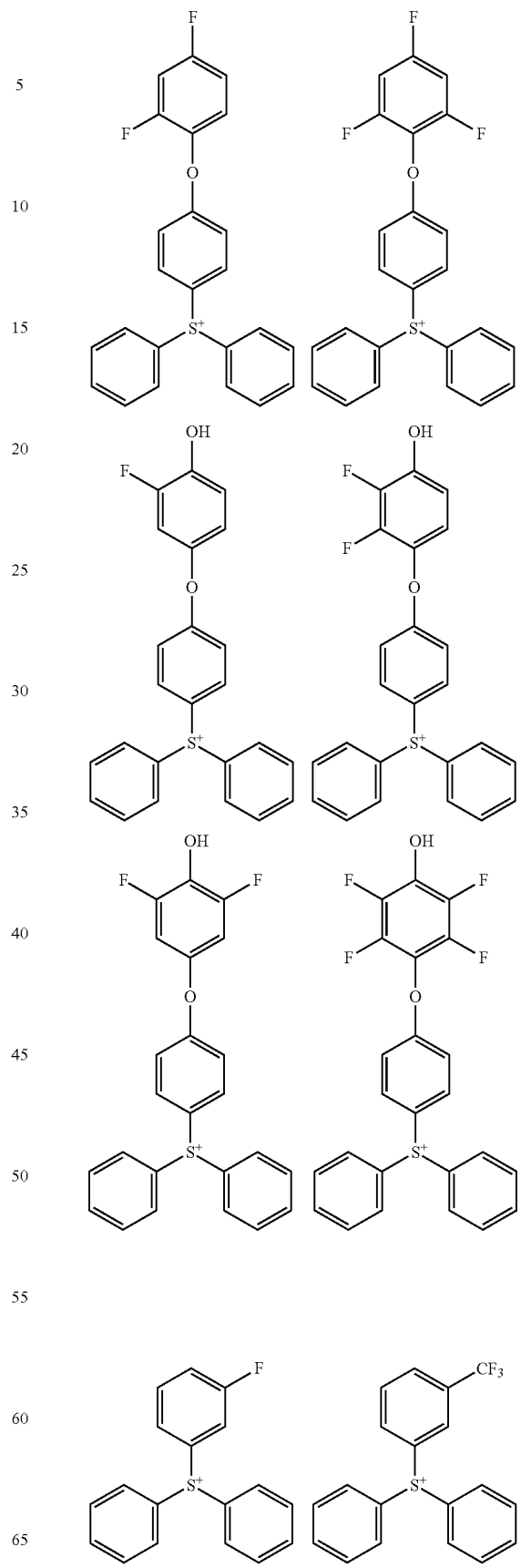

-continued
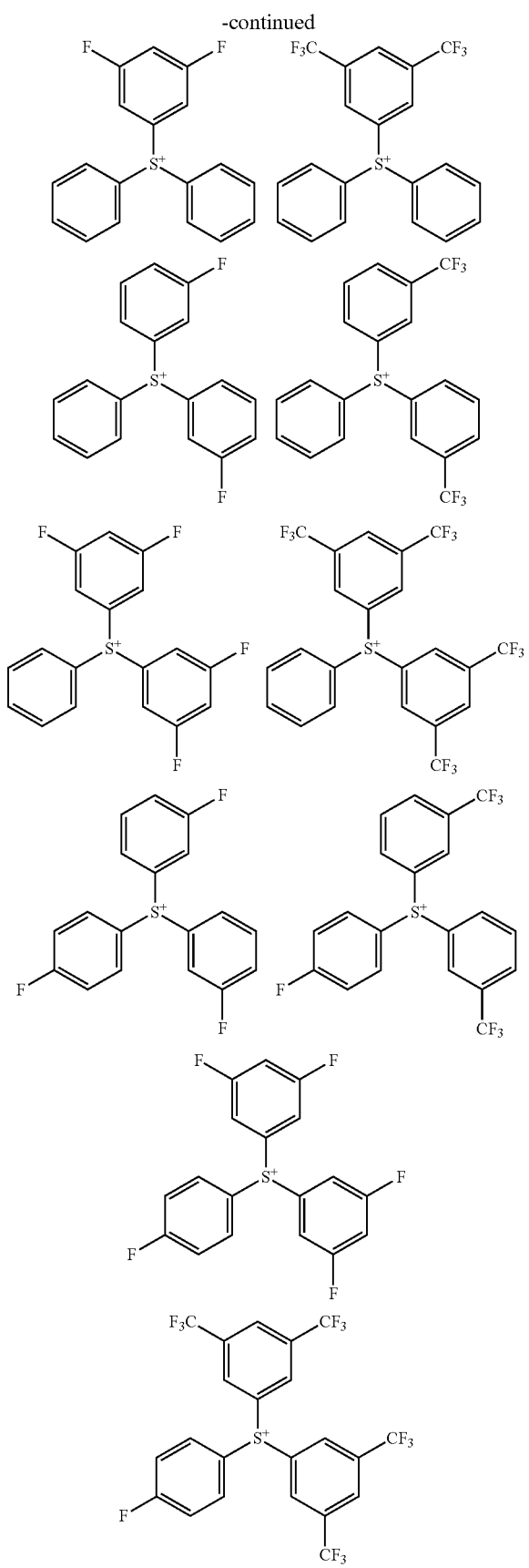
-continued
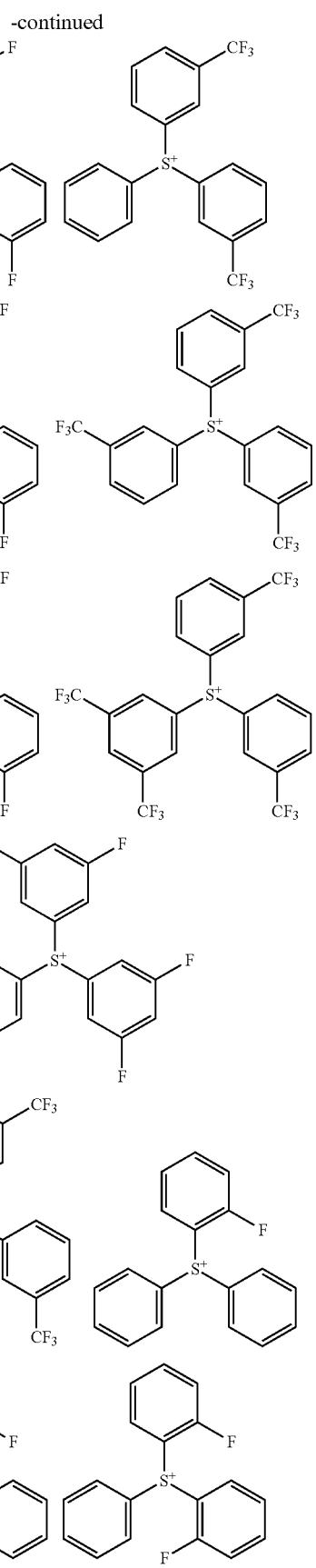

-continued
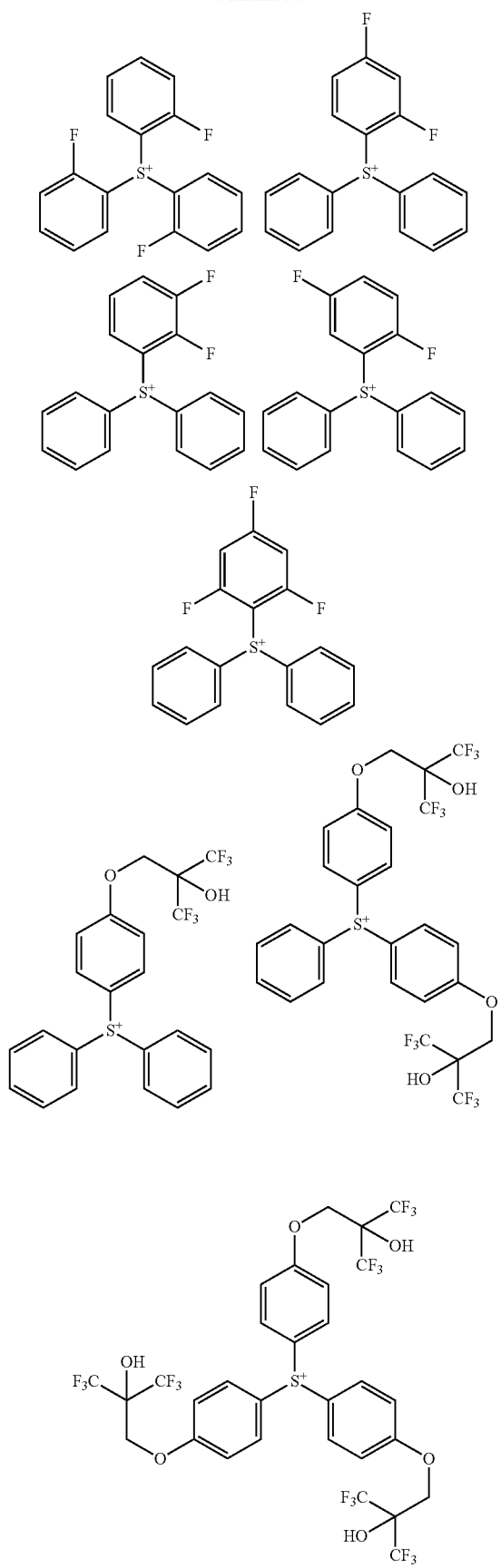
-continued
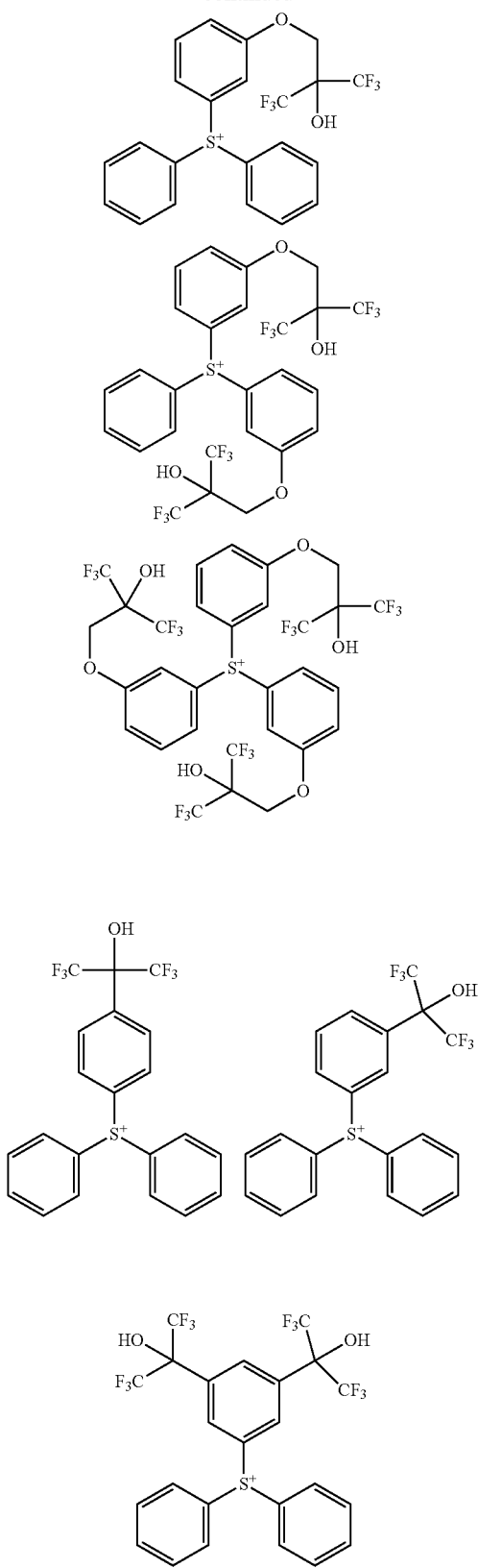

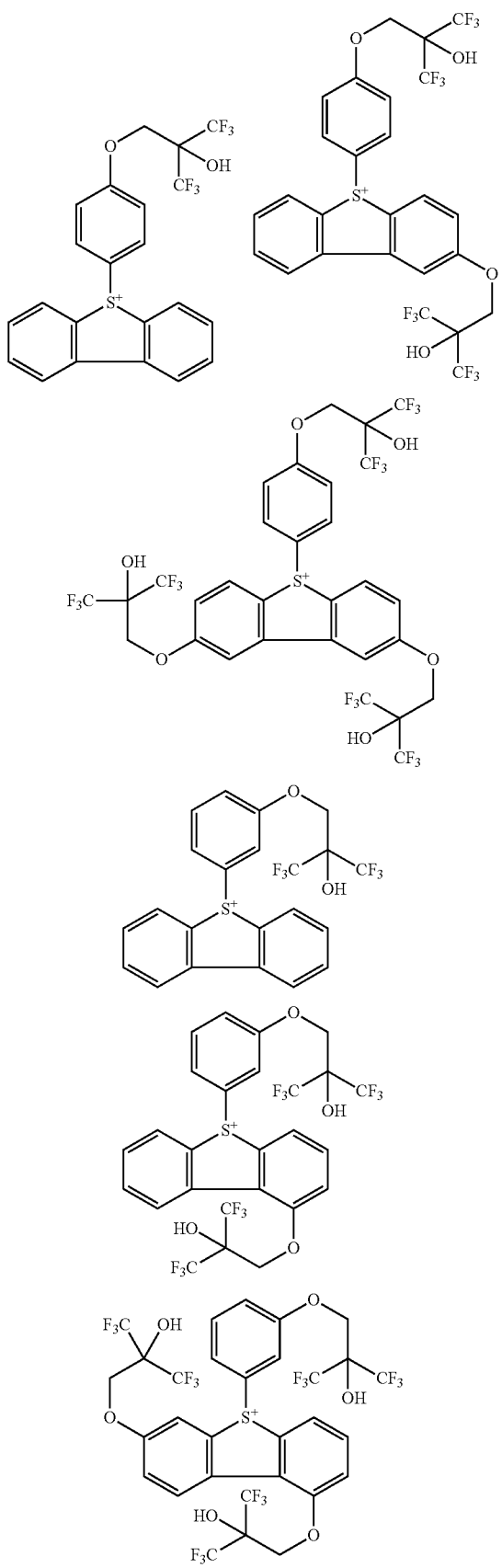
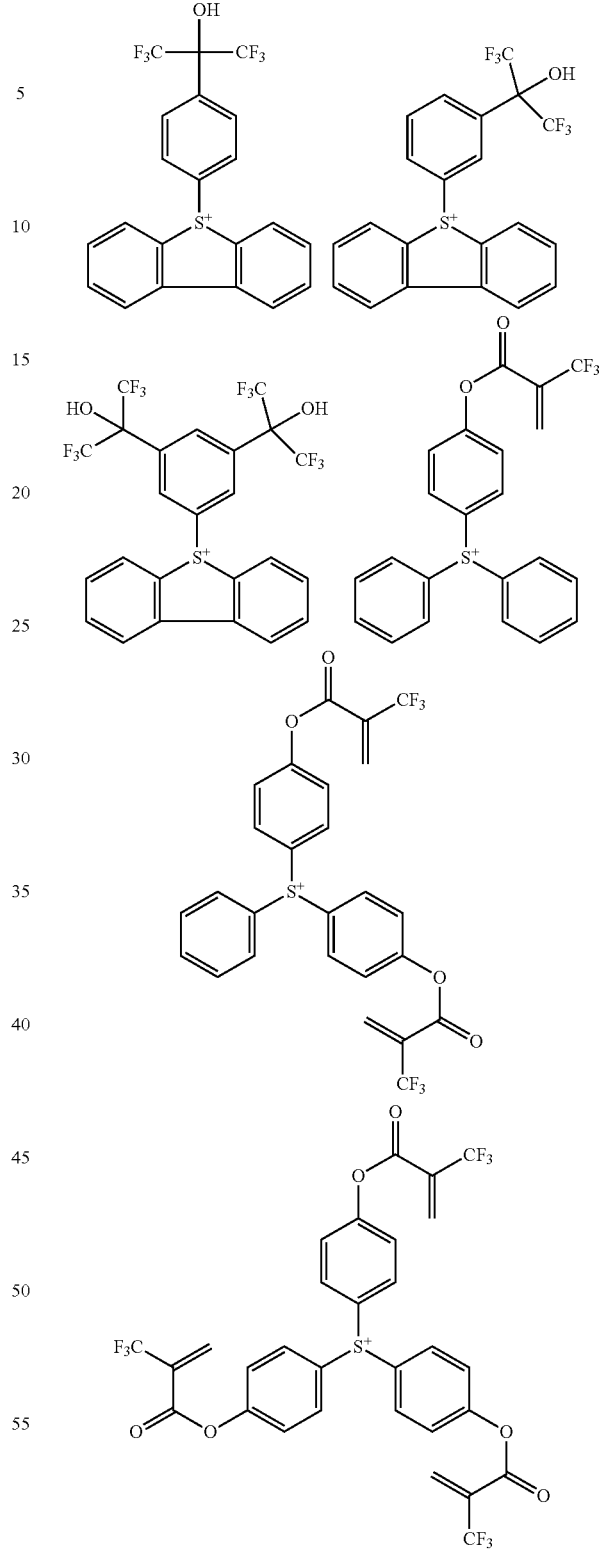
Of the sulfonium salts containing an anion of formula (1-3), preferred are those sulfonium salts having the formula (1-3-1):

(1-3-1)

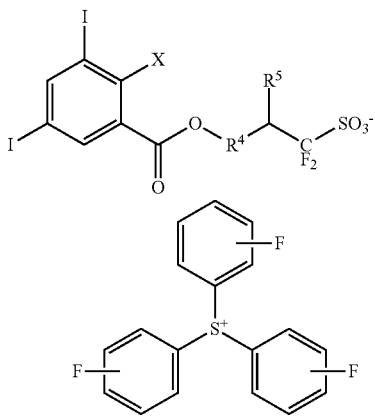

wherein $R^4$ is a single bond or a $C_1$-$C_6$ alkanediyl group, $R^5$ is hydrogen or trifluoromethyl, and X is a hydroxy group or iodine.

In the positive resist composition, the acid generator (A) is preferably present in an amount of 0.1 to 100 parts by weight, more preferably 1 to 50 parts by weight per 100 parts by weight of the base polymer (C) to be described later.

(B) Quencher

Component (B) is a quencher which is a sulfonium salt consisting of a cation and an anion, the cation containing at least two fluorine atoms or the anion and cation containing at least 5 fluorine atoms in total. The preferred anion is a carboxylate, sulfonamide, alkoxide or non-α-fluorinated sulfonate anion.

Preferably, the carboxylate anion has the formula (2-1), the sulfonamide anion has the formula (2-2), the alkoxide anion has the formula (2-3), and the non-α-fluorinated sulfonate anion has the formula (2-4).

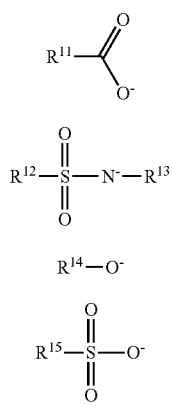

(2-1)
(2-2)
(2-3)
(2-4)

In formula (2-1), $R^{11}$ is fluorine or a $C_1$-$C_{40}$ hydrocarbyl group which may contain fluorine and/or a heteroatom exclusive of fluorine.

In formula (2-2), $R^{12}$ is fluorine or a $C_1$-$C_{40}$ hydrocarbyl group which may contain fluorine and/or a heteroatom exclusive of fluorine. $R^{13}$ is hydrogen or a $C_1$-$C_{20}$ hydrocarbyl group which may contain a heteroatom.

In formula (2-3), $R^{14}$ is a $C_1$-$C_8$ saturated hydrocarbyl group having at least two fluorine atoms or a $C_6$-$C_{10}$ aryl group having at least two fluorine atoms.

In formula (2-4), $R^5$ is a $C_1$-$C_{12}$ aliphatic hydrocarbyl group or $C_6$-$C_{10}$ aryl group. Any constituent —$CH_2$— in the aliphatic hydrocarbyl group may be replaced by —N(H)—, ether bond or ester bond, some or all of the hydrogen atoms in the aliphatic hydrocarbyl group may be substituted by a halogen atom, hydroxy moiety, carboxy moiety, $C_6$-$C_{10}$ aryl moiety, $C_1$-$C_{12}$ hydrocarbyloxy moiety, $C_2$-$C_{12}$ hydrocarbylcarbonyl moiety, or $C_1$-$C_{12}$ hydrocarbylcarbonyloxy moiety, some or all of the hydrogen atoms in the aryl group may be substituted by a halogen atom, hydroxy moiety, carboxy moiety, $C_1$-$C_{12}$ hydrocarbyloxy moiety, $C_2$-$C_{12}$ hydrocarbylcarbonyl moiety, or $C_1$-$C_{12}$ hydrocarbylcarbonyloxy moiety, with the proviso that $R^5$ has no fluorine at the α-position relative to the sulfo group.

The $C_1$-$C_{40}$ hydrocarbyl group represented by $R^{11}$ and $R^{12}$ may be saturated or unsaturated and straight, branched or cyclic. Examples thereof include $C_1$-$C_{40}$ alkyl groups, $C_3$-$C_{40}$ cyclic saturated hydrocarbyl groups, $C_2$-$C_{40}$ alkenyl groups, $C_2$-$C_{40}$ alkynyl groups, $C_3$-$C_{30}$ cyclic unsaturated aliphatic hydrocarbyl groups, $C_6$-$C_{40}$ aryl groups, $C_7$-$C_{40}$ aralkyl groups, and combinations thereof. In these groups, some hydrogen may be substituted by a moiety containing a heteroatom such as oxygen, sulfur, nitrogen, fluorine or halogen exclusive of fluorine, and some carbon may be replaced by a moiety containing a heteroatom such as oxygen, sulfur or nitrogen, so that the group may contain an ester bond, ether bond, thioether bond, carbonyl moiety, sulfonyl moiety, carbonate moiety, carbamate moiety, sulfone moiety, amino moiety, amide bond, hydroxy moiety, thiol moiety, nitro moiety, fluorine, chlorine, bromine, iodine or the like.

The $C_1$-$C_{20}$ hydrocarbyl group represented by $R^{13}$ may be saturated or unsaturated and straight, branched or cyclic. Examples thereof include $C_1$-$C_{20}$ alkyl groups, $C_3$-$C_{20}$ cyclic saturated hydrocarbyl groups, $C_2$-$C_{20}$ alkenyl groups, $C_2$-$C_{20}$ alkynyl groups, $C_3$-$C_{20}$ cyclic unsaturated aliphatic hydrocarbyl groups, $C_6$-$C_{20}$ aryl groups, $C_7$-$C_{20}$ aralkyl groups, and combinations thereof. In these groups, some hydrogen may be substituted by a moiety containing a heteroatom such as oxygen, sulfur, nitrogen or halogen, and some carbon may be replaced by a moiety containing a heteroatom such as oxygen, sulfur or nitrogen, so that the group may contain an ester bond, ether bond, thioether bond, carbonyl moiety, sulfonyl moiety, carbonate moiety, carbamate moiety, sulfone moiety, amino moiety, amide bond, hydroxy moiety, thiol moiety, nitro moiety, fluorine, chlorine, bromine, iodine or the like.

The $C_1$-$C_8$ saturated hydrocarbyl group having at least two fluorine atoms, represented by $R^{14}$, may be straight, branched or cyclic. Examples thereof include $C_1$-$C_8$ alkyl groups, $C_3$-$C_8$ cyclic saturated hydrocarbyl groups, and combinations thereof, in which at least 2 hydrogen atoms are substituted by fluorine atoms.

The $C_1$-$C_{12}$ aliphatic hydrocarbyl group $R^{11}$ may be straight, branched or cyclic. Examples thereof include $C_1$-$C_{12}$ alkyl groups, $C_3$-$C_{12}$ cyclic saturated hydrocarbyl groups, $C_2$-$C_{12}$ alkenyl groups, $C_2$-$C_{12}$ alkynyl groups, $C_3$-$C_{12}$ cyclic unsaturated aliphatic hydrocarbyl groups, and combinations thereof.

Examples of the carboxylate anion are shown below, but not limited thereto.

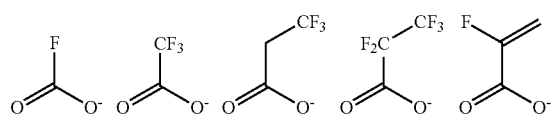

-continued
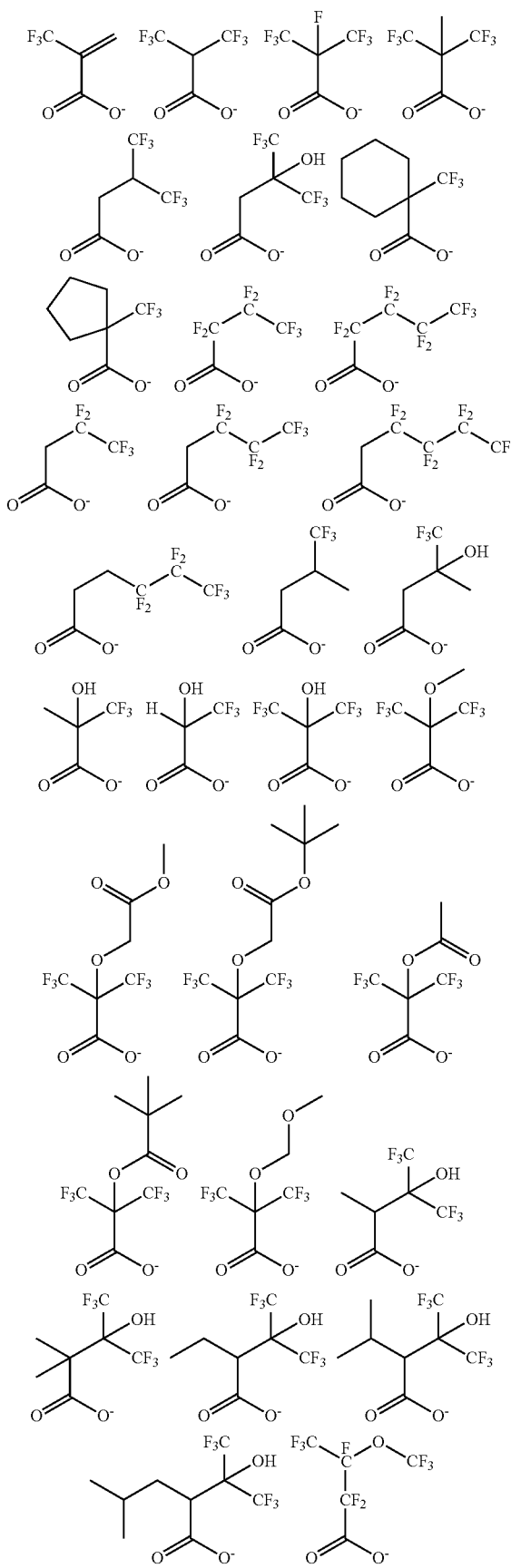
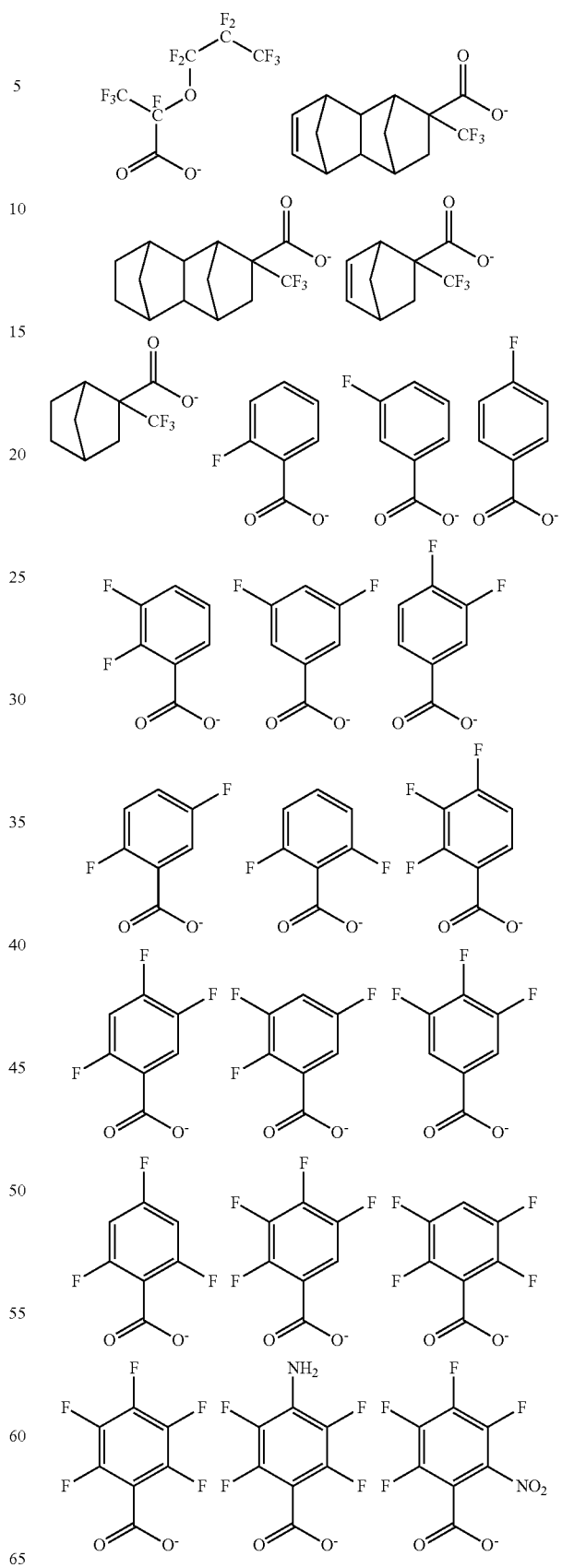

-continued
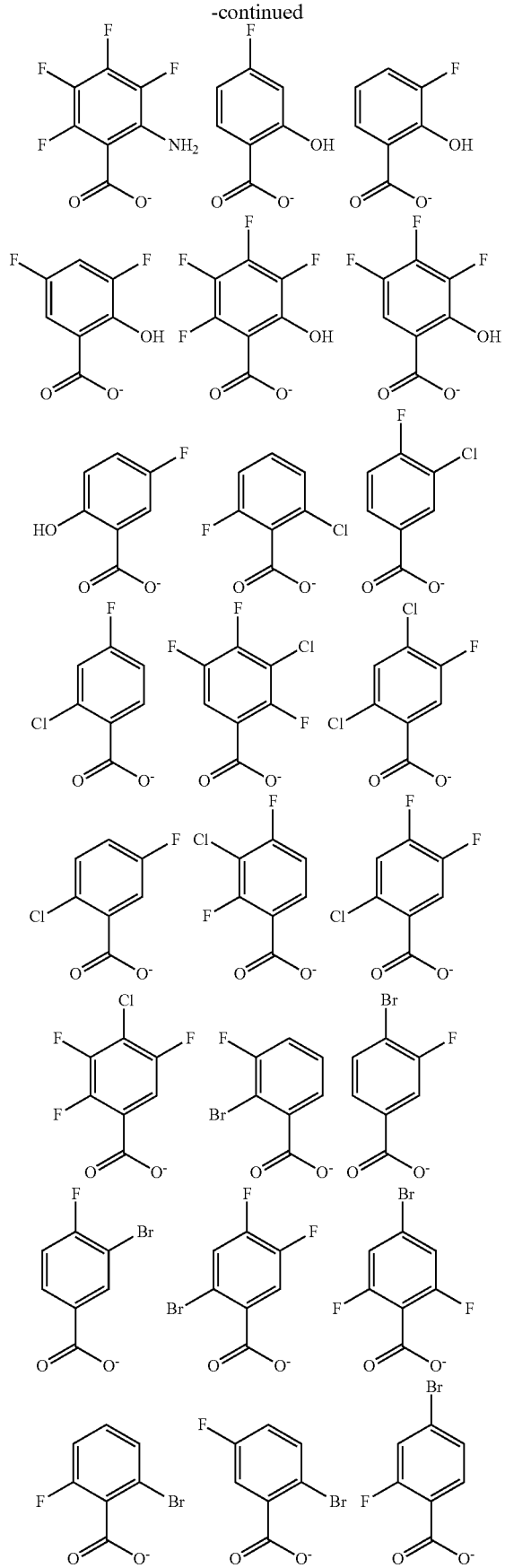
-continued
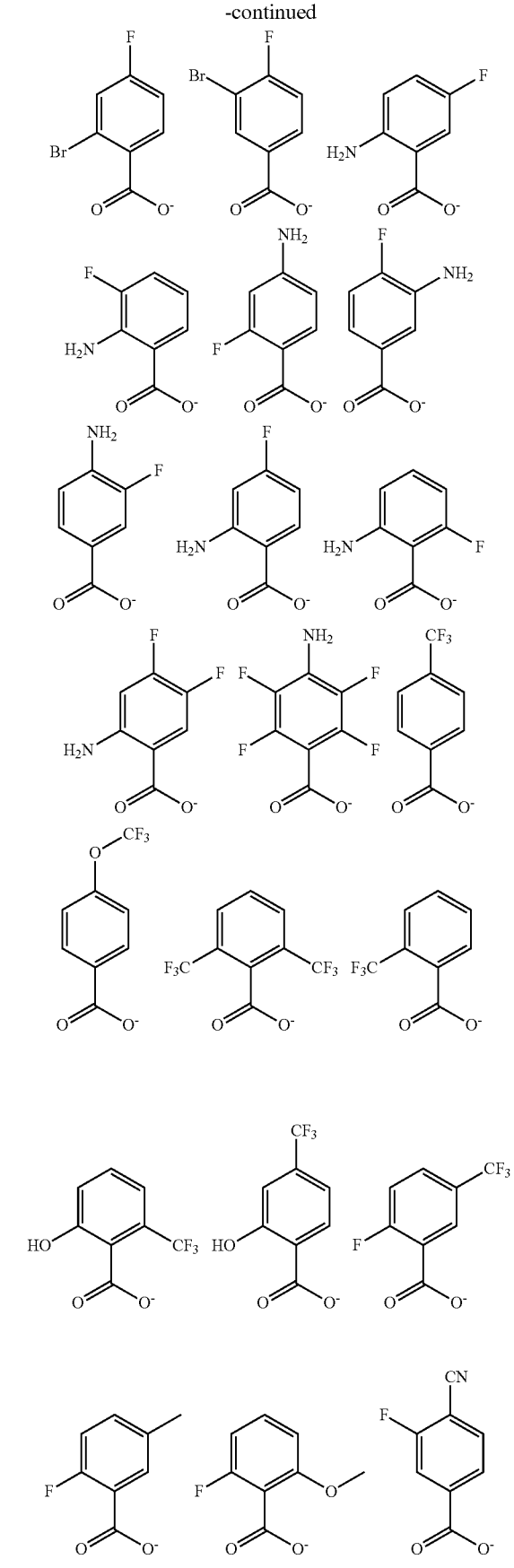

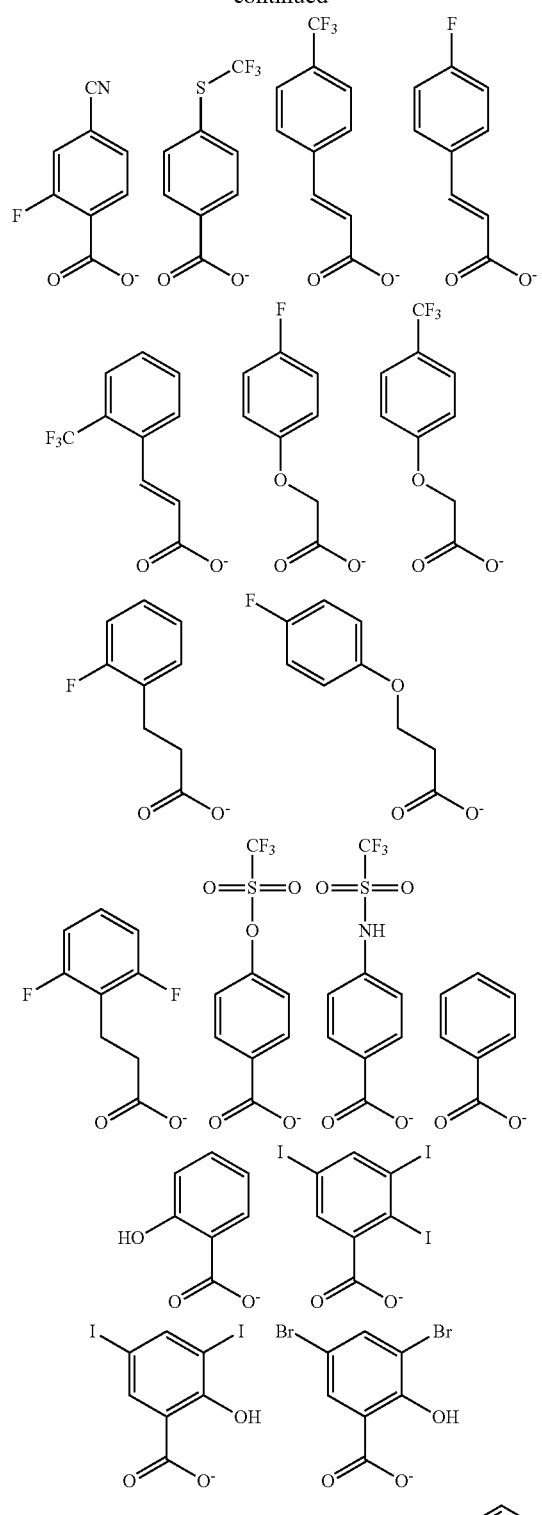
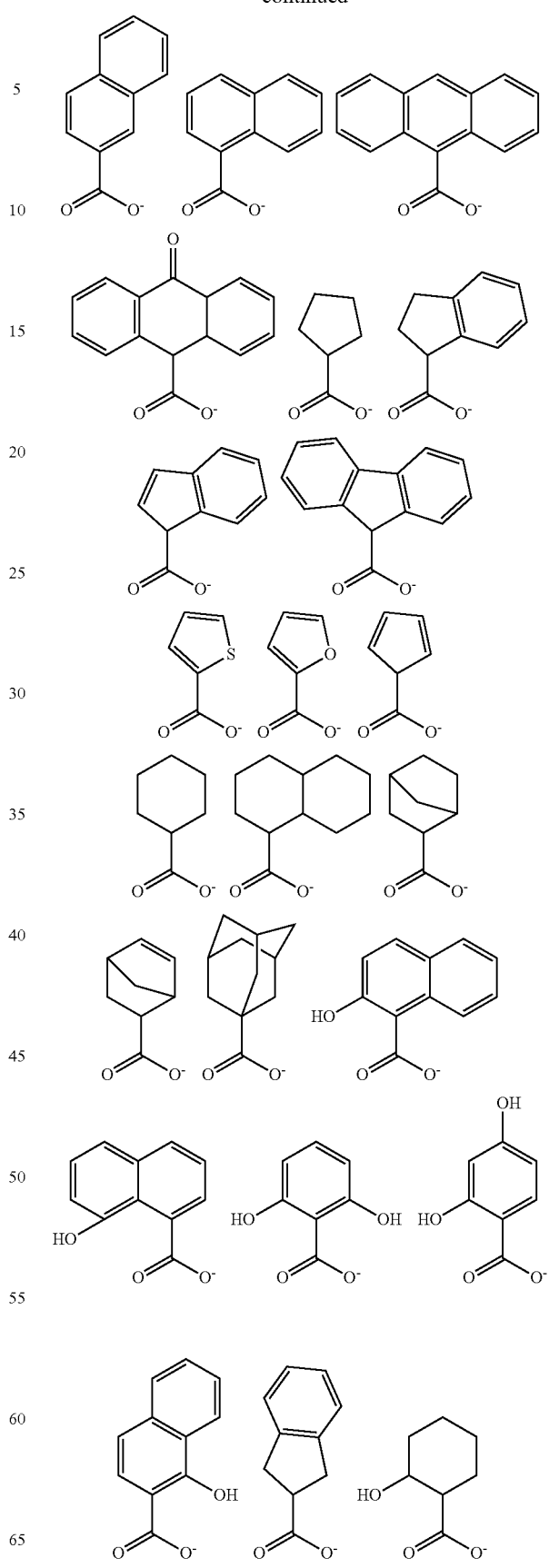

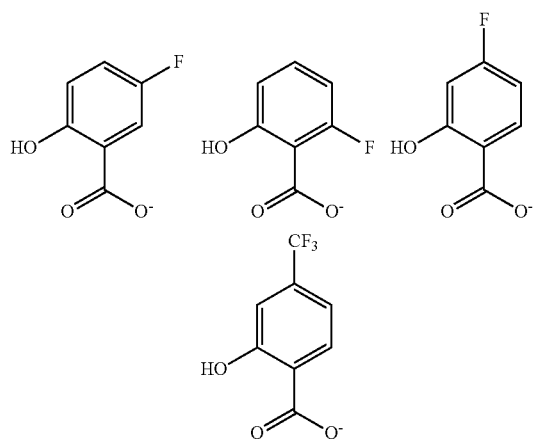
Examples of the sulfonamide anion are shown below, but not limited thereto.
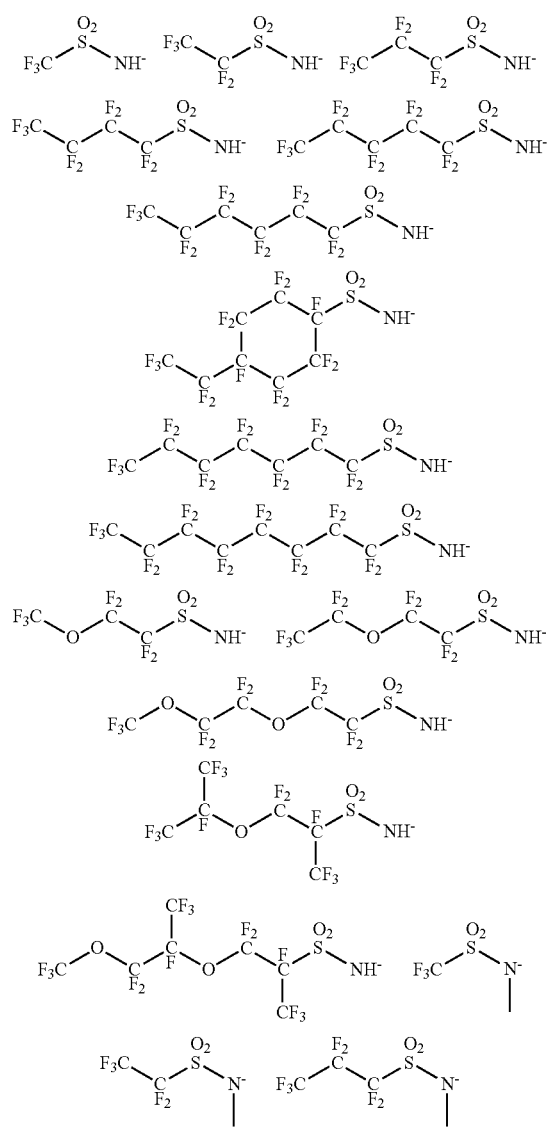
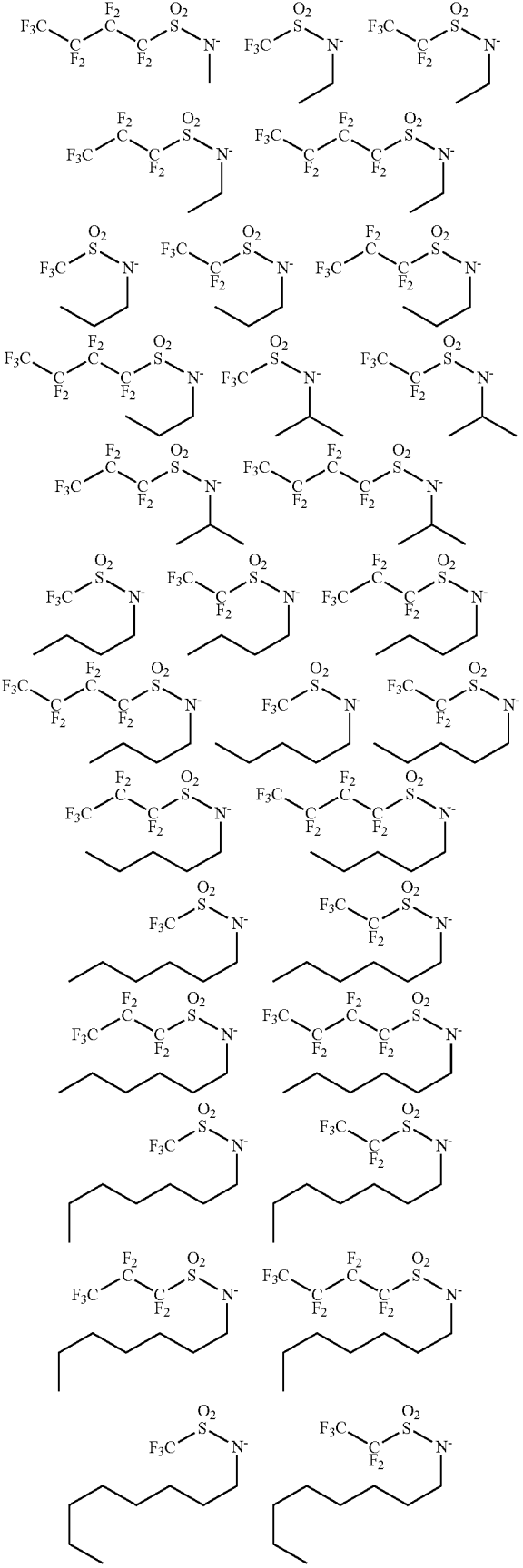

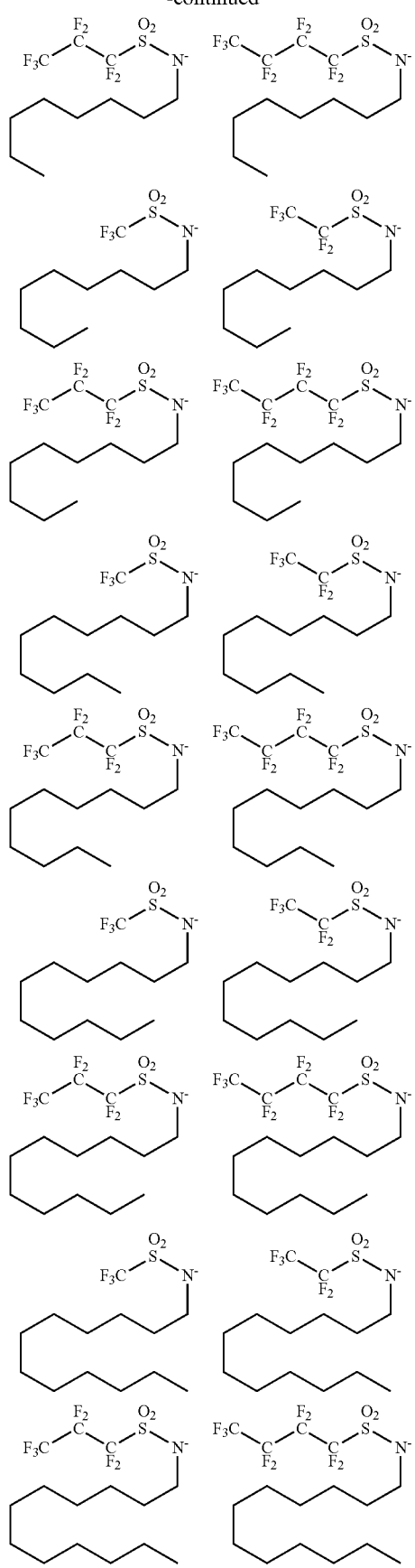
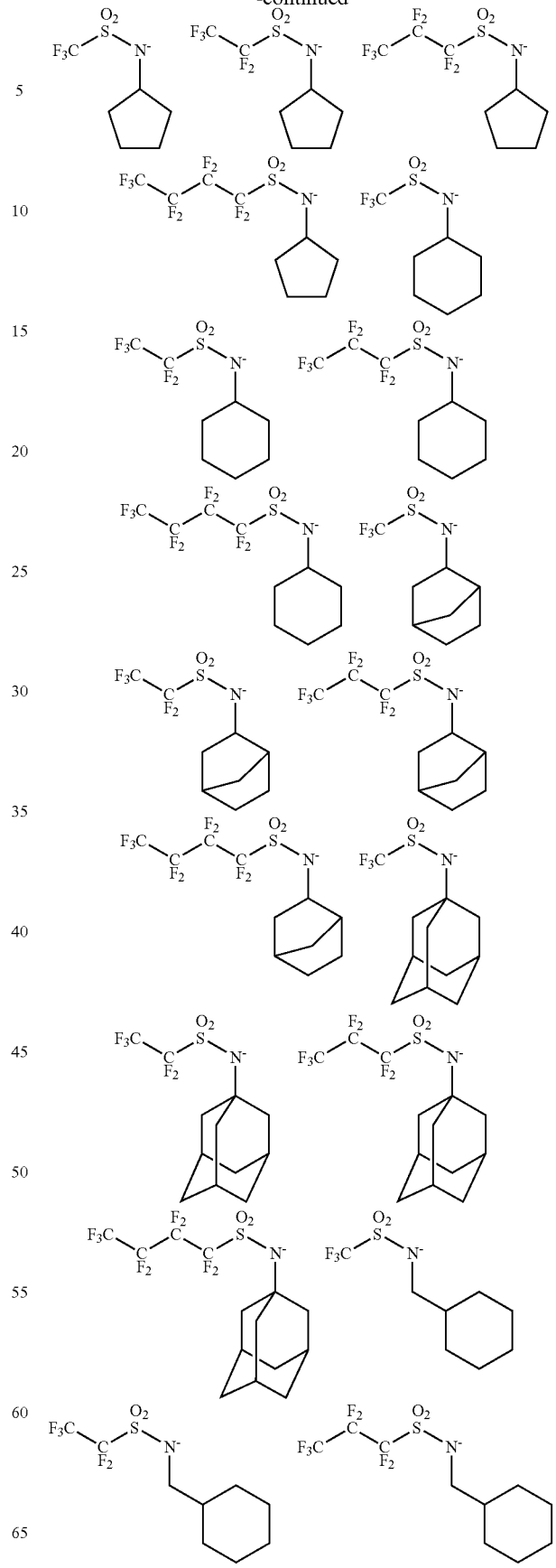

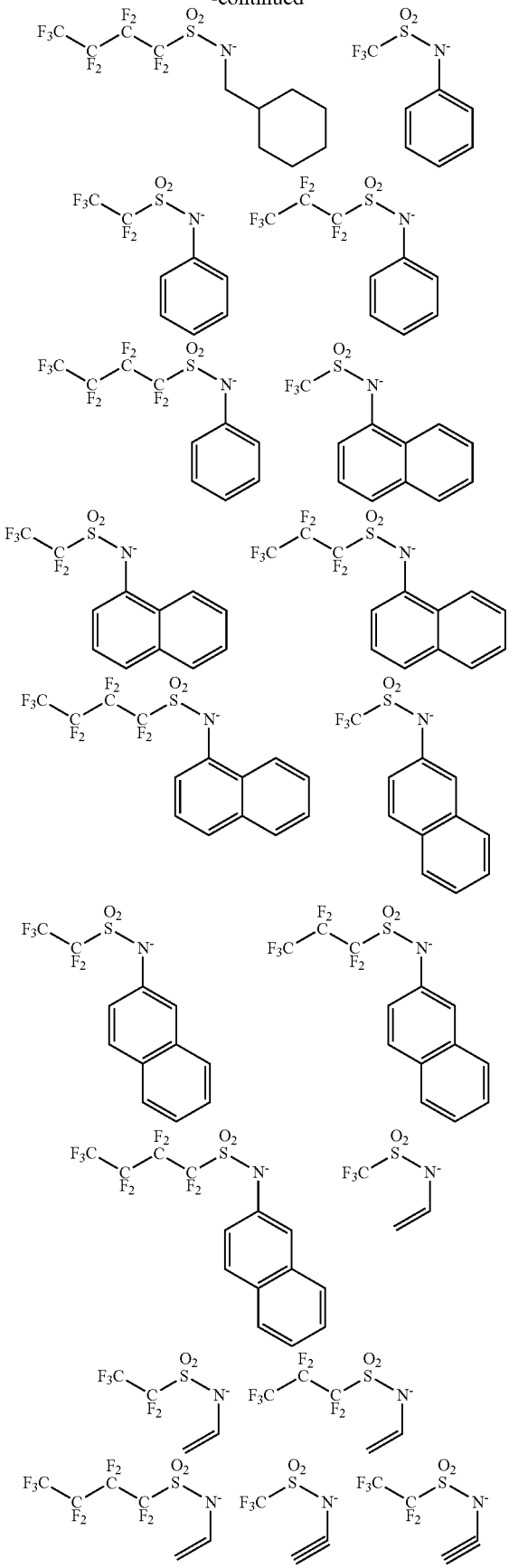
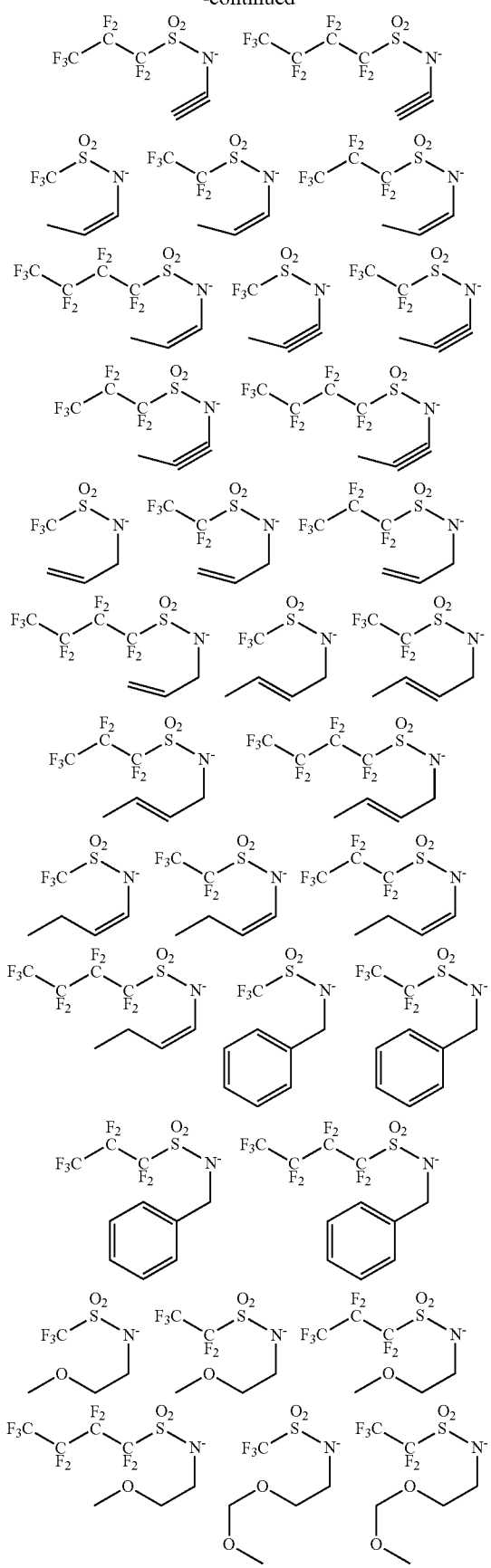

151
-continued
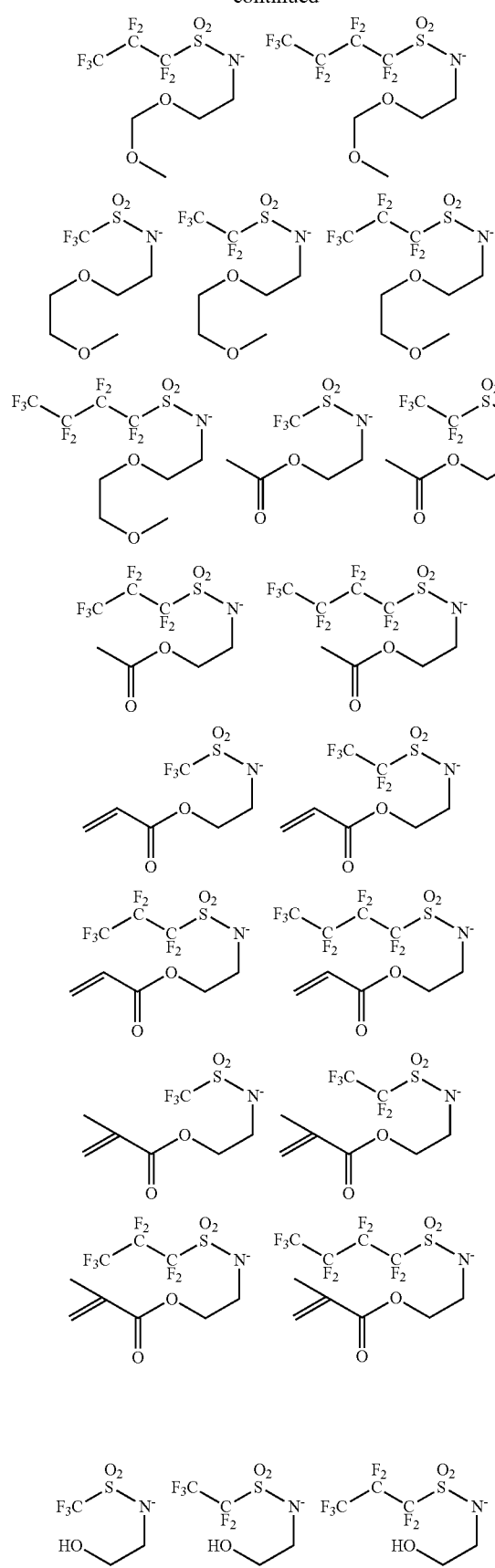
152
-continued
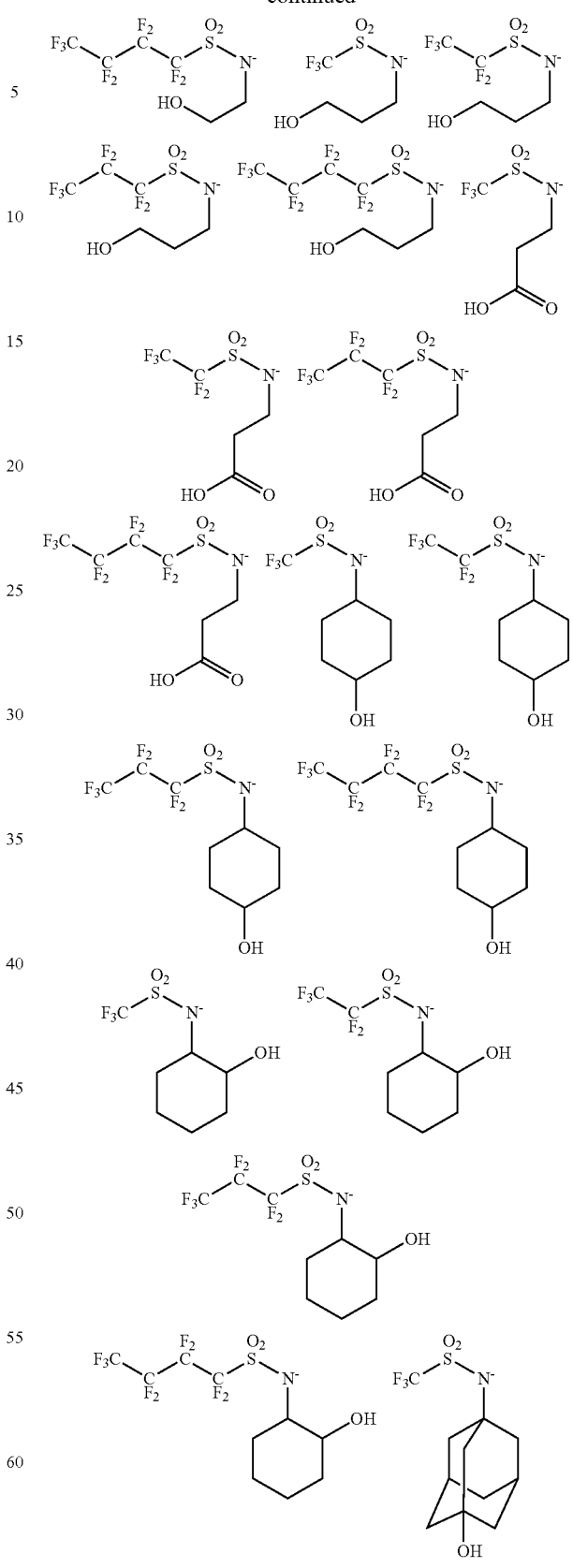

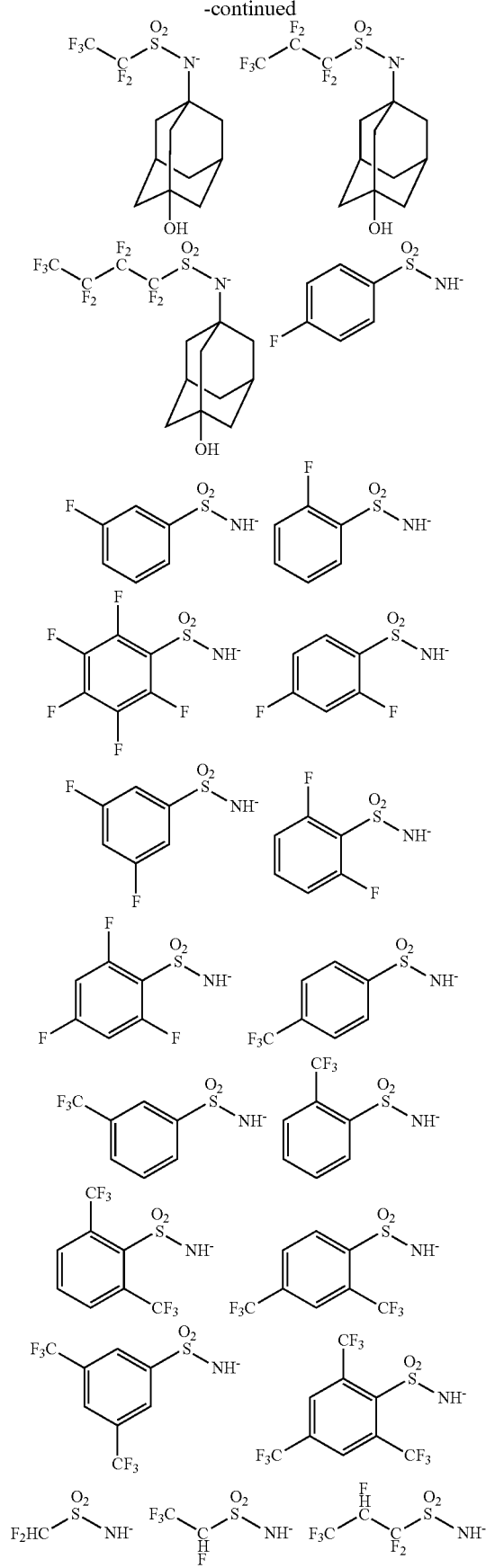
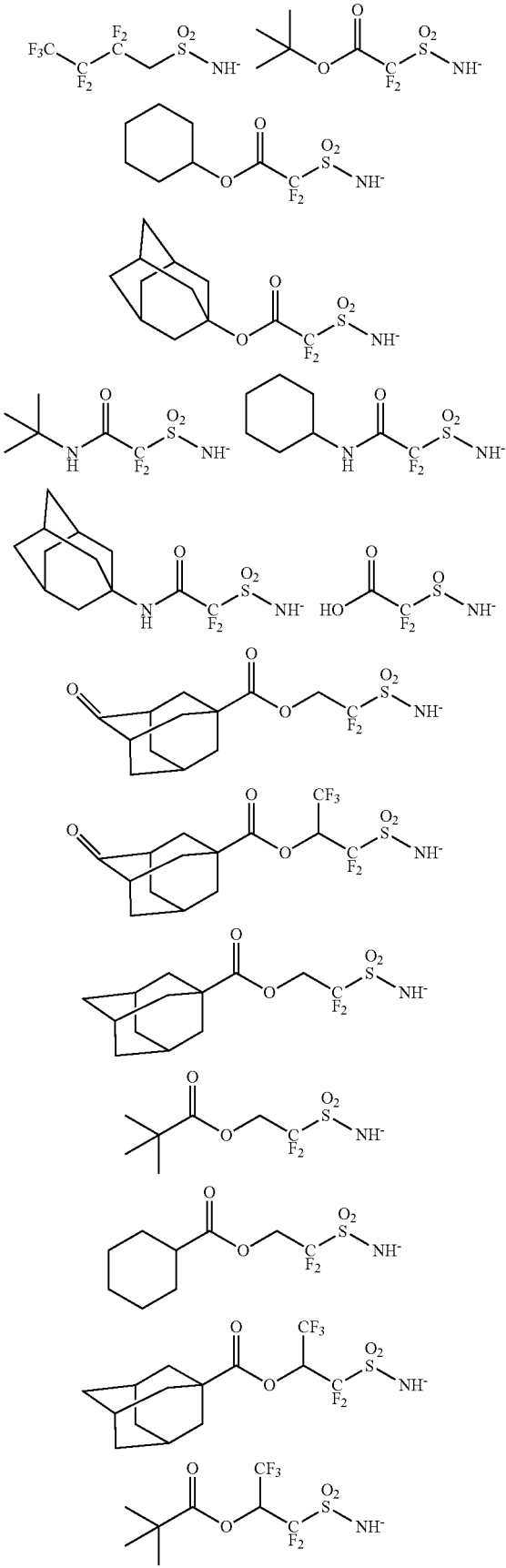

-continued
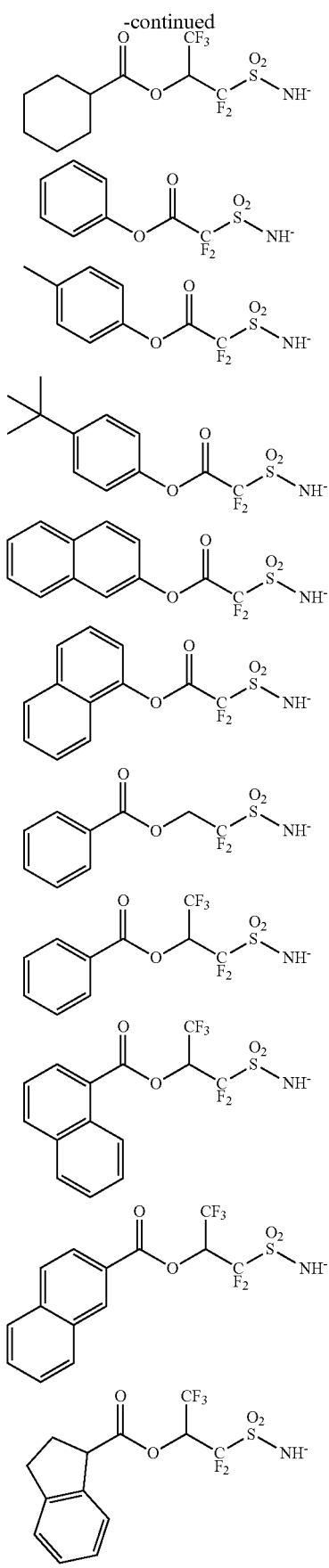
-continued
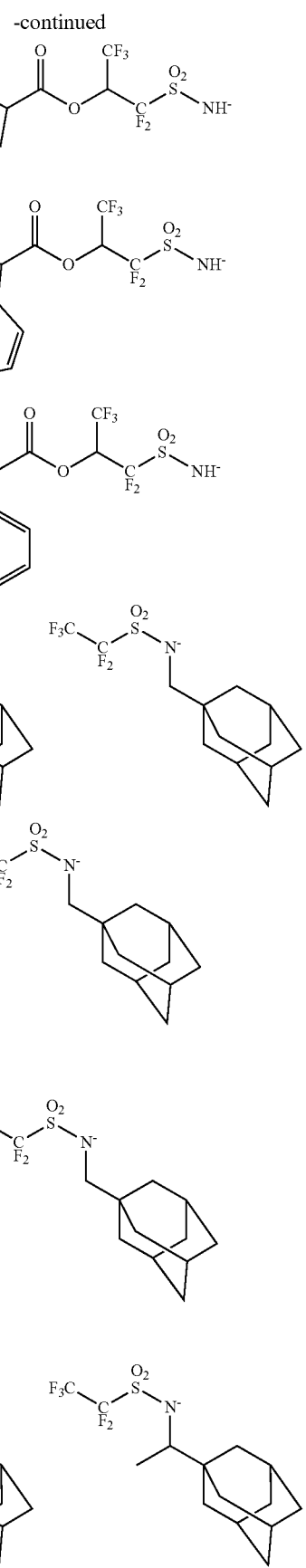

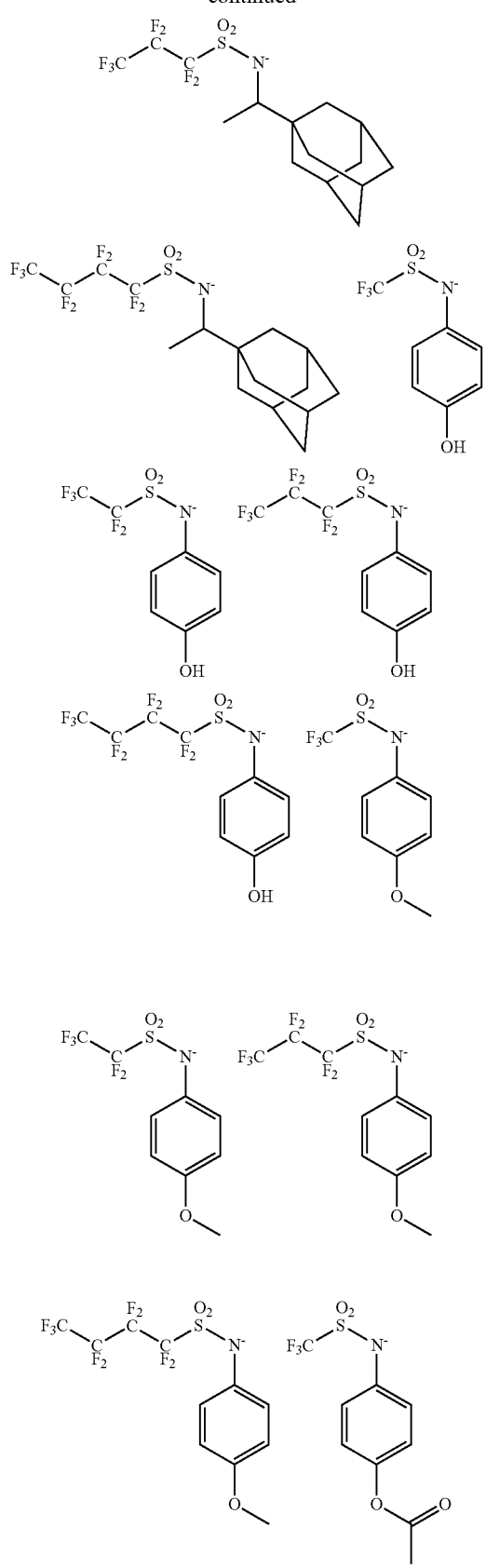
Examples of the alkoxide anion are shown below, but not limited thereto.
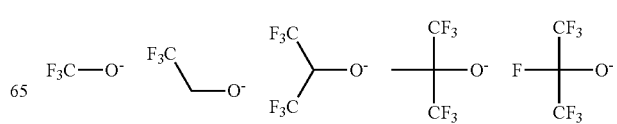

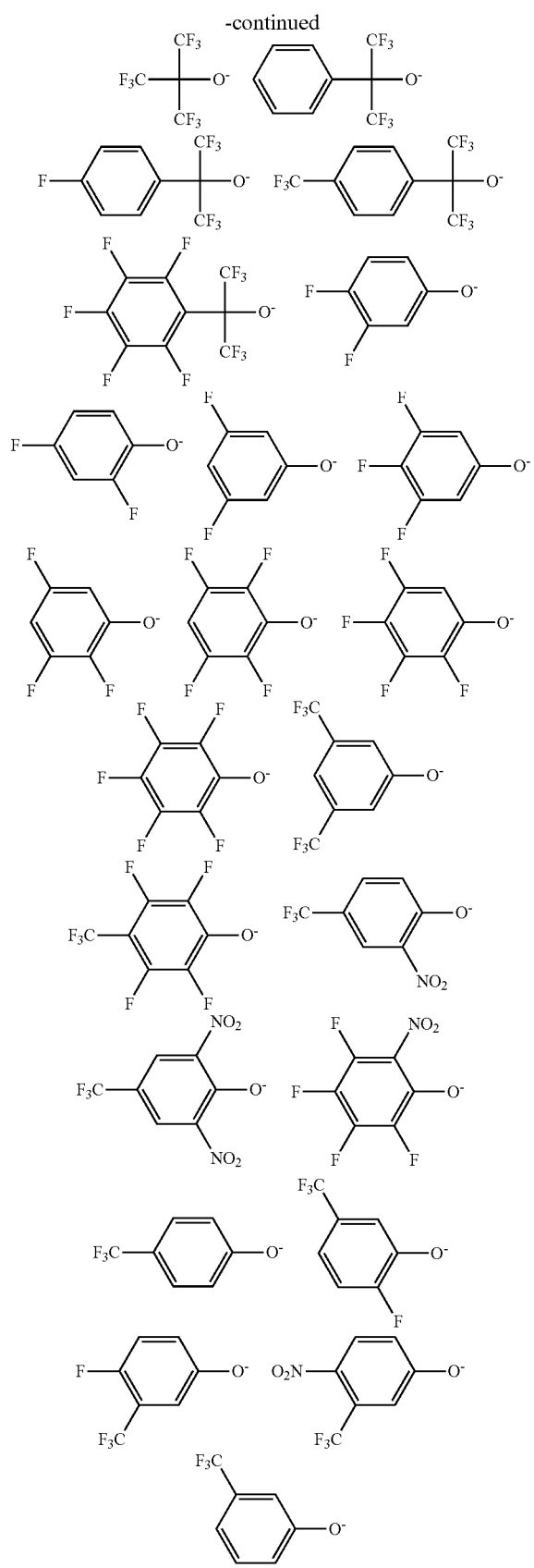
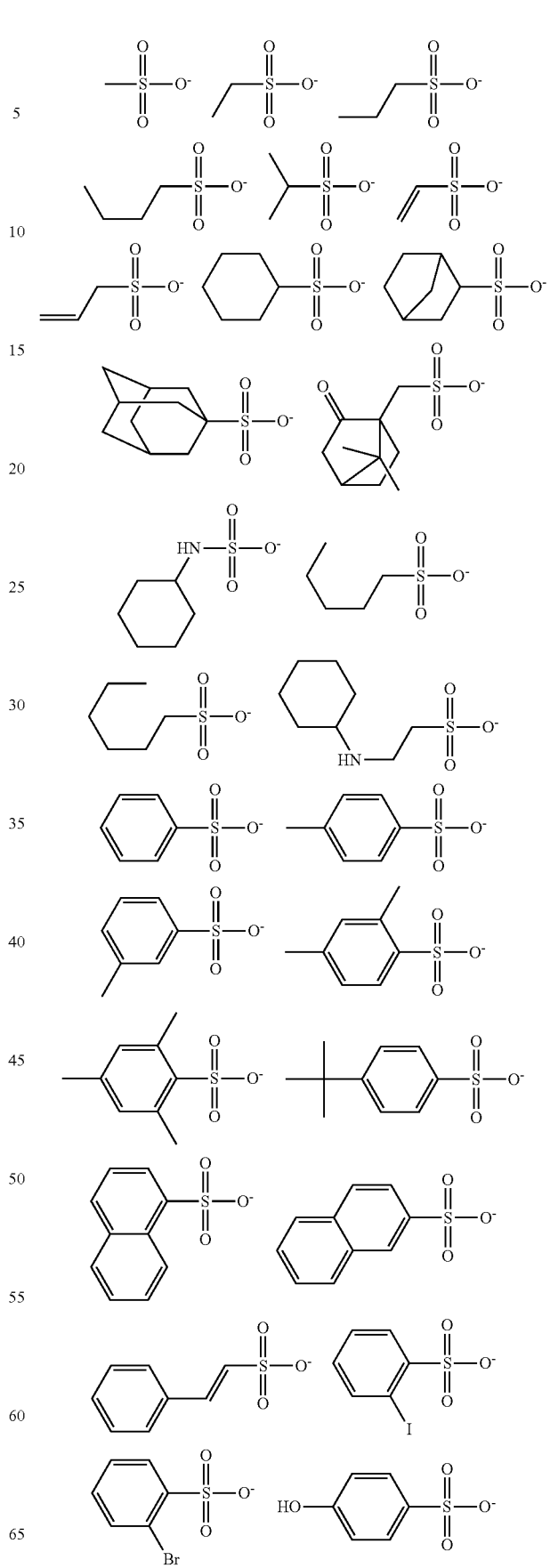
Examples of the non-α-fluorinated sulfonate anion are shown below, but not limited thereto.

161
-continued

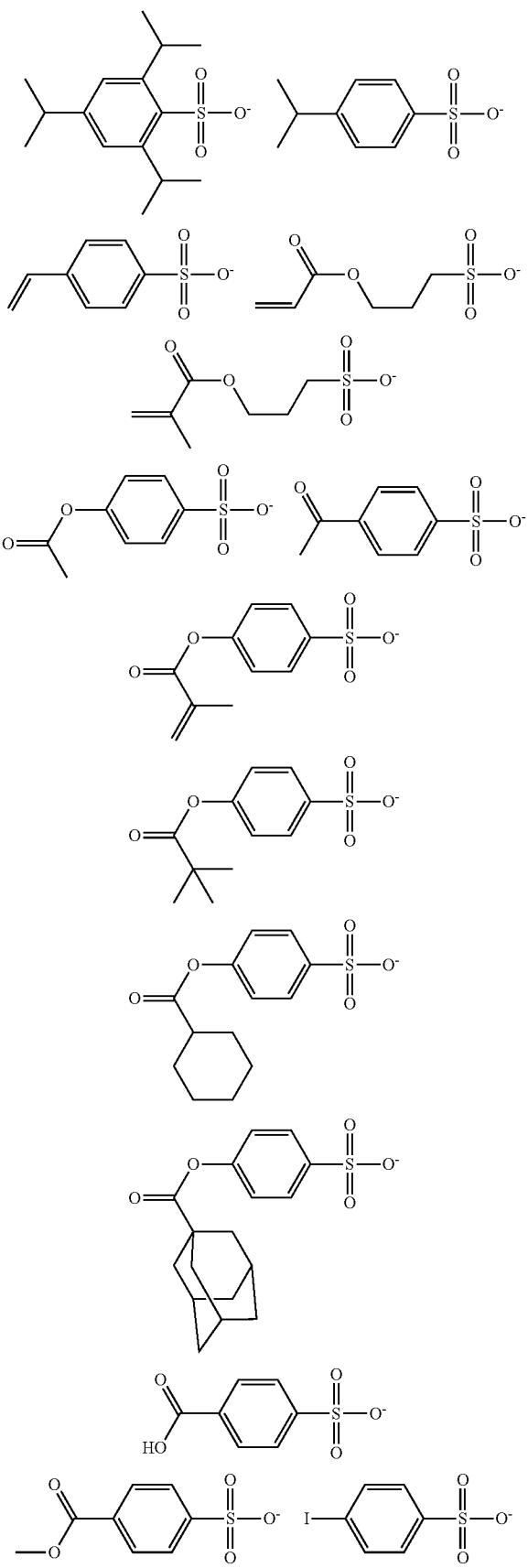

162
-continued

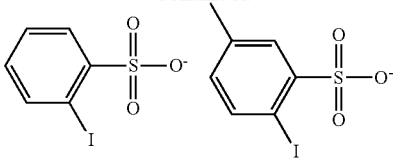

The sulfonium cation in the quencher (B) may or may not contain fluorine. Fluorine-containing sulfonium cations having formula (3) are preferred.

The preferred quencher (B) is a sulfonium salt in which the cation contains at least 3 fluorine atoms or the anion and cation contain at least 6 fluorine atoms in total.

In the positive resist composition, the quencher (B) is preferably present in an amount of 0.01 to 30 parts by weight, more preferably 0.02 to 20 parts by weight per 100 parts by weight of the base polymer (C) to be described later.

(C) Base Polymer

Component (C) is a base polymer comprising repeat units of at least one type selected from repeat units (a1) having a carboxy group whose hydrogen is substituted by an acid labile group and repeat units (a2) having a phenolic hydroxy group whose hydrogen is substituted by an acid labile group.

In a preferred embodiment, the repeat unit (a1) has the formula (a1) and the repeat unit (a2) has the formula (a2).

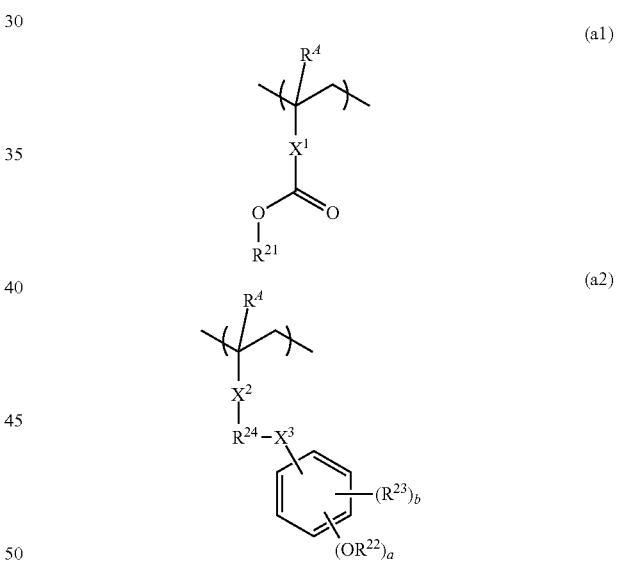

In formulae (a1) and (a2), $R^A$ is each independently hydrogen or methyl. $X^1$ is a single bond, phenylene group, naphthylene group, or a $C_1$-$C_{12}$ linking group containing at least one moiety selected from an ether bond, ester bond and lactone ring. $X^2$ is a single bond, ester bond or amide bond. $X^3$ is a single bond, ether bond or ester bond. $R^{21}$ and $R^{22}$ are each independently an acid labile group. $R^{23}$ is fluorine, trifluoromethyl, cyano or a $C_1$-$C_6$ saturated hydrocarbyl group. $R^{24}$ is a single bond or a $C_1$-$C_6$ alkanediyl group in which some carbon may be replaced by an ether bond or ester bond. The subscript "a" is 1 or 2, b is an integer of 0 to 4, and $1 \leq a+b \leq 5$.

Examples of the monomer from which repeat units (a1) are derived are shown below, but not limited thereto. Herein $R^A$ and $R^{21}$ are as defined above.

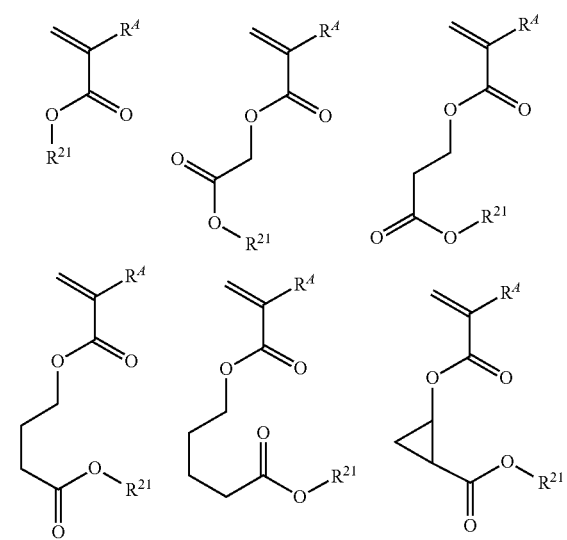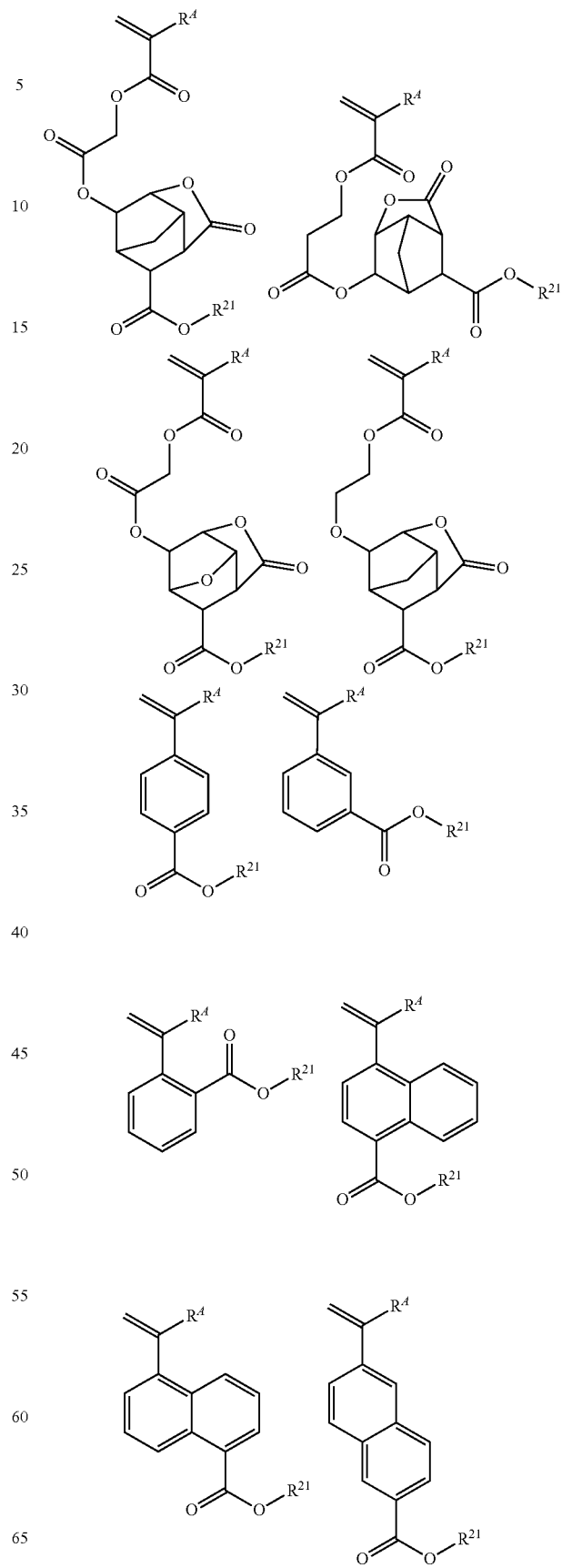

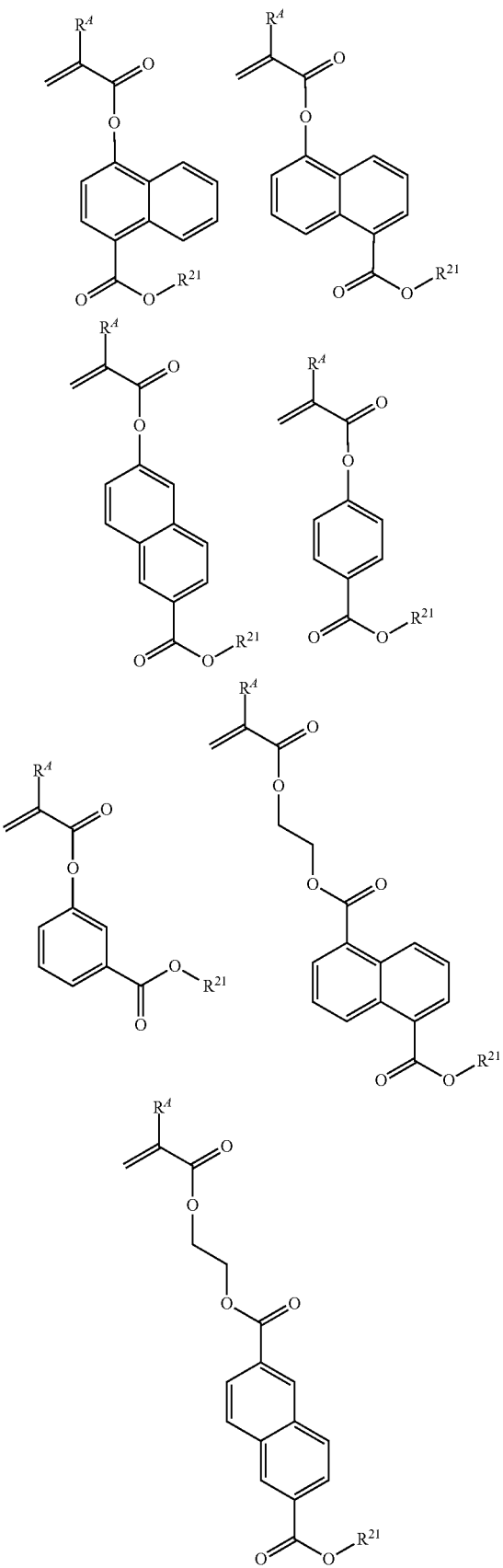
Examples of the monomer from which repeat units (a2) are derived are shown below, but not limited thereto. Herein $R^A$ and $R^{22}$ are as defined above.
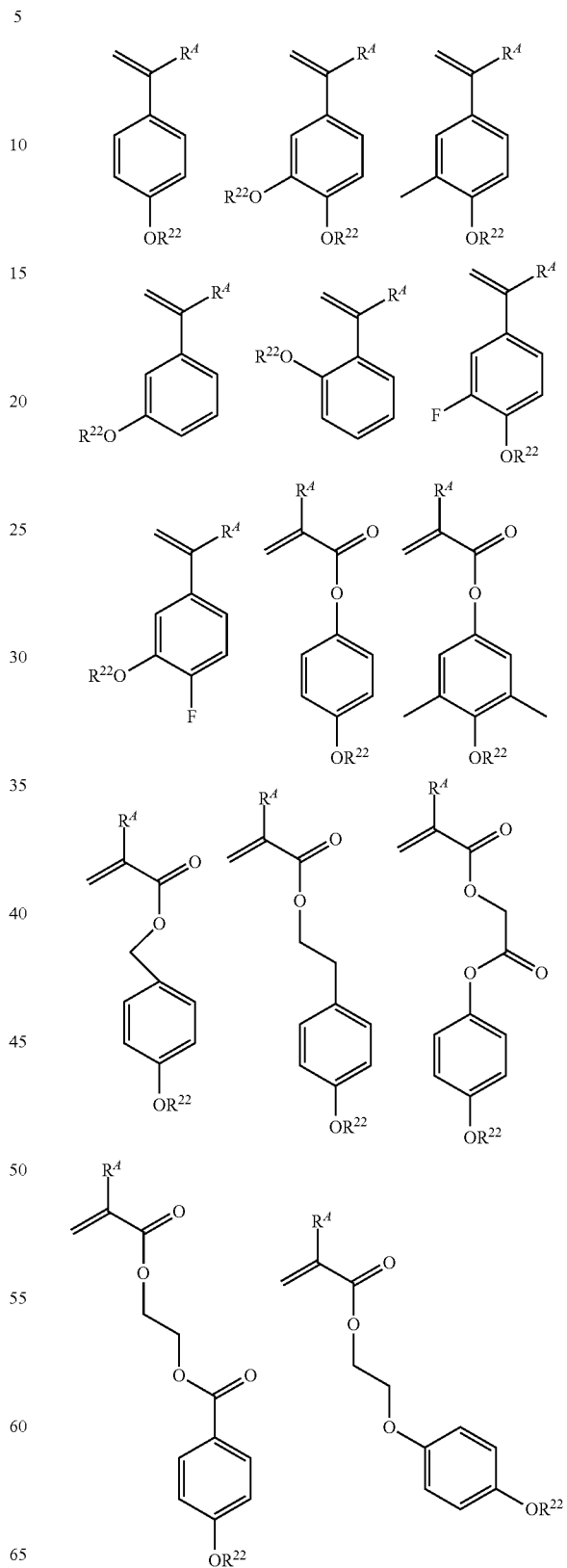

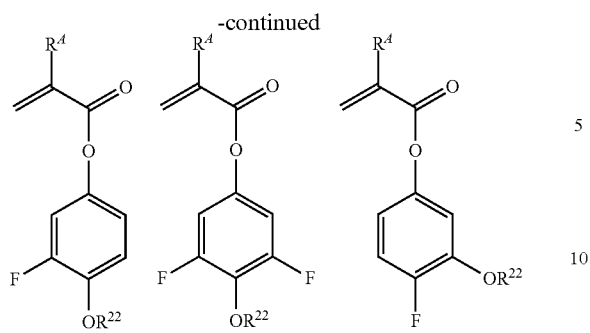

The acid labile groups represented by $R^{21}$ and $R^{22}$ may be selected from a variety of such groups, for example, those groups having the following formulae (AL-1) to (AL-3).

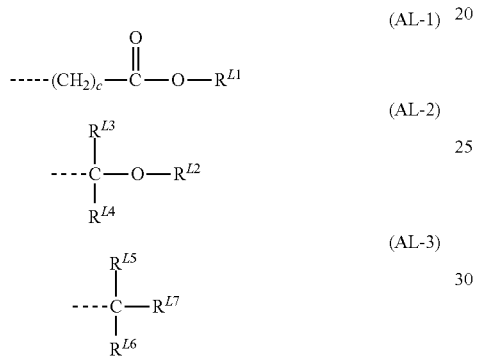

In formulae (AL-1), c is an integer of 0 to 6. $R^{L1}$ is a $C_4$-$C_{40}$, preferably $C_4$-$C_{15}$ tertiary hydrocarbyl group, a trihydrocarbylsilyl group in which each hydrocarbyl moiety is a $C_1$-$C_6$ saturated hydrocarbyl moiety, a $C_4$-$C_{20}$ saturated hydrocarbyl group containing a carbonyl moiety, ether bond or ester bond, or a group having formula (AL-3).

The tertiary hydrocarbyl group RY may be saturated or unsaturated and branched or cyclic. Examples thereof include tert-butyl, tert-pentyl, 1,1-diethylpropyl, 1-ethylcyclopentyl, 1-butylcyclopentyl, 1-ethylcyclohexyl, 1-butylcyclohexyl, 1-ethyl-2-cyclopentenyl, 1-ethyl-2-cyclohexenyl, and 2-methyl-2-adamantyl. Suitable trihydrocarbylsilyl groups include trimethylsilyl, triethylsilyl, and dimethyl-tert-butylsilyl. The saturated hydrocarbyl group containing a carbonyl moiety, ether bond or ester bond may be straight, branched or cyclic, preferably cyclic, and examples thereof include 3-oxocyclohexyl, 4-methyl-2-oxooxan-4-yl, 5-methyl-2-oxooxolan-5-yl, 2-tetrahydropyranyl, and 2-tetrahydrofuranyl.

Examples of the acid labile group having formula (AL-1) include tert-butoxycarbonyl, tert-butoxycarbonylmethyl, tert-pentyloxycarbonyl, tert-pentyloxycarbonylmethyl, 1,1-diethylpropyloxycarbonyl, 1,1-diethylpropyloxycarbonylmethyl, 1-ethylcyclopentyloxycarbonyl, 1-ethylcyclopentyloxycarbonylmethyl, 1-ethyl-2-cyclopentenyloxycarbonyl, 1-ethyl-2-cyclopentenyloxycarbonylmethyl, 1-ethoxyethoxycarbonylmethyl, 2-tetrahydropyranyloxycarbonylmethyl, and 2-tetrahydrofuranyloxycarbonylmethyl.

Other examples of the acid labile group having formula (AL-1) include groups having the formulae (AL-1)-1 to (AL-1)-10.

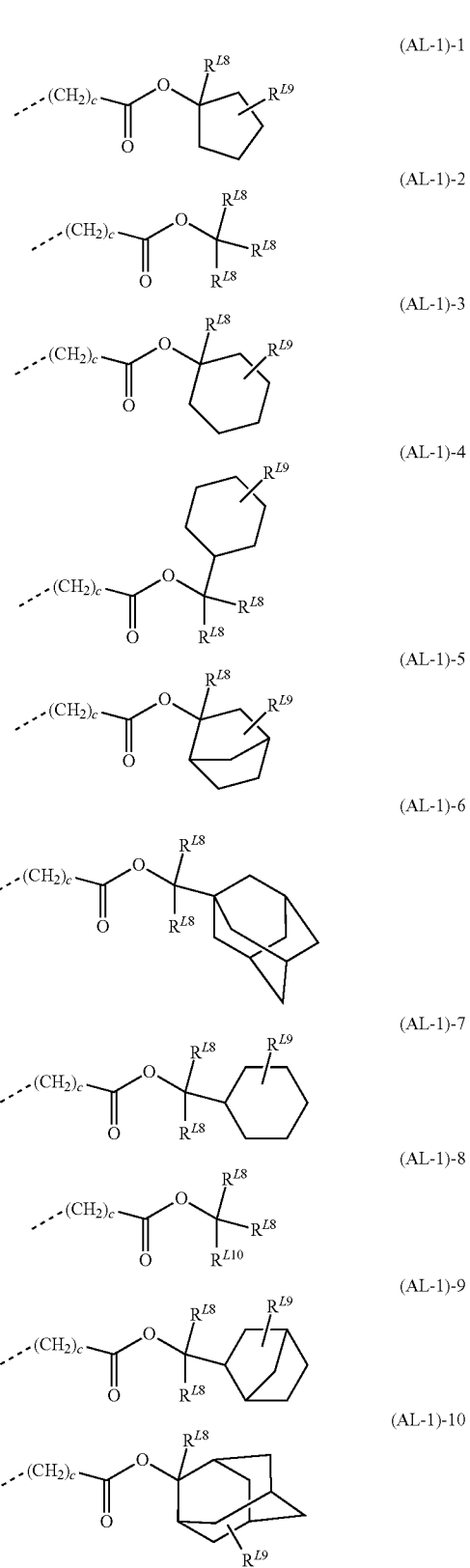

In formulae (AL-1)-1 to (AL-1)-10, c is as defined above. $R^{L8}$ is each independently a $C_1$-$C_{10}$ saturated hydrocarbyl group or $C_6$-$C_{20}$ aryl group. $R^{L9}$ is hydrogen or a $C_1$-$C_{10}$ saturated hydrocarbyl group. $R^{L10}$ is a $C_2$-$C_{10}$ saturated hydrocarbyl group or $C_6$-$C_{20}$ aryl group. The saturated hydrocarbyl group may be straight, branched or cyclic.

In formula (AL-2), $R^{L2}$ and $R^{L3}$ are each independently hydrogen or a $C_1$-$C_{18}$, preferably $C_1$-$C_{10}$ saturated hydrocarbyl group. The saturated hydrocarbyl group may be straight, branched or cyclic and examples thereof include methyl, ethyl, propyl, isopropyl, n-butyl, sec-butyl, tert-butyl, cyclopentyl, cyclohexyl, 2-ethylhexyl and n-octyl.

In formula (AL-2), $R^{L4}$ is a $C_1$-$C_{18}$, preferably $C_1$-$C_{10}$ hydrocarbyl group which may contain a heteroatom. The hydrocarbyl group may be saturated or unsaturated and straight, branched or cyclic and typical examples thereof include $C_1$-$C_{18}$ saturated hydrocarbyl groups, in which some hydrogen may be substituted by hydroxy, alkoxy, oxo, amino or alkylamino. Examples of the substituted saturated hydrocarbyl group are shown below.

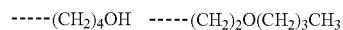
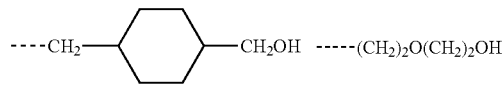
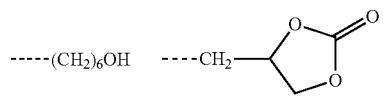

A pair of $R^{L2}$ and $R^{L3}$, $R^{L2}$ and $R^{L4}$, or $R^{L3}$ and $R^{L4}$ may bond together to form a ring with the carbon atom or carbon and oxygen atoms to which they are attached. $R^{L2}$ and $R^{L3}$, $R^{L2}$ and $R^{L4}$, and $R^{L3}$ and $R^{L4}$ taken together to form a ring are each independently a $C_1$-$C_{18}$, preferably $C_1$-$C_{10}$ alkanediyl group. The ring thus formed is preferably of 3 to 10, more preferably 4 to 10 carbon atoms.

Of the acid labile groups having formula (AL-2), suitable straight or branched groups include those having formulae (AL-2)-1 to (AL-2)-69, but are not limited thereto.

 (AL-2)-1

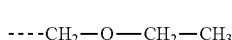 (AL-2)-2

 (AL-2)-3

 (AL-2)-4

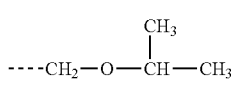 (AL-2)-5

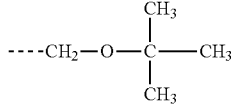 (AL-2)-6

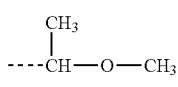 (AL-2)-7

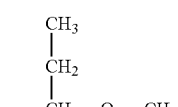 (AL-2)-8

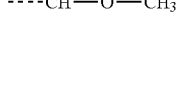 (AL-2)-9

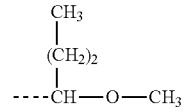 (AL-2)-9

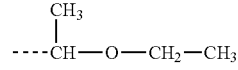 (AL-2)-10

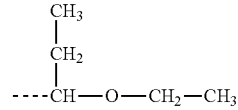 (AL-2)-11

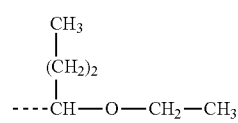 (AL-2)-12

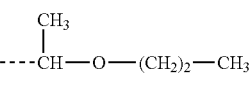 (AL-2)-13

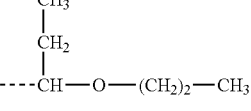 (AL-2)-14

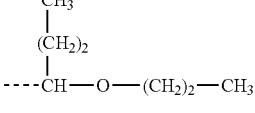 (AL-2)-15

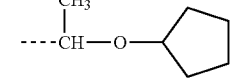 (AL-2)-16

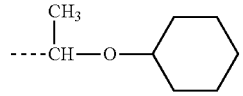 (AL-2)-17

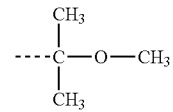 (AL-2)-18

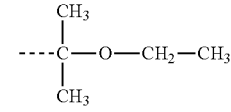 (AL-2)-19

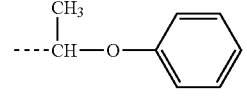 (AL-2)20

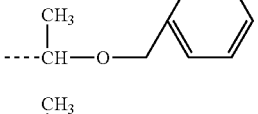 (AL-2)-21

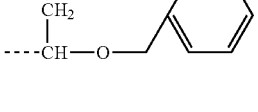 (AL-2)-22

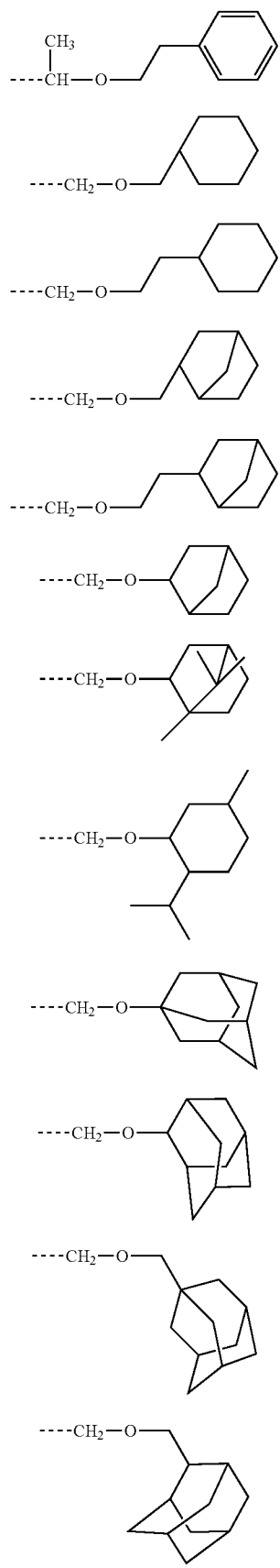
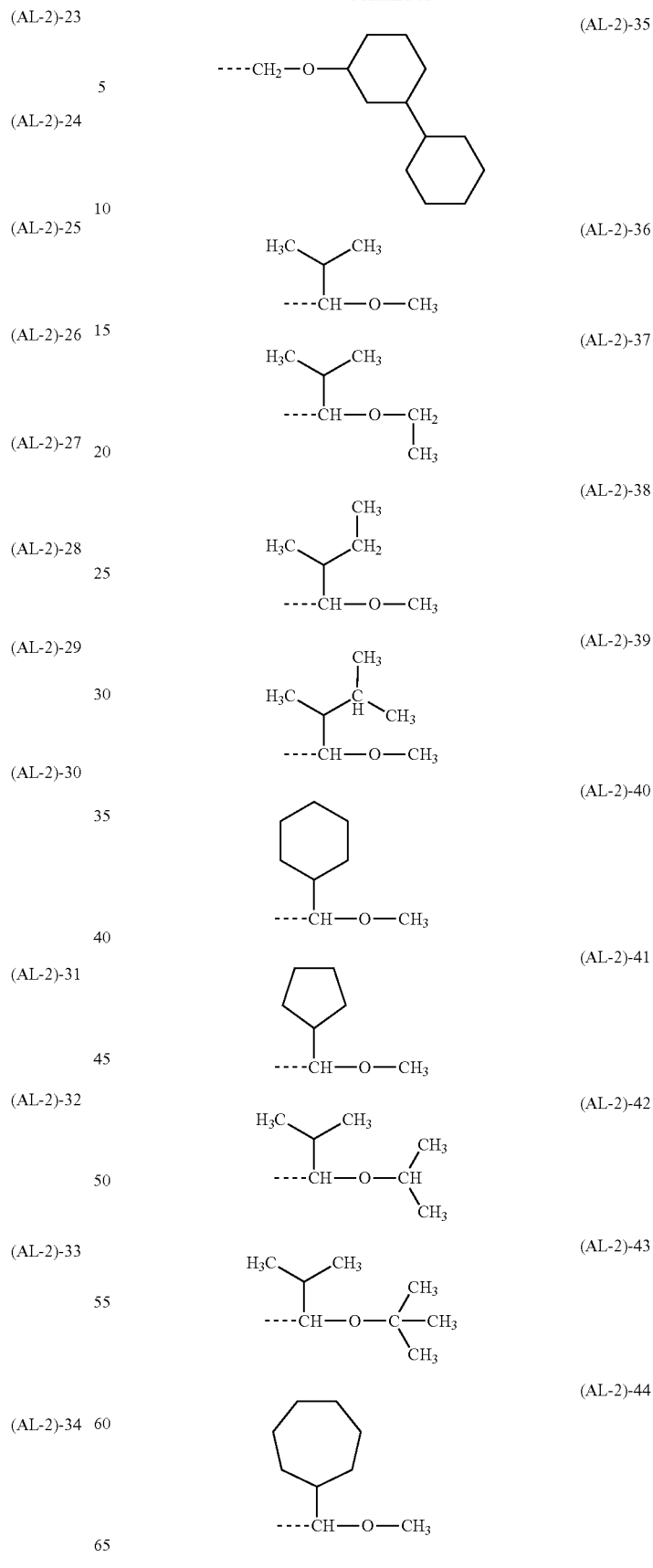

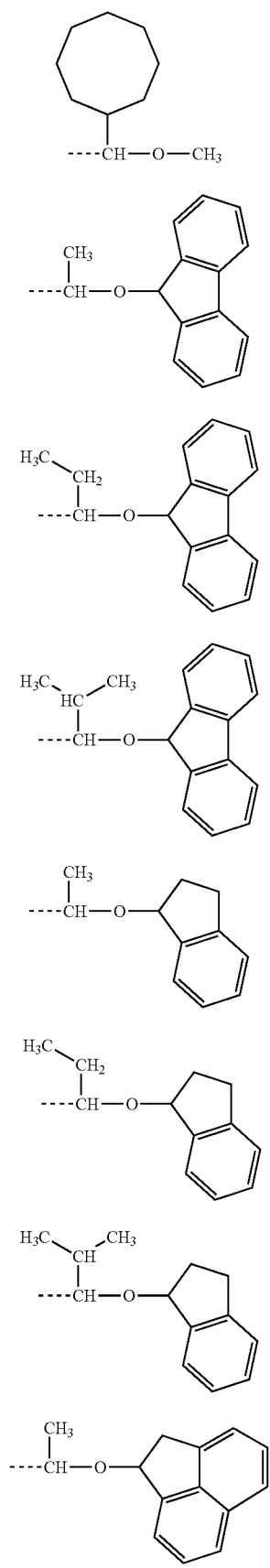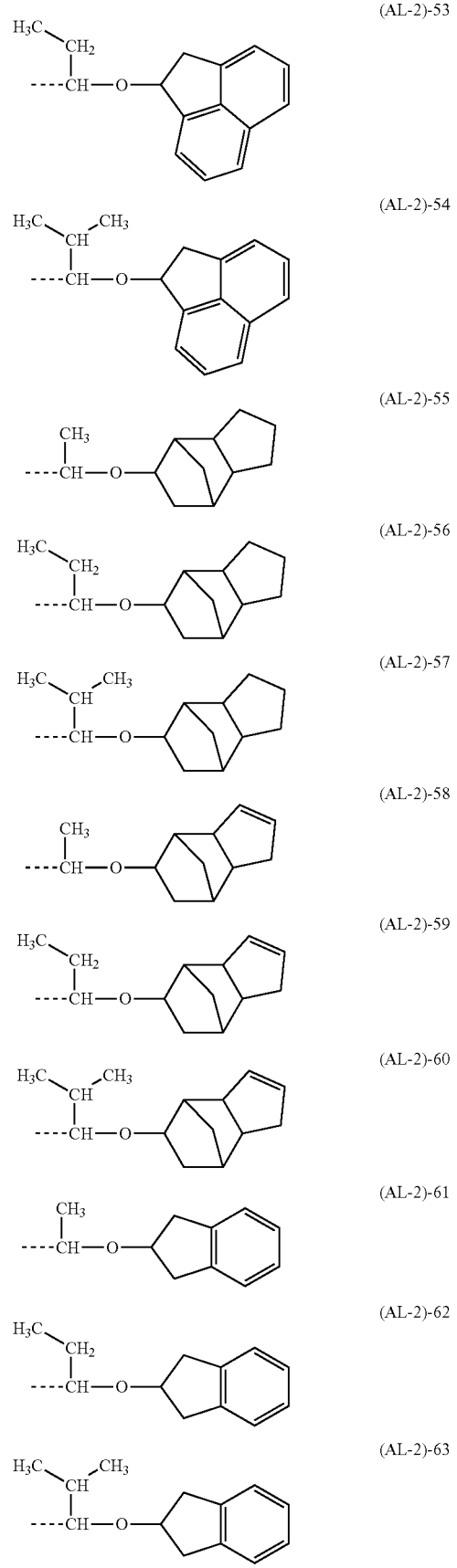

-continued

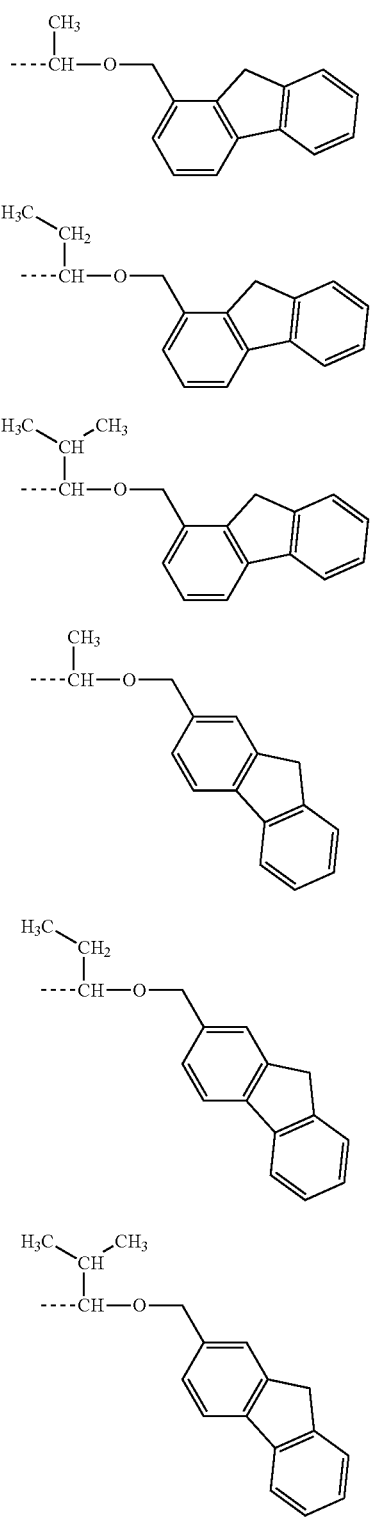

(AL-2)-64
(AL-2)-65
(AL-2)-66
(AL-2)-67
(AL-2)-68
(AL-2)-69

Of the acid labile groups having formula (AL-2), suitable cyclic groups include tetrahydrofuran-2-yl, 2-methyltetrahydrofuran-2-yl, tetrahydropyran-2-yl, and 2-methyltetrahydropyran-2-yl.

Also included are acid labile groups having the following formulae (AL-2a) and (AL-2b). The base polymer may be crosslinked within the molecule or between molecules with these acid labile groups.

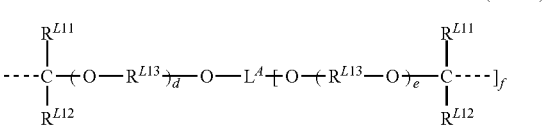

(AL-2a)

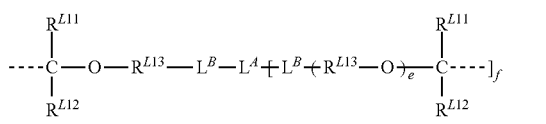

(AL-2b)

In formulae (AL-2a) and (AL-2b), $R^{L11}$ and $R^{L12}$ are each independently hydrogen or a $C_1$-$C_8$ saturated hydrocarbyl group which may be straight, branched or cyclic. Also, $R^{L11}$ and $R^{L12}$ may bond together to form a ring with the carbon atom to which they are attached, and in this case, $R^{L11}$ and $R^{L12}$ are each independently a $C_1$-$C_8$ alkanediyl group. $R^{L13}$ is each independently a $C_1$-$C_{10}$ saturated hydrocarbylene group which may be straight, branched or cyclic. The subscripts d and e are each independently an integer of 0 to 10, preferably 0 to 5, and f is an integer of 1 to 7, preferably 1 to 3.

In formulae (AL-2a) and (AL-2b), $L^A$ is a (f+1)-valent $C_1$-$C_{50}$ aliphatic saturated hydrocarbon group, (f+1)-valent $C_3$-$C_{50}$ alicyclic saturated hydrocarbon group, (f+1)-valent $C_6$-$C_{50}$ aromatic hydrocarbon group or (f+1)-valent $C_3$-$C_{50}$ heterocyclic group. In these groups, some carbon may be replaced by a heteroatom-containing moiety, or some carbon-bonded hydrogen may be substituted by a hydroxy, carboxy, acyl moiety or fluorine. $L^A$ is preferably a $C_1$-$C_{20}$ saturated hydrocarbon group such as saturated hydrocarbylene, trivalent saturated hydrocarbon or tetravalent saturated hydrocarbon group, or $C_6$-$C_{30}$ arylene group. The saturated hydrocarbon group may be straight, branched or cyclic. $L^B$ is —C(=O)—O—, —NH—C(=O)—O— or —NH—C(=O)—NH—.

Examples of the crosslinking acetal groups having formulae (AL-2a) and (AL-2b) include groups having the formulae (AL-2)-70 to (AL-2)-77.

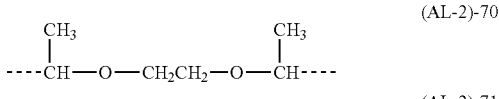

(AL-2)-70

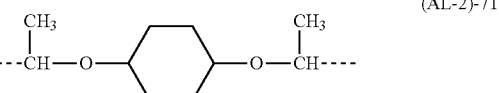

(AL-2)-71

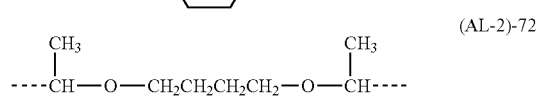

(AL-2)-72

(AL-2)-73

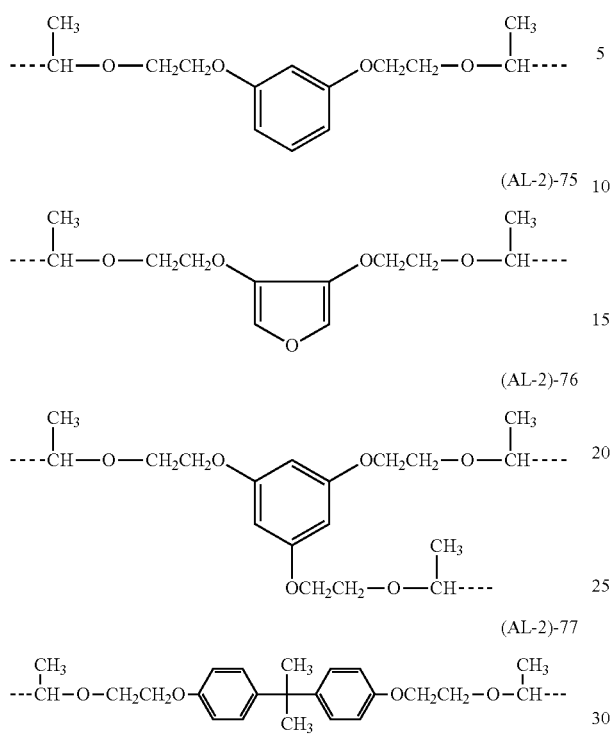

(AL-2)-74

(AL-2)-75

(AL-2)-76

(AL-2)-77

In formula (AL-3), $R^{L5}$, $R^{L6}$ and $R^{L7}$ are each independently a $C_1$-$C_{20}$ hydrocarbyl group which may contain a heteroatom such as oxygen, sulfur, nitrogen or fluorine. The hydrocarbyl group may be saturated or unsaturated and straight, branched or cyclic. Examples thereof include $C_1$-$C_{20}$ alkyl groups, $C_3$-$C_{20}$ cyclic saturated hydrocarbyl groups, $C_2$-$C_{20}$ alkenyl groups, $C_3$-$C_{20}$ cyclic unsaturated aliphatic hydrocarbyl groups, and $C_6$-$C_{10}$ aryl groups. A pair of $R^{L5}$ and $R^{L6}$, $R^{L5}$ and $R^{L7}$, or $R^{L6}$ and $R^{L7}$ may bond together to form a $C_3$-$C_{20}$ aliphatic ring with the carbon atom to which they are attached.

Examples of the group having formula (AL-3) include tert-butyl, 1,1-diethylpropyl, 1-ethylnorbornyl, 1-methylcyclopentyl, 1-ethylcyclopentyl, 1-isopropylcyclopentyl, 1-methylcyclohexyl, 2-(2-methyl)adamantyl, 2-(2-ethyl)adamantyl, and tert-pentyl.

Examples of the group having formula (AL-3) also include groups having the formulae (AL-3)-1 to (AL-3)-19.

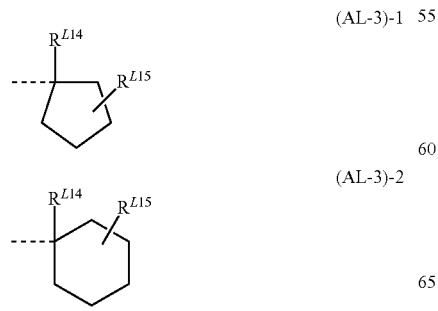

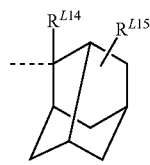

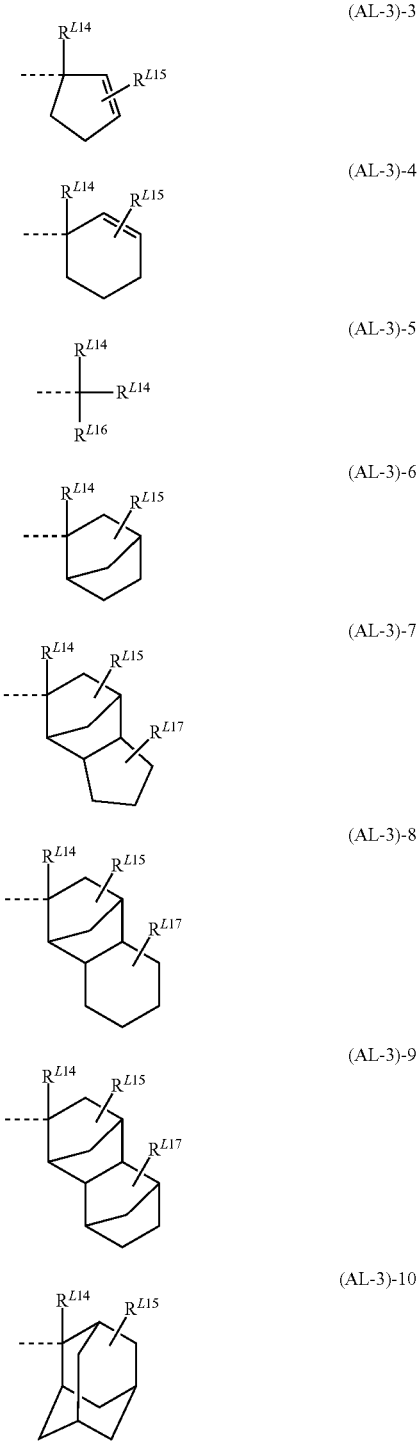

(AL-3)-12 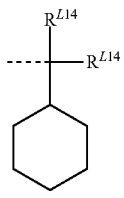

(AL-3)-13 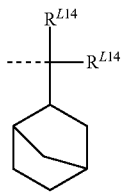

(AL-3)-14 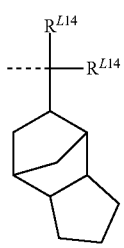

(AL-3)-15 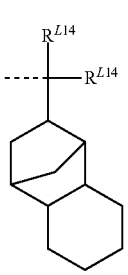

(AL-3)-16 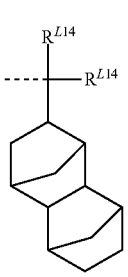

(AL-3)-17 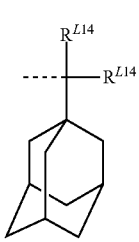

(AL-3)-18 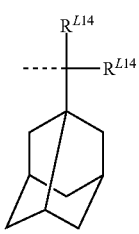

(AL-3)-19 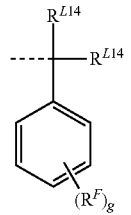

In formulae (AL-3)-1 to (AL-3)-19, $R^{L14}$ is each independently a $C_1$-$C_8$ saturated hydrocarbyl group or $C_6$-$C_{20}$ aryl group. $R^{L15}$ and $R^{L17}$ are each independently hydrogen or a $C_1$-$C_{20}$ saturated hydrocarbyl group. $R^{L16}$ is a $C_6$-$C_{20}$ aryl group. The saturated hydrocarbyl group may be straight, branched or cyclic. Typical of the aryl group is phenyl. $R^F$ is fluorine or trifluoromethyl, and g is an integer of 1 to 5.

Other examples of the group having formula (AL-3) include groups having the formulae (AL-3)-20 and (AL-3)-21. The base polymer may be crosslinked within the molecule or between molecules with these acid labile groups.

(AL-3)-20 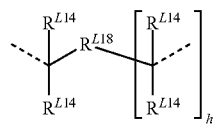

(AL-3)-21 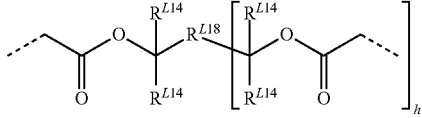

In formulae (AL-3)-20 and (AL-3)-21, $R^{L14}$ is as defined above. $R^{L18}$ is a $C_1$-$C_{20}$ (h+1)-valent saturated hydrocarbylene group or $C_6$-$C_{20}$ (h+1)-valent arylene group, which may contain a heteroatom such as oxygen, sulfur or nitrogen. The saturated hydrocarbylene group may be straight, branched or cyclic. The subscript h is an integer of 1 to 3

Examples of the monomer from which repeat units containing an acid labile group of formula (AL-3) are derived include (meth)acrylates having an exo-form structure represented by the formula (AL-3)-22.

(AL-3)-22 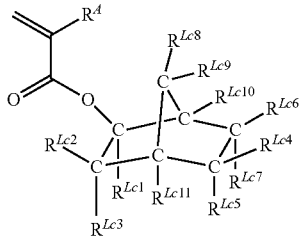

In formula (AL-3)-22, $R^A$ is as defined above. $R^{Lc1}$ is a $C_1$-$C_8$ saturated hydrocarbyl group or an optionally substituted $C_6$-$C_{20}$ aryl group; the saturated hydrocarbyl group may be straight, branched or cyclic. $R^{Lc2}$ to $R^{Lc11}$ are each independently hydrogen or a $C_1$-$C_{15}$ hydrocarbyl group which may contain a heteroatom; oxygen is a typical heteroatom. Suitable hydrocarbyl groups include $C_1$-$C_{15}$ alkyl groups and $C_6$-$C_{15}$ aryl groups. Alternatively, a pair of $R^{Lc2}$ and $R^{Lc3}$, $R^{Lc4}$ and $R^{Lc6}$, $R^{Lc4}$ and $R^{Lc7}$, $R^{Lc5}$ and $R^{Lc7}$, $R^{Lc5}$ and $R^{Lc11}$, $R^{Lc6}$ and $R^{Lc10}$, $R^{Lc8}$ and $R^{Lc9}$, or $R^{Lc9}$ and $R^{Lc10}$, taken together, may form a ring with the carbon atom to which they are attached, and in this event, the ring-forming group is a $C_1$-$C_{15}$ hydrocarbylene group which may contain a heteroatom. Also, a pair of $R^{Lc2}$ and $R^{Lc11}$, $R^{Lc8}$ and $R^{Lc11}$, or $R^{Lc4}$ and $R^{Lc6}$ which are attached to vicinal carbon atoms may bond together directly to form a double bond. The formula also represents an enantiomer.

Examples of the monomer having formula (AL-3)-22 are described in U.S. Pat. No. 6,448,420 (JP-A 2000-327633). Illustrative non-limiting examples of suitable monomers are given below. $R^A$ is as defined above.

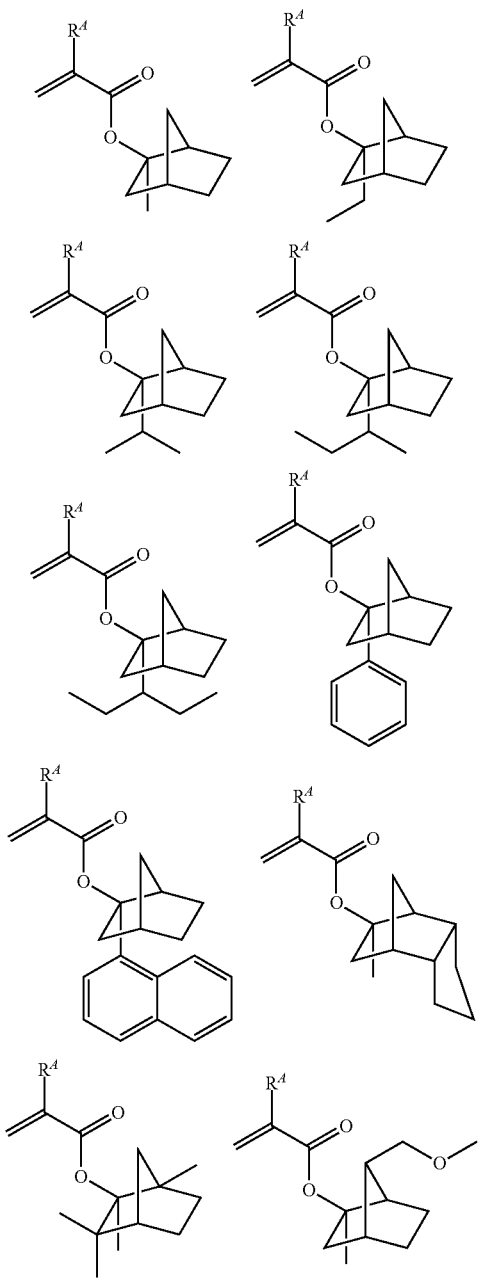

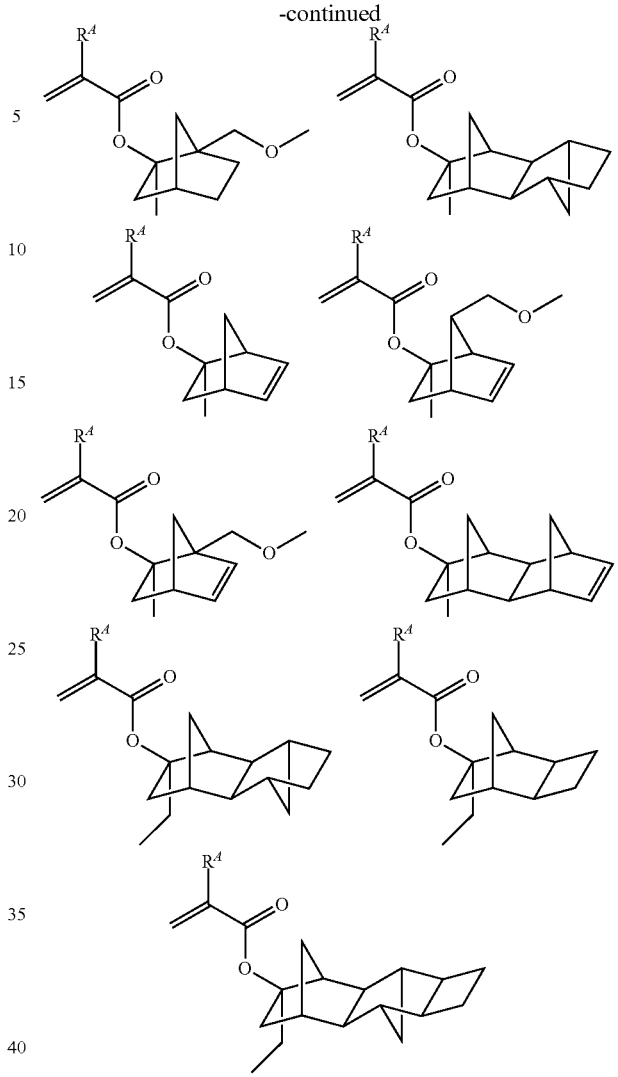

Examples of the monomer from which the repeat units having an acid labile group of formula (AL-3) are derived include (meth)acrylates having a furandiyl, tetrahydrofurandiyl or oxanorbornanediyl group as represented by the following formula (AL-3)-23.

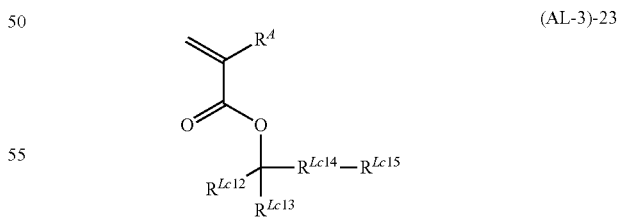

(AL-3)-23

In formula (AL-3)-23, $R^A$ is as defined above. $R^{Lc12}$ and $R^{Lc13}$ are each independently a $C_1$-$C_{10}$ hydrocarbyl group, or $R^{Lc12}$ and $R^{Lc13}$, taken together, may form an aliphatic ring with the carbon atom to which they are attached. $R^{Lc14}$ is furandiyl, tetrahydrofurandiyl or oxanorbornanediyl. $R^{Lc15}$ is hydrogen or a $C_1$-$C_{10}$ hydrocarbyl group which may contain a heteroatom. The hydrocarbyl group may be straight, branched or cyclic, and is typically a $C_1$-$C_{10}$ saturated hydrocarbyl group.

Examples of the monomer having formula (AL-3)-23 are shown below, but not limited thereto. Herein $R^A$ is as defined above.
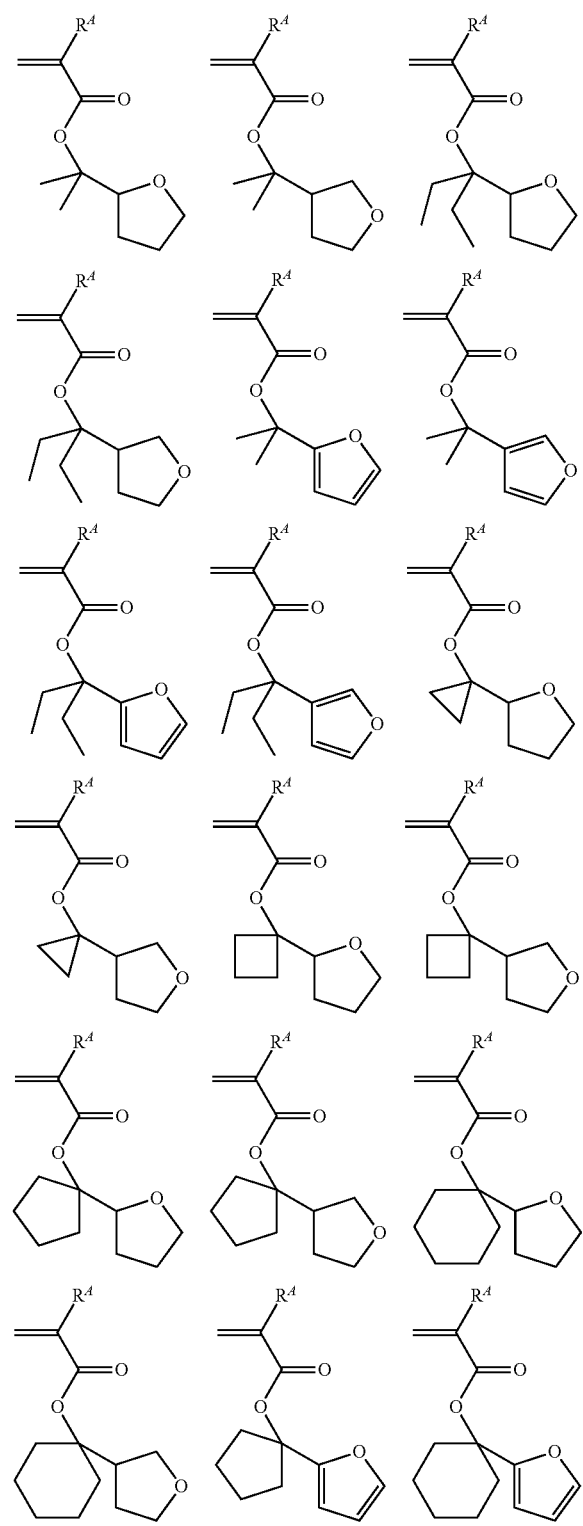
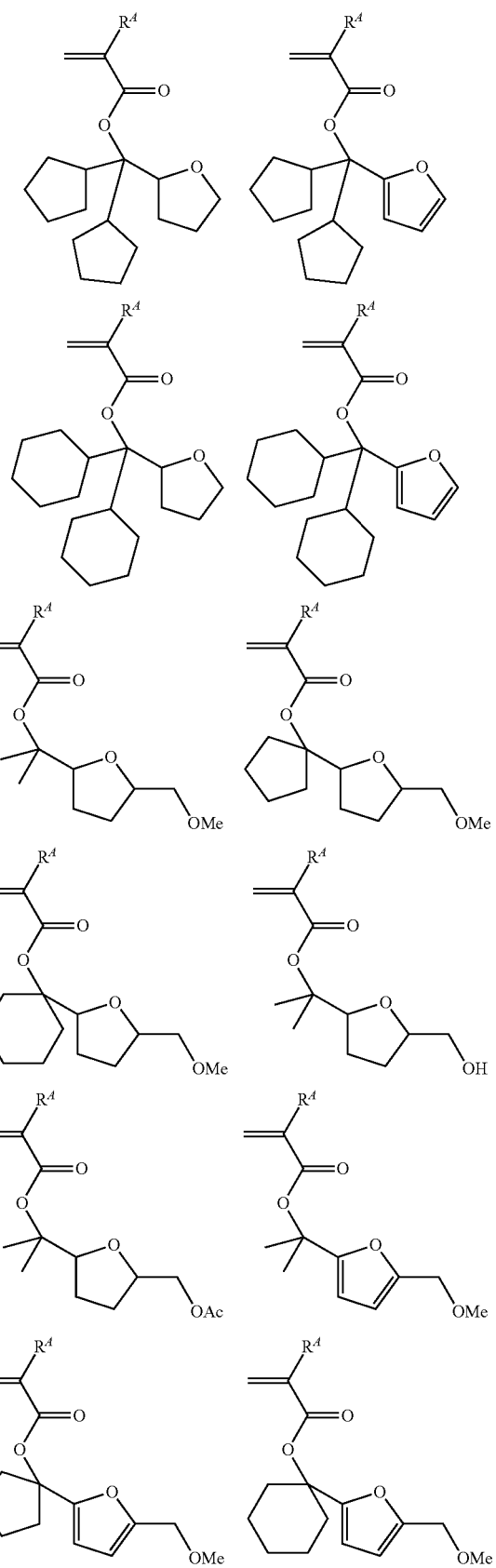

-continued
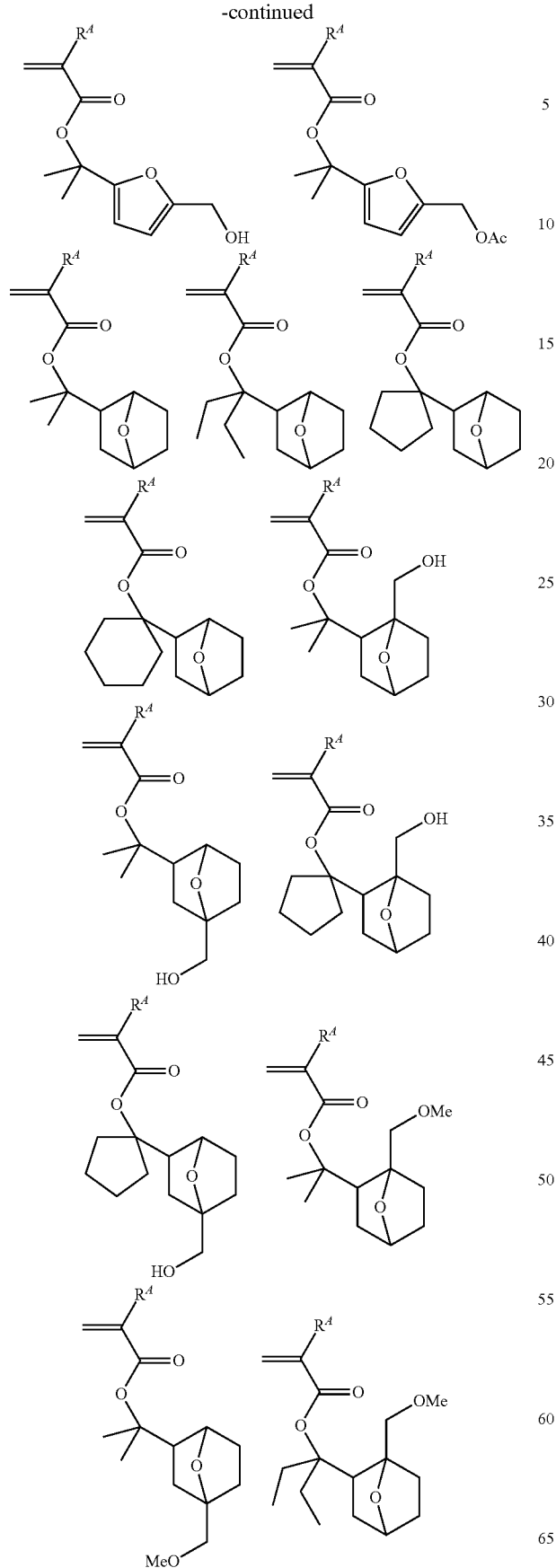
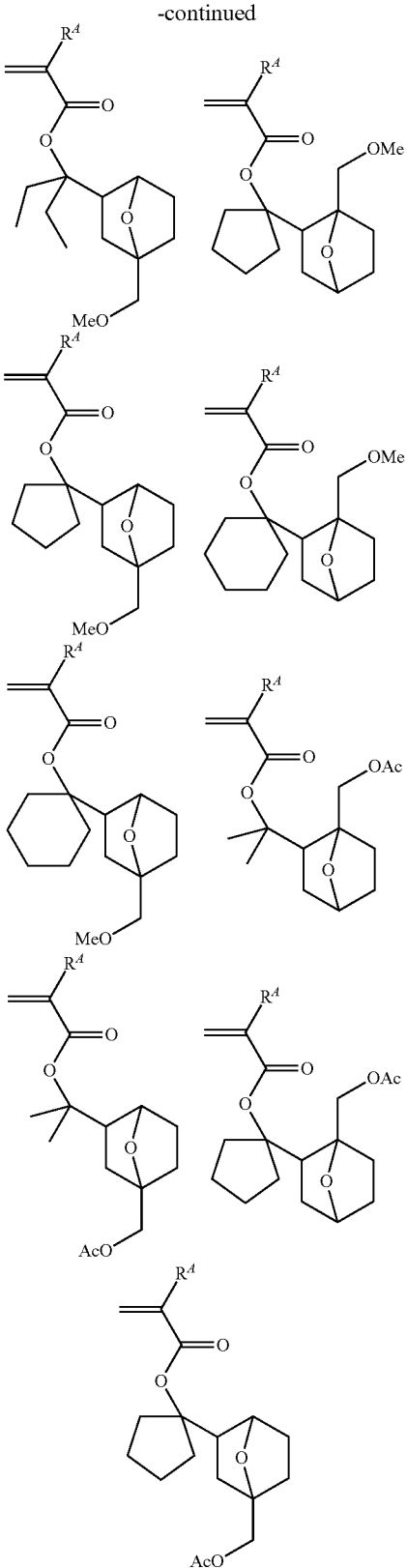
The base polymer may further include repeat units (b) having an adhesive group. The adhesive group is selected from hydroxy, carboxy, lactone ring, carbonate bond, thiocarbonate bond, carbonyl, cyclic acetal, ether bond, ester bond, sulfonic ester bond, cyano, amide, —O—C(=O)—S— and —O—C(=O)—NH—.
Examples of the monomer from which repeat units (b) are derived are given below, but not limited thereto. Herein $R^A$ is as defined above.
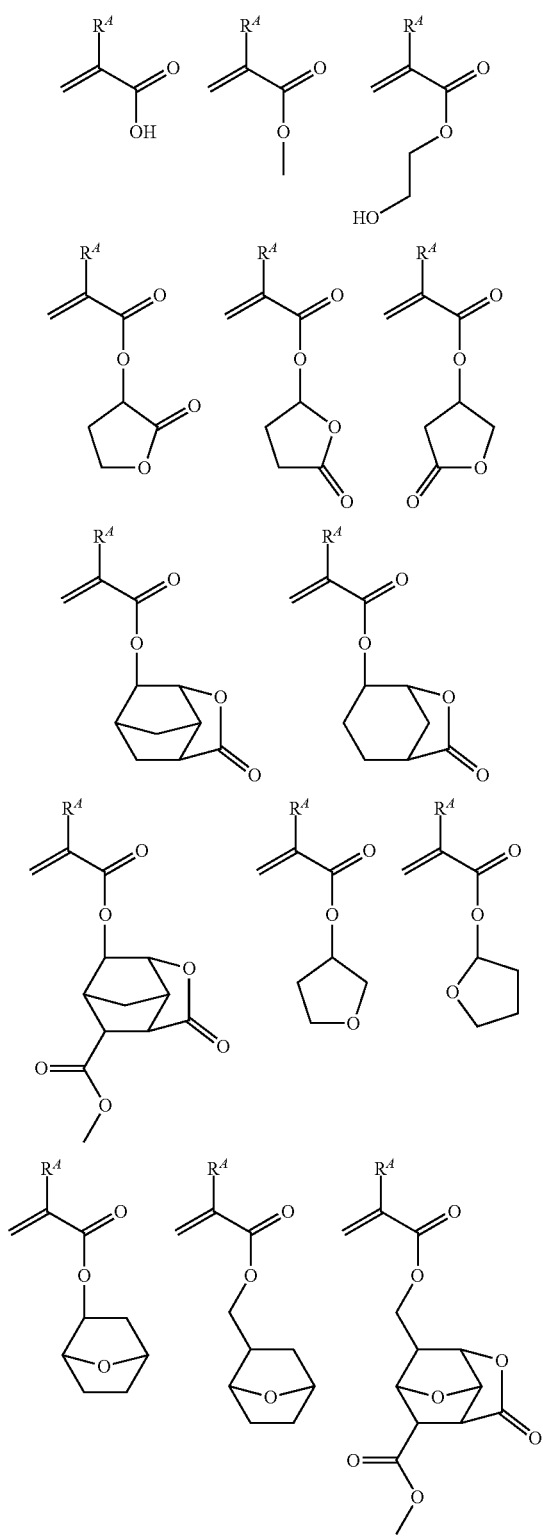
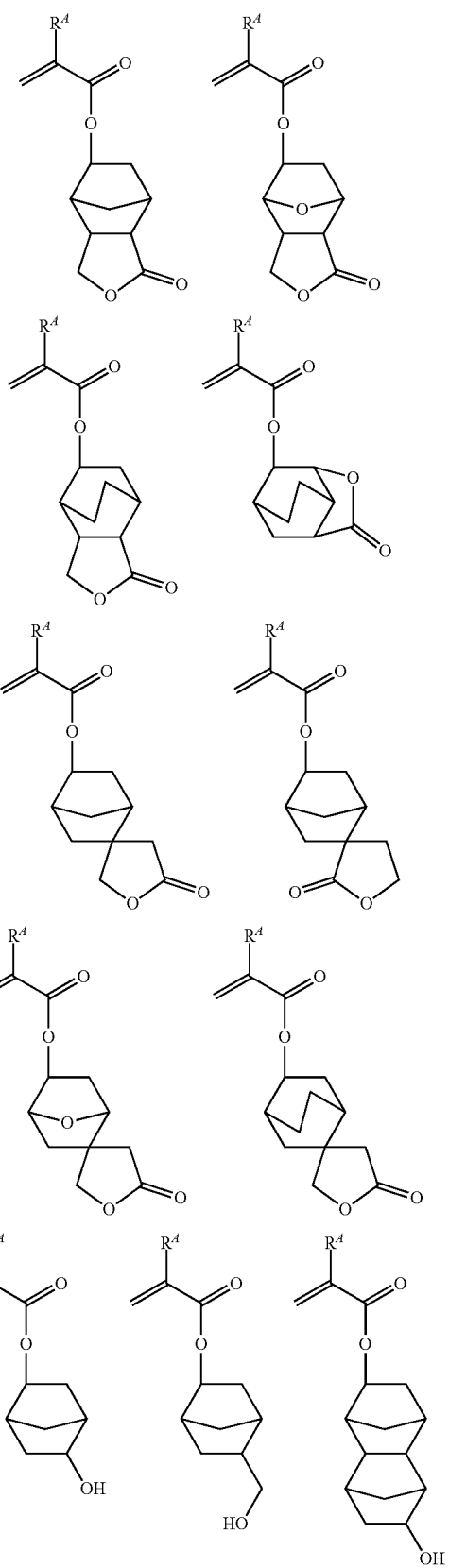

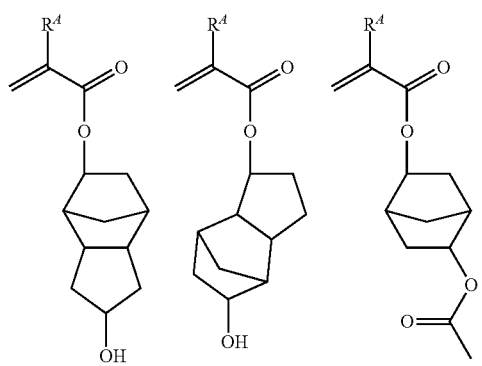
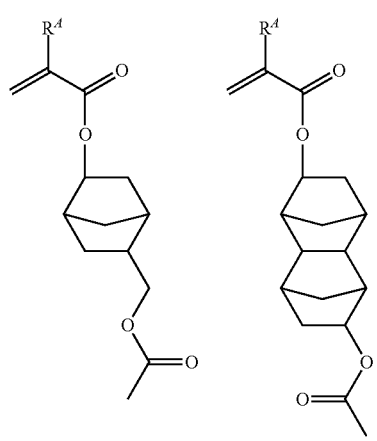
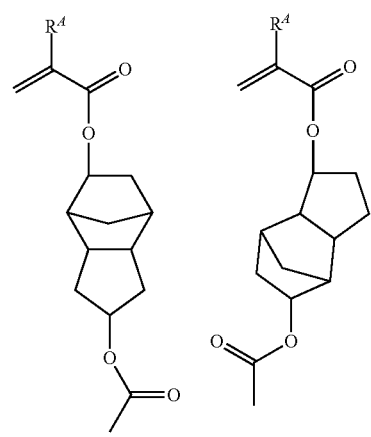
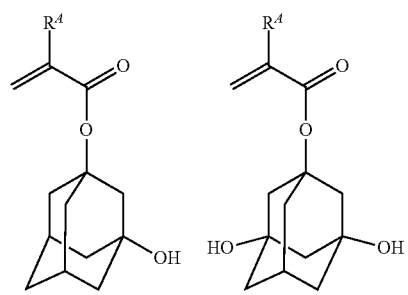
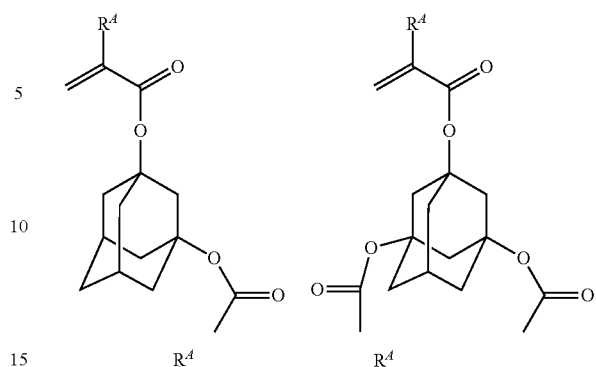
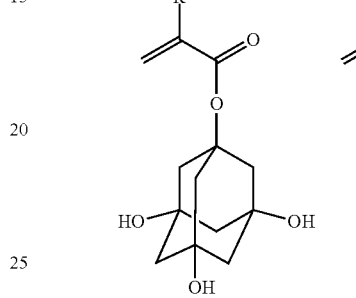
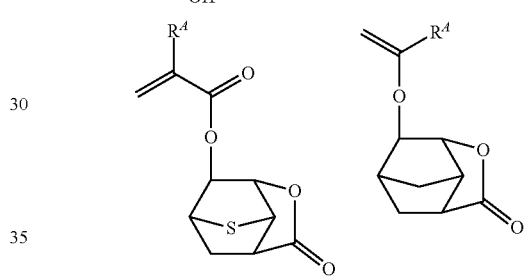
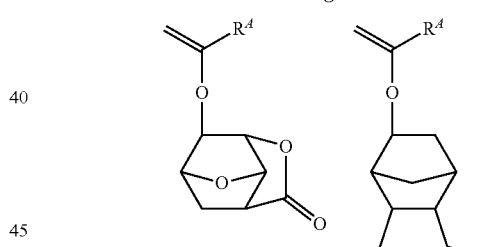
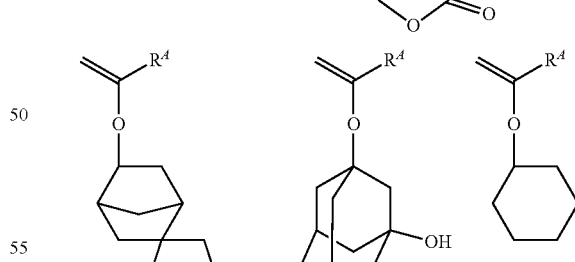
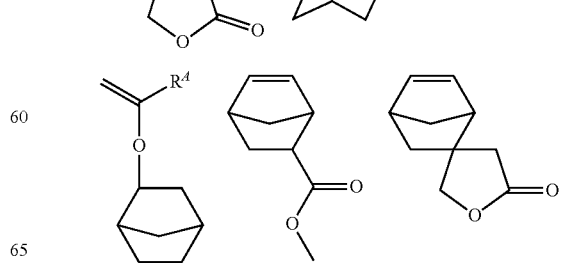

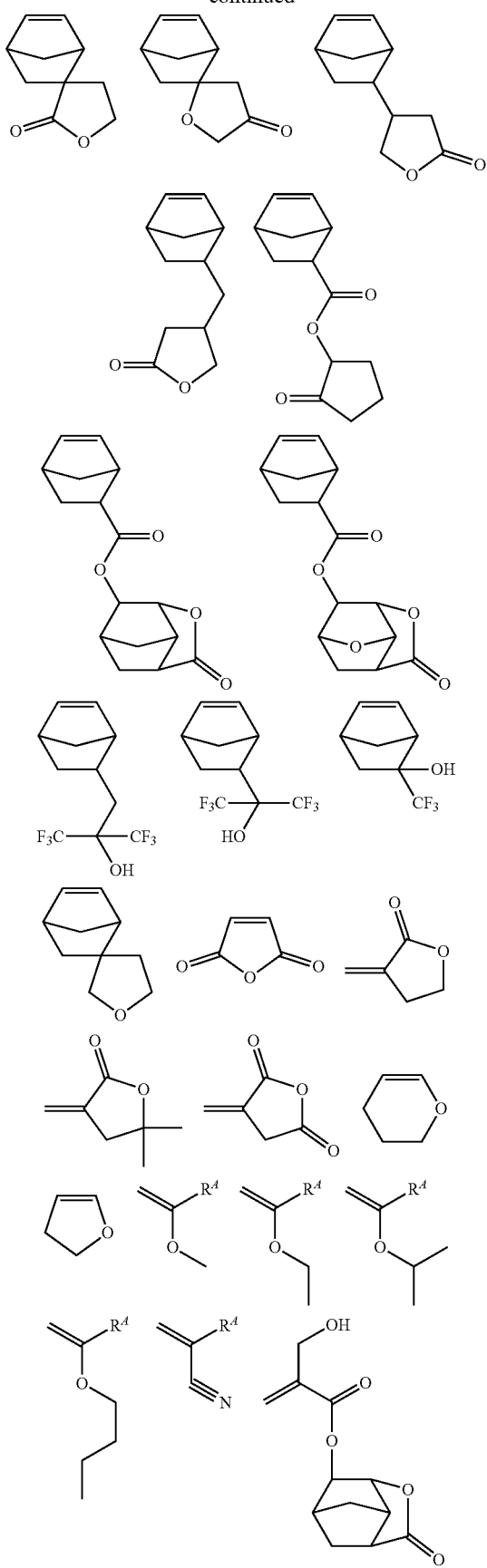
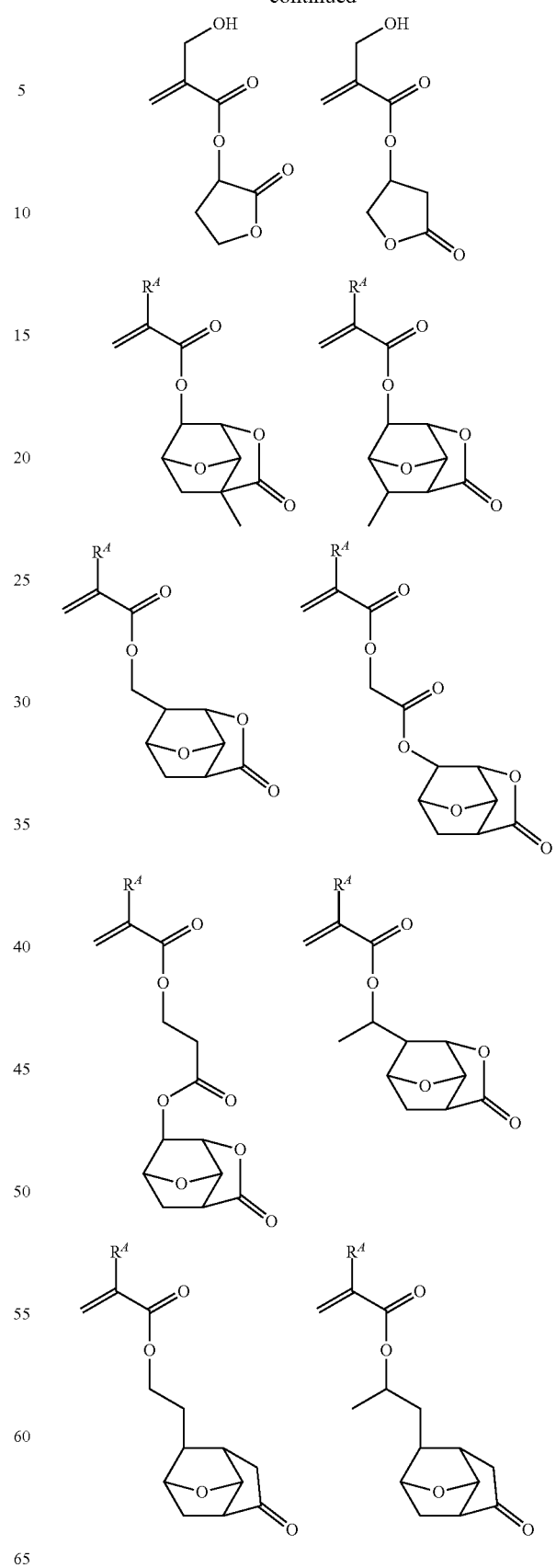

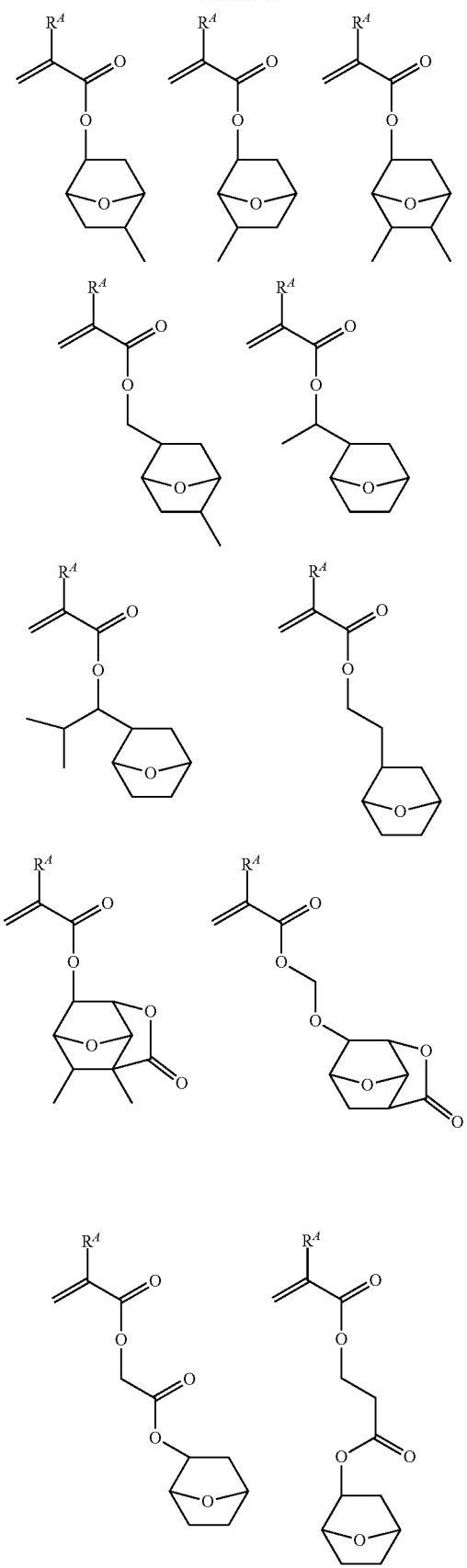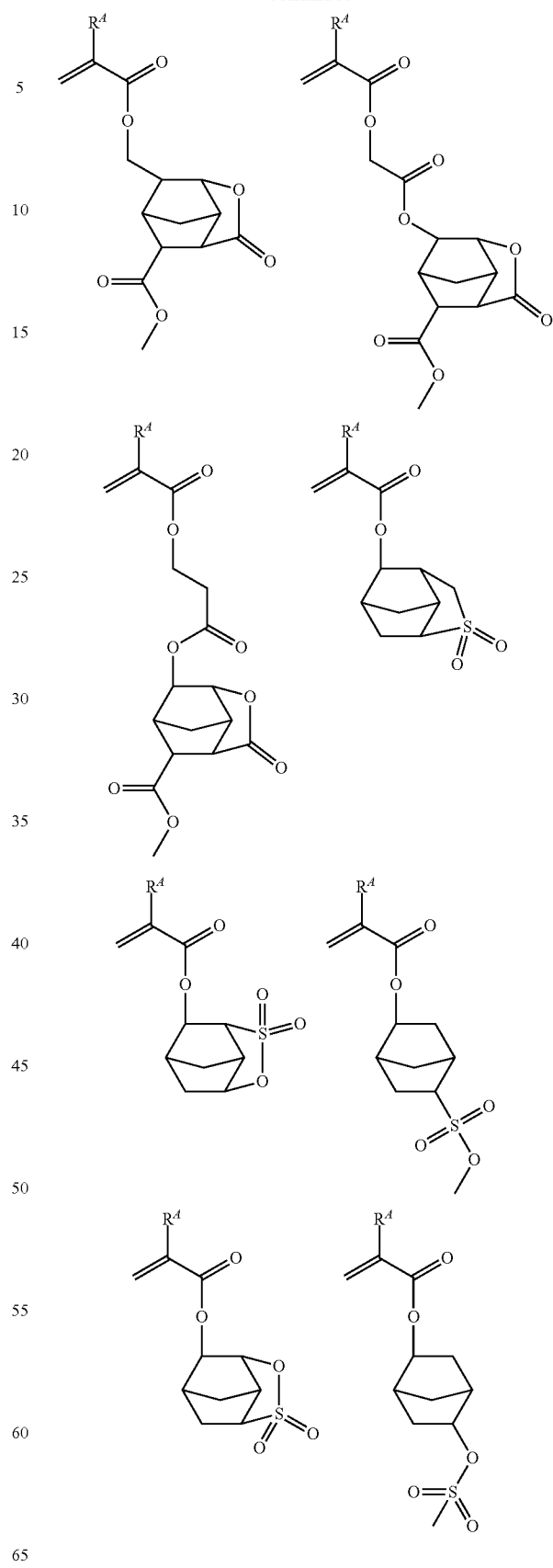

-continued
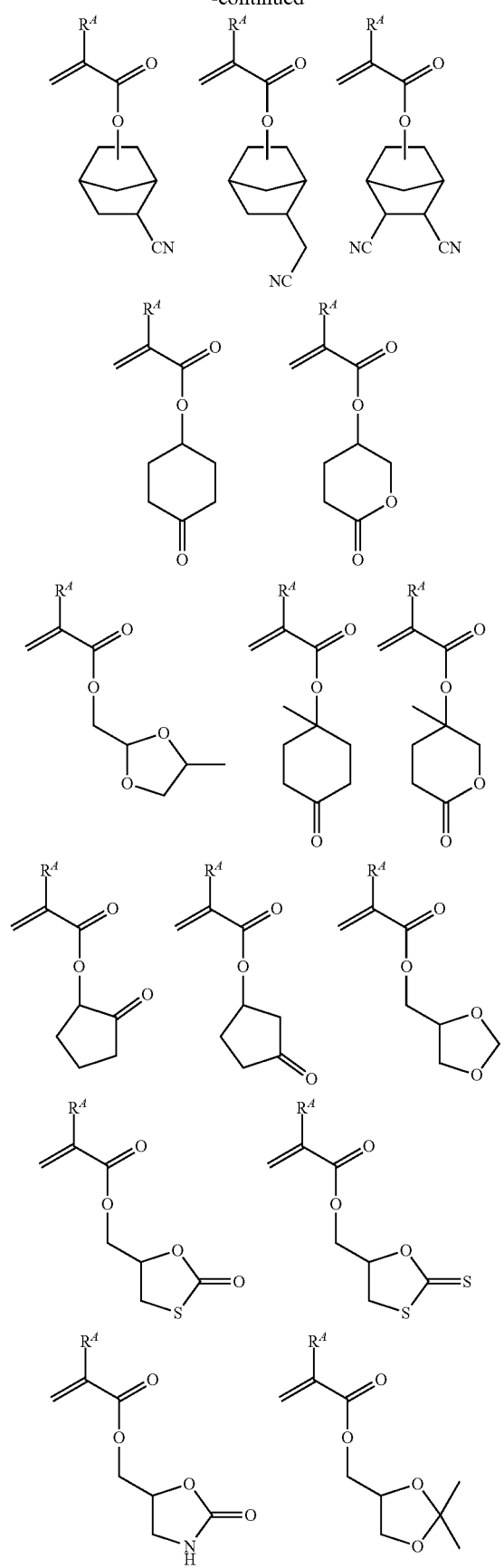
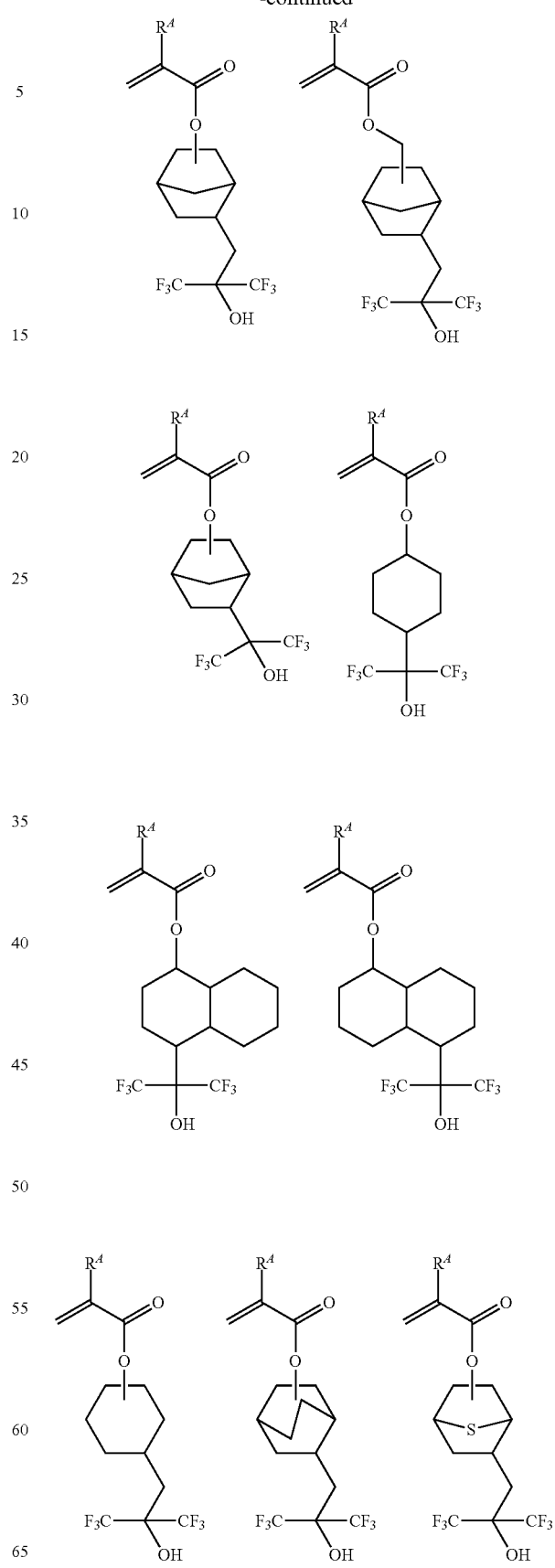

197
-continued
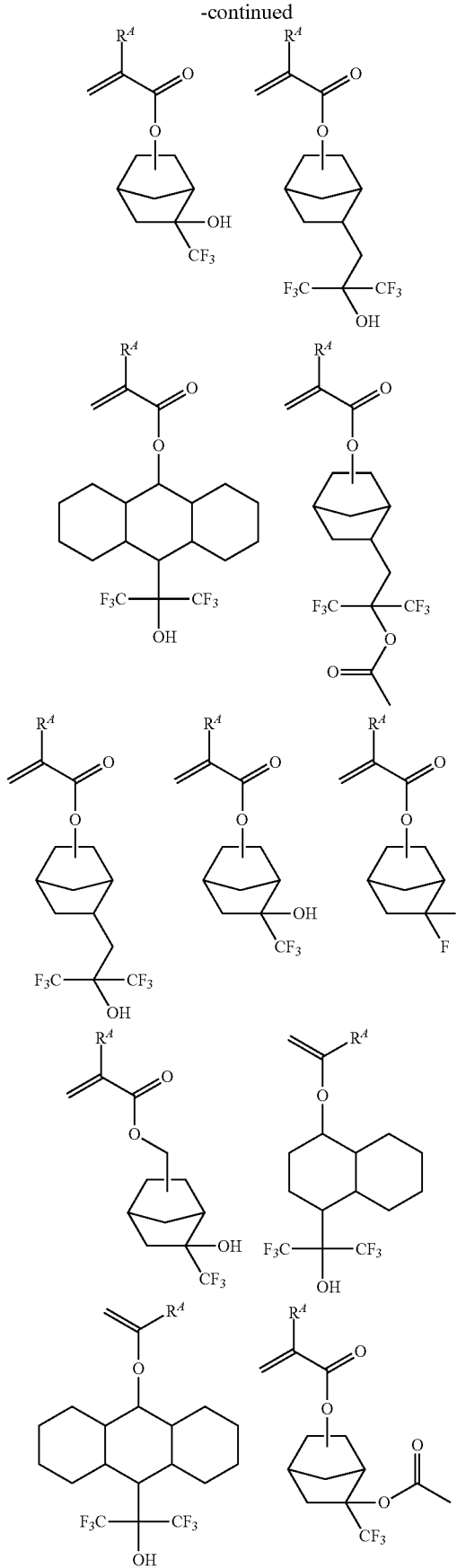
198
-continued
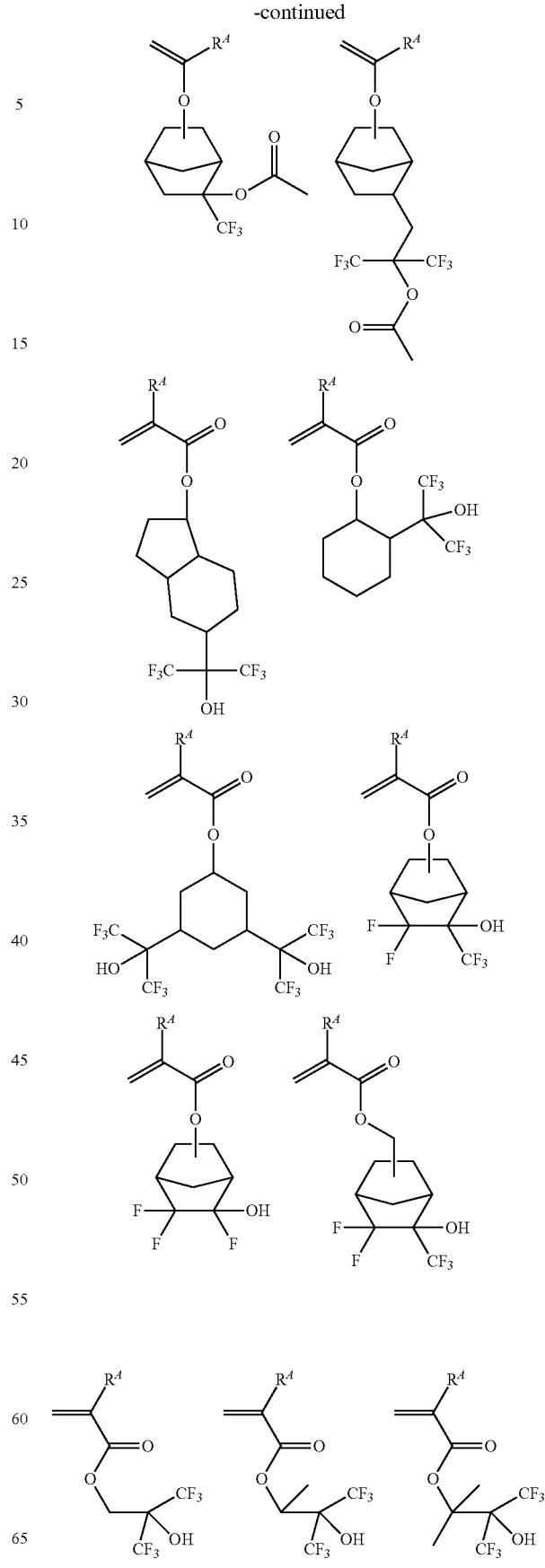

199
-continued
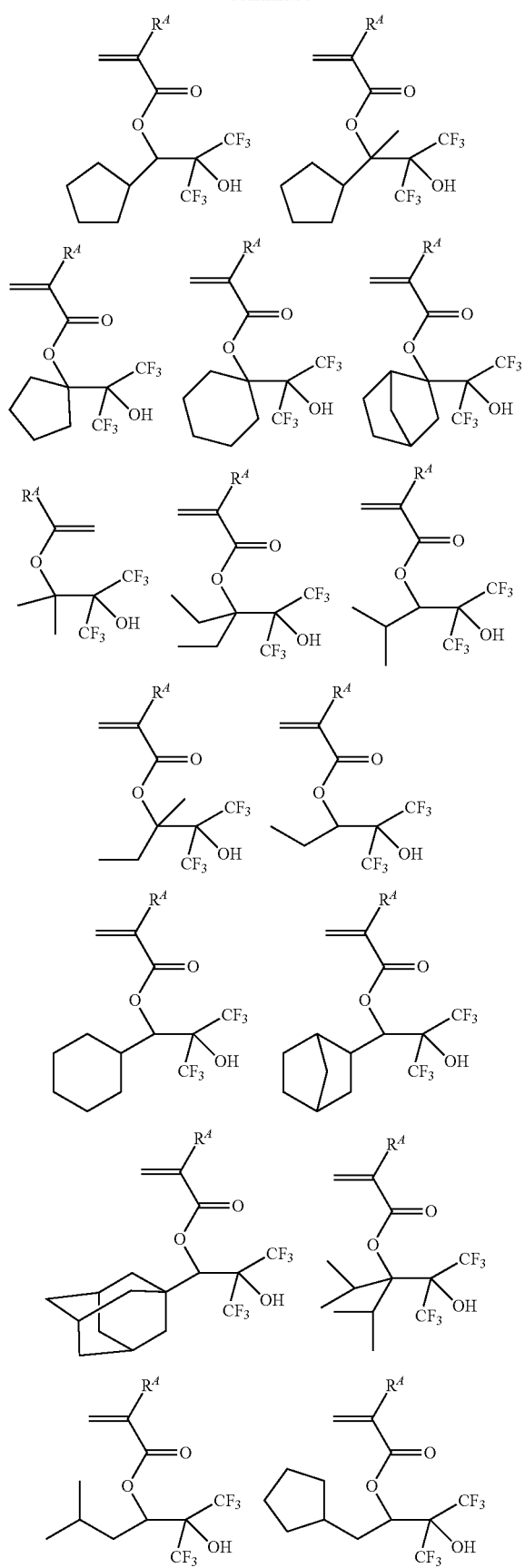
200
-continued
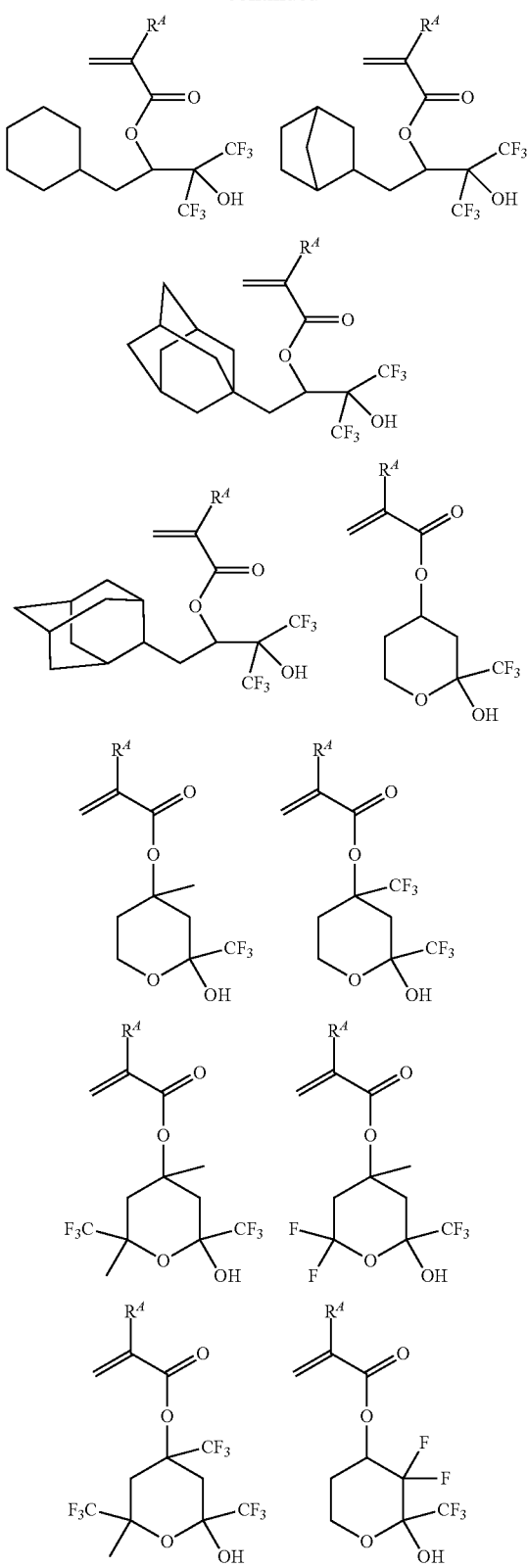

-continued
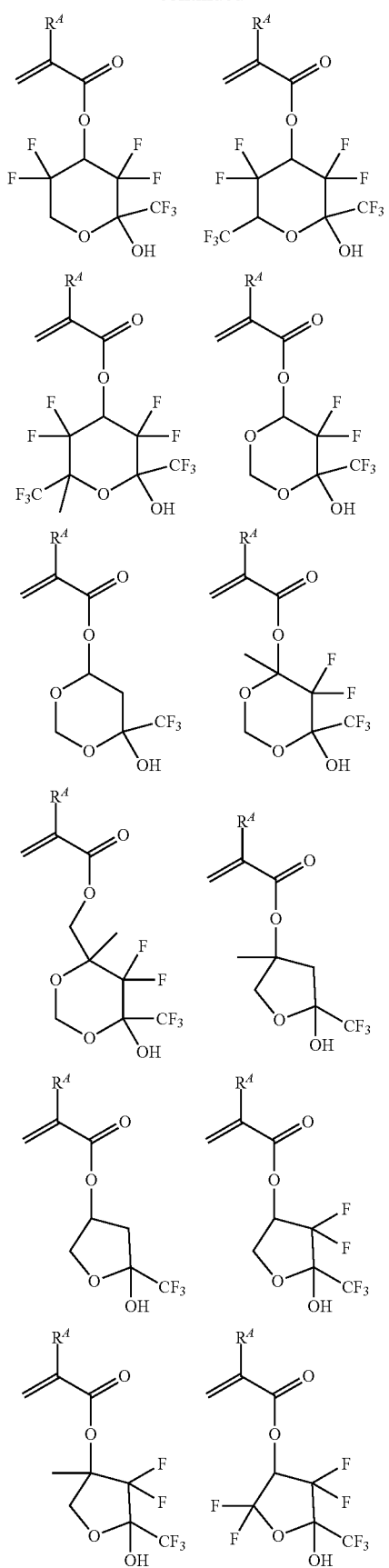
-continued
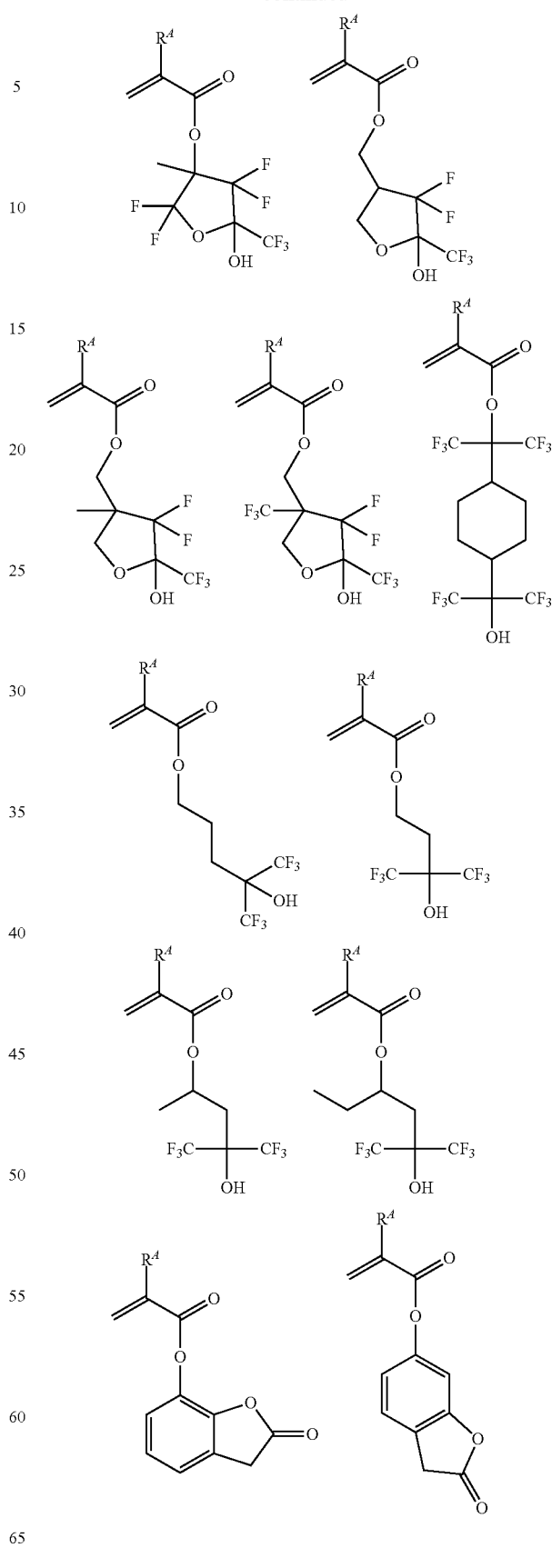

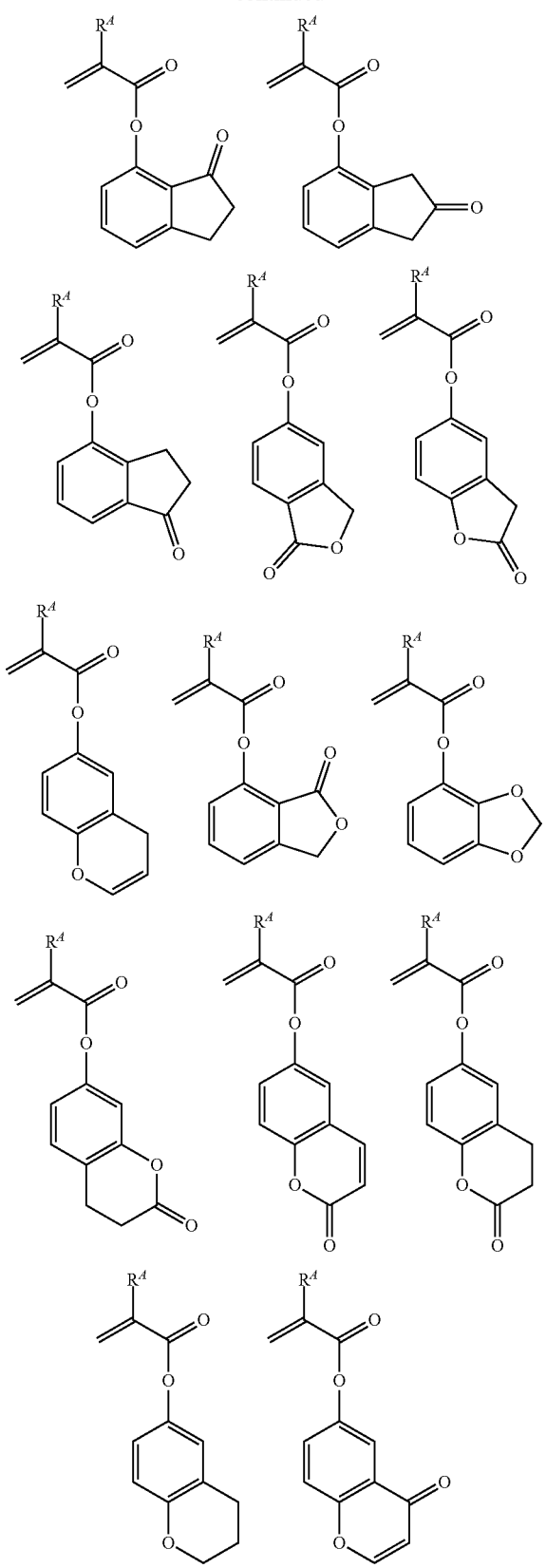
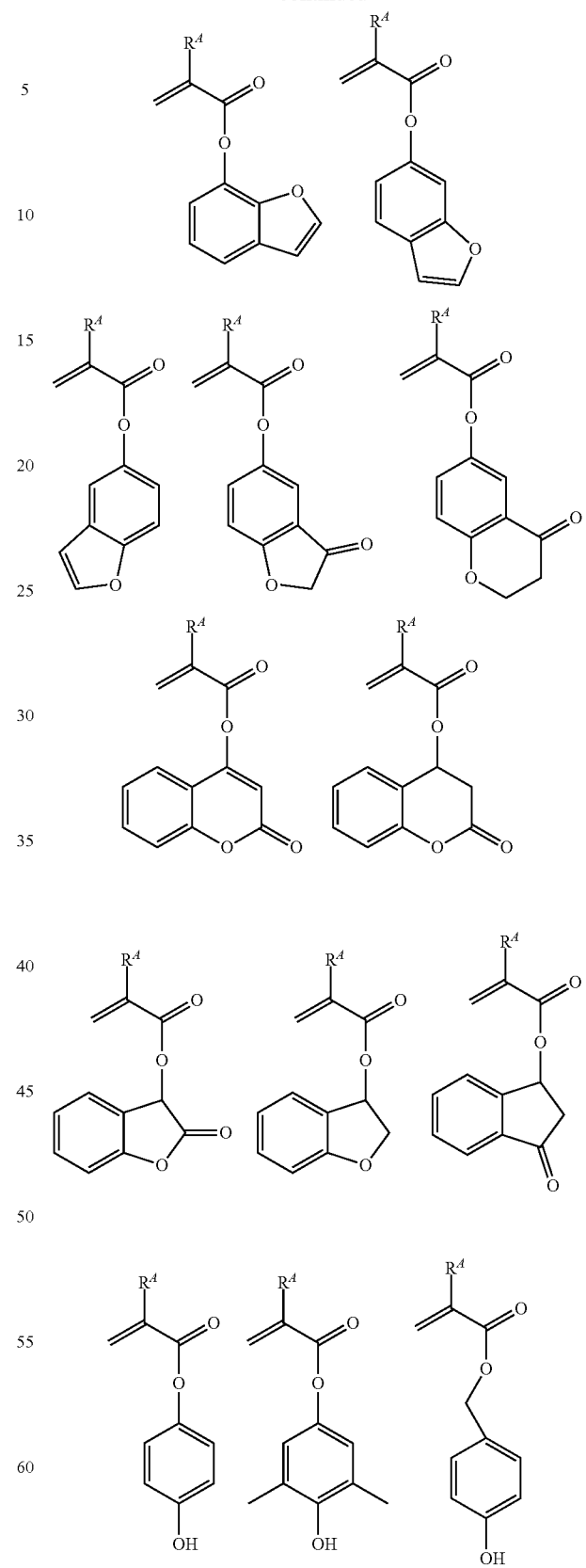

205
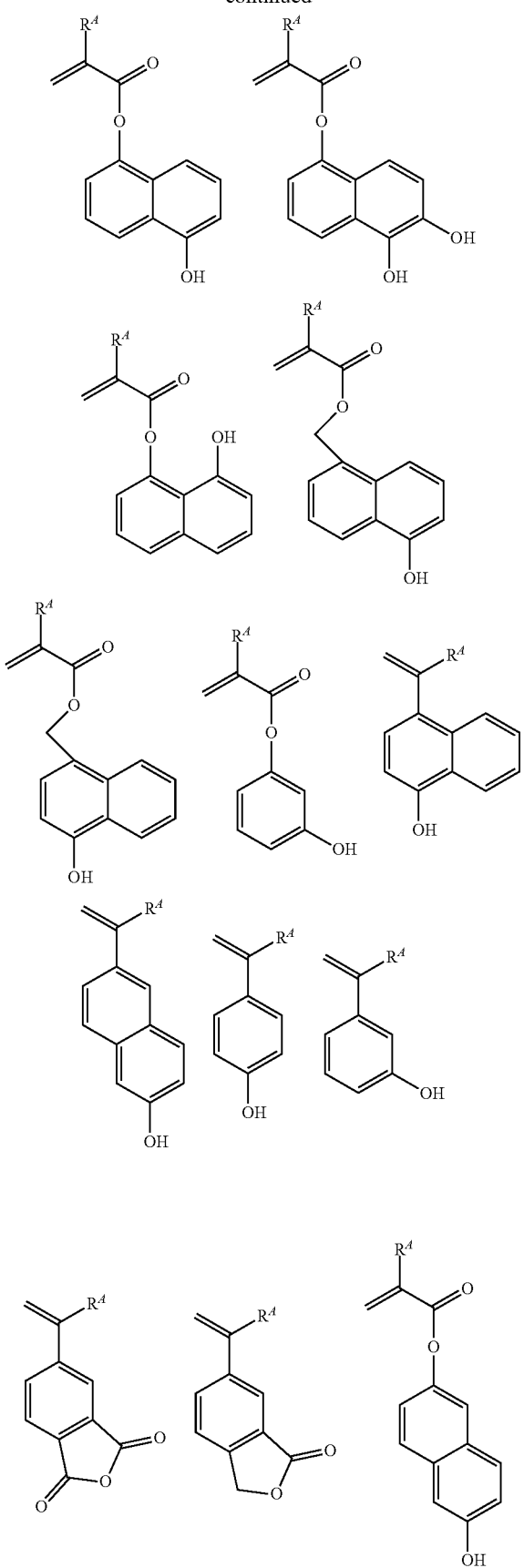
206
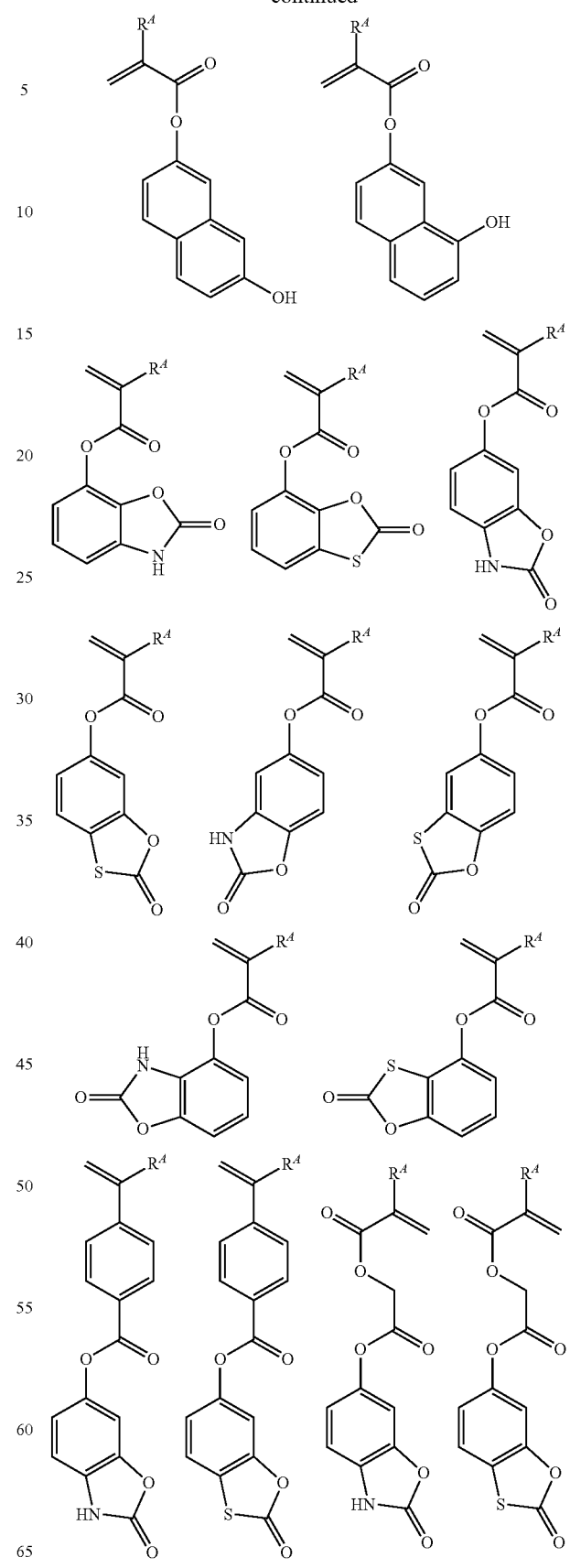

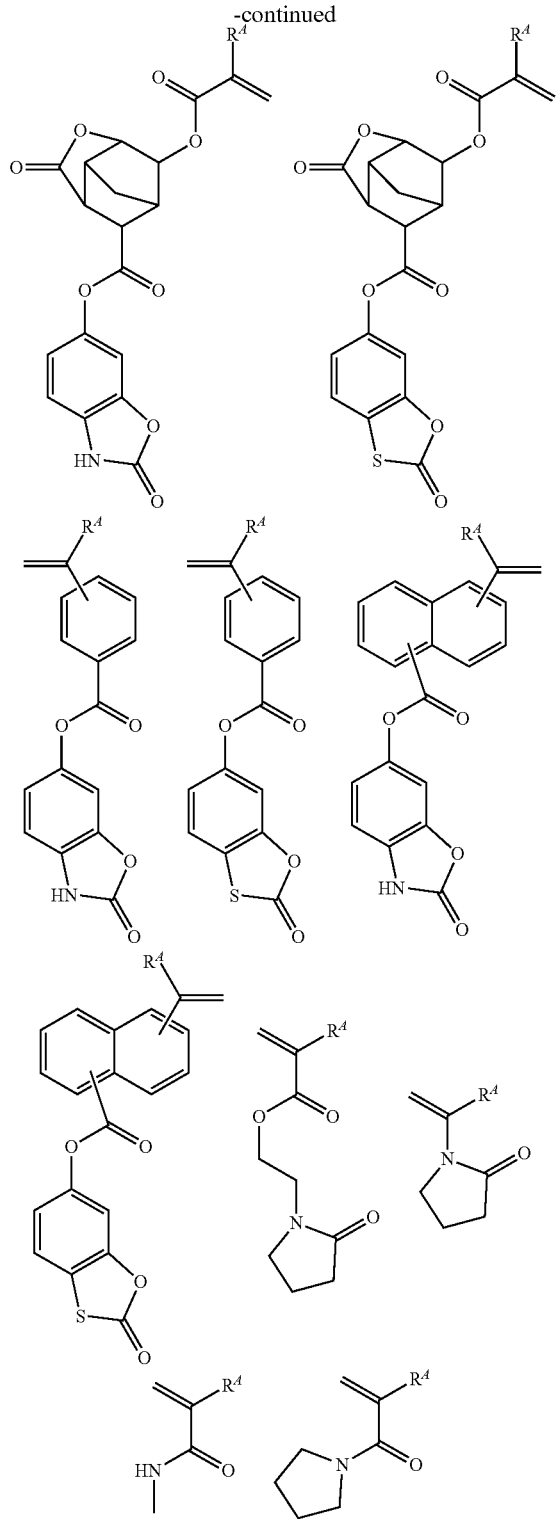

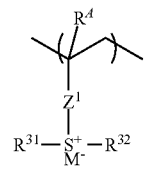

(c1)

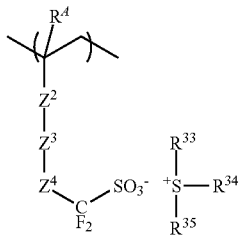

(c2)

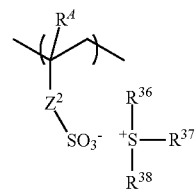

(c3)

The base polymer may further include repeat units (c) of at least one type selected from repeat units having the following formulae (c1), (c2) and (c3). These units are simply referred to as repeat units (c1), (c2) and (c3), which may be used alone or in combination of two or more types.

In formulae (c1) to (c3), $R^A$ is each independently hydrogen or methyl. $Z^1$ is a single bond, or a $C_1$-$C_6$ aliphatic hydrocarbylene group, phenylene group, naphthylene group, or a $C_7$-$C_{18}$ group obtained by combining the foregoing, or —O—$Z^{11}$—, —C(=O)—O—$Z^{11}$— or —C(=O)—NH—$Z^{11}$—, wherein $Z^{11}$ is a $C_1$-$C_6$ aliphatic hydrocarbylene group, phenylene group, naphthylene group, or a $C_7$-$C_{18}$ group obtained by combining the foregoing, which may contain a carbonyl moiety, ester bond, ether bond or hydroxy moiety. $Z^2$ is a single bond or ester bond. $Z^3$ is a single bond, —$Z^{31}$—C(=O)—O—, —$Z^{31}$—O—, or —$Z^{31}$—O—C(=O)—, wherein $Z^{31}$ is a $C_1$-$C_{12}$ hydrocarbylene group, phenylene group or a $C_7$-$C_{18}$ group obtained by combining the foregoing, which may contain a carbonyl moiety, ester bond, ether bond, bromine or iodine. $Z^4$ is methylene, 2,2,2-trifluoro-1,1-ethanediyl or carbonyl. $Z^5$ is a single bond, methylene, ethylene, phenylene, fluorinated phenylene, trifluoromethyl-substituted phenylene group, —O—$Z^{51}$—, —C(=O)—O—$Z^{51}$— or —C(=O)—NH—$Z^{51}$—, wherein $Z^{51}$ is a $C_1$-$C_6$ aliphatic hydrocarbylene group, phenylene group, fluorinated phenylene group, or trifluoromethyl-substituted phenylene group, which may contain a carbonyl moiety, ester bond, ether bond or hydroxy moiety.

In formulae (c1) to (c3), $R^{31}$ to $R^{38}$ are each independently halogen or a $C_1$-$C_{20}$ hydrocarbyl group which may contain a heteroatom. The hydrocarbyl group may be saturated or unsaturated and straight, branched or cyclic. Examples thereof include $C_1$-$C_{20}$ alkyl groups such as methyl, ethyl, n-propyl, isopropyl, n-butyl, isobutyl, sec-butyl, tert-butyl, n-pentyl, n-hexyl, n-octyl, n-nonyl, n-decyl, undecyl, dodecyl, tridecyl, tetradecyl, pentadecyl, heptadecyl, octadecyl, nonadecyl and icosyl; $C_3$-$C_{20}$ cyclic saturated hydrocarbyl groups such as cyclopropyl, cyclopentyl, cyclohexyl, cyclopropylmethyl, 4-methylcyclohexyl, cyclohexylmethyl, norbornyl, adamantyl; $C_2$-$C_{20}$ alkenyl groups such as vinyl, propenyl, butenyl, hexenyl; $C_3$-$C_{20}$ unsaturated alicyclic hydrocarbyl groups such as cyclohexenyl and norbornenyl; $C_2$-$C_{20}$ alkynyl groups such as ethynyl, propynyl, butynyl;

$C_6$-$C_{20}$ aryl groups such as phenyl, methylphenyl, ethylphenyl, n-propylphenyl, isopropylphenyl, n-butylphenyl, isobutylphenyl, sec-butylphenyl, tert-butylphenyl, naphthyl, methylnaphthyl, ethylnaphthyl, n-propylnaphthyl, isopropylnaphthyl, n-butylnaphthyl, isobutylnaphthyl, sec-butylnaphthyl, tert-butylnaphthyl; and $C_7$-$C_{20}$ aralkyl groups such as benzyl and phenethyl. In these groups, some hydrogen may be substituted by a moiety containing a heteroatom such as oxygen, sulfur, nitrogen or halogen, or some carbon may be replaced by a moiety containing a heteroatom such as oxygen, sulfur or nitrogen, so that the group may contain a hydroxy moiety, halogen, cyano moiety, carbonyl moiety, ether bond, ester bond, sulfonic ester bond, carbonate moiety, lactone ring, sultone ring, carboxylic anhydride or haloalkyl moiety.

Also, a pair of $R^{33}$ and $R^{34}$, or $R^{36}$ and $R^{37}$ may bond together to form a ring with the sulfur atom to which they are attached. Inter aha, rings of the following structure are preferred.

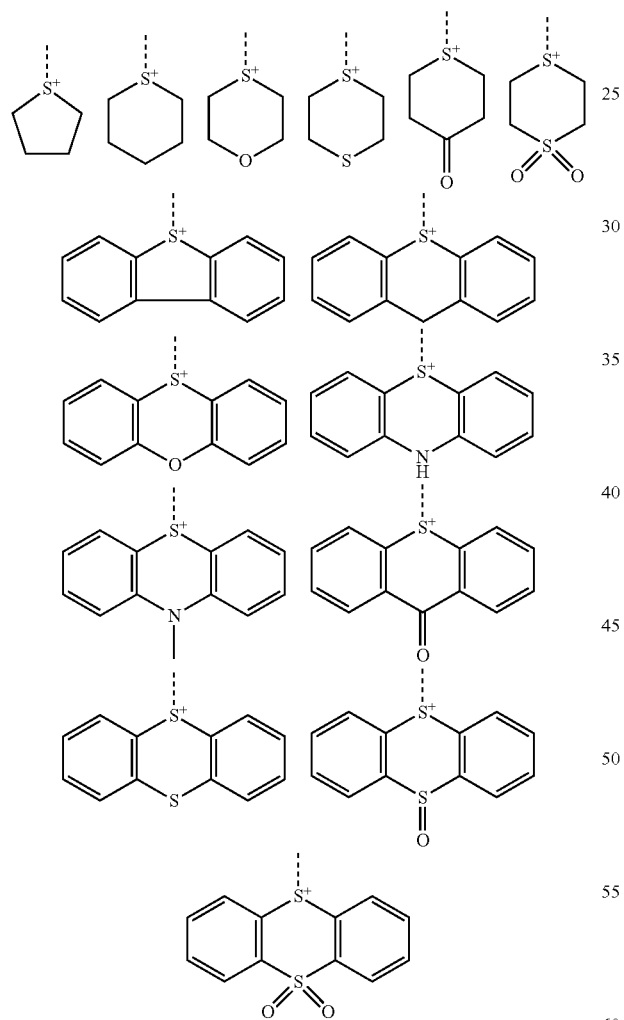

In formula (c1), M⁻ is a non-nucleophilic counter ion. Examples of the non-nucleophilic counter ion include halide ions such as chloride and bromide ions; fluoroalkylsulfonate ions such as triflate, 1,1,1-trifluoroethanesulfonate, and nonafluorobutanesulfonate; arylsulfonate ions such as tosylate, benzenesulfonate, 4-fluorobenzenesulfonate, and 1,2,3,4,5-pentafluorobenzenesulfonate; alkyl sulfonate ions such as mesylate and butanesulfonate; imide ions such as bis(trifluoromethylsulfonyl)imide, bis(perfluoroethylsulfonyl)imide and bis(perfluorobutylsulfonyl)imide; methide ions such as tris(trifluoromethylsulfonyl)methide and tris(perfluoroethylsulfonyl)methide.

Also included are sulfonate ions having fluorine substituted at α-position as represented by the formula (c1-1) and sulfonate ions having fluorine substituted at α-position and trifluoromethyl at β-position as represented by the formula (c1-2).

 (c1-1)

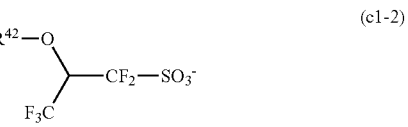 (c1-2)

In formula (c1-1), $R^{41}$ is hydrogen, or a $C_1$-$C_{20}$ hydrocarbyl group which may contain an ether bond, ester bond, carbonyl moiety, lactone ring, or fluorine atom. The hydrocarbyl group may be saturated or unsaturated and straight, branched or cyclic and examples thereof are as exemplified above for the hydrocarbyl group $R^{1a}$ in formula (1-1-1).

In formula (c1-2), $R^{42}$ is hydrogen, or a $C_1$-$C_{30}$ hydrocarbyl group or $C_2$-$C_{30}$ hydrocarbylcarbonyl group which may contain an ether bond, ester bond, carbonyl moiety or lactone ring. The hydrocarbyl group and hydrocarbyl moiety in the hydrocarbylcarbonyl group may be saturated or unsaturated and straight, branched or cyclic and examples thereof are as exemplified above for the hydrocarbyl group $R^{1a}$ in formula (1-1-1).

Examples of the cation in the monomer from which repeat unit (c1) is derived are shown below, but not limited thereto. $R^A$ is as defined above.

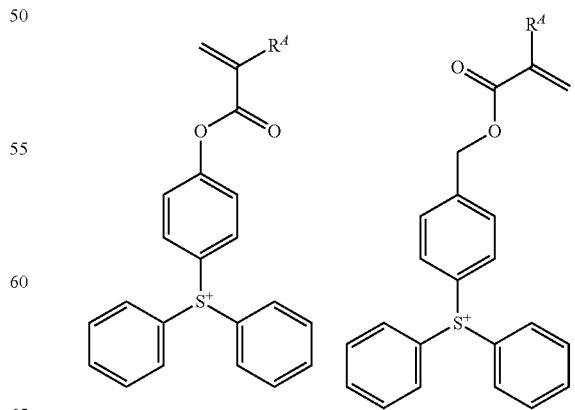

211
-continued
212
-continued
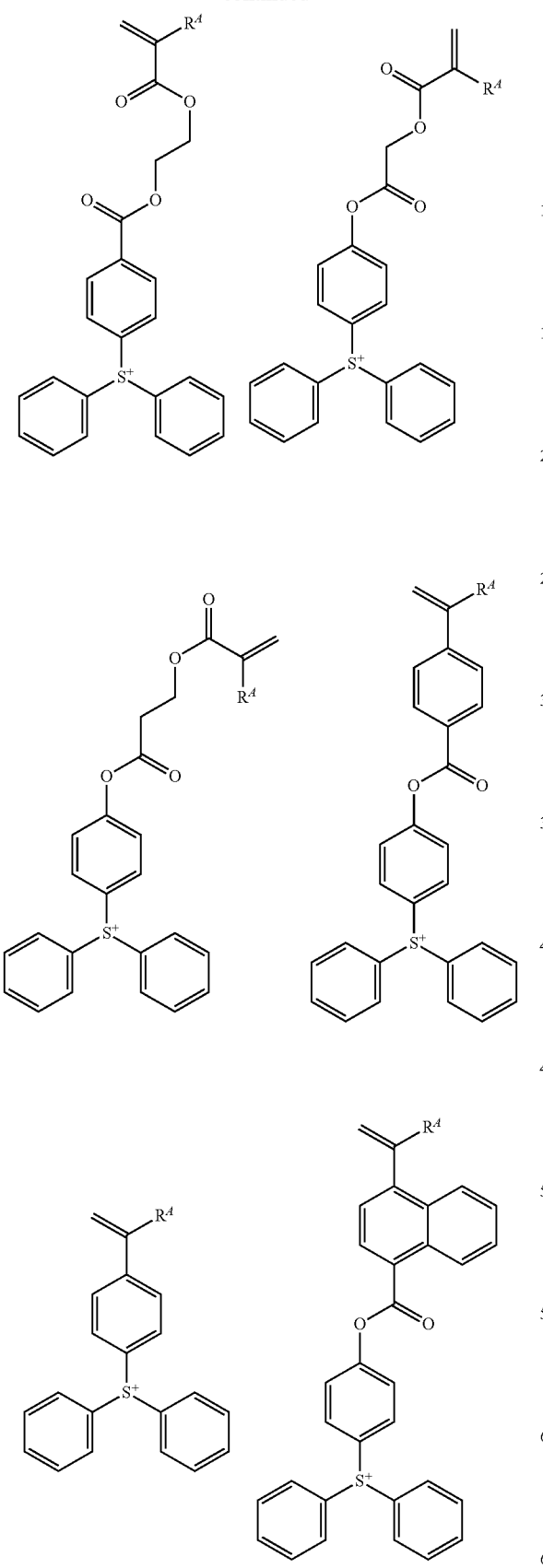
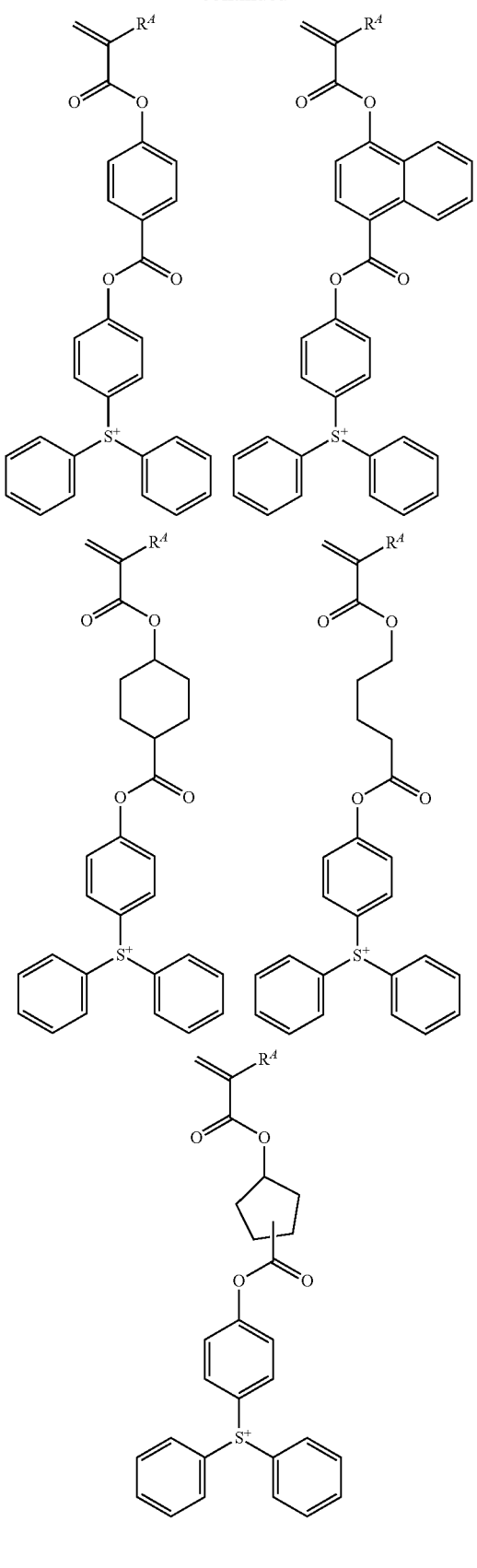

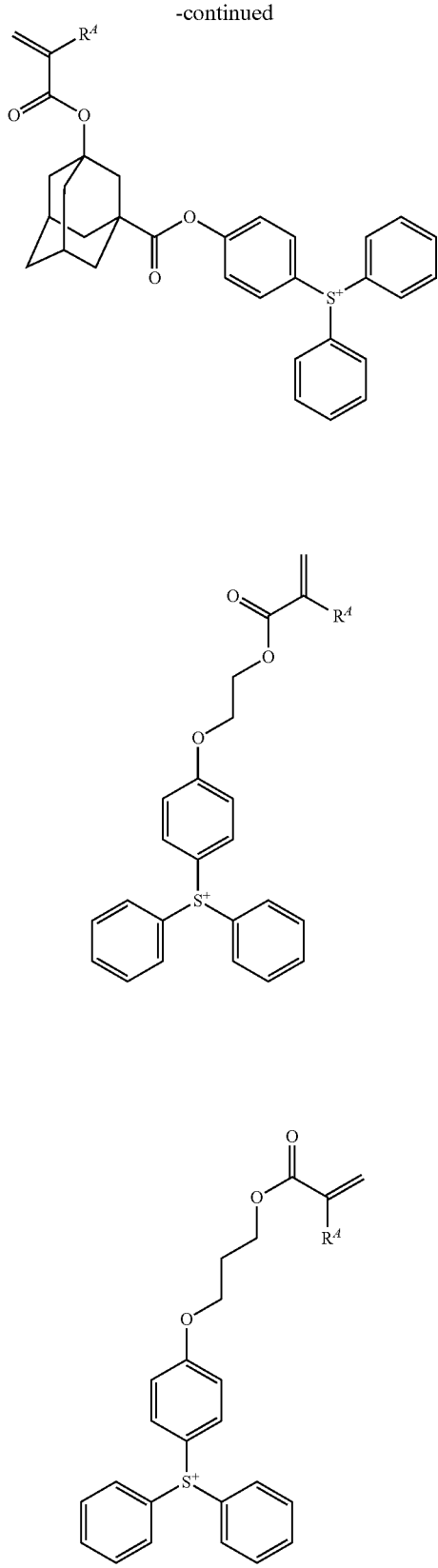
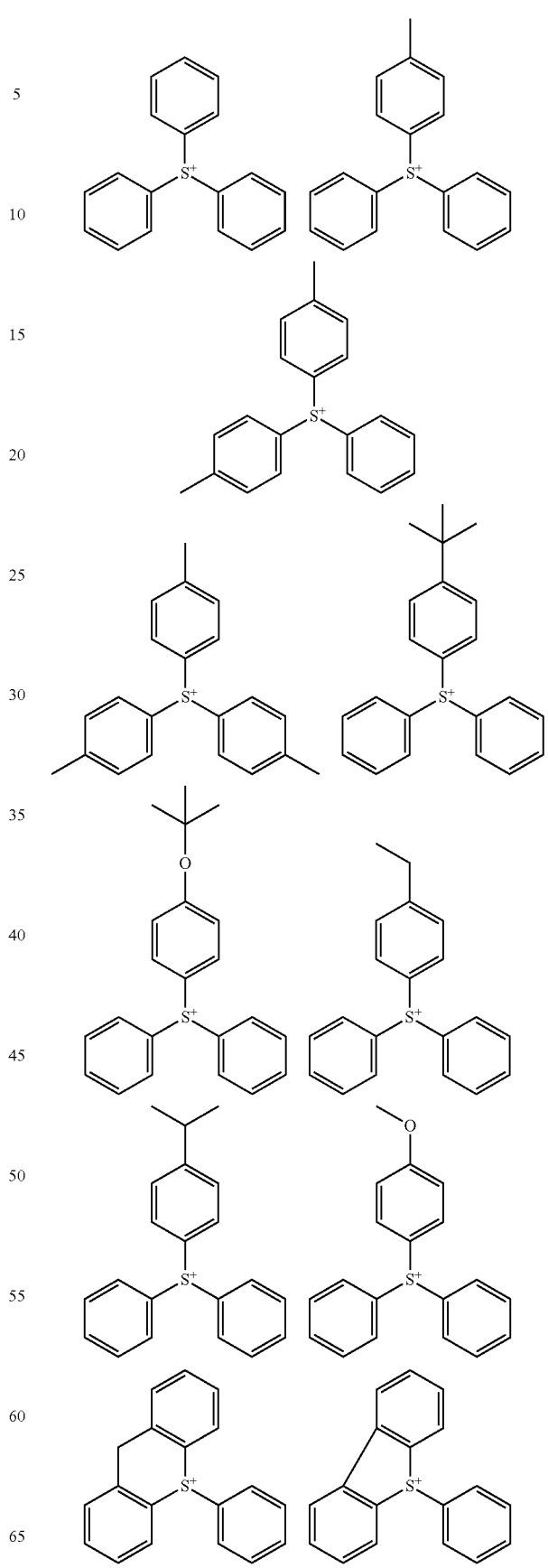
Examples of the cation in the monomer from which repeat unit (c2) or (c3) is derived are shown below, but not limited thereto.

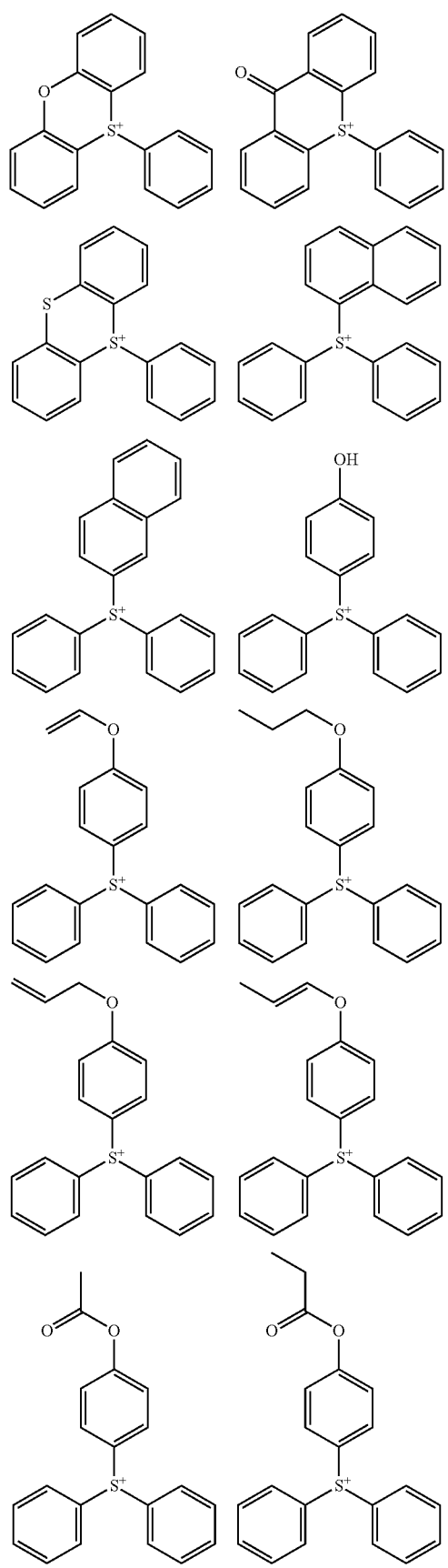
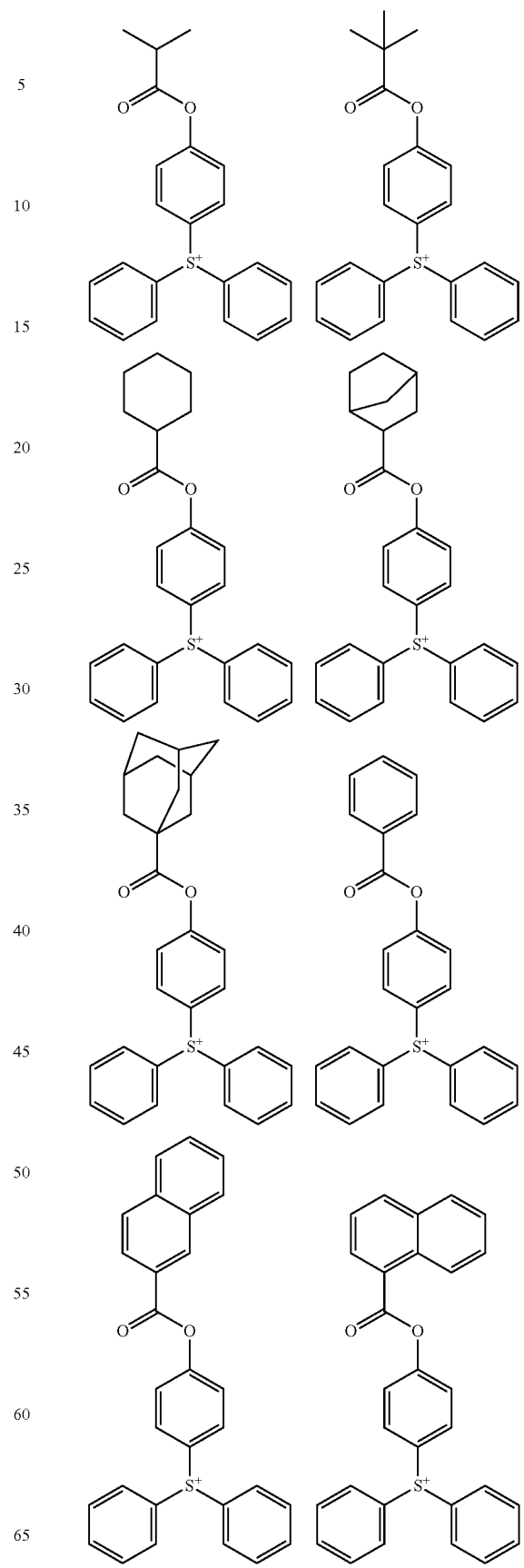

217
-continued
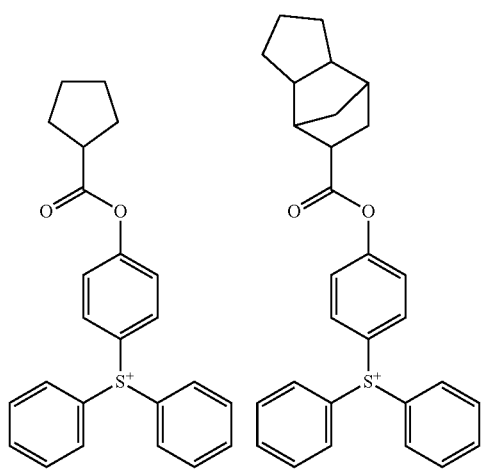
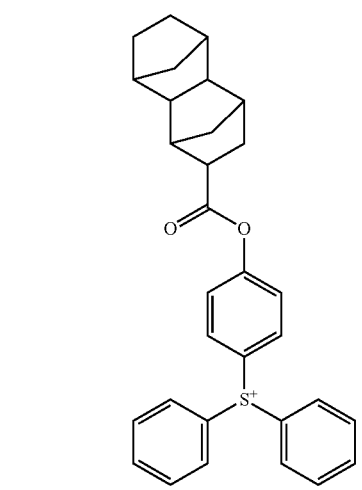
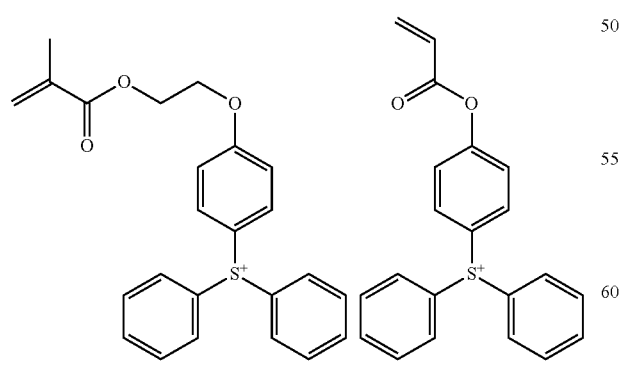
218
-continued
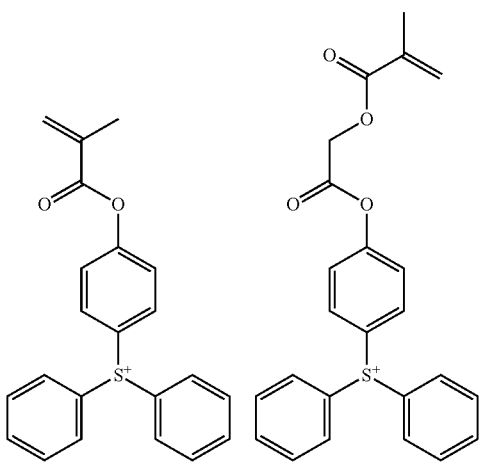
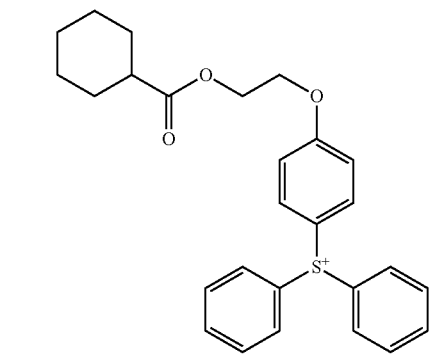
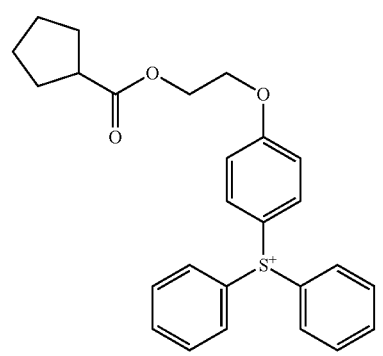
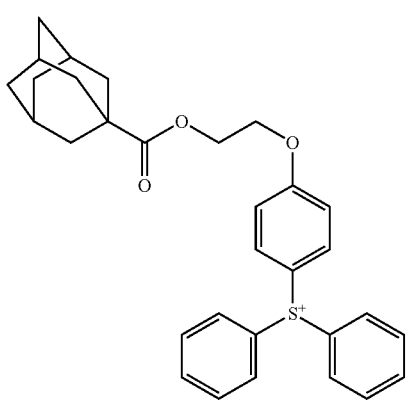

219
-continued
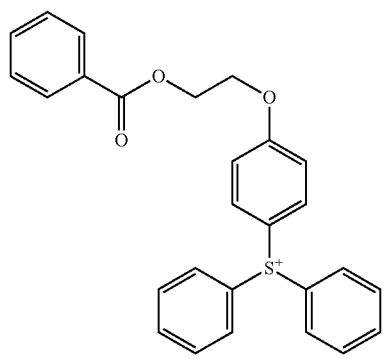
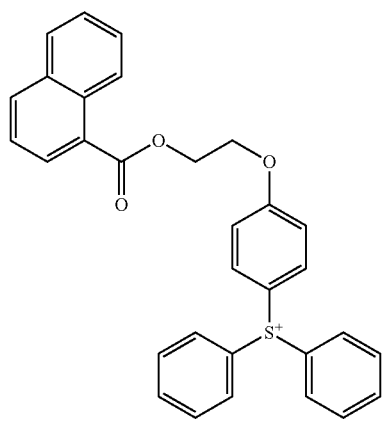
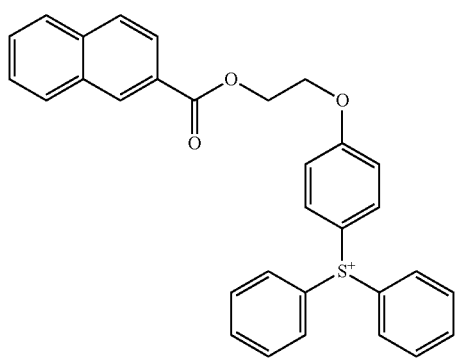
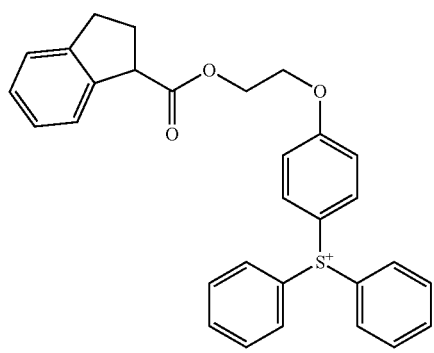
220
-continued
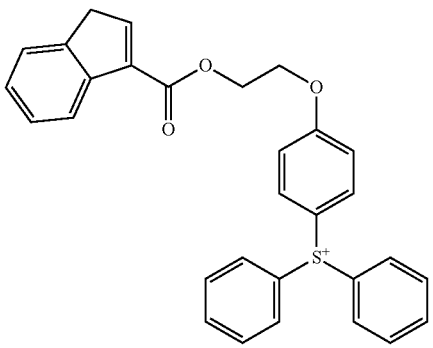
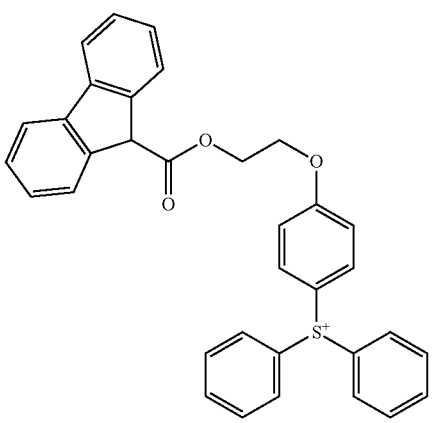
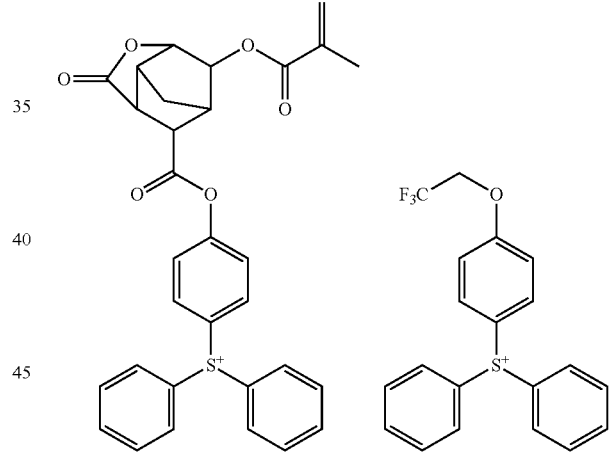
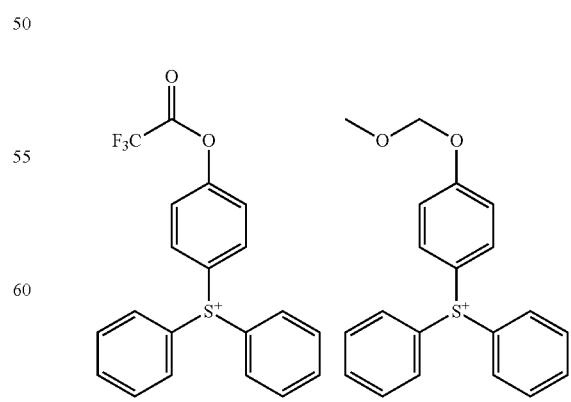

221
-continued
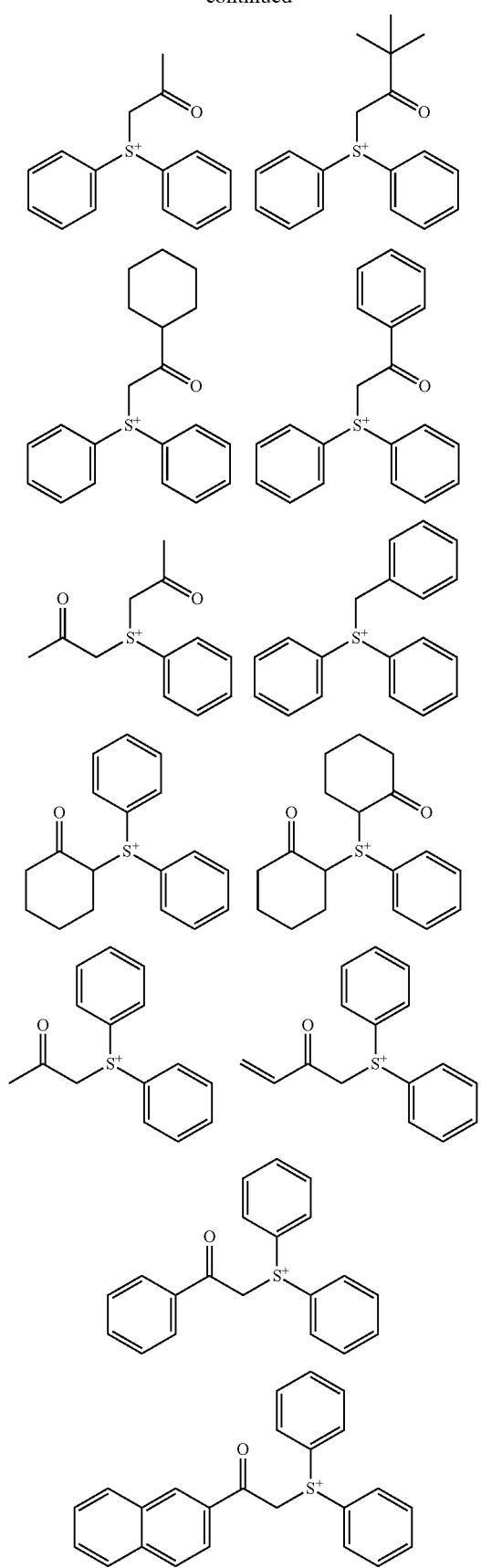
222
-continued
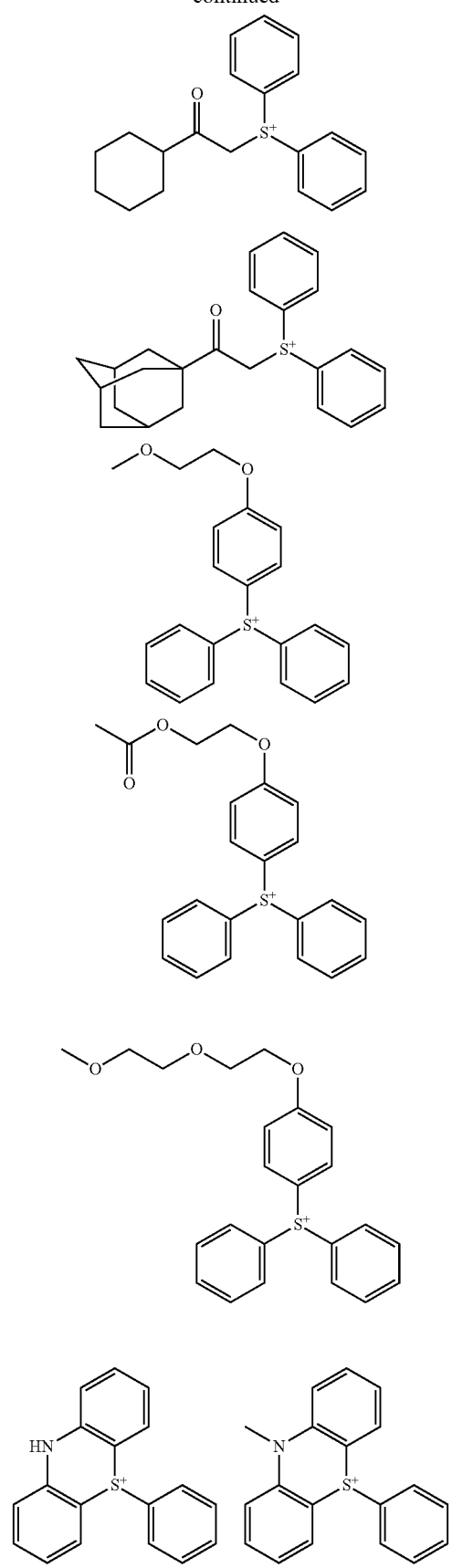

223
-continued
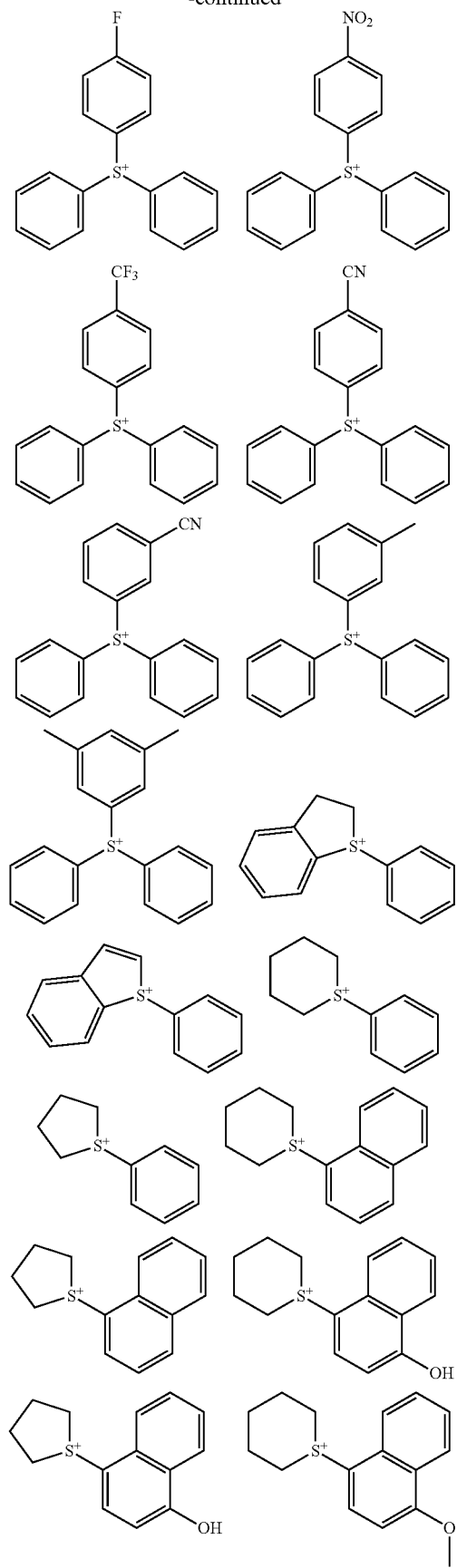
224
-continued
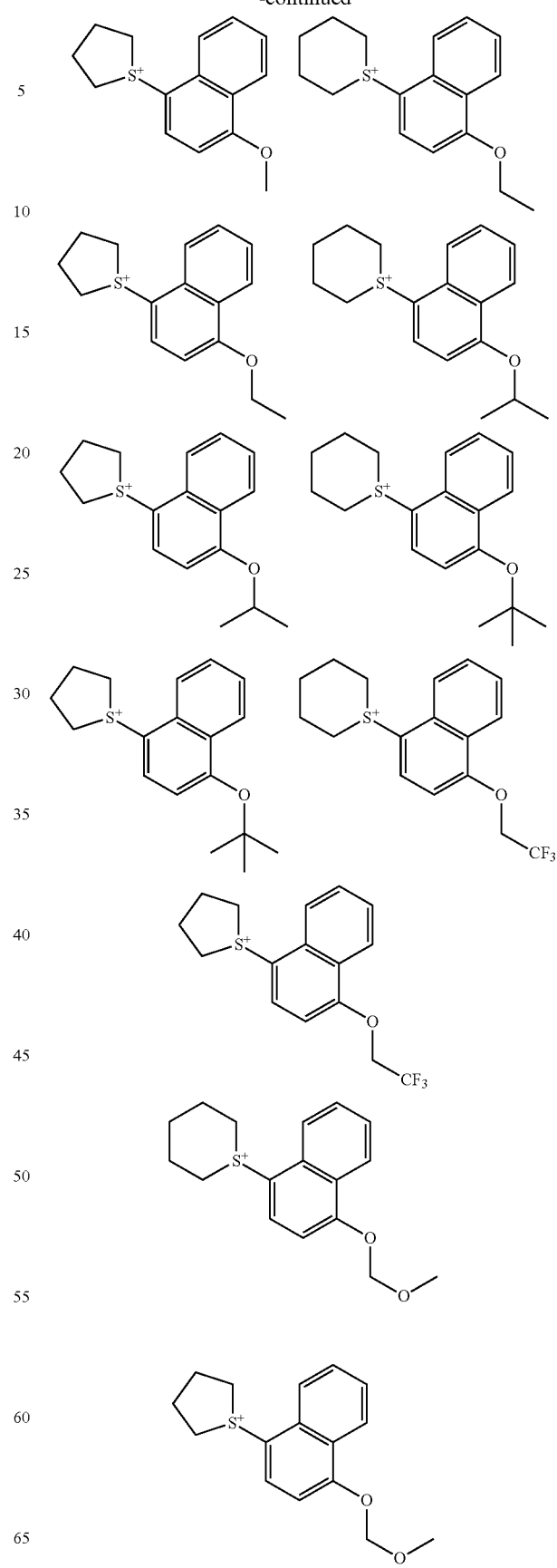

225
-continued
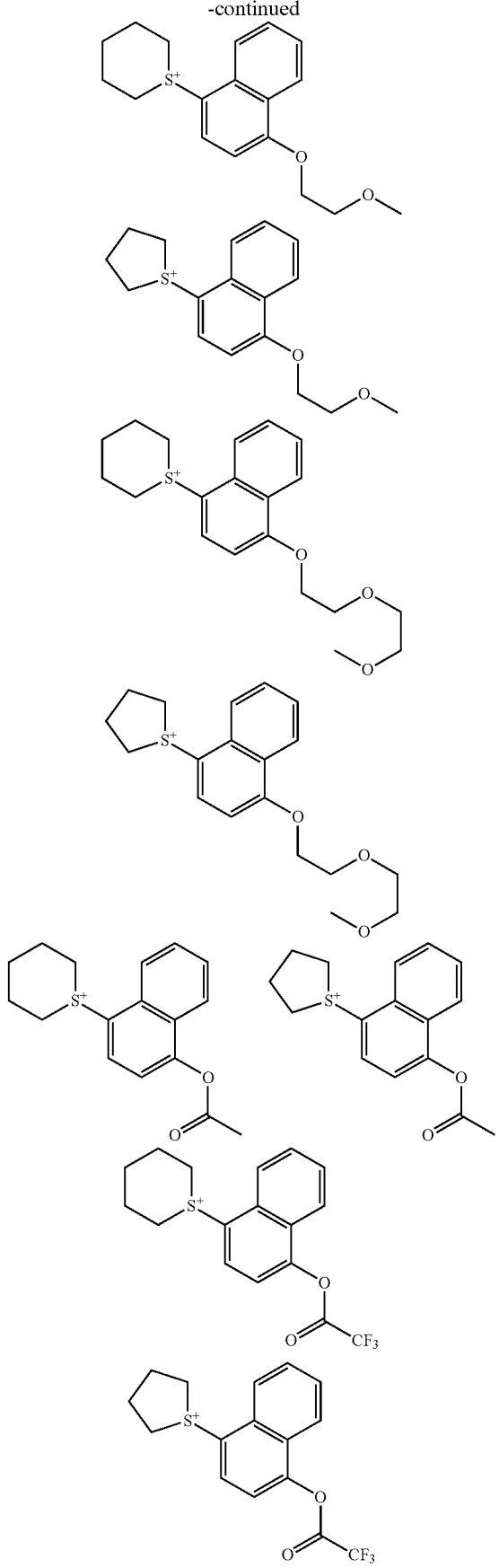
226
-continued
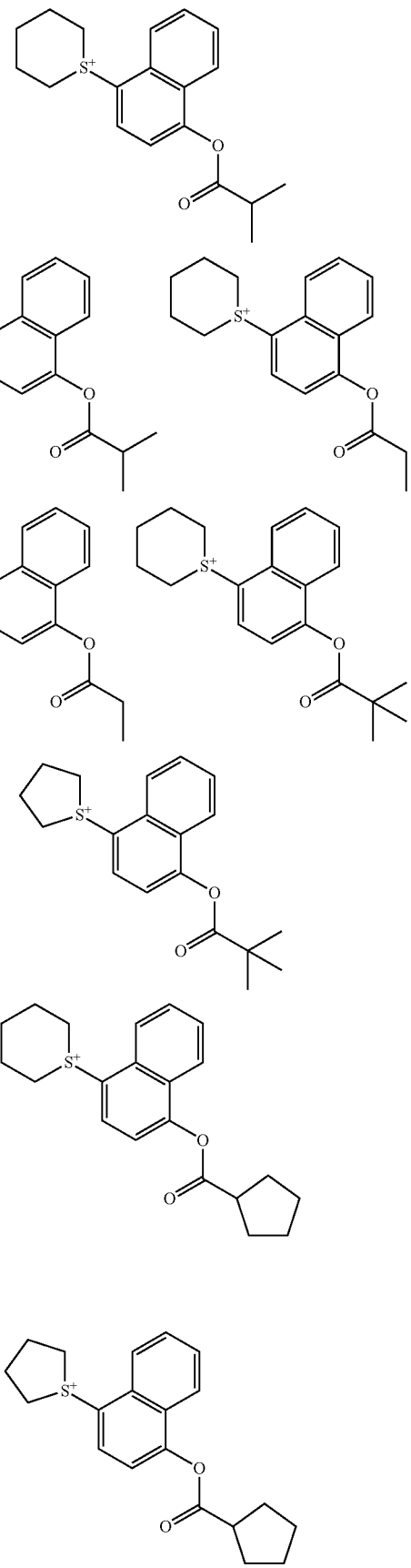

227
-continued
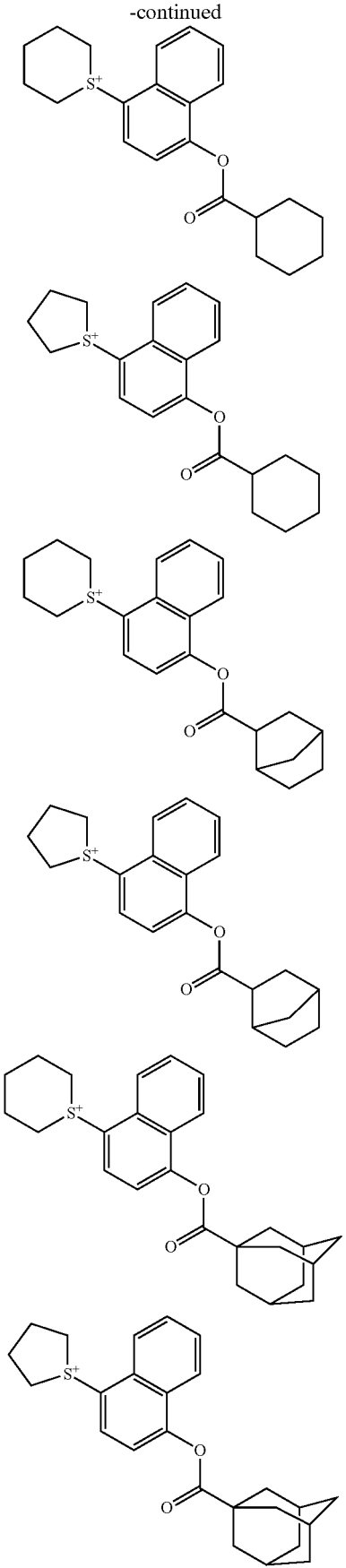
228
-continued
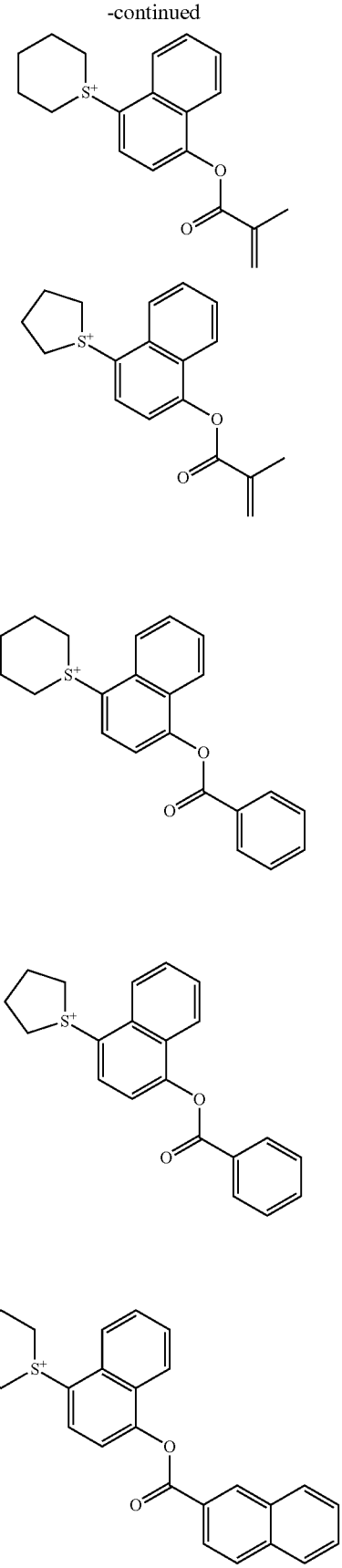

229
-continued
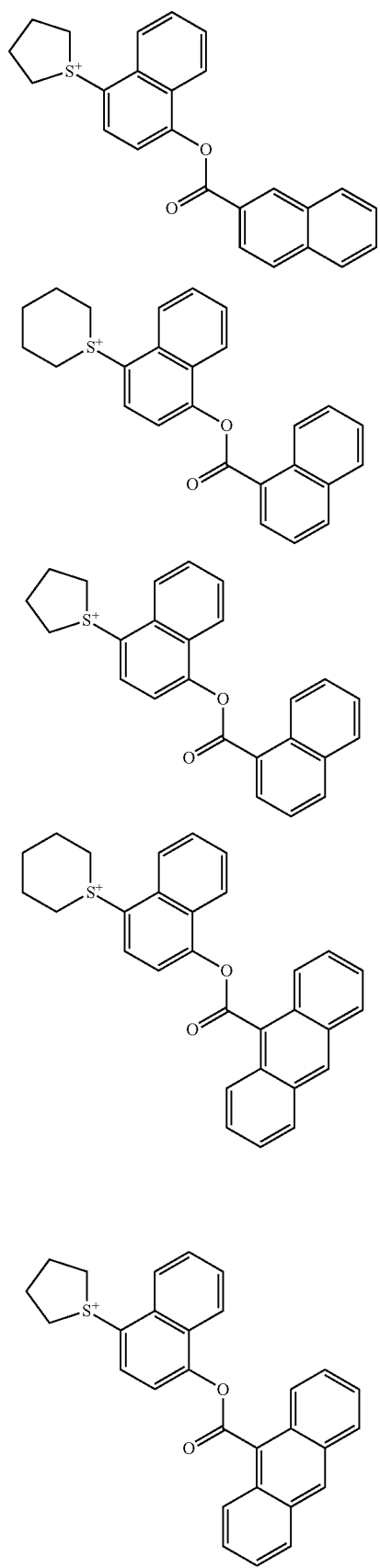
230
-continued
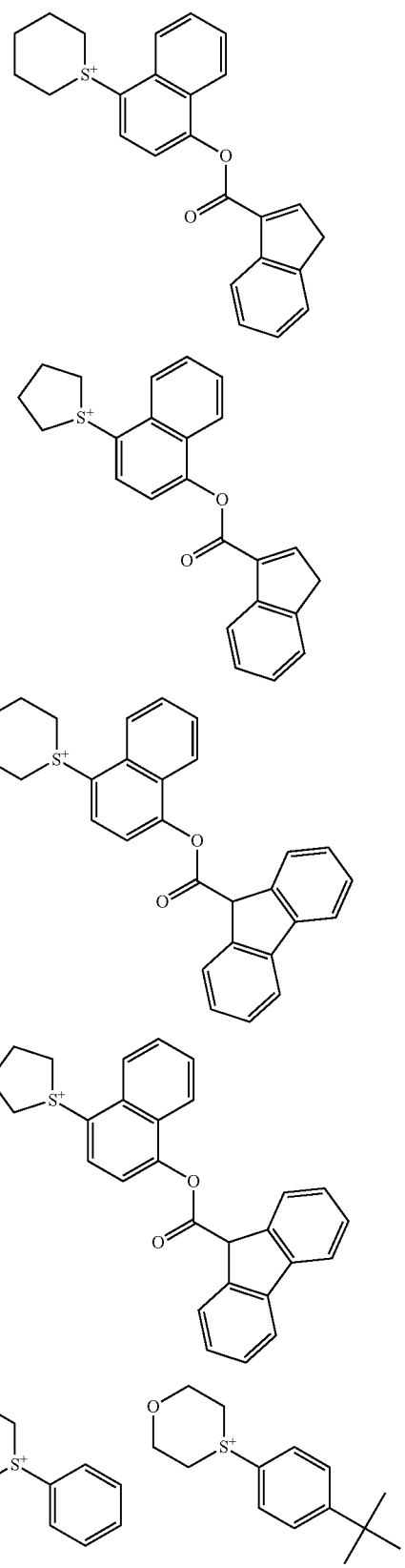

231
-continued
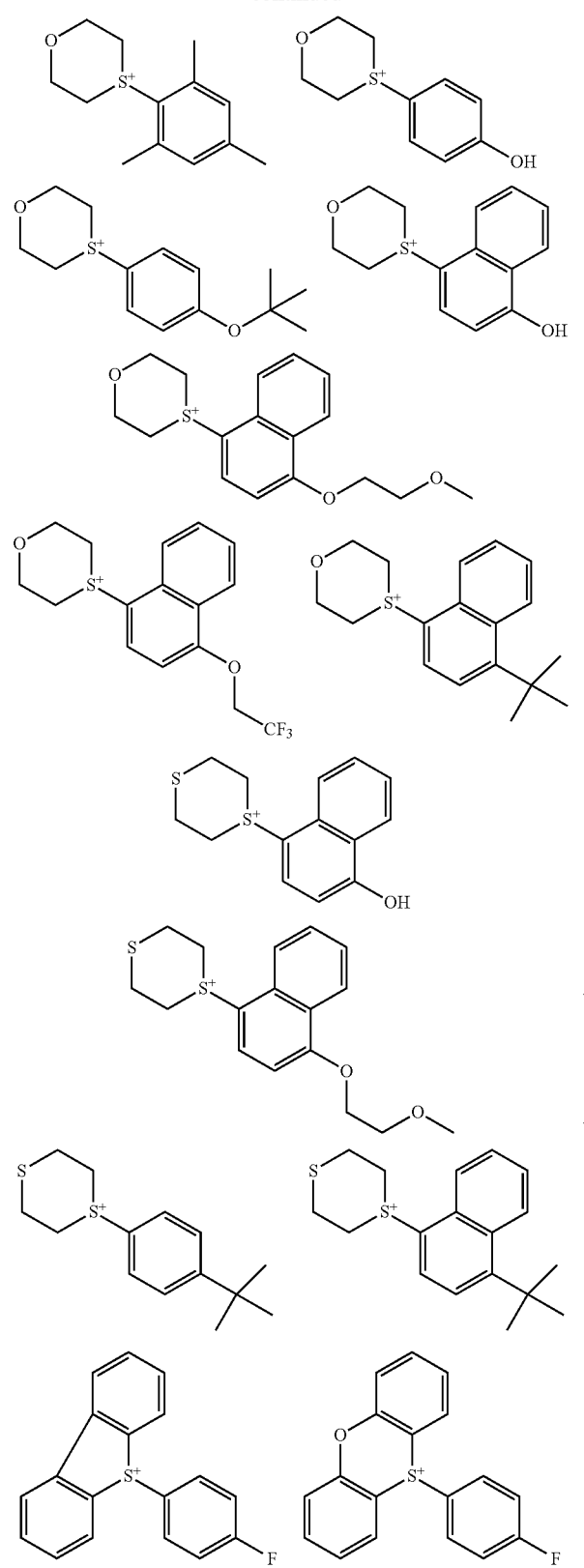
232
-continued
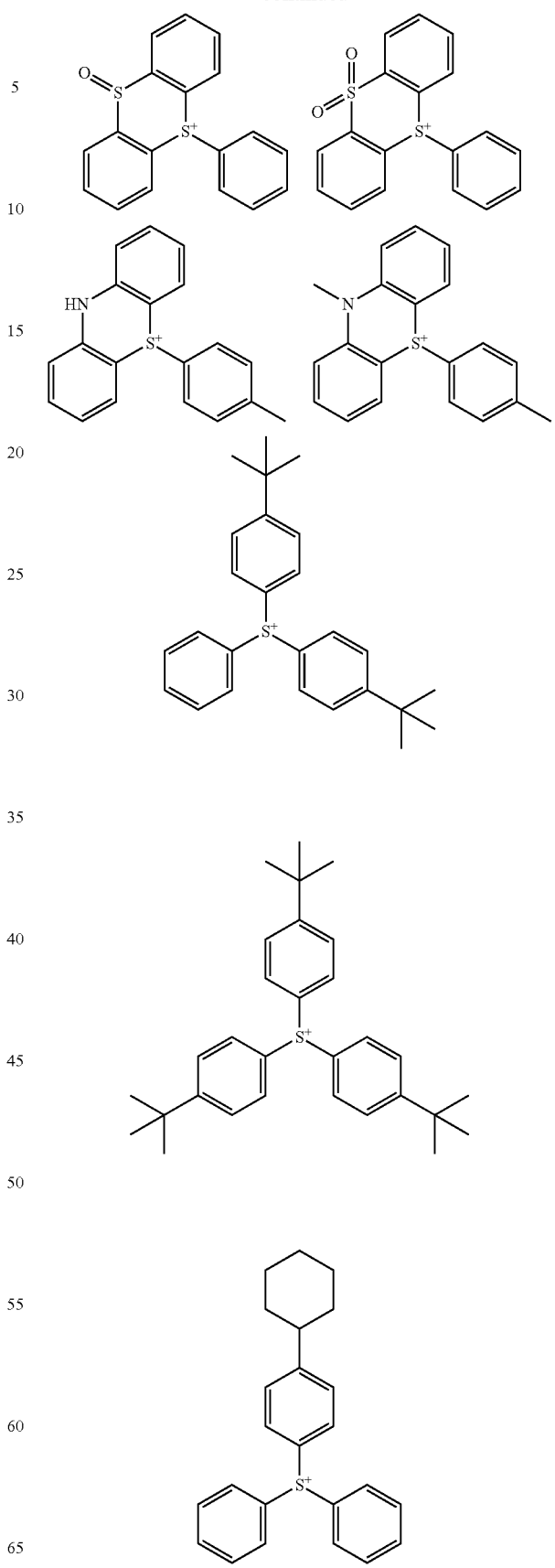

233
-continued
234
-continued
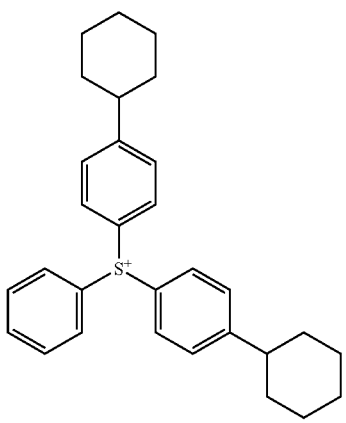
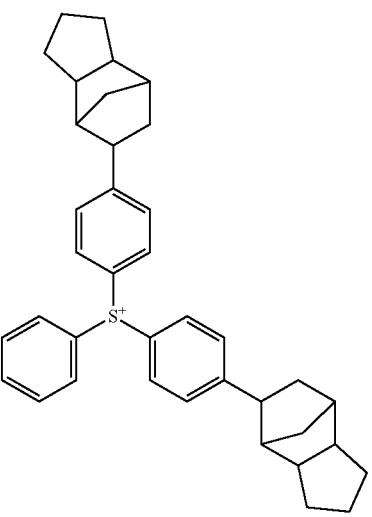
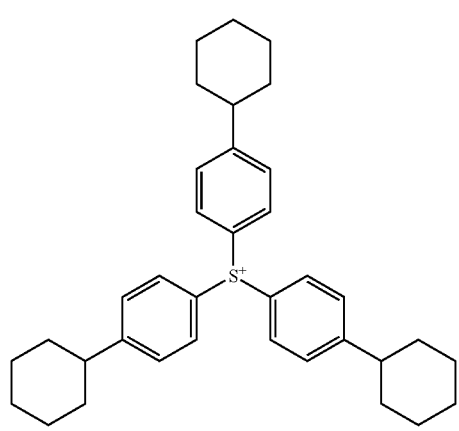
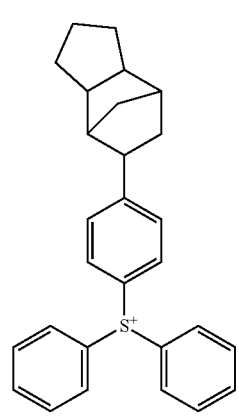
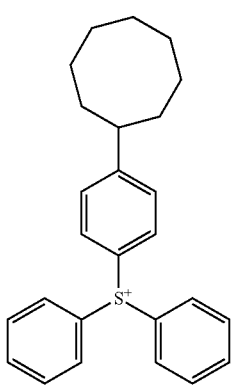

235
-continued
236
-continued
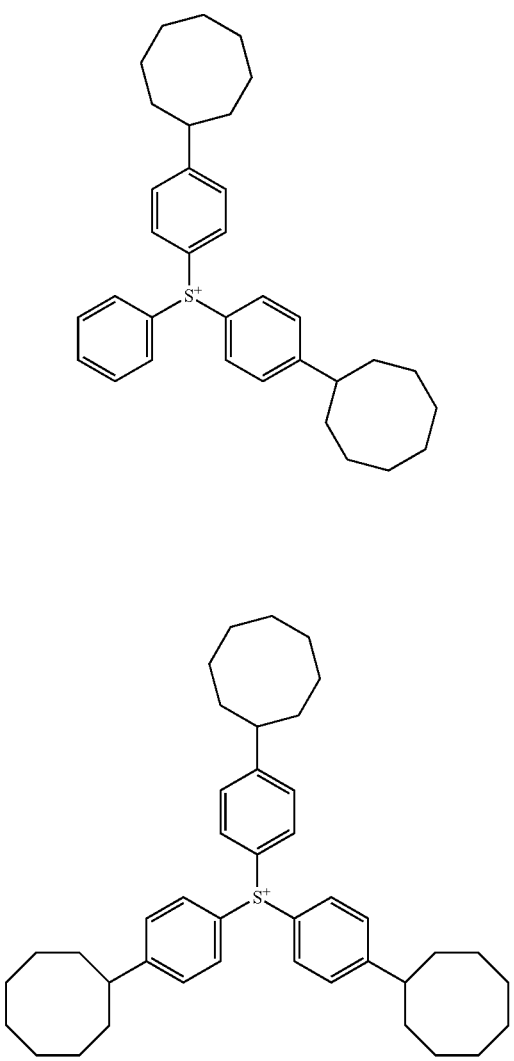
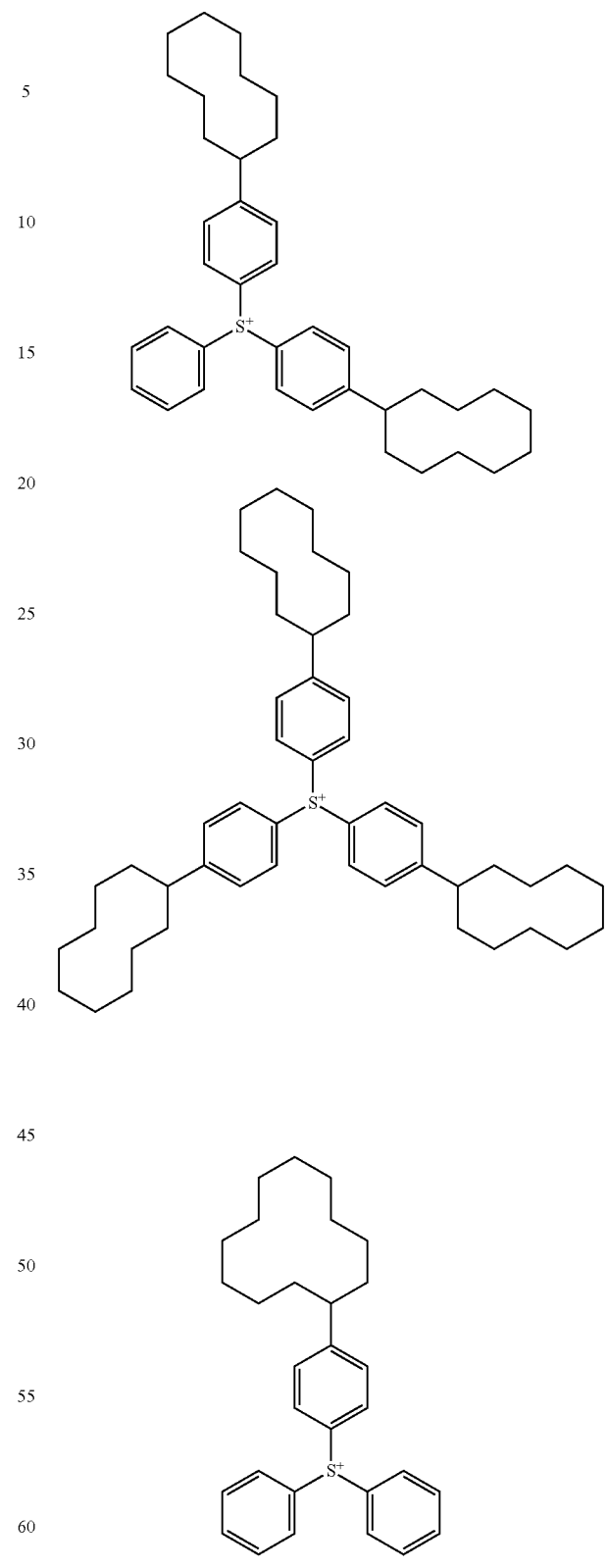

237
-continued
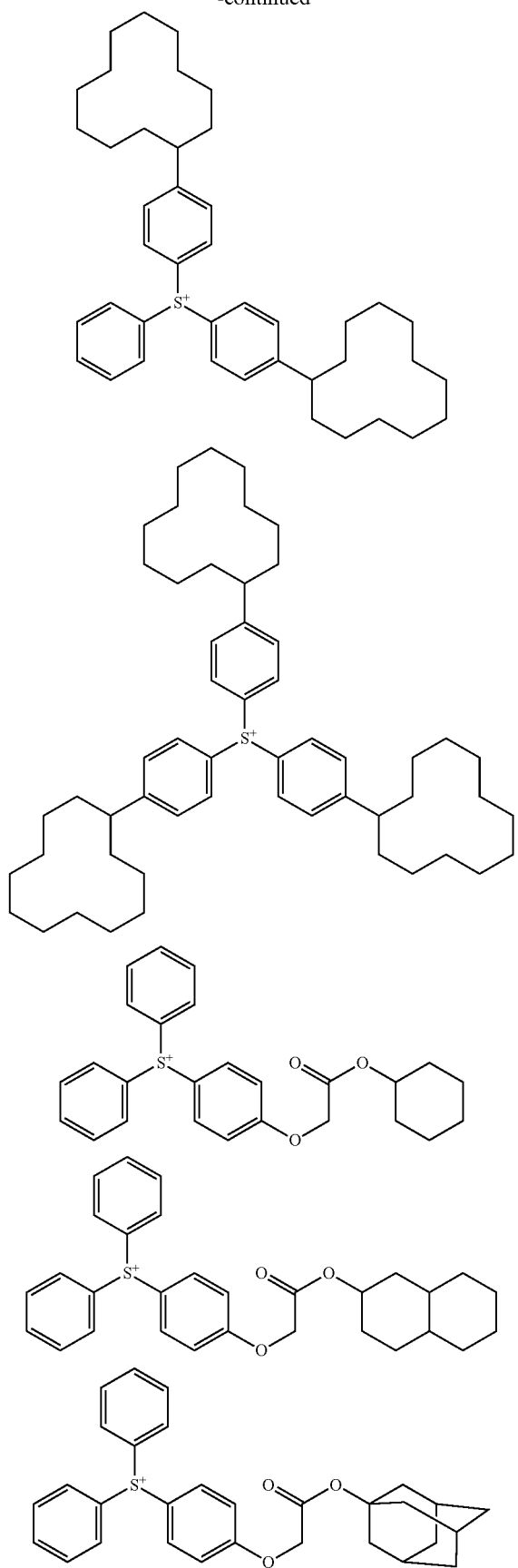
238
-continued
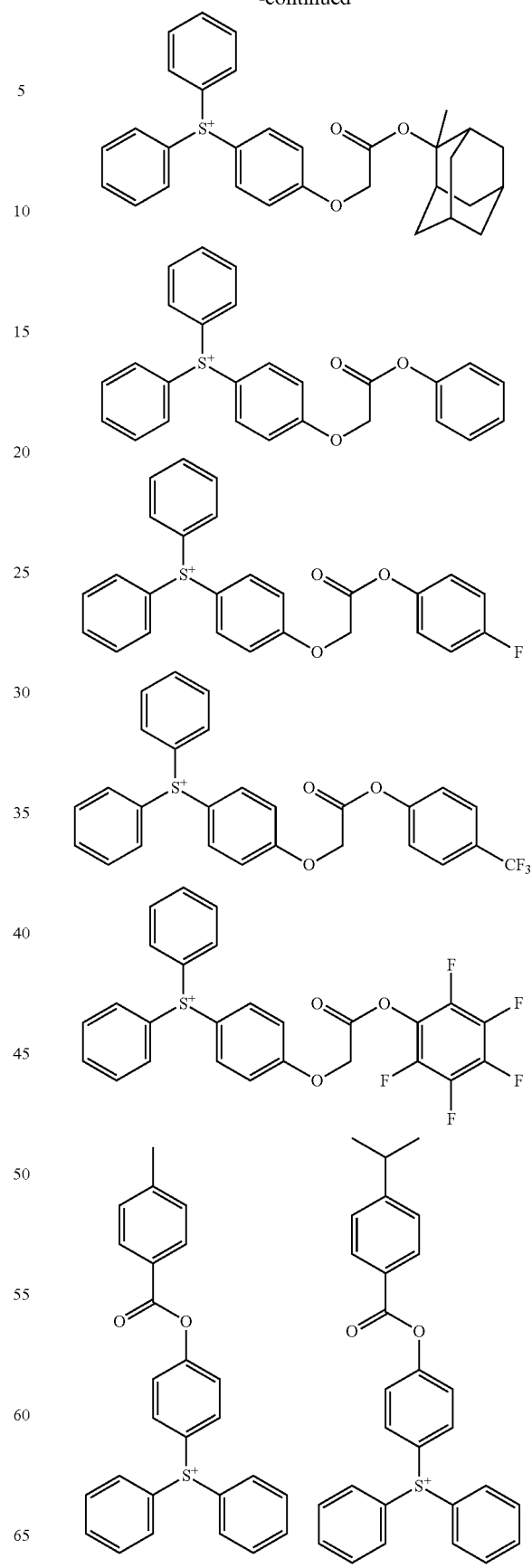

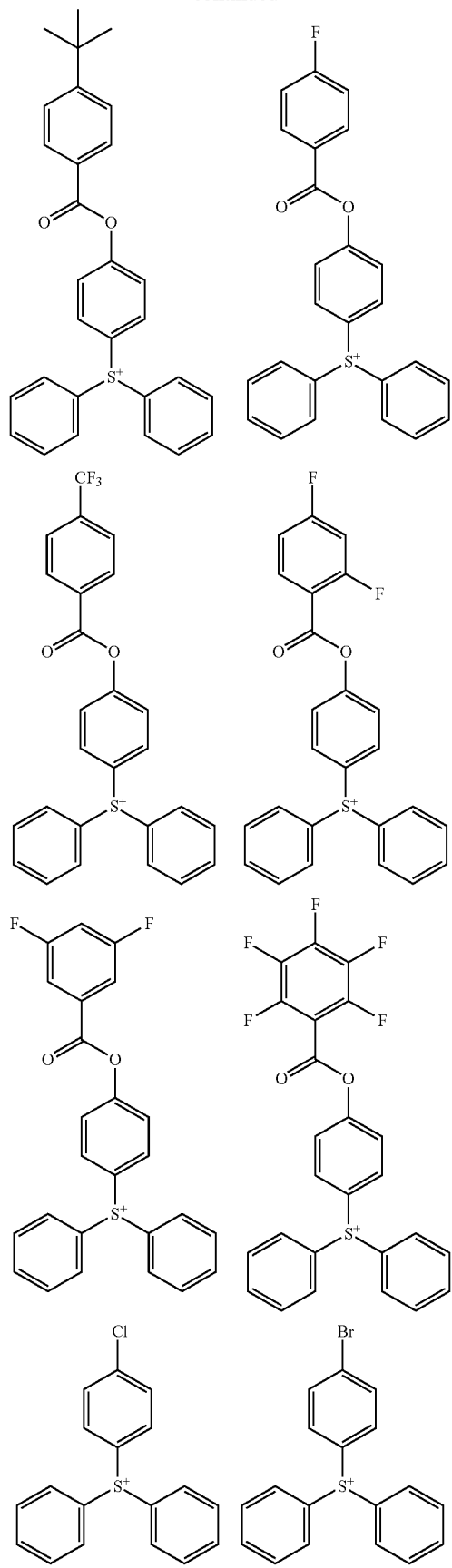
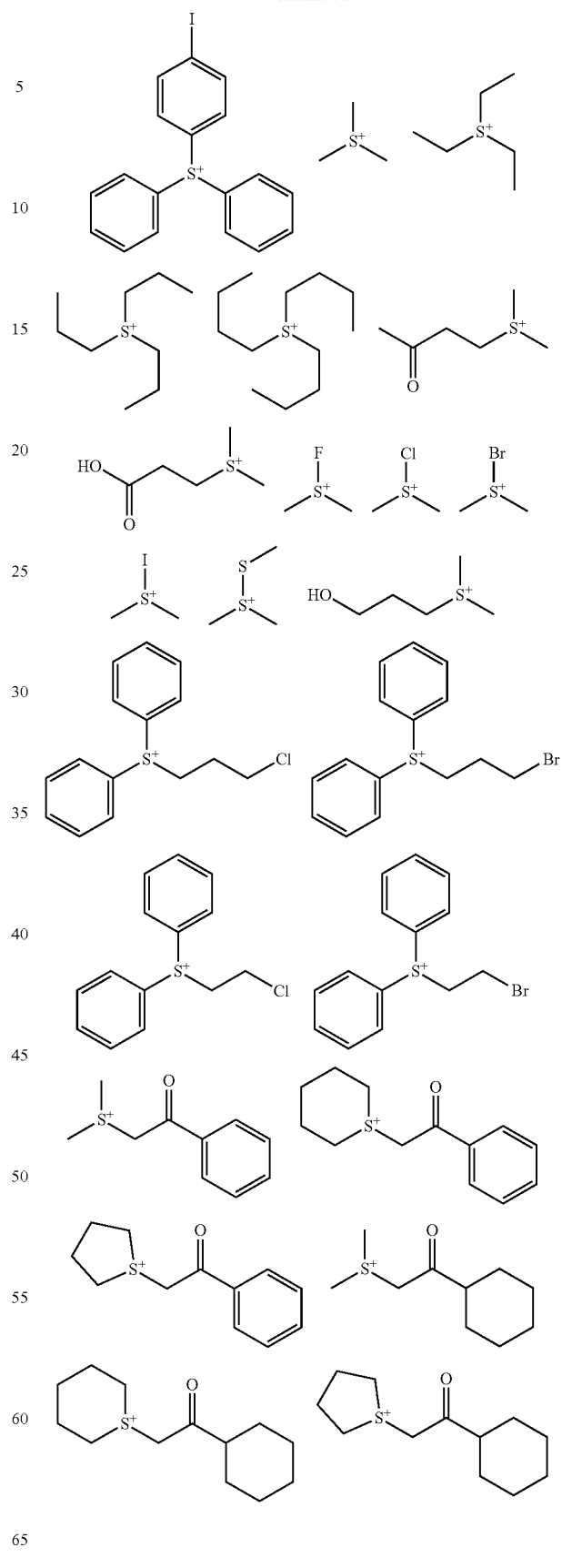

-continued
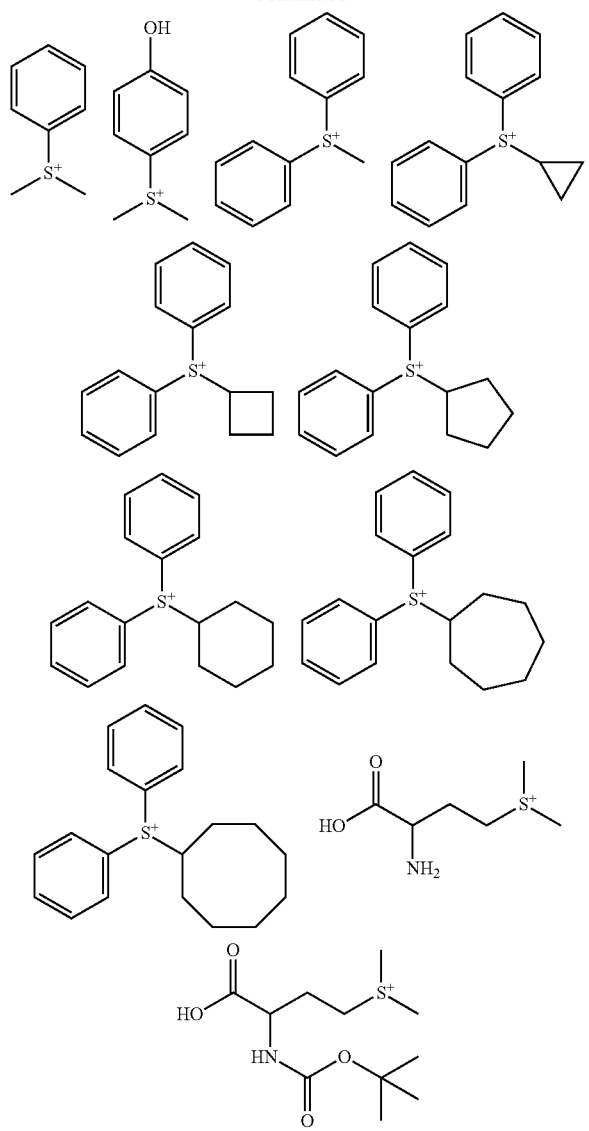
Examples of the anion in the monomer from which repeat unit (c2) is derived are shown below, but not limited thereto. $R^A$ is as defined above.
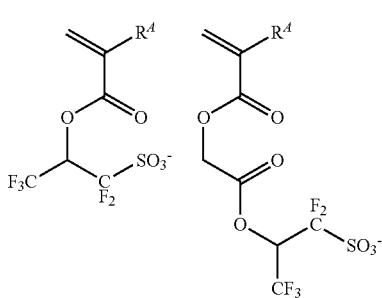
-continued
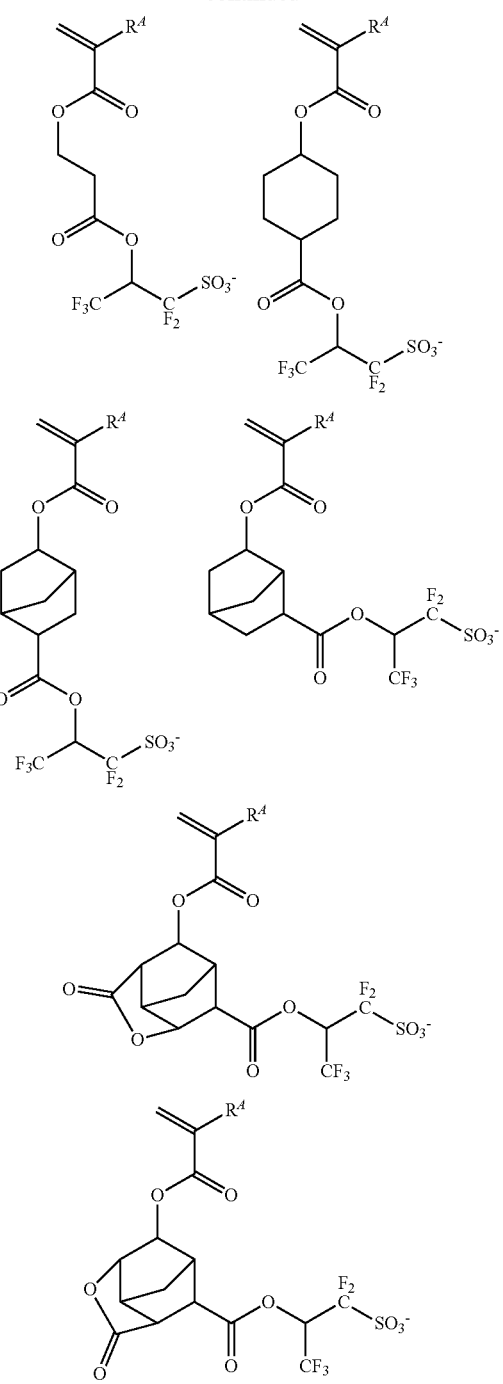

-continued
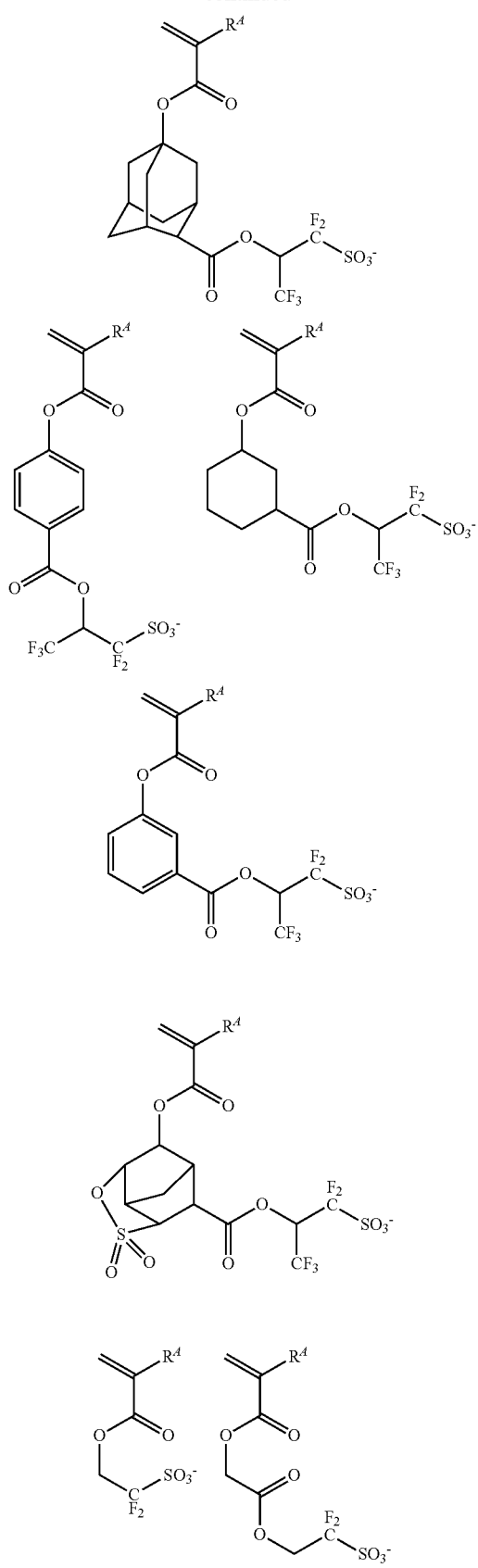
-continued
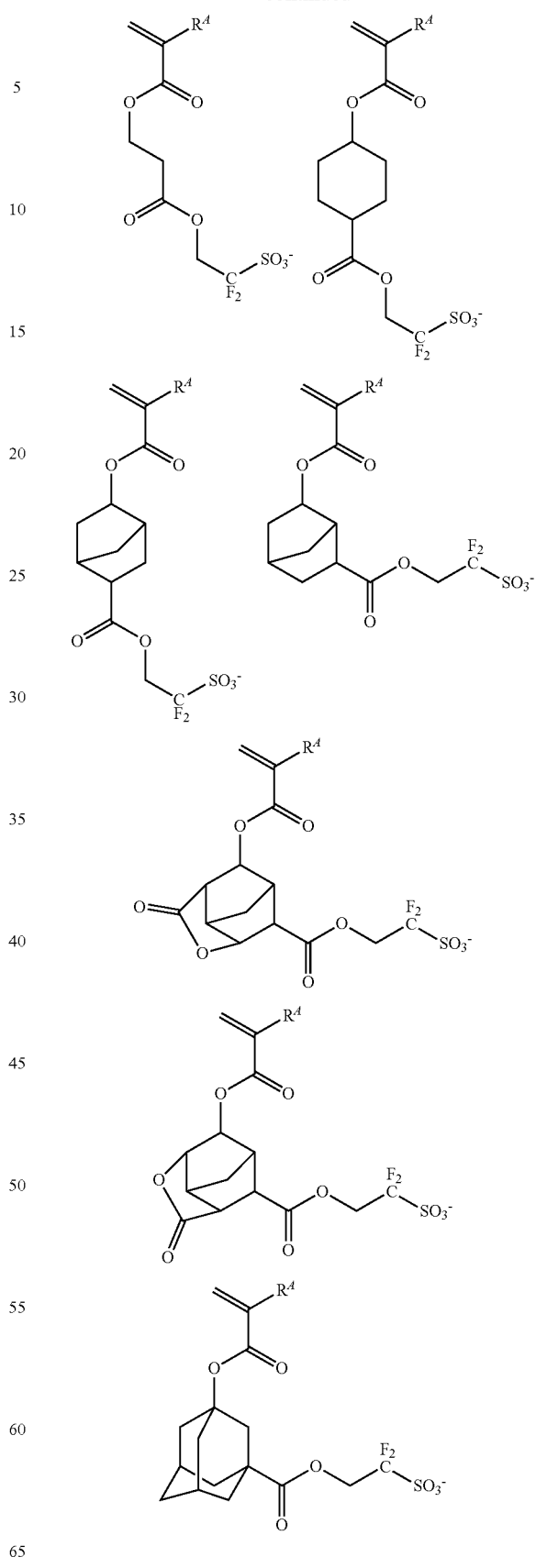

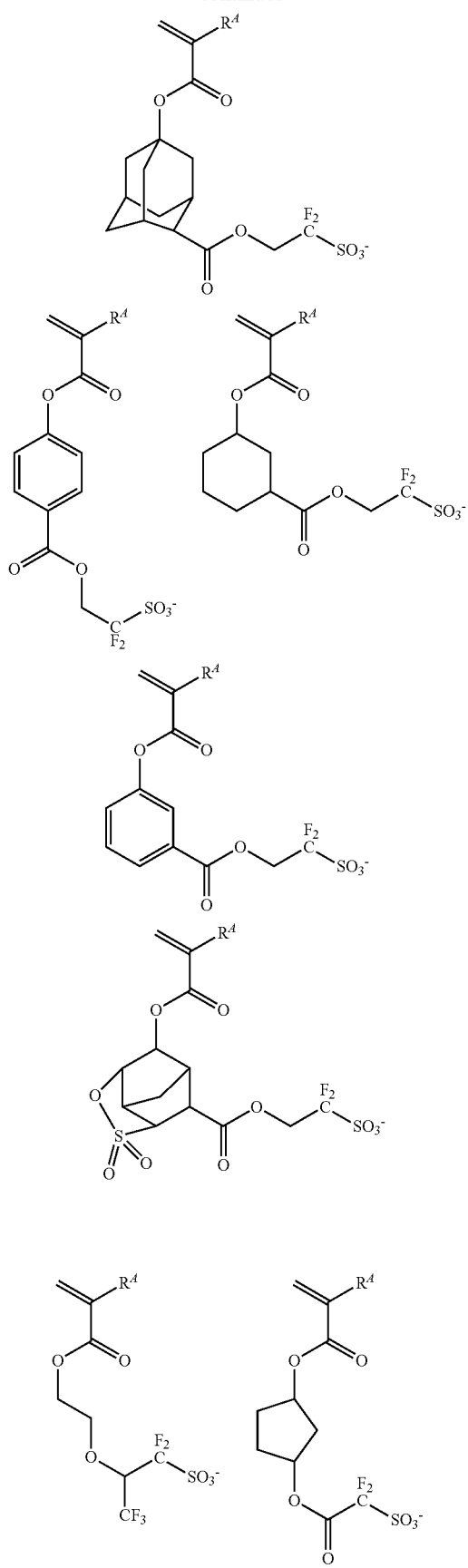
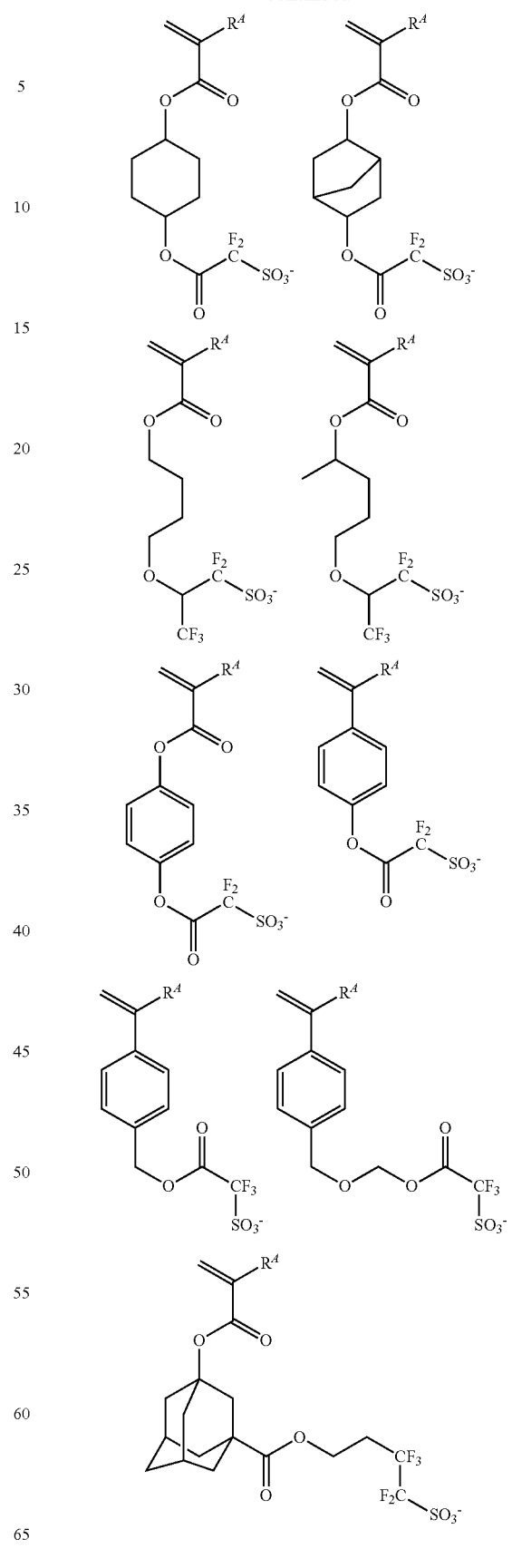

-continued
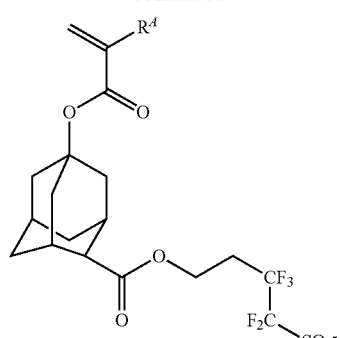
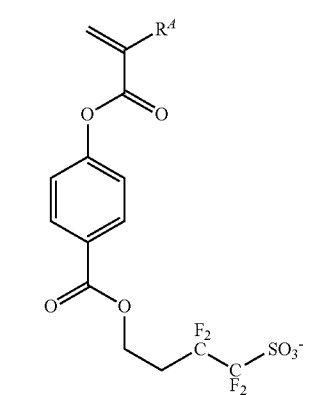
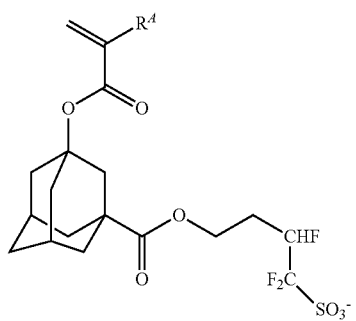
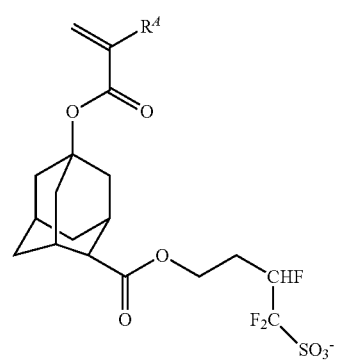
-continued
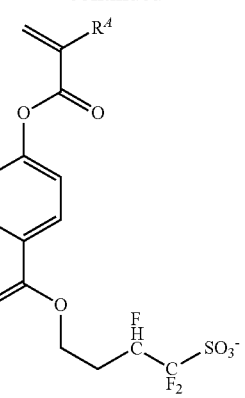
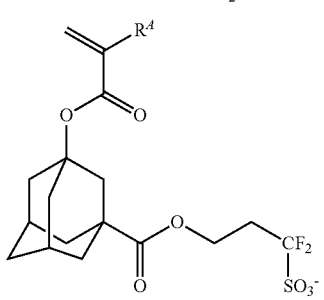
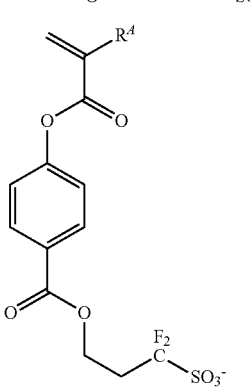
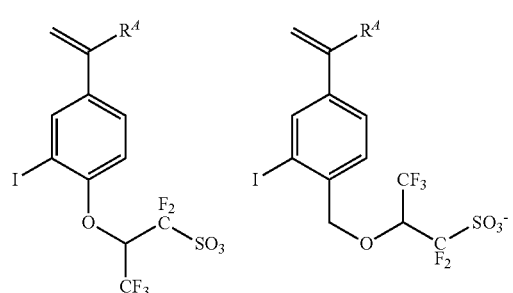
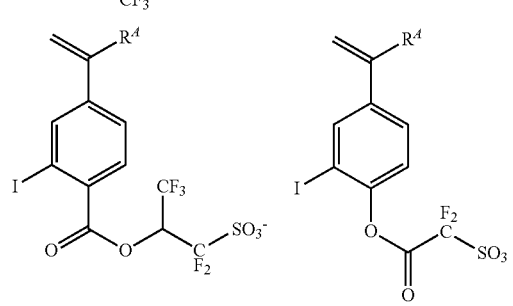

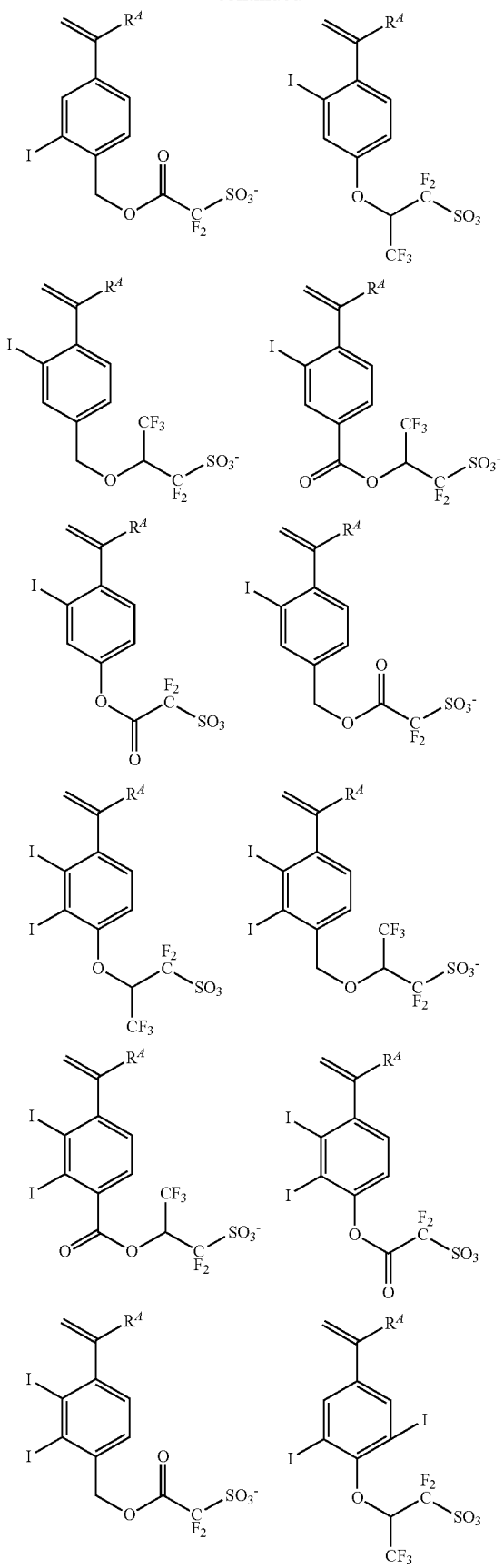
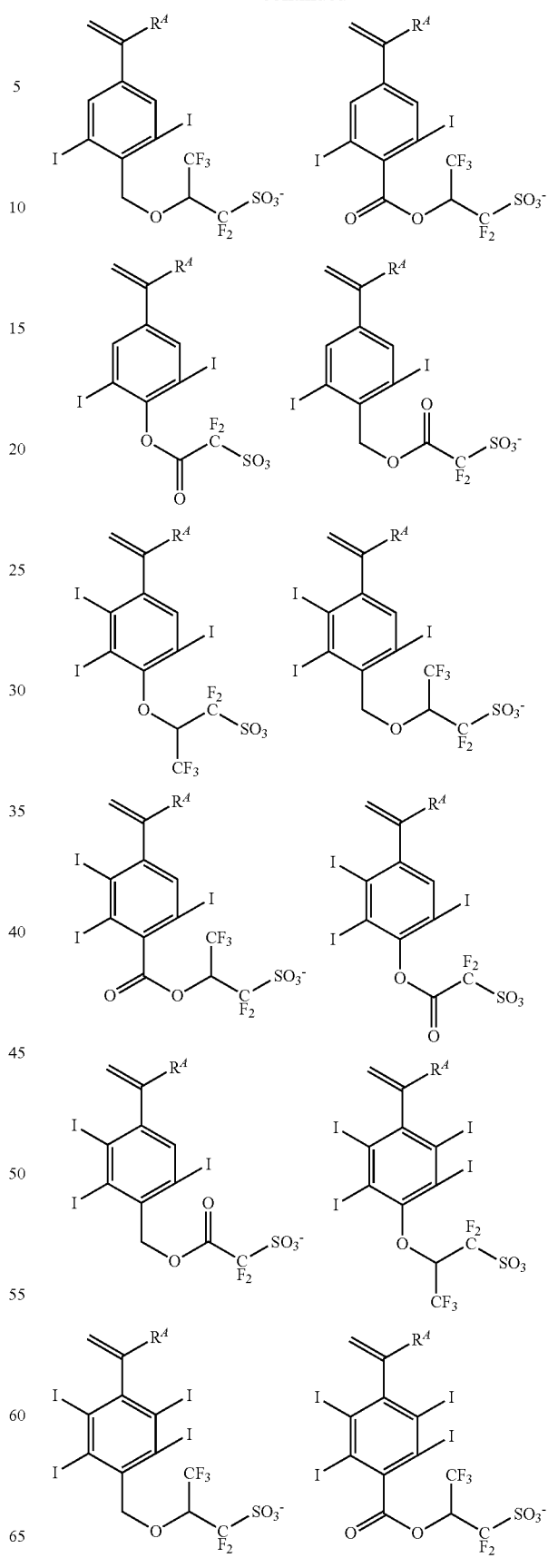

-continued
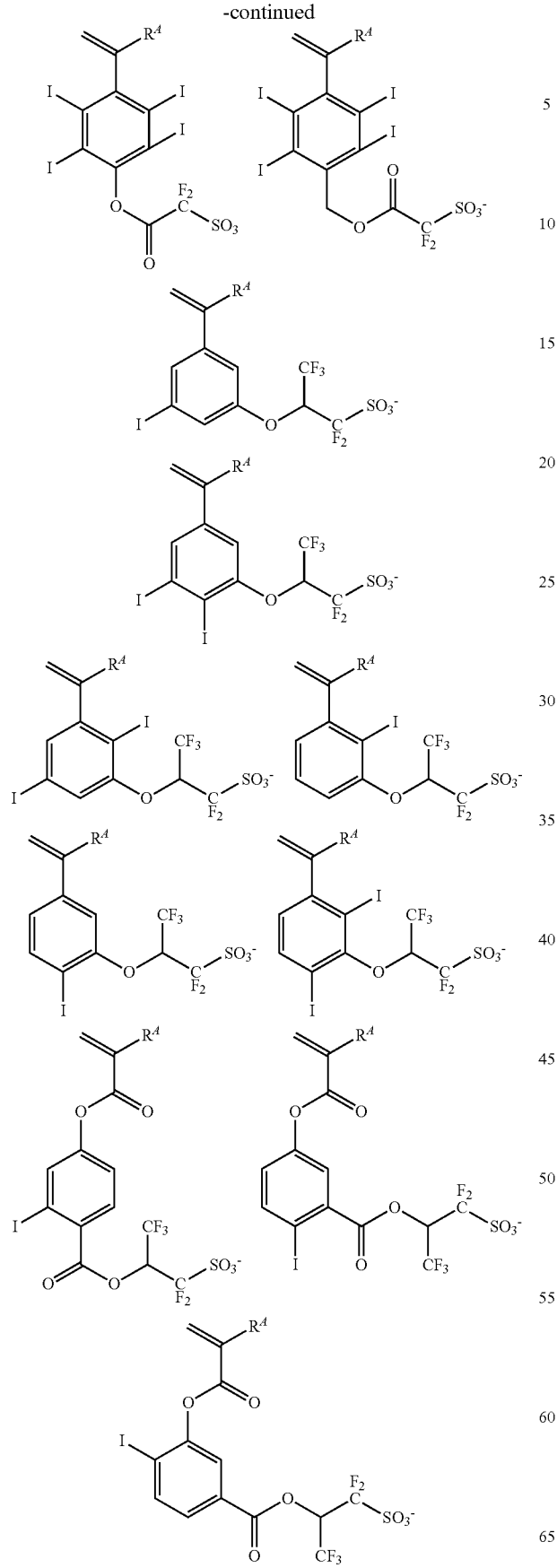
-continued
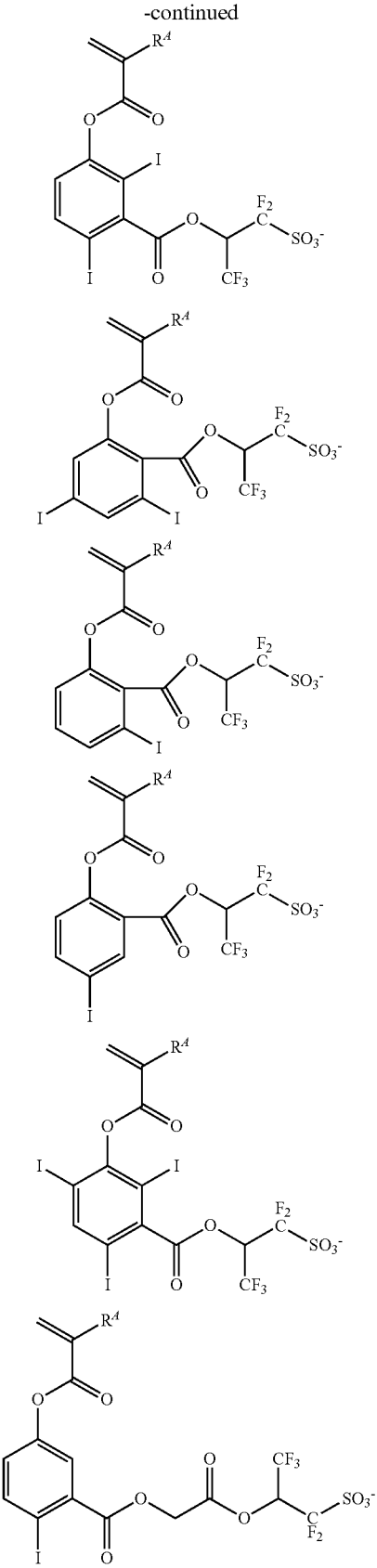

253
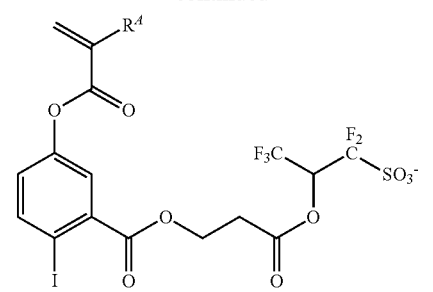
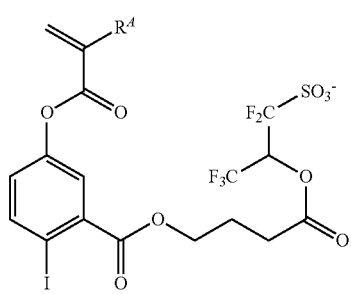
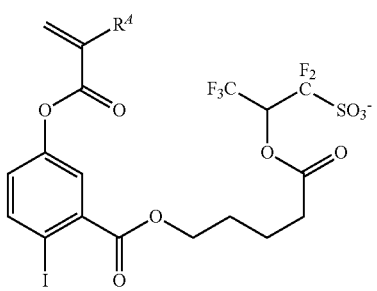
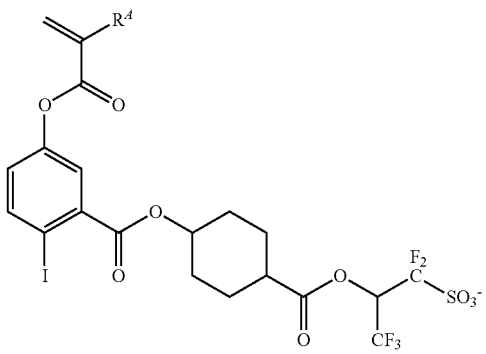
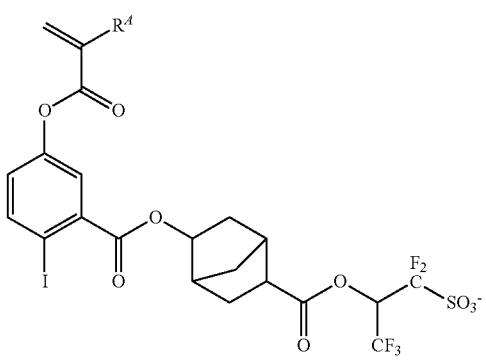
254
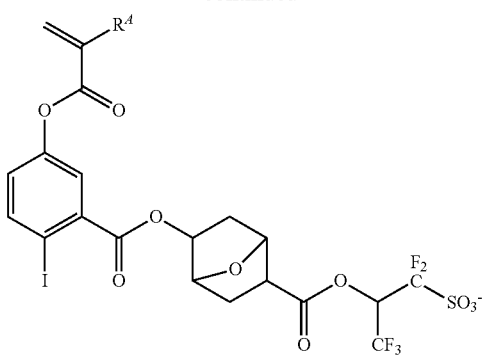
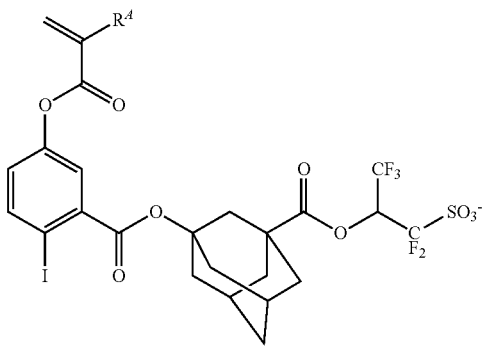
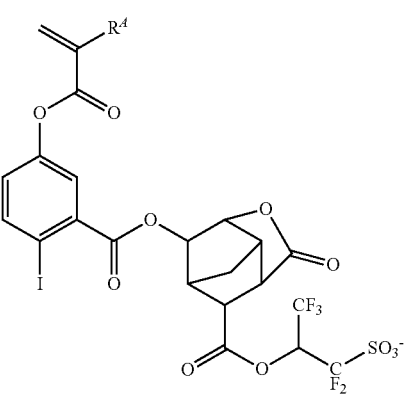
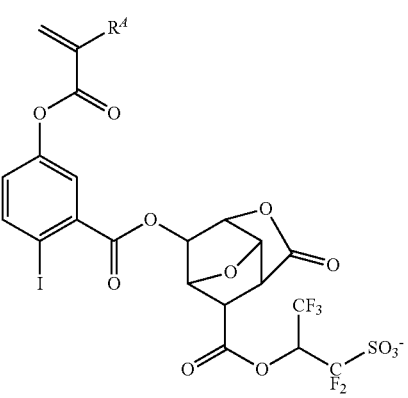

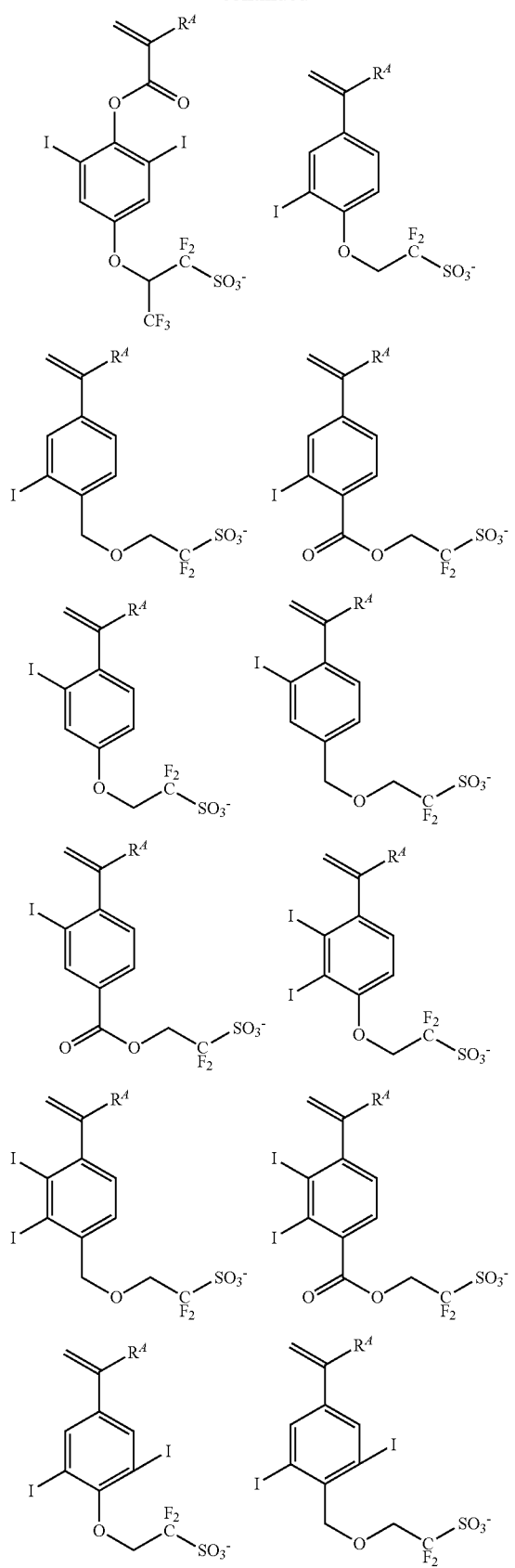
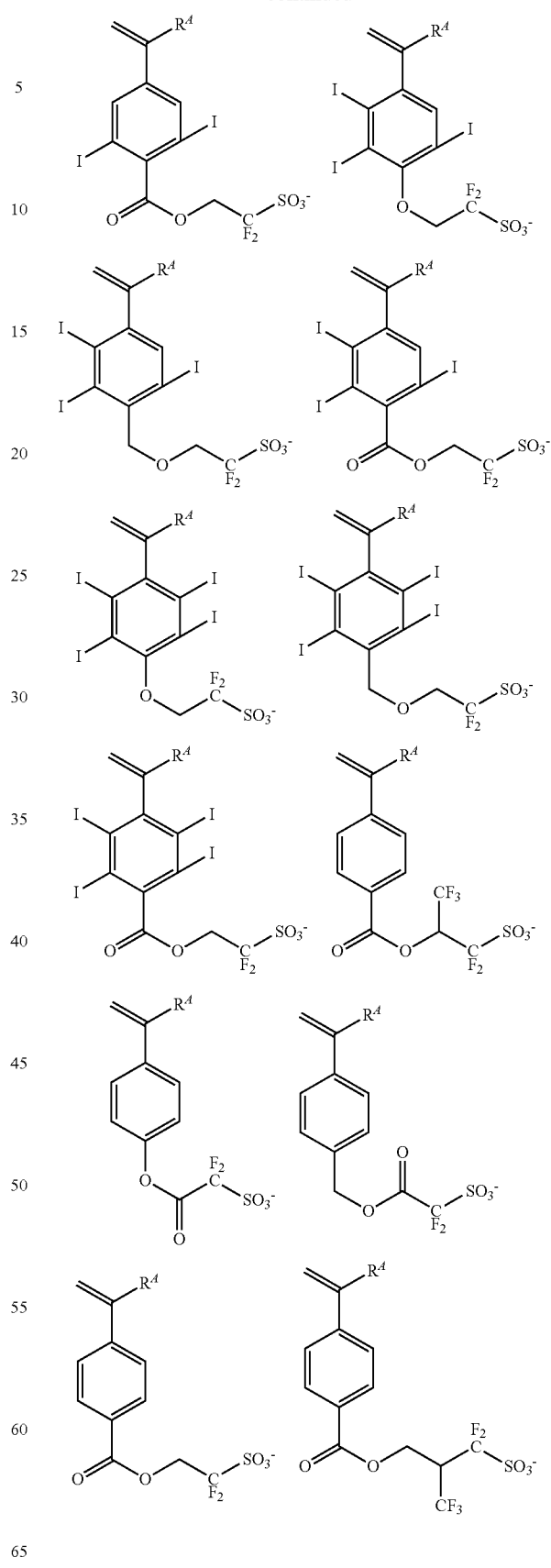

257
-continued
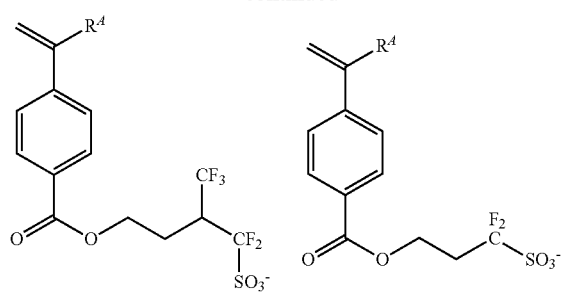
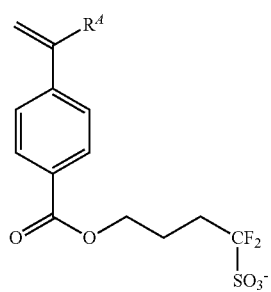
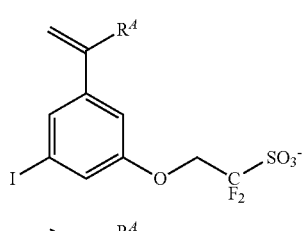
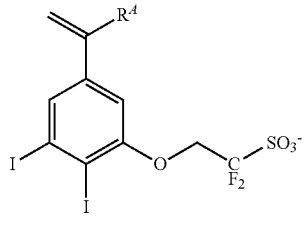
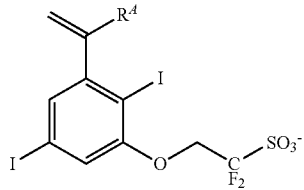
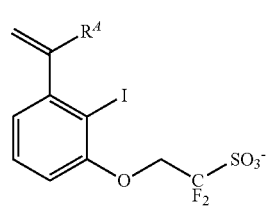
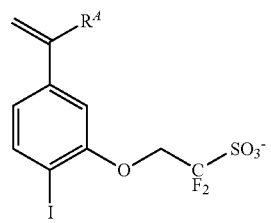
258
-continued
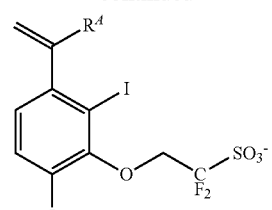
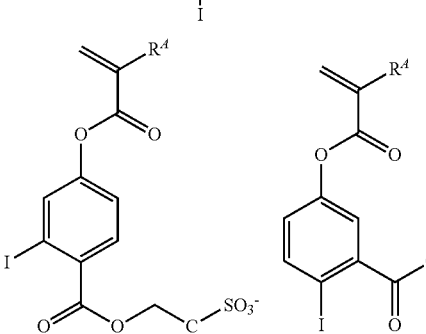
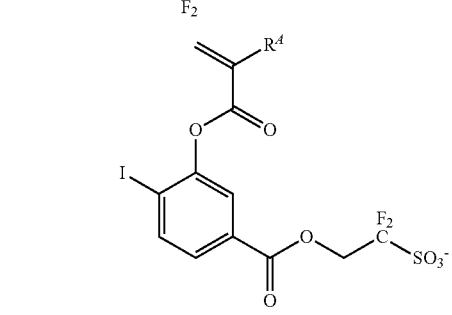
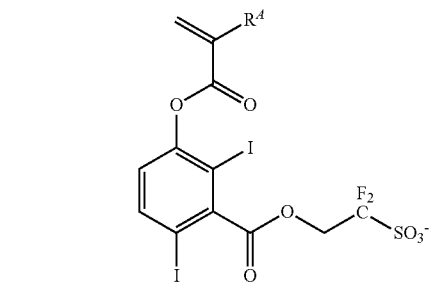
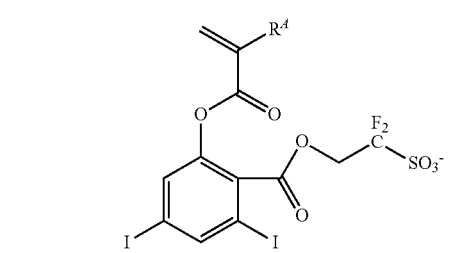
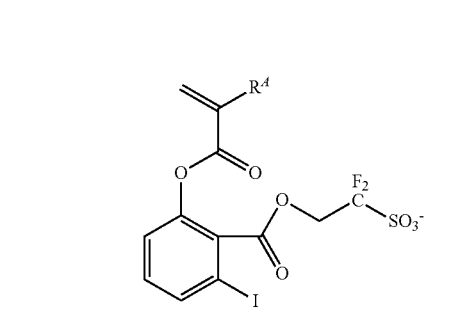

259
-continued
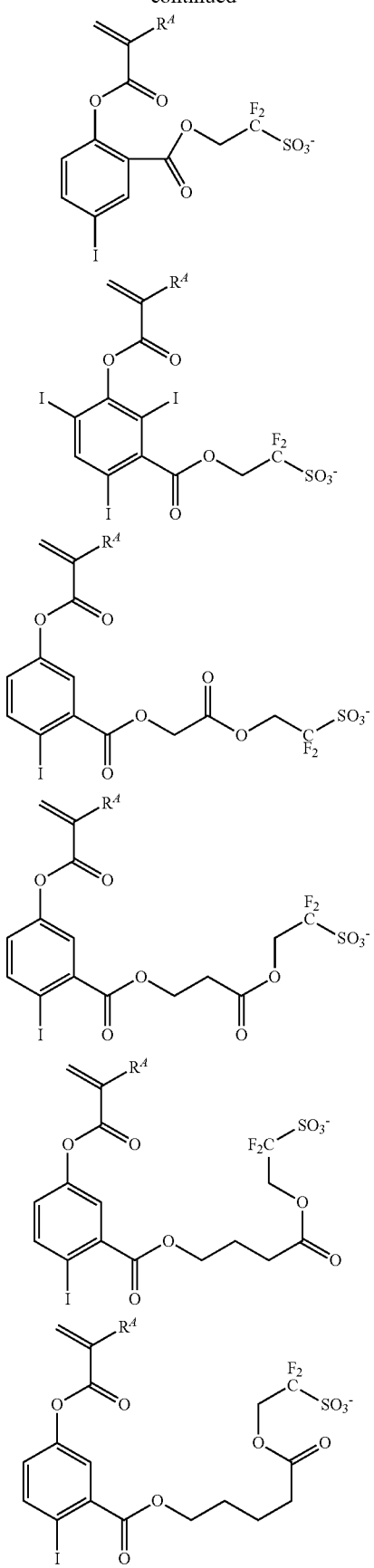
260
-continued
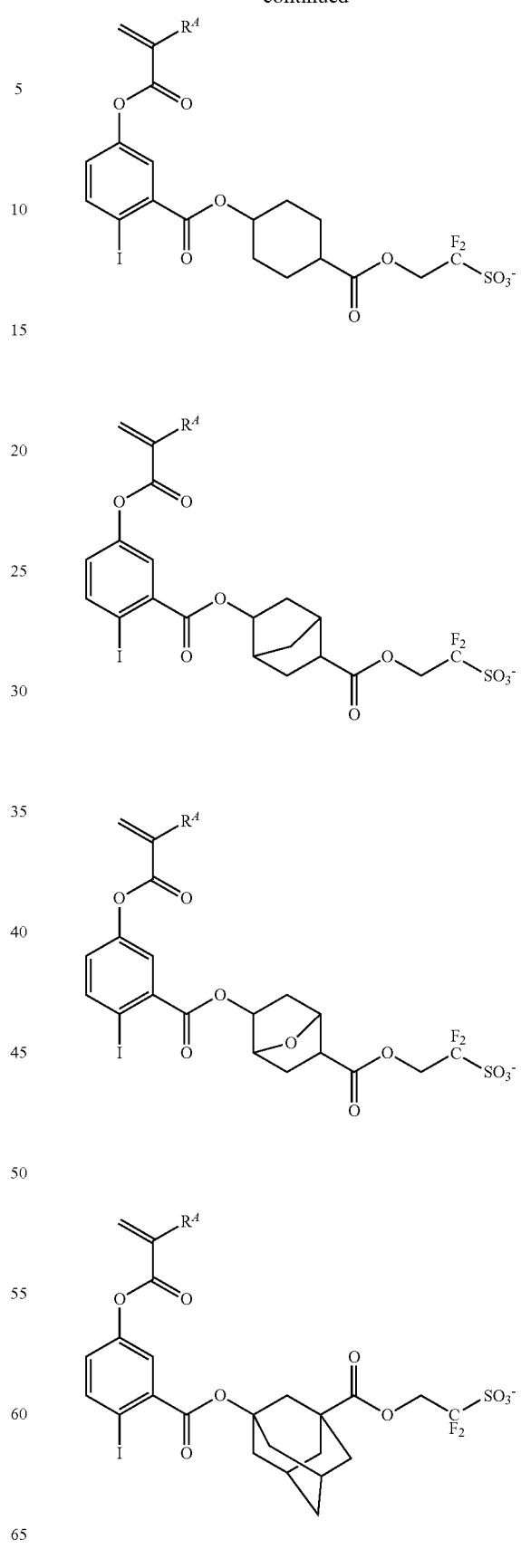

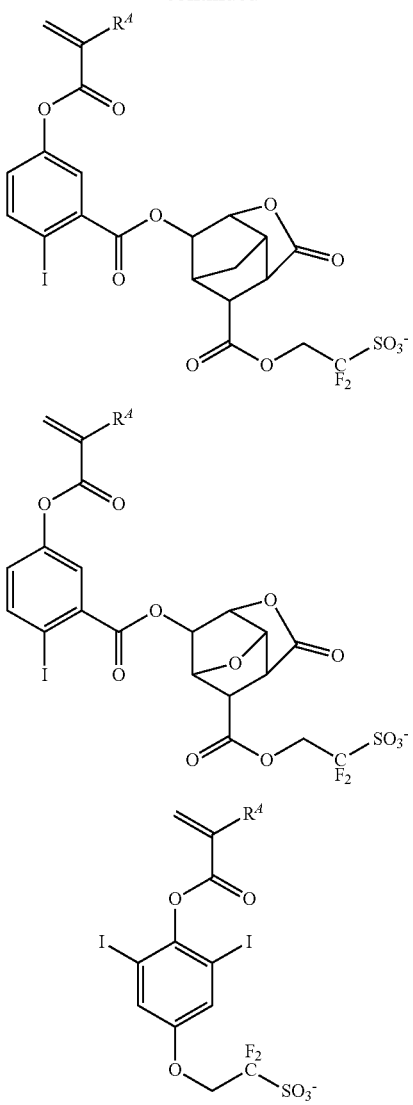

Examples of the anion in the monomer from which repeat unit (c3) is derived are shown below, but not limited thereto. $R^A$ is as defined above.

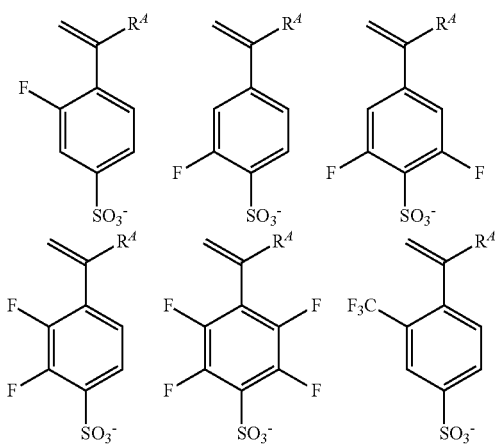

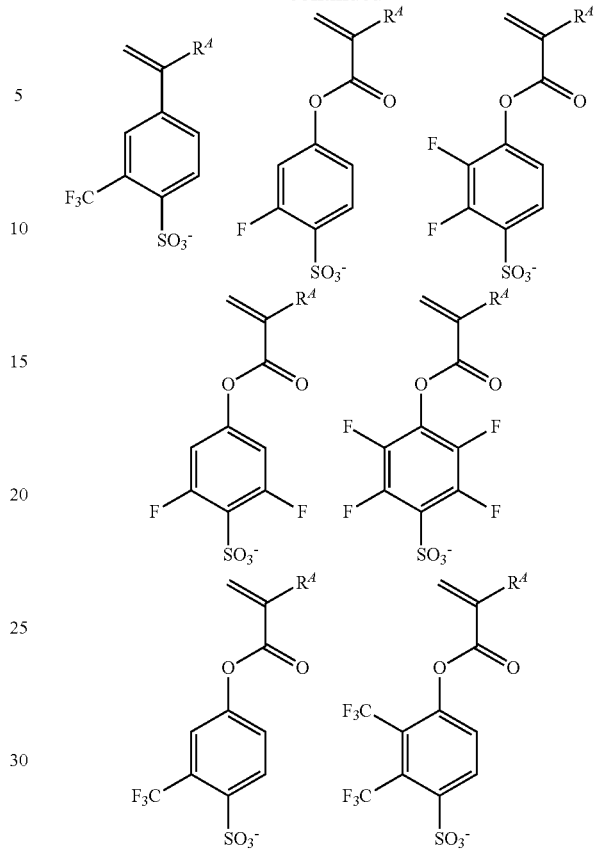

Besides the above-described repeat units, the base polymer may further include repeat units (d), which are derived from such monomers as styrene, acenaphthylene, indene, coumarin, and coumarone.

In the base polymer comprising repeat units (a1), (a2), (b), (c1), (c2), (c3), and (d), a fraction of these units is: preferably $0 \leq a1 < 1.0$, $0 \leq a2 < 1.0$, $0.1 \leq a1+a2 < 1.0$, $0.1 \leq b \leq 0.9$, $0 \leq c1 \leq 0.6$, $0 \leq c2 \leq 0.6$, $0 \leq c3 \leq 0.6$, $0 \leq c1+c2+c3 \leq 0.6$, and $0 \leq d \leq 0.5$; more preferably $0 \leq a1 \leq 0.8$, $0 \leq a2 \leq 0.8$, $0.2 \leq a1+a2 \leq 0.8$, $0.2 \leq b \leq 0.8$, $0 \leq c1 \leq 0.5$, $0 \leq c2 \leq 0.5$, $0 \leq c3 \leq 0.5$, $0 \leq c1+c2+c3 \leq 0.5$, and $0 \leq d \leq 0.4$; and even more preferably $0 \leq a1 \leq 0.7$, $0 \leq a2 \leq 0.7$, $0.3 \leq a1+a2 \leq 0.7$, $0.25 \leq b \leq 0.7$, $0 \leq c1 \leq 0.4$, $0 \leq c2 \leq 0.4$, $0 \leq c3 \leq 0.4$, $0 \leq c1+c2+c3 \leq 0.4$, and $0 \leq d \leq 0.3$. Notably, $a1+a2+b+c1+c2+c3+d=1.0$.

The base polymer may be synthesized by any desired methods, for example, by dissolving suitable monomers selected from the monomers corresponding to the foregoing repeat units in an organic solvent, adding a radical polymerization initiator thereto, and heating for polymerization. Examples of the organic solvent which can be used for polymerization include toluene, benzene, tetrahydrofuran (THF), diethyl ether, and dioxane. Examples of the polymerization initiator used herein include 2,2'-azobisisobutyronitrile (AIBN), 2,2'-azobis(2,4-dimethylvaleronitrile), dimethyl 2,2-azobis(2-methylpropionate), benzoyl peroxide, and lauroyl peroxide. Preferably the reaction temperature is 50 to 80° C., and the reaction time is 2 to 100 hours, more preferably 5 to 20 hours.

In the case of a monomer having a hydroxy group, the hydroxy group may be replaced by an acetal group susceptible to deprotection with acid, typically ethoxyethoxy, prior to polymerization, and the polymerization be followed by deprotection with weak acid and water. Alternatively, the hydroxy group may be replaced by an acetyl, formyl, pivaloyl or similar group prior to polymerization, and the polymerization be followed by alkaline hydrolysis.

When hydroxystyrene or hydroxyvinylnaphthalene is copolymerized, an alternative method is possible. Specifically, acetoxystyrene or acetoxyvinylnaphthalene is used instead of hydroxystyrene or hydroxyvinylnaphthalene, and after polymerization, the acetoxy group is deprotected by alkaline hydrolysis, for thereby converting the polymer product to hydroxystyrene or hydroxyvinylnaphthalene. For alkaline hydrolysis, a base such as aqueous ammonia or triethylamine may be used. Preferably the reaction temperature is −20° C. to 100° C., more preferably 0° C. to 60° C., and the reaction time is 0.2 to 100 hours, more preferably 0.5 to 20 hours.

The base polymer should preferably have a weight average molecular weight (Mw) in the range of 1,000 to 500,000, and more preferably 2,000 to 30,000, as measured by GPC versus polystyrene standards using tetrahydrofuran (THF) solvent. With too low a Mw, the resist composition may become less heat resistant. A polymer with too high a Mw may lose alkaline solubility and give rise to a footing phenomenon after pattern formation.

If a base polymer has a wide molecular weight distribution or dispersity (Mw/Mn), which indicates the presence of lower and higher molecular weight polymer fractions, there is a possibility that foreign matter is left on the pattern or the pattern profile is degraded. The influences of Mw and Mw/Mn become stronger as the pattern rule becomes finer. Therefore, the base polymer should preferably have a narrow dispersity (Mw/Mn) of 1.0 to 2.0, especially 1.0 to 1.5, in order to provide a resist composition suitable for micropatterning to a small feature size.

The base polymer may be a blend of two or more polymers which differ in compositional ratio, Mw or Mw/Mn.

(D) Organic Solvent

The positive resist composition may contain (D) an organic solvent. The organic solvent is not particularly limited as long as the foregoing components and other components are dissolvable therein. Examples of the organic solvent used herein are described in U.S. Pat. No. 7,537,880 (JP-A 2008-111103, paragraphs [0144]-[0145]). Exemplary solvents include ketones such as cyclohexanone, cyclopentanone, methyl-2-n-pentyl ketone, and 2-heptanone; alcohols such as 3-methoxybutanol, 3-methyl-3-methoxybutanol, 1-methoxy-2-propanol, 1-ethoxy-2-propanol, and diacetone alcohol (DAA); ethers such as propylene glycol monomethyl ether, ethylene glycol monomethyl ether, propylene glycol monoethyl ether, ethylene glycol monoethyl ether, propylene glycol dimethyl ether, and diethylene glycol dimethyl ether; esters such as propylene glycol monomethyl ether acetate (PGMEA), propylene glycol monoethyl ether acetate, ethyl lactate, ethyl pyruvate, butyl acetate, methyl 3-methoxypropionate, ethyl 3-ethoxypropionate, tert-butyl acetate, tert-butyl propionate, and propylene glycol mono-tert-butyl ether acetate; and lactones such as γ-butyrolactone, and mixtures thereof.

The organic solvent is preferably added in an amount of 100 to 10,000 parts, and more preferably 200 to 8,000 parts by weight per 100 parts by weight of the base polymer (C).

(E) Surfactant

The resist composition may further comprise (E) a surfactant. Exemplary surfactants are described in JP-A 2008-111103, paragraphs [0165]-[0166], Inclusion of a surfactant may improve or control the coating characteristics of the resist composition. When used, the surfactant is preferably added in an amount of 0.0001 to 10 parts by weight per 100 parts by weight of the base polymer (C). The surfactant may be used alone or in admixture.

(F) Other Acid Generator

The resist composition may further comprise (F) an acid generator other than component (A) (referred to as other acid generator, hereinafter). The acid generator is capable of generating a strong acid. As used herein, the term "strong acid" refers to a compound having a sufficient acidity to induce deprotection reaction of an acid labile group on the base polymer. The acid generator is typically a compound (PAG) capable of generating an acid upon exposure to actinic ray or radiation. Although the PAG used herein may be any compound capable of generating an acid upon exposure to high-energy radiation, those compounds capable of generating sulfonic acid, imide acid (imidic acid) or methide acid are preferred. Suitable PAGs include sulfonium salts, iodonium salts, sulfonyldiazomethane, N-sulfonyloxyimide, and oxime-O-sulfonate acid generators. Exemplary PAGs are described in JP-A 2008-111103, paragraphs [0122]-[0142] (U.S. Pat. No. 7,537,880).

Also included in the other acid generator are sulfonium salts having the formula (1-1) (exclusive of those salts containing fluorine in both anion and cation), iodonium salts having the formula (1-2), betaine type sulfonium compounds having the formula (2), and sulfonium salts having the formula (3-1) (exclusive of those salts containing fluorine in both anion and cation), and iodonium salts having the formula (3-2), as described in JP-A 2020-122956.

In the resist composition containing the other acid generator (F), its content is preferably 0.1 to 30 parts by weight, and more preferably 0.2 to 20 parts by weight per 100 parts by weight of the base polymer (C) although the content is not particularly limited as long as the benefits of the invention are not impaired.

(G) Other Quencher

The resist composition may further comprise (G) a quencher other than component (B) (referred to as other quencher, hereinafter).

The other quencher is typically selected from conventional basic compounds. Conventional basic compounds include primary, secondary, and tertiary aliphatic amines, mixed amines, aromatic amines, heterocyclic amines, nitrogen-containing compounds with carboxy group, nitrogen-containing compounds with sulfonyl group, nitrogen-containing compounds with hydroxy group, nitrogen-containing compounds with hydroxyphenyl group, alcoholic nitrogen-containing compounds, amide derivatives, imide derivatives, and carbamate derivatives. Also included are primary, secondary, and tertiary amine compounds, specifically amine compounds having a hydroxy group, ether bond, ester bond, lactone ring, cyano group, or sulfonic acid ester bond as described in JP-A 2008-111103, paragraphs [0146]-[0164], and compounds having a carbamate group as described in JP 3790649. Addition of such a basic compound is effective for further suppressing the diffusion rate of acid in the resist film or correcting the pattern profile.

Onium salts such as sulfonium salts, iodonium salts and ammonium salts of sulfonic acids which are not fluorinated at α-position as described in U.S. Pat. No. 8,795,942 (JP-A 2008-158339) and similar onium salts of carboxylic acid may also be used as the other quencher. While an α-fluorinated sulfonic acid, imide acid, and methide acid are necessary to deprotect the acid labile group of carboxylic acid ester, an α-non-fluorinated sulfonic acid or carboxylic acid are released by salt exchange with an α-non-fluorinated onium salt. An α-non-fluorinated sulfonic acid or carboxylic acid function as a quencher because they do not induce deprotection reaction.

Suitable other quenchers include sulfonium salts having an iodized phenyl group (exclusive of those salts containing fluorine in both anion and cation) as described in JP-A 2017-219836. Since iodine is highly absorptive to EUV of wavelength 13.5 nm, it generates secondary electrons upon EUV exposure. The energy of secondary electrons is transferred to the acid generator to promote its decomposition, contributing to a higher sensitivity.

Also useful are quenchers of polymer type as described in U.S. Pat. No. 7,598,016 (JP-A 2008-239918). The polymeric quencher segregates at the resist film surface and thus enhances the rectangularity of resist pattern. When a protective film is applied as is often the case in the immersion lithography, the polymeric quencher is also effective for preventing a film thickness loss of resist pattern or rounding of pattern top.

The other quencher (G) is preferably added in an amount of 0.001 to 20 parts, more preferably 0.01 to 10 parts by weight per 100 parts by weight of the base polymer (C) although the content is not particularly limited as long as the benefits of the invention are not impaired. The other quencher may be used alone or in admixture.

Other Components

With the foregoing components, the resist composition may further include other components such as a dissolution inhibitor, water repellency improver, and acetylene alcohol.

The inclusion of a dissolution inhibitor may lead to an increased difference in dissolution rate between exposed and unexposed areas and a further improvement in resolution. The dissolution inhibitor which can be used herein is a compound having at least two phenolic hydroxy groups on the molecule, in which an average of from 0 to 100 mol % of all the hydrogen atoms on the phenolic hydroxy groups are replaced by acid labile groups or a compound having at least one carboxy group on the molecule, in which an average of 50 to 100 mol % of all the hydrogen atoms on the carboxy groups are replaced by acid labile groups, both the compounds having a molecular weight of 100 to 1,000, and preferably 150 to 800. Typical are bisphenol A, trisphenol, phenolphthalein, cresol novolac, naphthalenecarboxylic acid, adamantanecarboxylic acid, and cholic acid derivatives in which the hydrogen atom on the hydroxy or carboxy group is replaced by an acid labile group, as described in U.S. Pat. No. 7,771,914 (JP-A 2008-122932, paragraphs [0155]-[0178]).

In the resist composition, the dissolution inhibitor is preferably added in an amount of 0 to 50 parts, more preferably 5 to 40 parts by weight per 100 parts by weight of the base polymer (C). The dissolution inhibitor may be used alone or in admixture.

The water repellency improver is added for improving the water repellency on surface of a resist film. The water repellency improver may be used in the topcoatless immersion lithography. Suitable water repellency improvers include polymers having a fluoroalkyl group and polymers having a specific structure with a 1,1,1,3,3,3-hexafluoro-2-propanol residue and are described in JP-A 2007-297590 and JP-A 2008-111103, for example. The water repellency improver to be added to the resist composition should be soluble in the alkaline developer and organic solvent developer. The water repellency improver of specific structure with a 1,1,1,3,3,3-hexafluoro-2-propanol residue is well soluble in the developer. A polymer having an amino group or amine salt copolymerized as repeat units may serve as the water repellent additive and is effective for preventing evaporation of acid during PEB, thus preventing any hole pattern opening failure after development. An appropriate amount of the water repellency improver is 0 to 20 parts, more preferably 0.5 to 10 parts by weight per 100 parts by weight of the base polymer (C). The water repellency improver may be used alone or in admixture.

Suitable acetylene alcohols are described in JP-A 2008-122932, paragraphs [0179]-[0182]. An appropriate amount of the acetylene alcohol blended is 0 to 5 parts by weight per 100 parts by weight of the base polymer (C). The acetylene alcohol may be used alone or in admixture.

Pattern Forming Process

The positive resist composition is used in the fabrication of various integrated circuits. Pattern formation using the resist composition may be performed by well-known lithography processes. The process generally involves the steps of applying the resist composition to form a resist film on a substrate, exposing the resist film to high-energy radiation, and developing the exposed resist film in a developer. If necessary, any additional steps may be added.

Specifically, the positive resist composition is first applied onto a substrate on which an integrated circuit is to be formed (e.g., Si, $SiO_2$, SiN, SiON, TiN, WSi, BPSG, SOG, or organic antireflective coating) or a substrate on which a mask circuit is to be formed (e.g., Cr, CrO, CrON, $MoSi_2$, or $SiO_2$) by a suitable coating technique such as spin coating, roll coating, flow coating, dipping, spraying or doctor coating. The coating is prebaked on a hot plate at a temperature of 60 to 150° C. for 10 seconds to 30 minutes, preferably at 80 to 120° C. for 30 seconds to 20 minutes. The resulting resist film is generally 0.01 to 2 μm thick.

The resist film is then exposed to a desired pattern of high-energy radiation such as UV, deep-UV, EB, EUV of wavelength 3 to 15 nm, x-ray, soft x-ray, excimer laser light, γ-ray or synchrotron radiation. When UV, deep-UV, EUV, x-ray, soft x-ray, excimer laser light, γ-ray or synchrotron radiation is used as the high-energy radiation, the resist film is exposed thereto directly or through a mask having a desired pattern in a dose of preferably about 1 to 200 $mJ/cm^2$, more preferably about 10 to 100 $mJ/cm^2$. When EB is used as the high-energy radiation, the resist film is exposed thereto directly or through a mask having a desired pattern in a dose of preferably about 0.1 to 100 $μC/cm^2$, more preferably about 0.5 to 50 $μC/cm^2$. It is appreciated that the inventive resist composition is suited in micropatterning using i-line of wavelength 365 nm, KrF excimer laser, ArF excimer laser, EB, EUV, x-ray, soft x-ray, γ-ray or synchrotron radiation, especially in micropatterning using EB or EUV.

After the exposure, the resist film may be baked (PEB) on a hot plate or in an oven at 50 to 150° C. for 10 seconds to 30 minutes, preferably at 60 to 120° C. for 30 seconds to 20 minutes.

After the exposure or PEB, the resist film is developed in a developer in the form of an aqueous base solution for 3 seconds to 3 minutes, preferably 5 seconds to 2 minutes by conventional techniques such as dip, puddle and spray techniques. A typical developer is a 0.1 to 10 wt %, preferably 2 to 5 wt % aqueous solution of tetramethylammonium hydroxide (TMAH), tetraethylammonium hydroxide (TEAH), tetrapropylammonium hydroxide (TPAH), or tetrabutylammonium hydroxide (TBAH). The resist film in the exposed area is dissolved in the developer whereas the resist film in the unexposed area is not dissolved. In this way, the desired positive pattern is formed on the substrate.

In an alternative embodiment, a negative pattern may be formed from the positive resist composition via organic solvent development. The developer used herein is preferably selected from among 2-octanone, 2-nonanone, 2-heptanone, 3-heptanone, 4-heptanone, 2-hexanone, 3-hexanone, diisobutyl ketone, methylcyclohexanone, acetophenone, methylacetophenone, propyl acetate, butyl acetate, isobutyl acetate, pentyl acetate, butenyl acetate, isopentyl acetate, propyl formate, butyl formate, isobutyl formate, pentyl formate, isopentyl formate, methyl valerate, methyl pentenoate, methyl crotonate, ethyl crotonate, methyl propionate, ethyl propionate, ethyl 3-ethoxypropionate, methyl lactate, ethyl lactate, propyl lactate, butyl lactate, isobutyl lactate, pentyl lactate, isopentyl lactate, methyl 2-hydroxyisobutyrate, ethyl 2-hydroxyisobutyrate, methyl benzoate, ethyl benzoate, phenyl acetate, benzyl acetate, methyl phenylacetate, benzyl formate, phenylethyl formate, methyl 3-phenylpropionate, benzyl propionate, ethyl phenylacetate, and 2-phenylethyl acetate, and mixtures thereof.

At the end of development, the resist film is rinsed. As the rinsing liquid, a solvent which is miscible with the developer and does not dissolve the resist film is preferred. Suitable solvents include alcohols of 3 to 10 carbon atoms, ether compounds of 8 to 12 carbon atoms, alkanes, alkenes, and alkynes of 6 to 12 carbon atoms, and aromatic solvents. Specifically, suitable alcohols of 3 to 10 carbon atoms include n-propyl alcohol, isopropyl alcohol, 1-butyl alcohol, 2-butyl alcohol, isobutyl alcohol, tert-butyl alcohol, 1-pentanol, 2-pentanol, 3-pentanol, tert-pentyl alcohol, neopentyl alcohol, 2-methyl-1-butanol, 3-methyl-1-butanol, 3-methyl-3-pentanol, cyclopentanol, 1-hexanol, 2-hexanol, 3-hexanol, 2,3-dimethyl-2-butanol, 3,3-dimethyl-1-butanol, 3,3-dimethyl-2-butanol, 2-ethyl-1-butanol, 2-methyl-1-pentanol, 2-methyl-2-pentanol, 2-methyl-3-pentanol, 3-methyl-1-pentanol, 3-methyl-2-pentanol, 3-methyl-3-pentanol, 4-methyl-1-pentanol, 4-methyl-2-pentanol, 4-methyl-3-pentanol, cyclohexanol, and 1-octanol. Suitable ether compounds of 8 to 12 carbon atoms include di-n-butyl ether, diisobutyl ether, di-sec-butyl ether, di-n-pentyl ether, diisopentyl ether, di-sec-pentyl ether, di-tert-pentyl ether, and di-n-hexyl ether. Suitable alkanes of 6 to 12 carbon atoms include hexane, heptane, octane, nonane, decane, undecane, dodecane, methylcyclopentane, dimethylcyclopentane, cyclohexane, methylcyclohexane, dimethylcyclohexane, cycloheptane, cyclooctane, and cyclononane. Suitable alkenes of 6 to 12 carbon atoms include hexene, heptene, octene, cyclohexene, methylcyclohexene, dimethylcyclohexene, cycloheptene, and cyclooctene. Suitable alkynes of 6 to 12 carbon atoms include hexyne, heptyne, and octyne. Suitable aromatic solvents include toluene, xylene, ethylbenzene, isopropylbenzene, tert-butylbenzene and mesitylene. The solvents may be used alone or in admixture.

Rinsing is effective for minimizing the risks of resist pattern collapse and defect formation. However, rinsing is not essential. If rinsing is omitted, the amount of solvent used may be reduced.

A hole or trench pattern after development may be shrunk by the thermal flow, RELACS® or DSA process. A hole pattern is shrunk by coating a shrink agent thereto, and baking such that the shrink agent may undergo crosslinking at the resist surface as a result of the acid catalyst diffusing from the resist layer during bake, and the shrink agent may attach to the sidewall of the hole pattern. The bake is preferably at a temperature of 70 to 180° C., more preferably 80 to 170° C., for a time of 10 to 300 seconds. The extra shrink agent is stripped and the hole pattern is shrunk.

EXAMPLES

Examples of the invention are given below by way of illustration and not by way of limitation. The abbreviation "pbw" is parts by weight.

Synthesis Examples 1-1 to 1-5

Synthesis of Base Polymers P-1 to P-5

Each of base polymers P-1 to P-5 was prepared by combining suitable monomers, effecting copolymerization reaction thereof in tetrahydrofuran (THF) solvent, pouring the reaction solution into methanol for crystallization, washing the precipitate with hexane, isolation, and drying. The resulting polymer was analyzed for composition by $^1$H-NMR spectroscopy, and for Mw and Mw/Mn by GPC versus polystyrene standards using THF solvent.

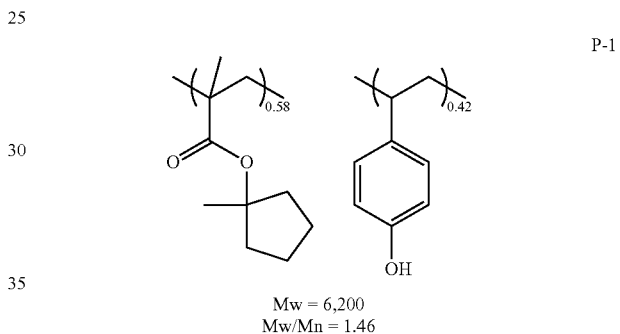

P-1

Mw = 6,200
Mw/Mn = 1.46

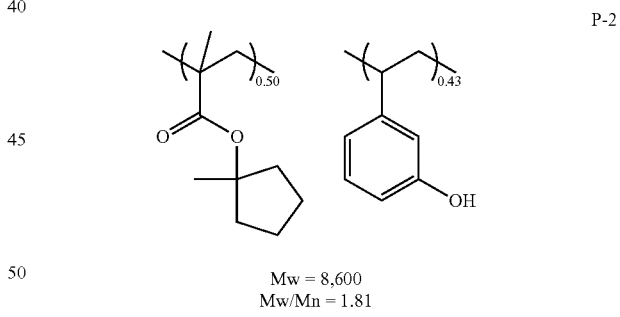

P-2

Mw = 8,600
Mw/Mn = 1.81

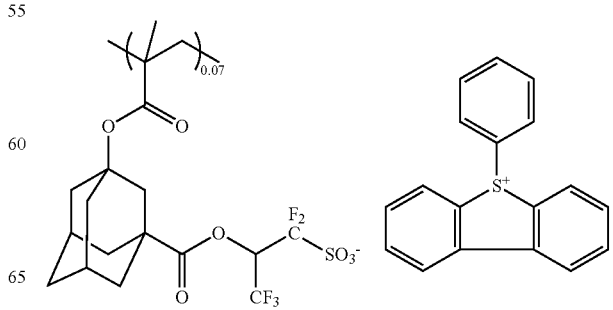

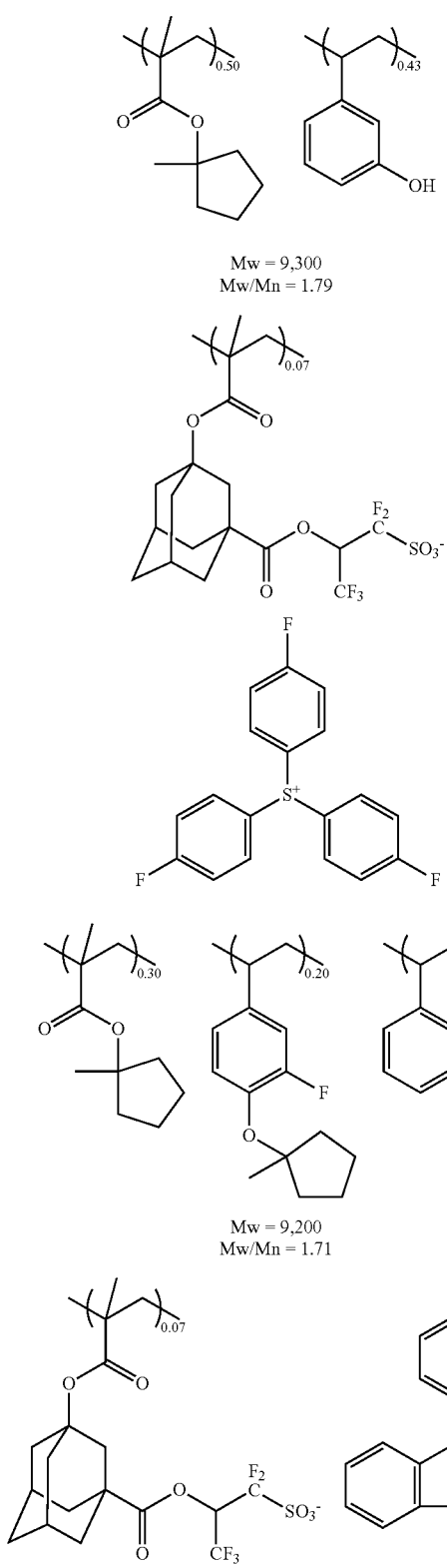
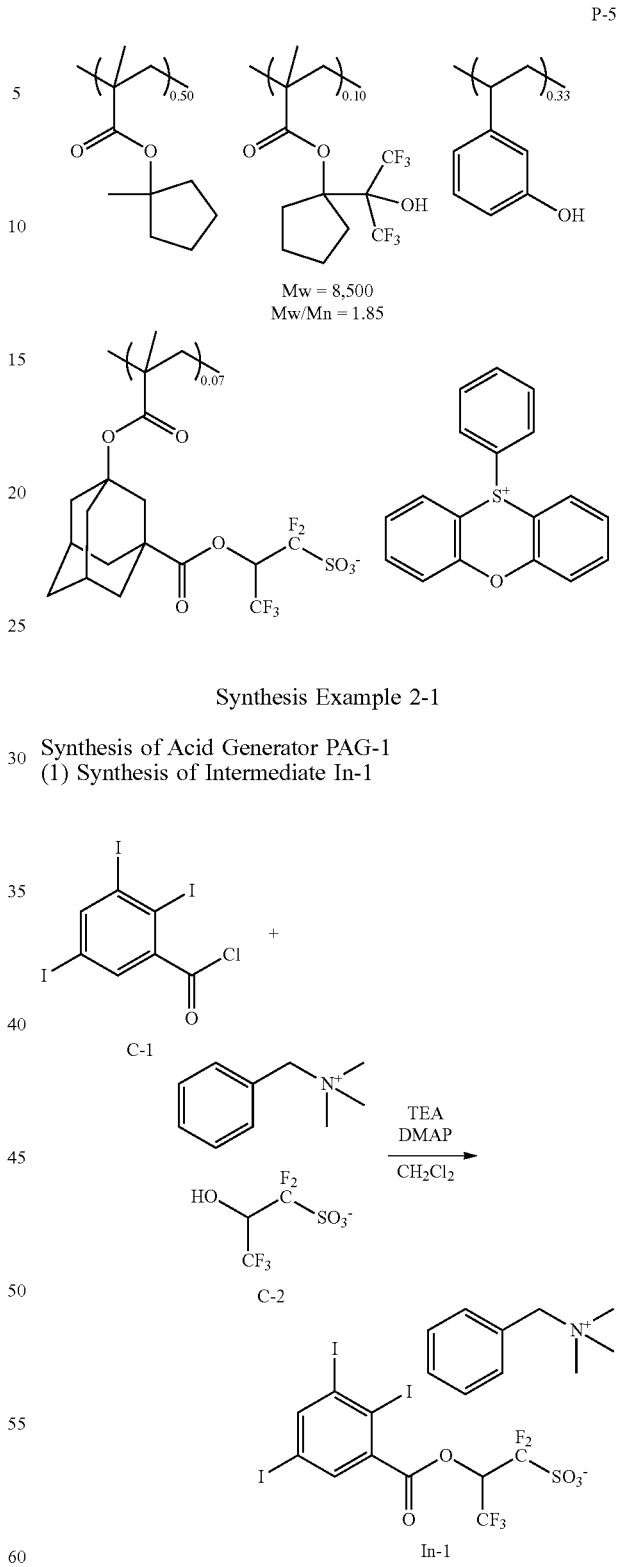
Synthesis Example 2-1
Synthesis of Acid Generator PAG-1
(1) Synthesis of Intermediate In-1
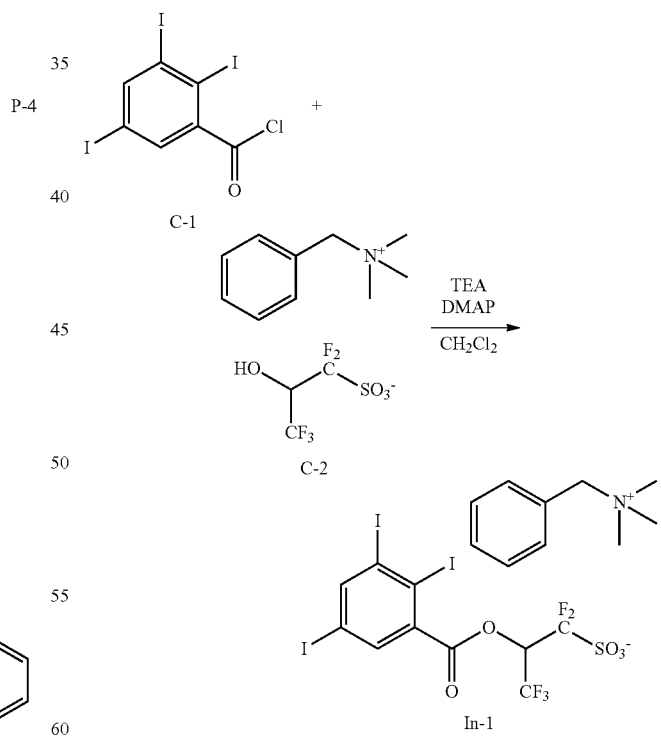
In 1,050 g of dichloromethane were dissolved 150 g of Compound C-1 and 87.6 of Compound C-2 which was synthesized according to the method described in JP-A 2016-218089 or US 20160334706. Under ice cooling, a solution of 32.7 g of triethylamine (TEA) and 2.8 g of N,N-dimethyl-4-aminopyridine (DMAP) in 100 g of dichloromethane was added to the above solution. After stirring was continued at room temperature for 1 hour, 300 g of a 10 wt % aqueous solution of sodium hydrogencarbonate was added to the solution, which was stirred at room temperature for 20 minutes. An organic layer was taken out, washed with deionized water, and concentrated under reduced pressure. To the residue was added 600 g of hexane. The thus precipitated crystal was recovered by filtration and dried in vacuum. There was obtained the end compound, Intermediate In-1 (amount 187 g, yield 94%). The results of $^1$H-NMR analysis are shown below.

$^1$H-NMR (500 MHz, DMSO-d6): δ=3.00 (9H, s), 4.50 (2H, s), 6.18 (1H, m), 7.52 (5H, s), 8.03 (1H, s), 8.44 (1H, s) ppm (2) Synthesis of Acid Generator PAG-1

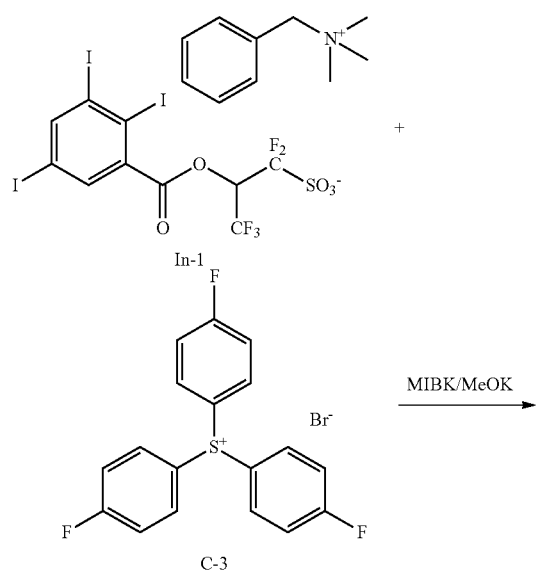

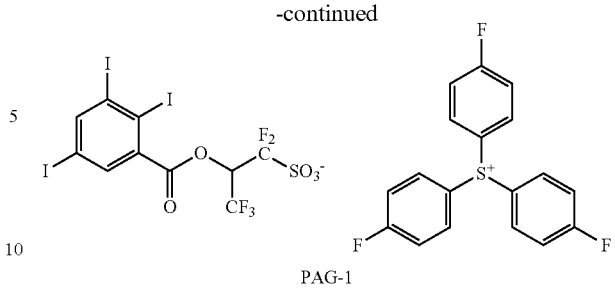

PAG-1

In a mixture of 84.7 g of methyl isobutyl ketone (MIBK) and 5 g of methanol, 17.2 g of In-1 and 8.74 g of Compound C-3 were dissolved. The solution was stirred at room temperature for 30 minutes. An organic layer was taken out, washed with deionized water, and concentrated under reduced pressure. To the residue was added 70 g of hexane. The thus precipitated crystal was recovered by filtration and dried in vacuum. There was obtained the target compound, PAG-1 (amount 17.5 g, yield 84%). The results of $^1$H- and $^{19}$F-NMR analyses are shown below.

$^1$H-NMR (500 MHz, DMSO-d6): δ=6.17 (1H, m), 7.63-7.68 (6H, m), 7.90-7.94 (6H, m), 8.03 (1H, s), 8.44 (1H, s) ppm $^{19}$F-NMR (500 MHz, DMSO-d6): δ=−121 (1F, m), −113 (1F, m), −105 (3F, s), −71.3 (3F, m) ppm Synthesis Examples 2-2 to 2-22

Synthesis of Acid Generators PAG-2 to PAG-22

Acid generators PAG-2 to PAG-22 were synthesized with reference to Synthesis Example 2-1. Their structure is shown below.

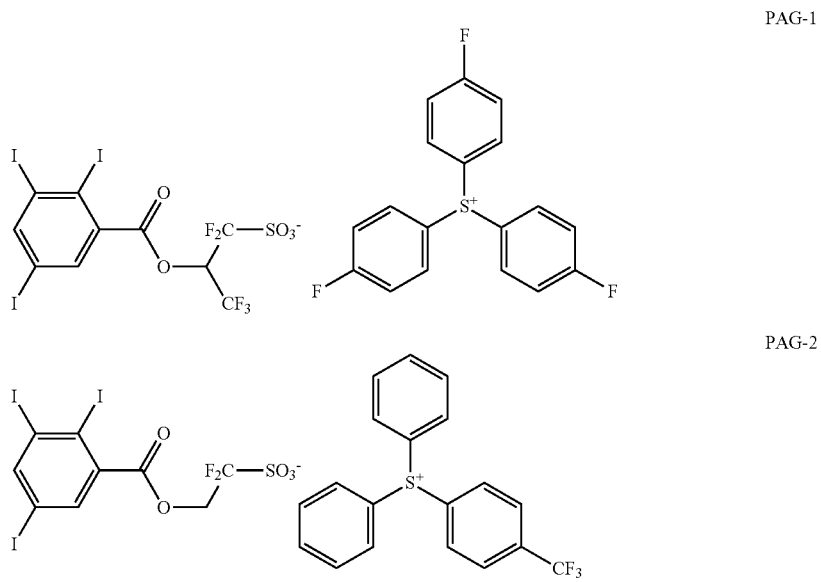

-continued
PAG-3
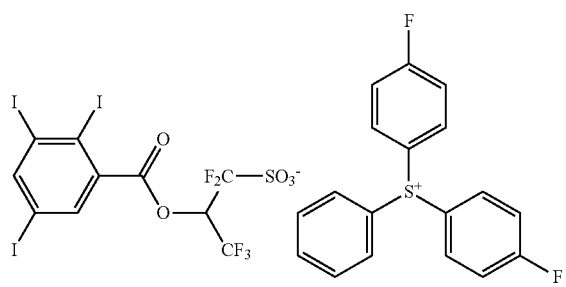
PAG-4
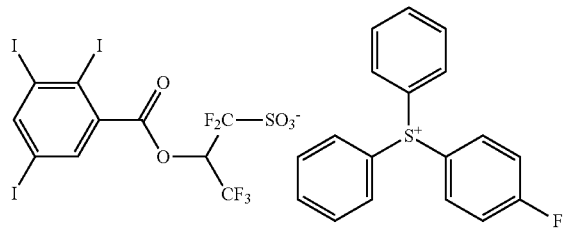
PAG-5
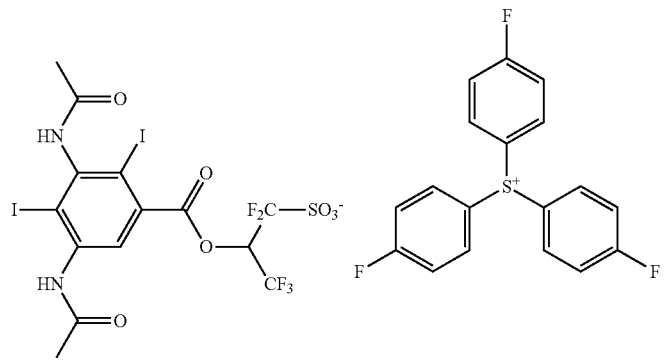
PAG-6
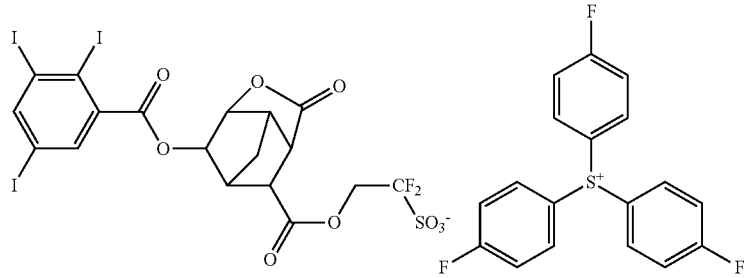
PAG-7
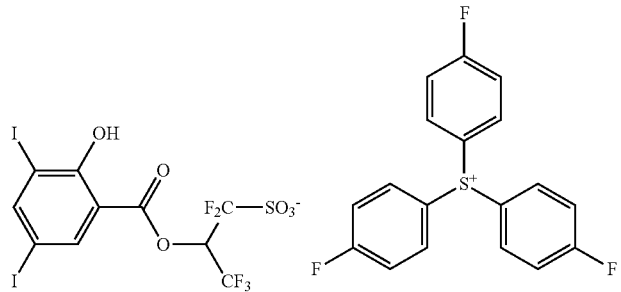

-continued
PAG-8
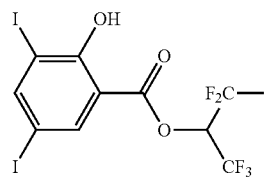 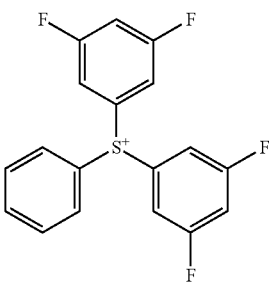
PAG-9
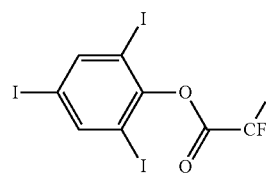 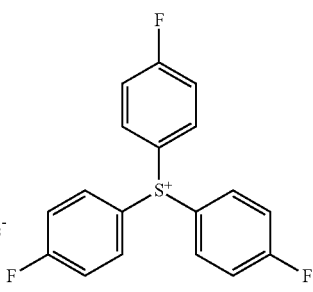
PAG-10
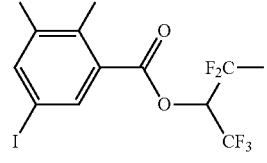 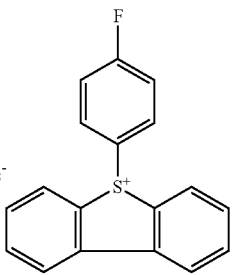
PAG-11
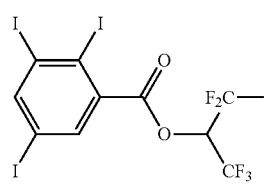 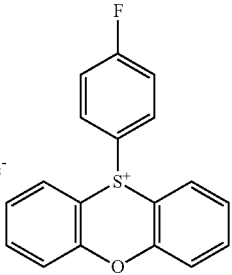
PAG-12
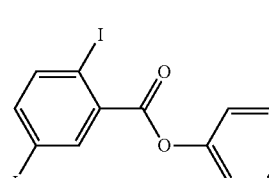 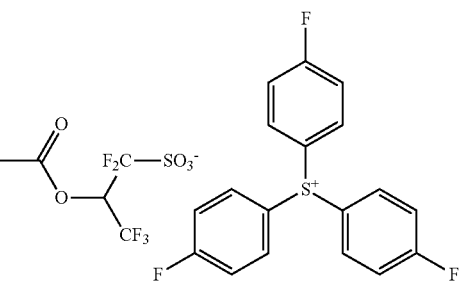

-continued
PAG-13
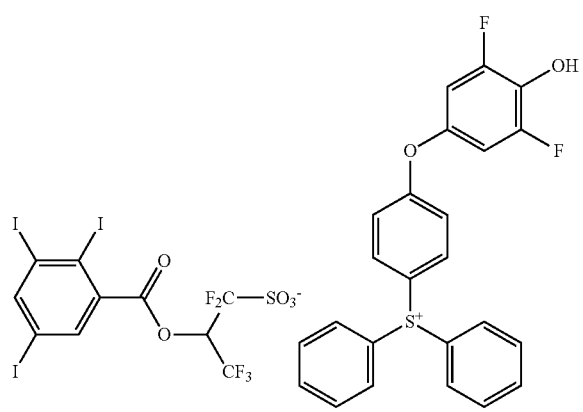
PAG-14
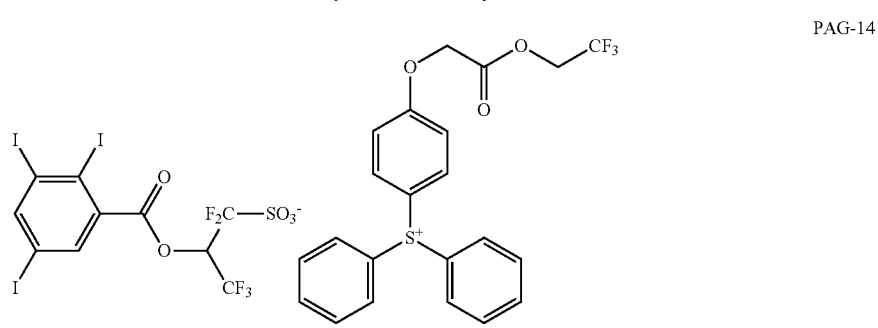
PAG-15
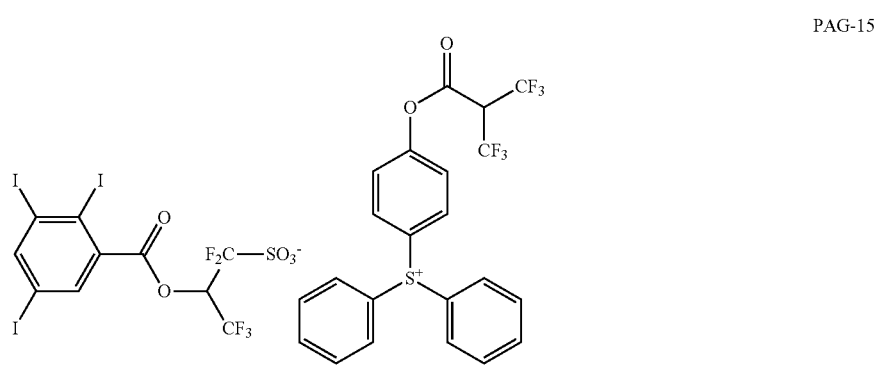
PAG-16
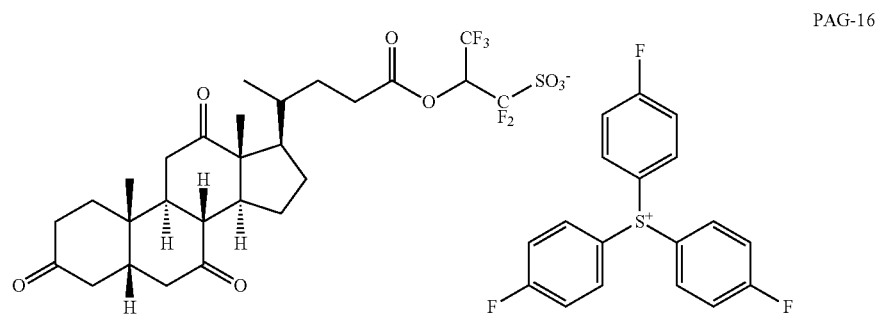

-continued
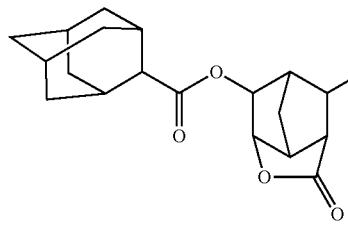
PAG-17
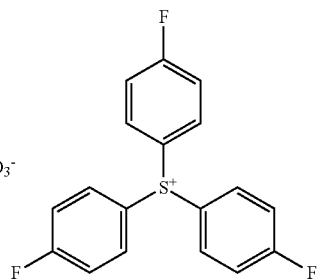
PAG-18
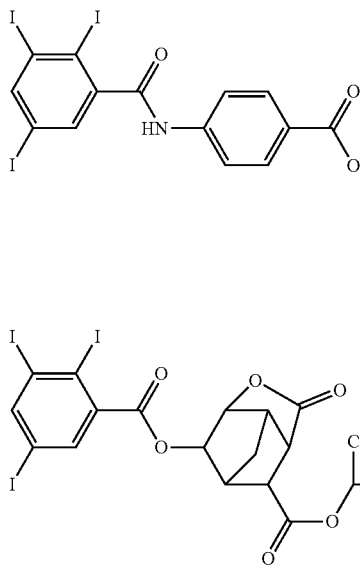
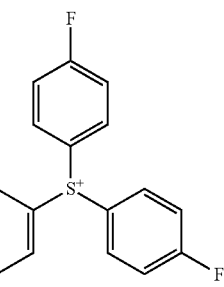
PAG-19
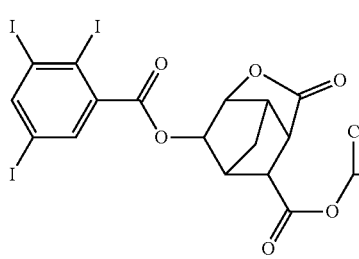
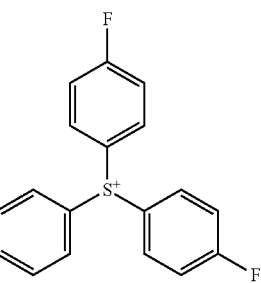
PAG-20
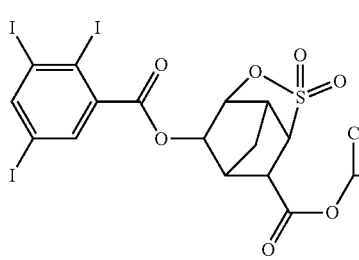
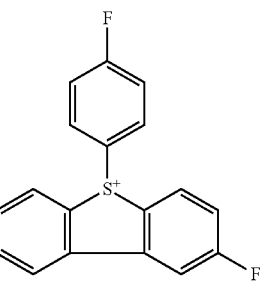
PAG-21
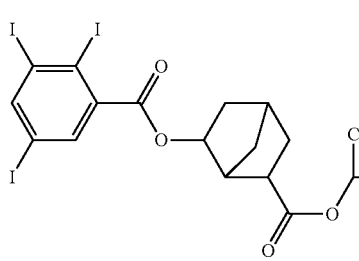
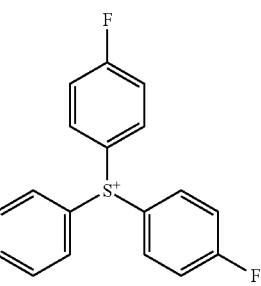

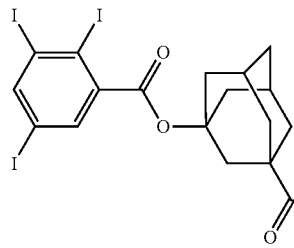

PAG-22

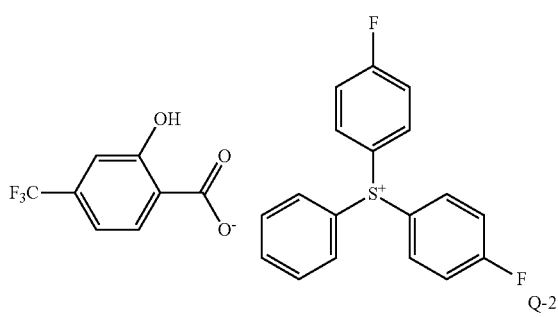

Examples 1 to 42 and Comparative Examples 1 to 6

Preparation and Evaluation of Positive Resist Compositions (1) Preparation of Positive Resist Composition Positive resist compositions were prepared by dissolving components in an organic solvent containing 50 ppm of surfactant Polyfox 636 (Omnova Solutions Inc.) in accordance with the formulation shown in Tables 1 to 4, and filtering through a filter with a pore size of 0.2 μm.

The components in Tables 1 to 4 are identified below.

Organic Solvent:

PGMEA=propylene glycol monomethyl ether acetate

DAA=diacetone alcohol

Comparative Acid Generators (cPAG-1, cPAG-2):

cPAG-1

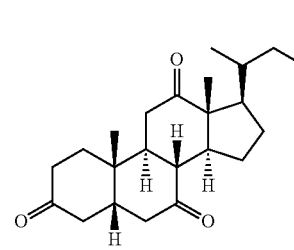 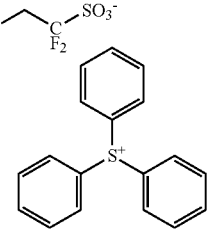

cPAG-2

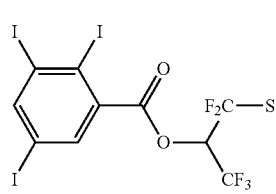 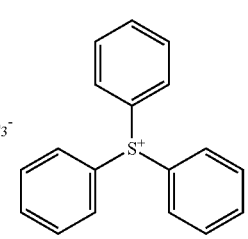

Quenchers: Q-1 to Q-26

Q-1

Q-2

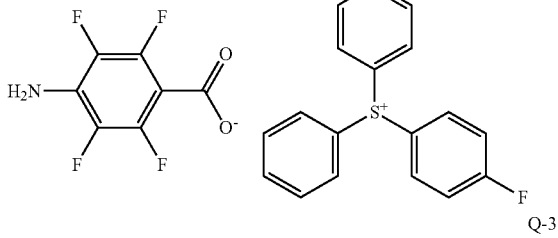

Q-3

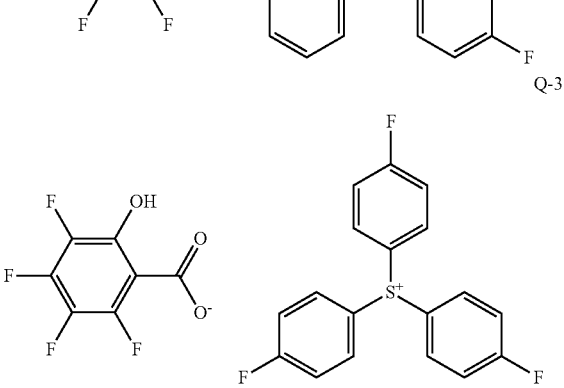

Q-4

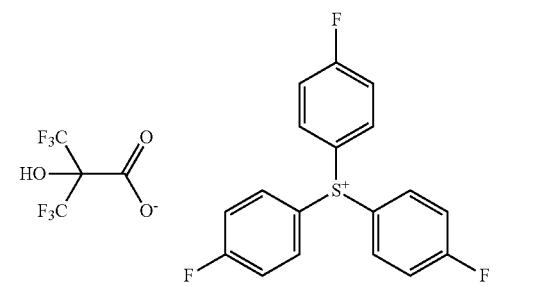

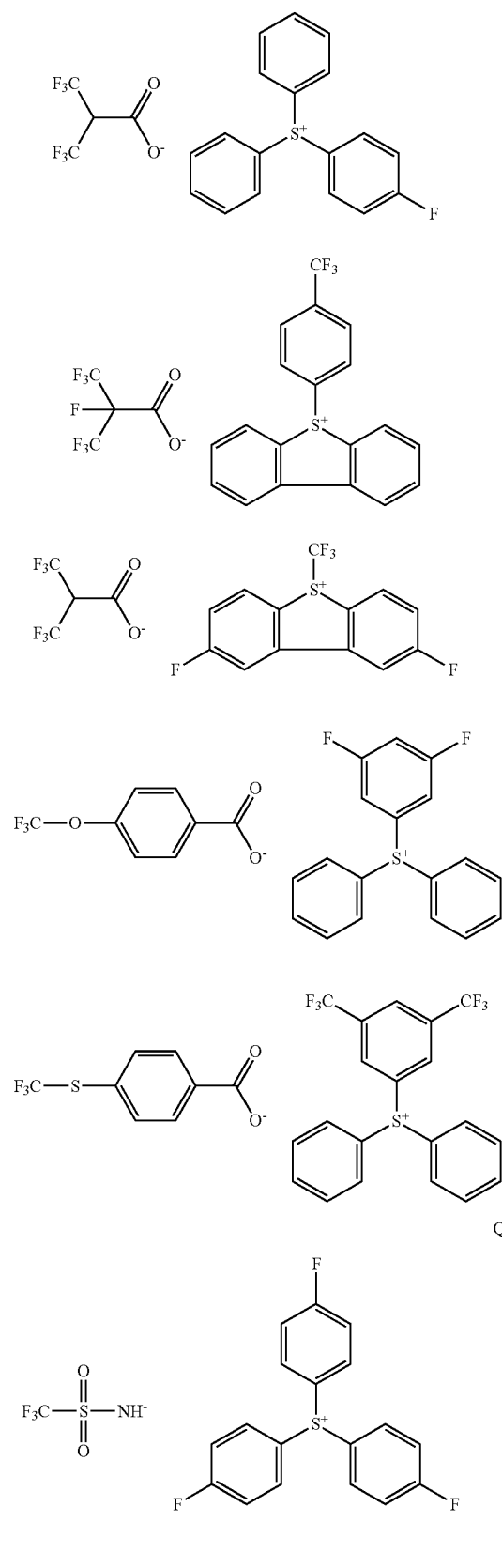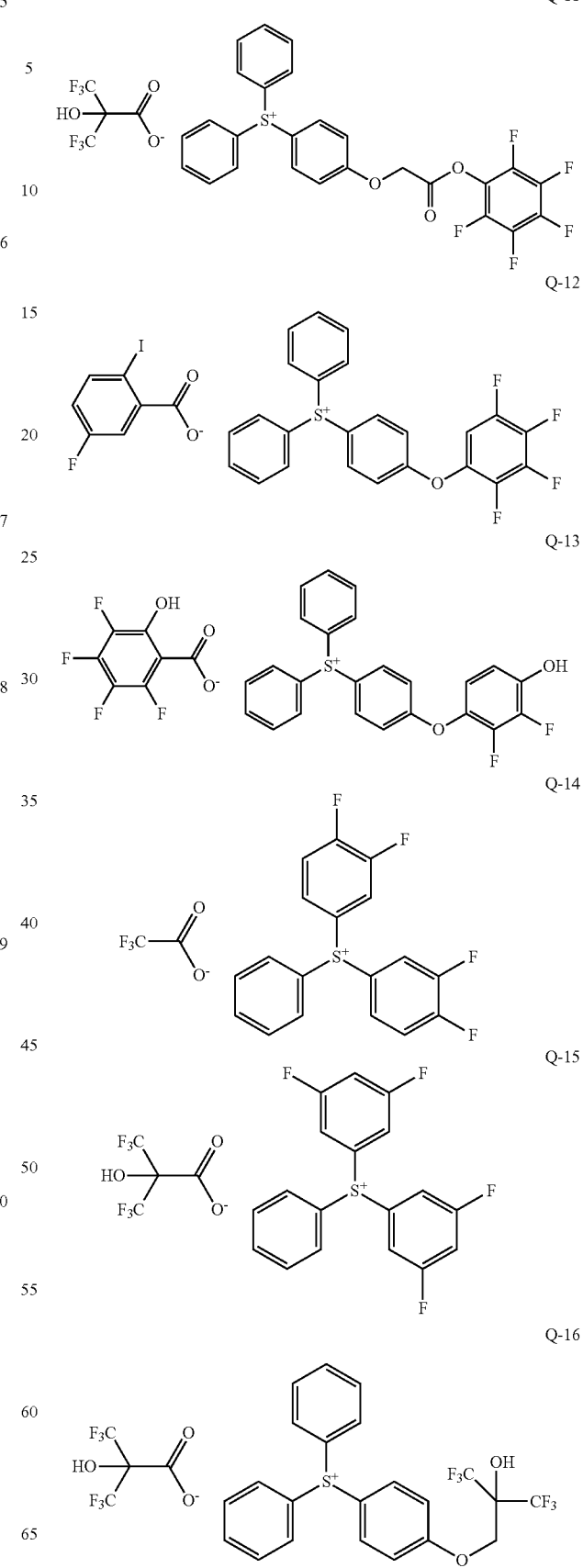

Q-17
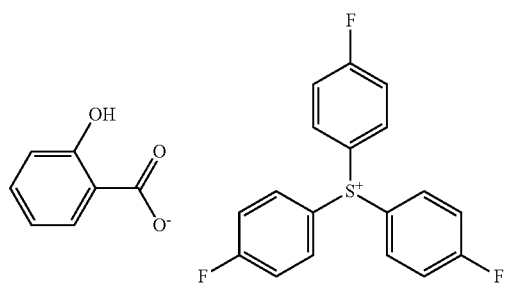
Q-18
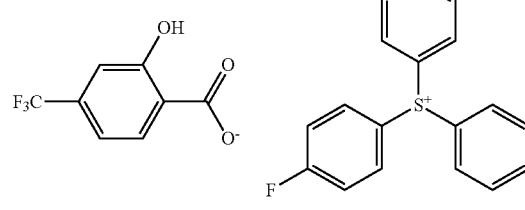
Q-19
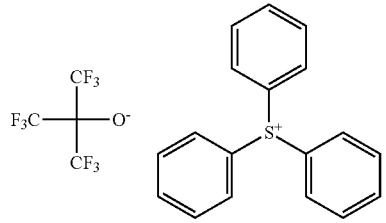
Q-20
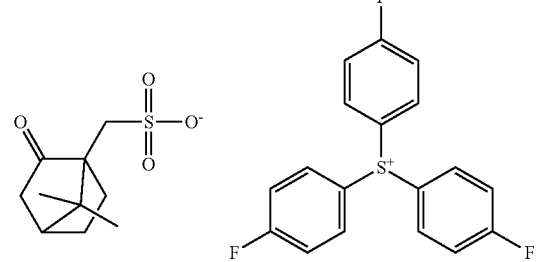
Q-21
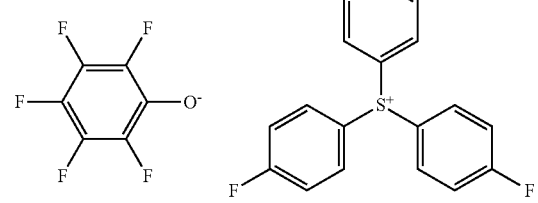
Q-22
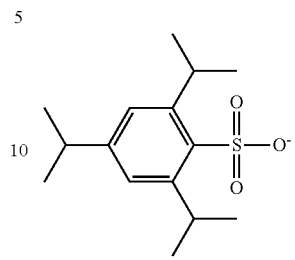
Q-23
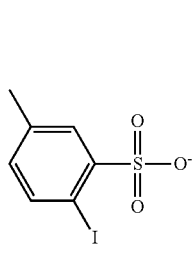 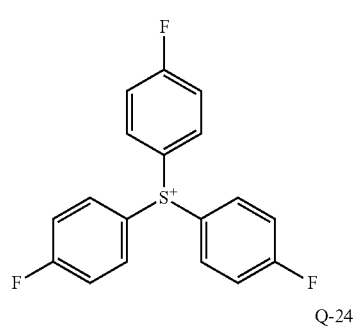
Q-24
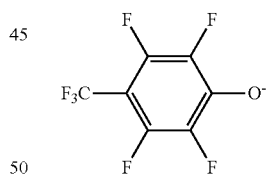 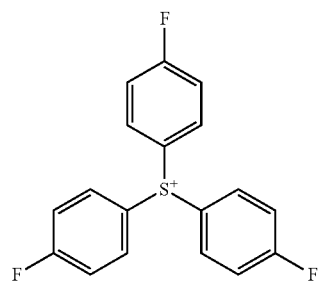
Q-25
Q-26
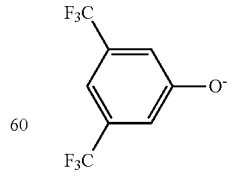 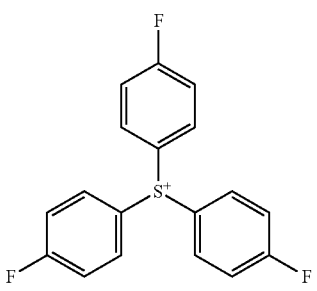

Comparative Quenchers: cQ-1 to cQ-5

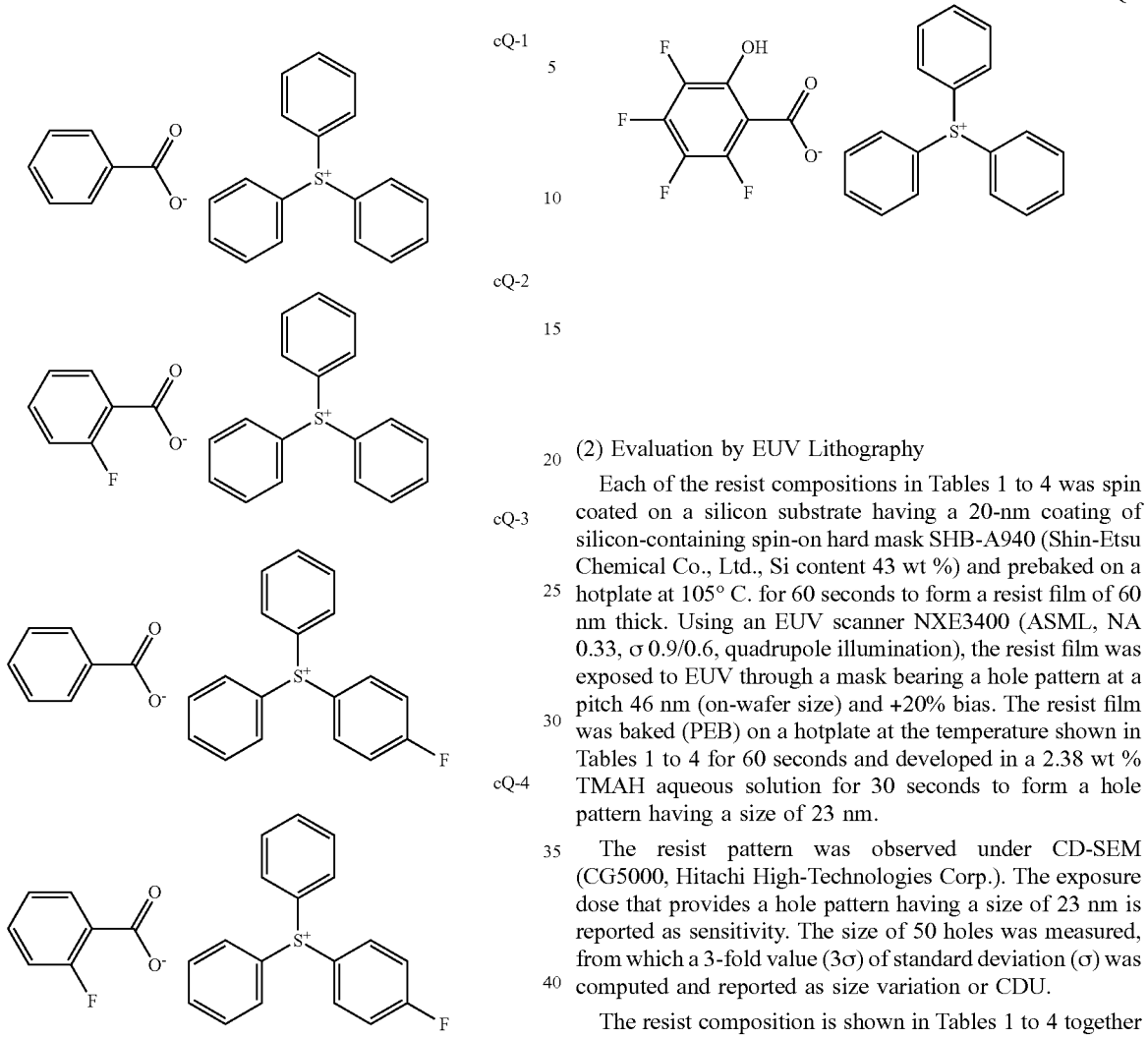

(2) Evaluation by EUV Lithography

Each of the resist compositions in Tables 1 to 4 was spin coated on a silicon substrate having a 20-nm coating of silicon-containing spin-on hard mask SHB-A940 (Shin-Etsu Chemical Co., Ltd., Si content 43 wt %) and prebaked on a hotplate at 105° C. for 60 seconds to form a resist film of 60 nm thick. Using an EUV scanner NXE3400 (ASML, NA 0.33, σ 0.9/0.6, quadrupole illumination), the resist film was exposed to EUV through a mask bearing a hole pattern at a pitch 46 nm (on-wafer size) and +20% bias. The resist film was baked (PEB) on a hotplate at the temperature shown in Tables 1 to 4 for 60 seconds and developed in a 2.38 wt % TMAH aqueous solution for 30 seconds to form a hole pattern having a size of 23 nm.

The resist pattern was observed under CD-SEM (CG5000, Hitachi High-Technologies Corp.). The exposure dose that provides a hole pattern having a size of 23 nm is reported as sensitivity. The size of 50 holes was measured, from which a 3-fold value (3σ) of standard deviation (σ) was computed and reported as size variation or CDU.

The resist composition is shown in Tables 1 to 4 together with the sensitivity and CDU of EUV lithography.

TABLE 1

|  |  | Polymer (pbw) | Acid generator (pbw) | Quencher (pbw) | Organic solvent (pbw) | PEB temp. (° C.) | Sensitivity (mJ/cm$^2$) | CDU (nm) |
| --- | --- | --- | --- | --- | --- | --- | --- | --- |
| Example | 1 | P-1 (100) | PAG-1 (30.3) | Q-1 (4.86) | PGMEA (2,000) DAA (500) | 80 | 29 | 2.6 |
|  | 2 | P-1 (100) | PAG-1 (30.3) | Q-2 (5.07) | PGMEA (2,000) DAA (500) | 80 | 27 | 2.6 |
|  | 3 | P-1 (100) | PAG-1 (30.3) | Q-3 (5.55) | PGMEA (2,000) DAA (500) | 80 | 28 | 2.6 |
|  | 4 | P-1 (100) | PAG-1 (30.3) | Q-4 (5.28) | PGMEA (2,000) DAA (500) | 80 | 26 | 2.4 |
|  | 5 | P-1 (100) | PAG-1 (30.3) | Q-5 (4.76) | PGMEA (2,000) DAA (500) | 80 | 30 | 2.5 |
|  | 6 | P-1 (100) | PAG-1 (30.3) | Q-6 (5.42) | PGMEA (2,000) DAA (500) | 80 | 29 | 2.4 |
|  | 7 | P-1 (100) | PAG-1 (30.3) | Q-7 (2.42) Q-8 (2.52) | PGMEA (2,000) DAA (500) | 80 | 28 | 2.5 |
|  | 8 | P-1 (100) | PAG-1 (30.3) | Q-9 (6.20) | PGMEA (2,000) DAA (500) | 80 | 29 | 2.4 |
|  | 9 | P-1 (100) | PAG-1 (30.3) | Q-10 (4.63) | PGMEA (2,000) DAA (500) | 80 | 28 | 2.5 |
|  | 10 | P-1 (100) | PAG-1 (30.3) | Q-11 (7.14) | PGMEA (2,000) DAA (500) | 80 | 30 | 2.4 |

TABLE 1-continued

|  | Polymer (pbw) | Acid generator (pbw) | Quencher (pbw) | Organic solvent (pbw) | PEB temp. (° C.) | Sensitivity (mJ/cm$^2$) | CDU (nm) |
|---|---|---|---|---|---|---|---|
| 11 | P-1 (100) | PAG-1 (30.3) | Q-12 (6.72) | PGMEA (2,000) DAA (500) | 80 | 29 | 2.4 |
| 12 | P-1 (100) | PAG-1 (30.3) | Q-13 (6.16) | PGMEA (2,000) DAA (500) | 80 | 29 | 2.3 |
| 13 | P-1 (100) | PAG-2 (29.2) | Q-4 (5.28) | PGMEA (2,000) DAA (500) | 80 | 28 | 2.4 |
| 14 | P-1 (100) | PAG-3 (29.8) | Q-4 (5.28) | PGMEA (2,000) DAA (500) | 80 | 27 | 2.4 |
| 15 | P-1 (100) | PAG-4 (30.8) | Q-4 (5.28) | PGMEA (2,000) DAA (500) | 80 | 26 | 2.4 |
| 16 | P-1 (100) | PAG-5 (34.3) | Q-4 (5.28) | PGMEA (2,000) DAA (500) | 80 | 29 | 2.4 |
| 17 | P-1 (100) | PAG-6 (34.2) | Q-4 (5.28) | PGMEA (2,000) DAA (500) | 80 | 28 | 2.2 |
| 18 | P-1 (100) | PAG-7 (27.5) | Q-4 (5.28) | PGMEA (2,000) DAA (500) | 80 | 28 | 2.4 |
| 19 | P-1 (100) | PAG-8 (28.1) | Q-4 (5.28) | PGMEA (2,000) DAA (500) | 80 | 28 | 2.5 |
| 20 | P-1 (100) | PAG-9 (28.4) | Q-4 (5.28) | PGMEA (2,000) DAA (500) | 80 | 29 | 2.3 |

TABLE 2

|  |  | Polymer (pbw) | Acid generator (pbw) | Quencher (pbw) | Organic solvent (pbw) | PEB temp. (° C.) | Sensitivity (mJ/cm$^2$) | CDU (nm) |
|---|---|---|---|---|---|---|---|---|
| Example | 21 | P-1 (100) | PAG-10 (27.7) | Q-4 (5.28) | PGMEA (2,000) DAA (500) | 80 | 27 | 2.4 |
|  | 22 | P-2 (100) | PAG-11 (10.2) | Q-4 (5.28) | PGMEA (2,000) DAA (500) | 85 | 29 | 2.4 |
|  | 23 | P-3 (100) | PAG-12 (9.1) | Q-4 (5.28) | PGMEA (2,000) DAA (500) | 85 | 26 | 2.2 |
|  | 24 | P-4 (100) | PAG-13 (11.2) | Q-4 (5.28) | PGMEA (2,000) DAA (500) | 85 | 25 | 2.4 |
|  | 25 | P-5 (100) | PAG-14 (11.3) | Q-4 (5.28) | PGMEA (2,000) DAA (500) | 85 | 37 | 2.3 |
|  | 26 | P-5 (100) | PAG-15 (11.7) | Q-4 (5.28) | PGMEA (2,000) DAA (500) | 85 | 28 | 2.1 |
|  | 27 | P-5 (100) | PAG-16 (9.3) | Q-4 (5.28) | PGMEA (2,000) DAA (500) | 85 | 31 | 2.6 |
|  | 28 | P-5 (100) | PAG-17 (8.2) | Q-14 (3.94) | PGMEA (2,000) DAA (500) | 80 | 31 | 2.5 |
|  | 29 | P-5 (100) | PAG-18 (8.2) | Q-15 (3.76) | PGMEA (2,000) DAA (500) | 80 | 34 | 2.2 |

TABLE 3

|  |  | Polymer (pbw) | Acid generator (pbw) | Quencher (pbw) | Organic solvent (pbw) | PEB temp. (° C.) | Sensitivity (mJ/cm$^2$) | CDU (nm) |
|---|---|---|---|---|---|---|---|---|
| Example | 30 | P-5 (100) | PAG-18 (8.2) | Q-16 (6.70) | PGMEA (2,000) DAA (500) | 80 | 26 | 2.6 |
|  | 31 | P-5 (100) | PAG-19 (12.0) | Q-17 (4.54) | PGMEA (2,000) DAA (500) | 80 | 33 | 2.4 |
|  | 32 | P-5 (100) | PAG-20 (12.4) | Q-18 (4.72) | PGMEA (2,000) DAA (500) | 80 | 32 | 2.4 |
|  | 33 | P-5 (100) | PAG-20 (12.4) | Q-19 (4.98) | PGMEA (2,000) DAA (500) | 80 | 27 | 2.3 |
|  | 34 | P-5 (100) | PAG-20 (12.4) | Q-20 (5.48) | PGMEA (2,000) DAA (500) | 80 | 24 | 2.6 |
|  | 35 | P-5 (100) | PAG-20 (12.4) | Q-21 (4.46) | PGMEA (2,000) DAA (500) | 80 | 27 | 2.3 |
|  | 36 | P-5 (100) | PAG-20 (12.4) | Q-22 (6.00) | PGMEA (2,000) DAA (500) | 80 | 22 | 2.6 |
|  | 37 | P-5 (100) | PAG-20 (12.4) | Q-23 (6.13) | PGMEA (2,000) DAA (500) | 80 | 26 | 2.2 |
|  | 38 | P-5 (100) | PAG-20 (12.4) | Q-24 (5.23) | PGMEA (2,000) DAA (500) | 80 | 27 | 2.2 |

TABLE 3-continued

|  | Polymer (pbw) | Acid generator (pbw) | Quencher (pbw) | Organic solvent (pbw) | PEB temp. (° C.) | Sensitivity (mJ/cm$^2$) | CDU (nm) |
|---|---|---|---|---|---|---|---|
| 39 | P-5 (100) | PAG-20 (12.4) | Q-25 (5.50) | PGMEA (2,000) DAA (500) | 80 | 26 | 2.3 |
| 40 | P-1 (100) | PAG-20 (31.0) | Q-26 (5.46) | PGMEA (2,000) DAA (500) | 80 | 26 | 2.4 |
| 41 | P-1 (100) | PAG-21 (29.2) | Q-26 (5.46) | PGMEA (2,000) DAA (500) | 80 | 29 | 2.3 |
| 42 | P-1 (100) | PAG-22 (30.2) | Q26 (5.46) | PGMEA (2,000) DAA (500) | 80 | 30 | 2.2 |

TABLE 4

| | | Polymer (pbw) | Acid generator (pbw) | Quencher (pbw) | Organic solvent (pbw) | PEB temp. (° C.) | Sensitivity (mJ/cm$^2$) | CDU (nm) |
|---|---|---|---|---|---|---|---|---|
| Comparative Example | 1 | P-1 (100) | cPAG-1 (24.2) | Q-1 (4.86) | PGMEA (2,000) DAA (500) | 80 | 35 | 3.0 |
| | 2 | P-1 (100) | cPAG-1 (29.8) | cQ-1 (4.02) | PGMEA (2,000) DAA (500) | 80 | 33 | 2.8 |
| | 3 | P-1 (100) | cPAG-2 (24.2) | cQ-2 (4.02) | PGMEA (2,000) DAA (500) | 80 | 30 | 3.4 |
| | 4 | P-1 (100) | PAG-1 (29.8) | cQ-3 (4.02) | PGMEA (2,000) DAA (500) | 80 | 33 | 2.8 |
| | 5 | P-1 (100) | PAG-1 (29.8) | cQ-4 (4.20) | PGMEA (2,000) DAA (500) | 80 | 32 | 2.8 |
| | 6 | P-1 (100) | PAG-1 (29.8) | cQ-5 (4.7) | PGMEA (2,000) DAA (500) | 80 | 30 | 2.8 |

It is evident from Tables 1 to 4 that the positive resist compositions comprising an acid generator in the form of a sulfonium salt consisting of a fluorine-containing sulfonate anion and a fluorine-containing sulfonium cation and a quencher in the form of a sulfonium salt containing at least two fluorine atoms in its cation or containing at least 5 fluorine atoms in its anion and cation exhibit a high sensitivity and improved CDU.

Japanese Patent Application No. 2020-166646 is incorporated herein by reference.

Although some preferred embodiments have been described, many modifications and variations may be made thereto in light of the above teachings. It is therefore to be understood that the invention may be practiced otherwise than as specifically described without departing from the scope of the appended claims.

The invention claimed is:

1. A positive resist composition comprising:
(A) an acid generator in the form of a sulfonium salt consisting of a sulfonate anion having at least one fluorine atom and a sulfonium cation having at least one fluorine atom,
(B) a quencher in the form of a sulfonium salt consisting of a cation and an anion, the cation containing at least two fluorine atoms or the anion and cation containing at least 5 fluorine atoms in total, and
(C) a base polymer comprising repeat units of at least one type selected from repeat units (a1) having a carboxy group whose hydrogen is substituted by an acid labile group and repeat units (a2) having a phenolic hydroxy group whose hydrogen is substituted by an acid labile group,
wherein the sulfonate anion in the acid generator (A) has the formula (1-1) or (1-2):

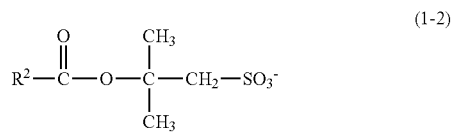

wherein $R^1$ is fluorine or a $C_1$-$C_{40}$ hydrocarbyl group which may contain a heteroatom exclusive of iodine, and $R^2$ is a $C_1$-$C_{40}$ hydrocarbyl group which may contain a heteroatom exclusive of iodine.

2. The resist composition of claim 1 wherein the quencher (B) is a sulfonium salt in which the cation contains at least 3 fluorine atoms or the anion and cation contain at least 6 fluorine atoms in total.

3. A positive resist composition comprising:
(A) an acid generator in the form of a sulfonium salt consisting of a sulfonate anion having at least one fluorine atom and a sulfonium cation having at least one fluorine atom,
(B) a quencher in the form of a sulfonium salt consisting of a cation and an anion, the cation containing at least two fluorine atoms or the anion and cation containing at least 5 fluorine atoms in total, and
(C) a base polymer comprising repeat units of at least one type selected from repeat units (a1) having a carboxy group whose hydrogen is substituted by an acid labile group and repeat units (a2) having a phenolic hydroxy group whose hydrogen is substituted by an acid labile group,
wherein the sulfonate anion in the acid generator (A) further contains an iodine atom, and wherein the sulfonate anion has the formula (1-3):

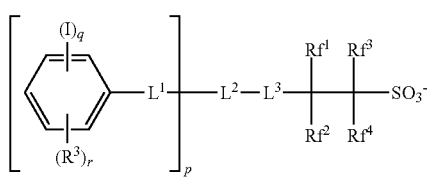

wherein p is an integer of 1 to 3, q is an integer of 1 to 5, r is an integer of 0 to 3, and q+r is from 1 to 5, $L^1$ is a single bond, ether bond, ester bond, amide bond, imide bond or a $C_1$-$C_6$ straight or branched saturated hydrocarbylene group in which any constituent —$CH_2$— may be replaced by an ether bond or ester bond, $L^2$ is a single bond or $C_1$-$C_{20}$ straight or branched hydrocarbylene group which may contain a heteroatom in case of p=1, and a $C_1$-$C_{20}$ straight or branched (p+1)-valent hydrocarbon group which may contain a heteroatom in case of p=2 or 3, $L^3$ is a single bond, ether bond or ester bond, $Rf^1$ to $Rf^4$ are each independently hydrogen, fluorine or trifluoromethyl, at least one of $Rf^1$ to $Rf^4$ being fluorine or trifluoromethyl, and $Rf^1$ and $Rf^2$, taken together, may form a carbonyl group, $R^3$ is a hydroxy group, carboxy group, fluorine, chlorine, bromine, or amino group, or a $C_1$-$C_{20}$ hydrocarbyl group, $C_1$-$C_{20}$ hydrocarbyloxy group, $C_2$-$C_{20}$ hydrocarbyloxycarbonyl group, $C_2$-$C_{20}$ hydrocarbyloxycarbonyl group, $C_2$-$C_{20}$ hydrocarbylcarbonyloxy group, or $C_1$-$C_{20}$ hydrocarbylsulfonyloxy group, which may contain fluorine, chlorine, bromine, hydroxy, amino or ether bond, or —N($R^{3A}$)($R^{3B}$), —N($R^{3C}$)—C(=O)—$R^{3D}$ or —N($R^{3C}$)—C(=O)—O—$R^{3D}$, wherein $R^{3A}$ and $R^{3B}$ are each independently hydrogen or a $C_1$-$C_6$ saturated hydrocarbyl group, $R^{3C}$ is hydrogen or a $C_1$-$C_6$ saturated hydrocarbyl group, in which some or all hydrogen may be substituted by a halogen, hydroxy moiety, $C_1$-$C_6$ saturated hydrocarbyloxy moiety, $C_2$-$C_6$ saturated hydrocarbylcarbonyl moiety, or $C_2$-$C_6$ saturated hydrocarbylcarbonyloxy moiety, and $R^{3D}$ is a $C_1$-$C_{16}$ aliphatic hydrocarbyl group, $C_6$-$C_{12}$ aryl group or $C_7$-$C_{15}$ aralkyl group, in which some or all hydrogen may be substituted by a halogen, hydroxy moiety, $C_1$-$C_6$ saturated hydrocarbyloxy moiety, $C_2$-$C_6$ saturated hydrocarbylcarbonyl moiety, or $C_2$-$C_6$ saturated hydrocarbylcarbonyloxy moiety.

4. The resist composition of claim 1 wherein the anion of the sulfonium salt as quencher (B) is a carboxylate, sulfonamide, alkoxide or non-α-fluorinated sulfonate anion.

5. The resist composition of claim 4 wherein the carboxylate anion has the formula (2-1), the sulfonamide anion has the formula (2-2), the alkoxide anion has the formula (2-3), and the non-a-fluorinated sulfonate anion has the formula (2-4):

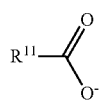

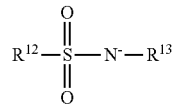

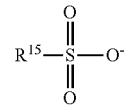

wherein $R^{11}$ is fluorine or a $C_1$-$C_{40}$ hydrocarbyl group which may contain fluorine or a heteroatom exclusive of fluorine, $R^{12}$ is fluorine or a $C_1$-$C_{40}$ hydrocarbyl group which may contain fluorine or a heteroatom exclusive of fluorine, $R^{13}$ is hydrogen or a $C_1$-$C_{20}$ hydrocarbyl group which may contain a heteroatom, $R^{14}$ is a $C_1$-$C_8$ saturated hydrocarbyl group having at least two fluorine atoms or a $C_6$-$C_{10}$ aryl group having at least two fluorine atoms, $R^{15}$ is a $C_1$-$C_{12}$ aliphatic hydrocarbyl group or $C_6$-$C_{10}$ aryl group, any constituent —$CH_2$— in the aliphatic hydrocarbyl group may be replaced by —N(H)—, ether bond, or ester bond, some or all of the hydrogen atoms in the aliphatic hydrocarbyl group may be substituted by a halogen atom, hydroxy moiety, carboxy moiety, $C_6$-$C_{10}$ aryl moiety, $C_1$-$C_{12}$ hydrocarbyloxy moiety, $C_2$-$C_{12}$ hydrocarbylcarbonyl moiety, or $C_1$-$C_{12}$ hydrocarbylcarbonyloxy moiety, some or all of the hydrogen atoms in the aryl group may be substituted by a halogen atom, hydroxy moiety, carboxy moiety, $C_1$-$C_{12}$ hydrocarbyloxy moiety, $C_2$-$C_{12}$ hydrocarbylcarbonyl moiety, or $C_1$-$C_{12}$ hydrocarbylcarbonyloxy moiety, with the proviso that $R^{15}$ has no fluorine at the α-position relative to the sulfo group.

6. The resist composition of claim 1 wherein in the sulfonium salt (A), the sulfonium cation having at least one fluorine atom has the formula (3):

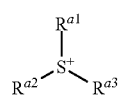

wherein $R^{a1}$ is a $C_1$-$C_{20}$ hydrocarbyl group substituted with at least one fluorine, which may contain at least one atom selected from oxygen, sulfur, nitrogen, and halogen exclusive of fluorine, $R^{a2}$ and $R^{a3}$ are each independently a $C_1$-$C_{20}$ hydrocarbyl group or $C_1$-$C_{20}$ hydrocarbyl group substituted with at least one fluorine, which may contain at least one atom selected from oxygen, sulfur, nitrogen, and halogen exclusive of fluorine, $R^{a1}$ and $R^{a2}$, or $R^{a2}$ and $R^{a3}$ may bond together to form a ring with the sulfur atom to which they are attached.

7. The resist composition of claim 1 wherein the repeat unit (a1) has the formula (a1) and the repeat unit (a2) has the formula (a2):

(a1)

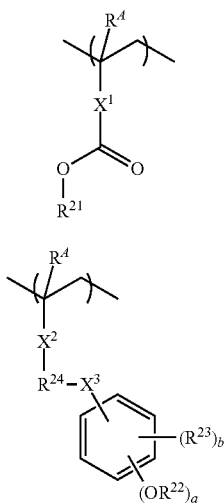

(a2)

wherein RA is each independently hydrogen or methyl,
X$^1$ is a single bond, phenylene group, naphthylene group, or a C$_1$-C$_{12}$ linking group containing at least one moiety selected from an ether bond, ester bond and lactone ring,
X$^2$ is a single bond, ester bond or amide bond,
X$^3$ is a single bond, ether bond or ester bond,
R$^{21}$ and R$^{22}$ are each independently an acid labile group,
R$^{23}$ is fluorine, trifluoromethyl, cyano or a C$_1$-C$_6$ saturated hydrocarbyl group,
R$^{24}$ is a single bond or a C$_1$-C$_6$ alkanediyl group in which some carbon may be replaced by an ether bond or ester bond,
a is 1 or 2, b is an integer of 0 to 4, and 1≤a+b≤5.

8. The resist composition of claim 1 wherein the base polymer further comprises repeat units containing an adhesive group selected from among hydroxy, carboxy, lactone ring, carbonate, thiocarbonate, carbonyl, cyclic acetal, ether bond, ester bond, sulfonic ester bond, cyano, amide bond, —O—C(=O)—S—, and —O—C(=O)—NH—.

9. The resist composition of claim 1, further comprising (D) an organic solvent.

10. The resist composition of claim 1, further comprising (E) a surfactant.

11. A pattern forming process comprising the steps of applying the positive resist composition of claim 1 to form a resist film on a substrate, exposing the resist film to high-energy radiation, and developing the exposed resist film in a developer.

12. The pattern forming process of claim 11 wherein the high-energy radiation is i-line, KrF excimer laser, ArF excimer laser, EB, or EUV of wavelength 3 to 15 nm.

13. A sulfonium salt having the formula (1-3-1):

(1-3-1)

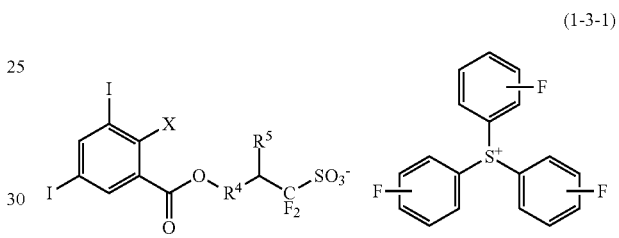

wherein R$^4$ is a single bond or C$_1$-C$_6$ alkanediyl group, R$^5$ is hydrogen or trifluoromethyl, and X is hydroxy or iodine.

* * * * *